US007960613B2

(12) United States Patent
Taramino et al.

(10) Patent No.: US 7,960,613 B2
(45) Date of Patent: Jun. 14, 2011

(54) PLANTS WITH ALTERED ROOT ARCHITECTURE, INVOLVING THE RUM1 GENE, RELATED CONSTRUCTS AND METHODS

(75) Inventors: Graziana Taramino, Wilmington, DE (US); Hajime Sakai, Newark, DE (US); Mai Komatsu, Wilmington, DE (US); Xiaomu Niu, Johnston, IA (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 37 days.

(21) Appl. No.: 12/261,358

(22) Filed: Oct. 30, 2008

(65) Prior Publication Data

US 2009/0178159 A1 Jul. 9, 2009

Related U.S. Application Data

(63) Continuation-in-part of application No. 12/030,455, filed on Feb. 13, 2008.

(60) Provisional application No. 60/889,637, filed on Feb. 13, 2007.

(51) Int. Cl.

| | |
|---|---|
| ***C12N 15/29*** | (2006.01) |
| ***C12N 15/82*** | (2006.01) |
| ***C12N 5/04*** | (2006.01) |
| ***A01H 5/00*** | (2006.01) |
| ***A01H 5/10*** | (2006.01) |

(52) U.S. Cl. .................... 800/298; 536/24.1; 435/320.1; 435/419

(58) Field of Classification Search ........................ None
See application file for complete search history.

(56) References Cited

U.S. PATENT DOCUMENTS

| | | | | |
|---|---|---|---|---|
| 2004/0034888 | A1 | 2/2004 | Liu et al. | |
| 2004/0045049 | A1 | 3/2004 | Zhang et al. | |
| 2004/0045059 | A1 | 3/2004 | Tillman et al. | |
| 2004/0122592 | A1 | 6/2004 | Fuessley et al. | |
| 2004/0214272 | A1 | 10/2004 | La Rosa et al. | |
| 2004/0216190 | A1 | 10/2004 | Kovalic | |
| 2006/0107345 | A1 | 5/2006 | Alexandrov et al. | |
| 2007/0022495 | A1 | 1/2007 | Reuber et al. | |
| 2007/0130645 | A1 * | 6/2007 | Wu et al. ....................... | 800/278 |

OTHER PUBLICATIONS

Benfey et al (1990, Science 250:959-966).*
Benfey et al (1989, EMBO J, 8(8):2195-2202).*
Woll et al., Maize Genetics Cooperation Newsletter, Isolation of a New Root Mutant rum1 Affected in Lateral and Seminal Root Initiation, 2004, vol. 78:59-60.
Woll et al., Isolation, Characterization, and Pericycle-Specific Transcriptome Analyses of the Novel Maize Lateral and Seminal Root Initiation Mutant rum1, Plant Physiology, 2005, vol. 139:1255-1267.
Fukaki et al., Lateral Root Formation Is Blocked by a Gain-Of-Function Mutation in the Solitary-Root/1AA14 Gene of *Arabidopsis*, The Plant Journal, 2002, vol. 29:153-168.
Tatematsu et al., MASSUGU2 Encodes AUX/IAA19, An Auxin-Regulated Protein That Functions Together With the Transcriptional Activator NPH4/ARF7 to Regulate Differential Growth Responses of Hypocotyl and Formation of Lateral Roots in *Arabidopdid thaliana*, Plant Cell, 2004, vol. 16:379-393.
Okushima et al., Functional Genomic Analysis of the Auxin Response Factor Gene Family Members in *Arabidopsis thaliana*: Unique and Overlapping Functions of ARF7 and ARF19, Plant Cell, 2005, vol. 17:444-463.
National Center for Biotechnology Information General Identifier No. 34911088, Nov. 9, 2004, Direct Submission.
National Center for Biotechnology Information General Identifier No. 15229343, May 22, 2008.
National Center for Biotechnology Information General Identifer No. 2388689, Sep. 10, 1997, G. Hagen et al., Direct Submission.
National Center for Biotechnology Information General Identifier No. 125553286, Feb. 9, 2007, J. Yu et al., The Genomes of *Oryza sativa*: A History of Duplications.
National Center for Biotechnology Information General Identifier No. 15227275, May 22, 2008.
National Center for Biotechnology Information General Identifier No. 22328628, May 22, 2008.
National Center for Biotechnology Information General Identifier No. 1532612, Sep. 12, 1996, Y. Kohara et al., Expression Map of the *C. elegans* Genome.
Jain et al., Structure and Expression Analysis of Early Auxin-Responsive AUX/IAA Gene Family in Rice (*Oryza sativa*), Funct. Integr. Genomics, 2006, vol. 6:47-59.
Tiwari et al., AUX/IAA Proteins Contain a Potent Transcriptional Repression Domain, Plant Cell, 2004, vol. 16:533-543.
National Center for Biotechnology Information General Identifier No. 117572683, Accession No. EF030816, Nov. 11, 2006. Abrahams et al., Expression Patterns of Three Genes in the Stem of Lucerne (*Medicago sativa*).
Abrahams et al., Plant Mol. Biol., Expression Patterns of Three Genes in the Stem of Lucerne (*Medicago sativa*), vol. 27, p. 513-528, 1995.
National Center for Biotechnology Information General Identifier No. 117572684, Accession No. EF030817, Nov. 11, 2006, Abrahams et al., Expression Patterns of Three Genes in the Stem of Lucerne (*Medicago sativa*).
Tiwari et al., Methods in mol. Biol., Aux/IAA Proteins Contain a Potent Transcriptional Repression Domain, vol. 323, p. 237-244, 2006.

(Continued)

*Primary Examiner* — Stuart F. Baum

(57) ABSTRACT

The present disclosure is directed to isolated nucleic acid fragments comprising a root-preferred maize NAS2 promoter, a functional fragment thereof, and end-uses and methods utilizing said fragments. Functional fragment NAS2 promoters include those containing the Root Motif 1, the CAAT box, and the TATA box; the Pyrimidine Box, the Pyrimidine-rich Stretch, the QAR, the Root Motif 1, the CAAT box, and the TATA box; and the Pyrimidine Box, the Pyrimidine-rich Stretch, the QAR, the Root Motif 1, and the CAAT box.

9 Claims, 22 Drawing Sheets

OTHER PUBLICATIONS

Crawford, et al., "Evolutionary Analysis of TATA-less Proximal Promoter Function", Molecular Biology and Evolution, vol. 16(2), pp. 194-207 (1999).

Davuluri, et al., "CART Classification of Human 5' UTR Sequences", Genome Research, vol. 10, pp. 1807-1816 (2000).

Guerineau, et al., "Effect of Two Consensus Sequences Preceding the Translation Initiator Codon . . . ", Plant Molecular Biology, vol. 18, pp. 815-818 (1992).

Joshi, C. P., "An Inspection of the Domain Between Putative TATA Box and Translation Start . . . ", Nucleic Acids Research, vol. 15(16), pp. 6643-6653 (1987).

Kozak, M., "Influences of mRNA Secondary Structure on Initiation by Eukaryotic Ribosomes", Proc. Natl. Acad. Sci. USA, vol. 83, pp. 2850-2854 (1986).

Kozak, M., "The Scanning Model for Translation: An Update", The Journal of Cell Biology, vol. 108, pp. 229-241 (1989).

Pugh, B. F., and Tjian, R., "Transcription from a TATA-less Promoter Requires a Multisubunit TFIID Complex", Genes & Development, vol. 5, pp. 1935-1945 (1991).

* cited by examiner

Fig.16

Modified Hoagland's solutions -
16X concentrations for semi-hydroponics maize growth.

| Nutrient | 1 mM $KNO_3$ | 2 mM $KNO_3$ | 3 mM $KNO_3$ | 4 mM $KNO_3$ |
|---|---|---|---|---|
| $KNO_3$ | 16 mM | 32 mM | 48 mM | 64 mM |
| KCl | 48 mM | 32 mM | 16 mM | ------- |
| $KH_2PO_4$ | 11 mM | 11 mM | 11 mM | 11 mM |
| $MgSO_4$ | 16 mM | 16 mM | 16 mM | 16 mM |
| $CaCl_2 \cdot 2H_2O$ | 16 mM | 16 mM | 16 mM | 16 mM |
| Sprint 330 | 1.6 g/L | 1.6 g/L | 1.6 g/L | 1.6 g/L |
| $H_3BO_3$ | 24 μM | 24 μM | 24 μM | 24 μM |
| 5 mM $MnCl_2 \cdot 4H_2O$ | 8 μM | 8 μM | 8 μM | 8 μM |
| 5 mM $ZnSO_4 \cdot 7\ H_2O$ | 8 M | 8 μM | 8 μM | 8 μM |
| 0.5 mM $CuSO_4 \cdot 5\ H_2O$ | 800 nM | 800 nM | 800 nM | 800 nM |
| 0.5 mM $H_2MoO_4 \cdot H_2O$ | 800 nM | 800 nM | 800 nM | 800 nM |

Dilute 16X with tap water and determine the pH of the final mixture.

Add 3-12 mL $H_2SO_4$ if the pH is above 6.5.

Optimum pH is 5.0 - 5.5

Fig.17

The effect of different nitrate concentrations on the growth and development of Gaspe Bay Flint derived maize lines.

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

Fig.18

```
                         *****************   *     ***      *  ************** *
SEQ ID NO:24             MSPPLEPHDYIGLSAAAAAAPPTPTPTSSSSSSSSPA--PRLTLRLGLPGSESPDRDRDC
SEQ ID NO:29             MSPPLEPHDYIGLSAVAAAAPPTPTPTSSSSSSSSPA--PRLTLRLGLPGSESPDRDRDC
SEQ ID NO:39             MSPPLEPHDYIGLSAAAAAAPPTP--TSSSSSSSSPA--PRLTLRLGLPGSESPDRDRDR
SEQ ID NO:25             MSPPLEPHDYIGLSAAAAAAPPTP--TSSSSSSSSPA--PRLTLRLGLPGSESPDRDRDC
SEQ ID NO:66             MSPPLEPHDYIGLSAAAASPTPSSSSCSSSPNPGGEARGPRLTLRLGLPGSESPER----

                            * *** * *****      *     ******   * **               *  **
SEQ ID NO:24             --CEDVAATLSLGPLPAA----AAVSAKRAFPDPAQRPGASKASDA------KQQASPAA
SEQ ID NO:29             --CEDVAATLSLGPLPAA----AAVSAKRAFPDPAQRPGASKASDA------KQQASPAA
SEQ ID NO:39             DRCEDVAAALSLGPLPATPKAPAAVSAKRAFPDPAQRPGAAKASDD------KQ-ASPAA
SEQ ID NO:25             --CEDVAATLSLGPLPAA----AAVSAKRAFPDPAQRPGASKASDA------KQQASPAA
SEQ ID NO:65             ---EVVAAGLTLGPLPPTTTKAAS---KRAFPDSSPRHGASSGSVAAAAACQDKAAPAAA

                         *****                                      * ***************
SEQ ID NO:24             PPAAKAQVVGWPPVRNYRKNTLAAATASRSKAPAEEAASGAGPMYVKVSMDGAPYLRKVD
SEQ ID NO:29             PPAAKAQVVGWPPVRNYRKNTLAAATASRSKAPAEEAASGAGPMYVKVSMDGAPYLRKVD
SEQ ID NO:39             PPAAKAQVVGWPPVRNYRKNTLAASASRSKAPAAEDAASAARPMYVKVSMDGAPYLRKVD
SEQ ID NO:25             PPAAK-----------------------SKAPAEEAASGAGPMYVKVSMDGAPYLRKVD
SEQ ID NO:65             PPAAKAQVVGWPPVRNYRKNTLAASASKGK--GEDKGTAEGGPLYVKVSMDGAPYLRKVD

                         **** ***** ** ******* ***** ***  ******** *** ************
SEQ ID NO:24             IKMYSGYEDLSLALEKMFSCFIAGQSGLHKSSSKDRLTNGSKVDALKDQEYVLTYEDKDA
SEQ ID NO:29             IKMYSSYEDLSLALEKMFSCFIAGQSGLHKSSSKDRLTNGSKVDALKDQEYVLTYEDKDA
SEQ ID NO:39             IKMYSSYEDLSVALQKMFSCFIAGQSGLHKSSSKDRLTNGSKVDALKDQEYVLTYEDKDA
SEQ ID NO:25             IKMYSSYEDLSLALEKMFSCFIAGQSGLHKSSSKDRLTNGSKVDALKDQEYVLTYEDKDA
SEQ ID NO:65             LKMYSSYEDLSMALEKMFSCFITGQSGLRKSSNRDRLTNGSKADALQDQEYVLTYEDKDA

                         *********** ** ************* *****   ** **
SEQ ID NO:24             DWMLVGDLPWDYFTSICRKLKIMRGSDAVGIAPRTVEQTGQNK
SEQ ID NO:29             DWMLVGDLPWDYFTSICRKLKIMRGSDAVGIAPRTVEQTGQNK
SEQ ID NO:39             DWMLVGDLPWDYFTSICRKLKIMRGSDAVGIAPRTIEQTGQNK
SEQ ID NO:25             DWMLVGDLPWDYFTSICRKLKIMRGSDAVGIAPRTVEQTGQNK
SEQ ID NO:65             DWMLVGDLPWDLFTTICRKLKIMRGSDAAGIAPRSIEQSGQSR
```

Fig.19

% Identity

| | SEQ ID NO:24 (B73-Mu-wt) | SEQ ID NO:29 (B73) | SEQ ID NO:39 (B73) | SEQ ID NO:25 (mutant) | SEQ ID NO:65 (gi:34911088) |
|---|---|---|---|---|---|
| SEQ ID NO:24 (B73-Mu-wt) | | 99.3 | 87.0 | 97.1 | 67.3 |
| SEQ ID NO:29 (B73) | | | 87.0 | 97.1 | 67.3 |
| SEQ ID NO:39 (B73) | | | | 88.9 | 68.6 |
| SEQ ID NO:25 (mutant) | | | | | 66.3 |
| SEQ ID NO:65 (gi:34911088) | | | | | |

SEQUENCE LISTING

```
<160> NUMBER OF SEQ ID NOS: 79

<210> SEQ ID NO 1
<211> LENGTH: 24
<212> TYPE: DNA
<213> ORGANISM: artificial sequence
<220> FEATURE:
<223> OTHER INFORMATION: primer

<400> SEQUENCE: 1
```

accttagtta cacaggcaca cggt 24

<210> SEQ ID NO 2
<211> LENGTH: 24
<212> TYPE: DNA
<213> ORGANISM: artificial sequence
<220> FEATURE:
<223> OTHER INFORMATION: primer

<400> SEQUENCE: 2
ggtgatggga ttttcgcatt atta 24

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
ggattccttt atgacggggt 20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
agtaacaacc aaggcatcgg 20

<210> SEQ ID NO 5
<211> LENGTH: 24
<212> TYPE: DNA
<213> ORGANISM: artificial sequence
<220> FEATURE:
<223> OTHER INFORMATION: primer

<400> SEQUENCE: 5
ggcatgggtc tctcataaag tcat 24

<210> SEQ ID NO 6
<211> LENGTH: 24
<212> TYPE: DNA
<213> ORGANISM: artificial sequence
<220> FEATURE:
<223> OTHER INFORMATION: primer

<400> SEQUENCE: 6
cgacgtatat ggctgagaac ccta 24

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
agacgagtta aacctccatc atgc 24

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8
cctaccccaa cttgcttgag acta 24

<210> SEQ ID NO 9
<211> LENGTH: 24
<212> TYPE: DNA
<213> ORGANISM: artificial sequence
<220> FEATURE:
<223> OTHER INFORMATION: primer

<400> SEQUENCE: 9
atctcgcgaa cgtgtgcaga ttct 24

<210> SEQ ID NO 10
<211> LENGTH: 23
<212> TYPE: DNA
<213> ORGANISM: artificial sequence
<220> FEATURE:
<223> OTHER INFORMATION: primer

<400> SEQUENCE: 10
tcgatctttc ccggaactct gac 23

<210> SEQ ID NO 11
<211> LENGTH: 23
<212> TYPE: DNA
<213> ORGANISM: artificial sequence
<220> FEATURE:
<223> OTHER INFORMATION: primer

<400> SEQUENCE: 11
gaagagatcg gctgaacaag agg 23

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
gaactgcgag acggtgacct 20

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
tgacttctat gaaaatcggc ag 22

<210> SEQ ID NO 14
<211> LENGTH: 22
<212> TYPE: DNA
<213> ORGANISM: artificial sequence
<220> FEATURE:
<223> OTHER INFORMATION: primer

<400> SEQUENCE: 14
ccatgagata atggaagaga ac 22

-continued

<210> SEQ ID NO 15
<211> LENGTH: 23
<212> TYPE: DNA
<213> ORGANISM: artificial sequence
<220> FEATURE:
<223> OTHER INFORMATION: primer

<400> SEQUENCE: 15
ggagtaaaga tccgacccgc ttg 23

<210> SEQ ID NO 16
<211> LENGTH: 23
<212> TYPE: DNA
<213> ORGANISM: artificial sequence
<220> FEATURE:
<223> OTHER INFORMATION: primer

<400> SEQUENCE: 16
cacaatcggc tccaaccttg tac 23

<210> SEQ ID NO 17
<211> LENGTH: 24
<212> TYPE: DNA
<213> ORGANISM: artificial sequence
<220> FEATURE:
<223> OTHER INFORMATION: primer

<400> SEQUENCE: 17
ggtctgatca cgacccatga gatc 24

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
ctcggattca gagcttgatt ggag 24

<210> SEQ ID NO 19
<211> LENGTH: 4098
<212> TYPE: DNA
<213> ORGANISM: Zea mays

<400> SEQUENCE: 19
gtgtctcgac agtagtgagt ggtatagcct tcttcggatg cttcaaggcc ctagaaatca 60
atatgtgatc aaccaaaagg aatcaattcc atttgcttca actgtcgaaa gcataatgta 120
tgtctaaata tgtactctct ctaacttacc atttataact aggatgcttg tcaggtttta 180
aaggaatcct gggacttgcg gttggaggag agatctaagt ataaccttgt tttagggggt 240
gtttggattc cctgacttta gtccatgtca tgtctgattt aacacggacc gaacaaatca 300
aacacacctt tttaaaaaaa atccacagac ttggtggtta gaagagggat ccgtatataa 360
ccttatacta gtcctatttg ttggtcaatt gttatggacg ccatgtcagc ttcatgtagc 420
tggaaaaggt agtagttaaa aagccttcgt atgaaacgat agttacgata cgatgtgatt 480
agcttgggaa cggcccgttt gtcccgtgga tgtgattgct tgcacctgcc ttggcaatag 540
cacggccgat tactagctac agctgactcg gcggcggcgt ccacttgtga gccggagtag 600
gacgtactag cacaatgcac aaaccgaccc cgcccagcac cagcagactc cctcccacac 660
atcgagacca cagaccagcg gcggcgaccc aaccaaccaa gcacaaagca ccgcgcgaca 720
agacgacaag gctcccggaa aagagagaaa aaacaggcga gagaaattcg ttaaaaatcc 780

-continued

```
tcccggtcgg ccacttttat taccagcact ctagcagcaa gtcgtcgctc ccaccccacc    840
tcaccatctc cactccaaac aaggggaagg cgagcgacag acaaacccac cctatcgccc    900
ctcctctgtc tcctctcttg cccacccgcc ccaatgtcgc cgcccctcga gccccacgac    960
tacatcggcc tctccgccgt ggccgcggcc gcgccgccga ccccgacccc gacctcctcc   1020
tcctcttcgt cctcctcgcc ggccccccgt ctcacccttc gcctcggcct gccgggctcc   1080
gagtcccccg accgcgaccg ggactgctgc gaggacgtcg ccgccacgct ctccctcggc   1140
ccgctgccgg cggccgccgc cgtctccgcc aagcgcgcct tcccggaccc cgcccagcgc   1200
cccggcgctt ccaaggctag cgacgccaag cagcaggctt cccccgccgc gccgccggcc   1260
gccaagtaag acccagctct cgatccgtcg caggcgttac tgttttggcc cggggttgca   1320
ccccgcctgg gcgggtgacc gatgcggtgc gctctcgatc cgtgcagagc gcaggtggtt   1380
ggatggccgc ccgtgcgcaa ctaccggaag aataccctcg ccgccgcgac cgcctccagg   1440
agcaaggcgc cggcggagga ggccgcgtcc ggagctgggc ccatgtacgt gaaggtgagc   1500
atggatggcg cgccctacct caggaaggtg gacatcaaga tgtactccag ctacgaggac   1560
ctctccctgg cgctcgagaa gatgttcagc tgcttcatcg ctggtgagtg gtgttcggtt   1620
ctatgcctct gttccatgct tttccctctt gttcacggac atttttcgaa gcttgtcgat   1680
tggatccgtt gtgatgtact aggatttaat actacaaata agtaggagtt tgaataattt   1740
tgtcgaataa aagttgcttt cttgaaacaa agattcataa gacttgtatg aagatagcat   1800
tcatacagcg atgtgttatg catgtataat tataaacaaa caccaggcac aatgcaaaac   1860
atacggtcat tttgtgcaca ccgagatatt tctgcttatc atgccacgaa ctccacctga   1920
cttggctgca ctgctctgtc tttatcatag ttccgtgtag ctctactaac ggacaagtaa   1980
ttgggacaca cgcacagttt tcacggccta acaaataatg ccatacaaat cactgaacag   2040
tttttgcata gtatatcttt ttttcacaag gatatttact tagcctgtga ttttaaaggt   2100
caaagtggtc tgcataaatc atcgagcaaa gacaggctca ctaatggctc aaaggtggat   2160
gctctcaaag atcaggagta tgtccttaca tatgaggata aggatgcaga ctggatgctt   2220
gtcggtgatc ttccctggga gtaagtacct tatattgtca tatattactt tcaatataac   2280
tatagacctt gcccttaacc ctagcctctg tatgcgtaaa tcatagagta gattaccttc   2340
ggggttggag gagctcacca ttagggcggt tctttgccta ccgacagcga ggaacggcgg   2400
tggcctcaca gtctcacaca ggggcagtga ggtgtggcgg caggcttccc ttcactgacc   2460
gcggaacaga atagatcaga tcagtgtttt cttgtgggga agagttggta acagcgaaca   2520
ttgggtcccg taccggttgc tcttcccctt ttatatgcac ggtgcgagcg ggagccgcaa   2580
ccaataggtt gttacgcccc ctgatcacgg cgcattatga taggatagga tcgactcggt   2640
ccataactga atcgattgaa atcaacccaa caaagtttag tttatttgtt gttaatgtta   2700
ttggcaatta ttagcgacat attatatgac tgaaaagaat accattgaca ttatttctcc   2760
acttgtaaat gcatcacgtt attaccacca gtagctcgtt gtagtgttaa tttttcctca   2820
actagctacg gtgacatgca aataacaaaa ggatgaaaaa aatgcacaat gtacttatgg   2880
tgtaggtatt gaacatatct gttctatatt ttggtaaaac tgattaccat gtataagctt   2940
catatcagta caagatacca ctcaagatgc aagtgctgac cttgtttgtt cctttgcagt   3000
tattttacct ctatctgccg gaagctcaaa atcatgaggg gctctgatgc tgttggaata   3060
ggtatgtaca atgtgtgaca atagatcttg acattctgca tgtattatgt gcatatgtta   3120
cagccttgca ggacgaattt attatttccc aaacacttat atttgcagtt aacttatact   3180
```

atgcagtagc tatatttctc tctcttttta ttttctgcat gtattagctg caactgtatc 3240
ctggcaacca acggattgta gcttgaatgc atagatcatt tatcctggct ggtagctgag 3300
cataaactta agtgaacaat aagacgatta aatattaatc ggaagaaaca gttgctgttt 3360
cggtgcctga atctgaaact tcagtttgga agatgccttt tcttgtctgc aaccaagacc 3420
actggctctc gcatttggtc cttcatttct gaatttaggt gcatttttc attttgctac 3480 aatgtttctt gtatgattct gaactatgtc cattgcatgc agctccacga accgtcgagc 3540
agacaggtca gaacaaataa gctttggcct ttgcctgcat ccaaggaaga catctgagct 3600
agctgggaga ctatgttgaa ggctgaagcc tgaaatagtt gccgggaatc gtcaaaaccc 3660
gtcaagtgtt tagtgtagtt ttcacgtgtc cttgagacat gtgcatttgt atgtctgtga 3720
cgtgatccgt tagatcgtgc aatcgtaggt tgctgttctt gtgccctttg aaggccagac 3780
agatcaggga gctctctgct tccttagtgc acttgctttg cagcattcct tgttattcta 3840
ctctgaaatc atacatcatg ccacaagaac cgatggttcg tgatgtcaag agagctgccc 3900
taattgttcc attgtaacct cgtaattgtg ttcttccgca ggagaaattg gtgctgcact 3960
cagcttccta ccacatcaac actagtaccg cacagcaaca gcgcatgtta cagaggtatg 4020
cgtttggggt ttgtcatggc tcaccagtca ccgttttttt gggttctgtg aatctggtga 4080
gaataaattg tacaaccg 4098

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
ggaaggcgag cgacagacaa ac 22

<210> SEQ ID NO 21
<211> LENGTH: 24
<212> TYPE: DNA
<213> ORGANISM: artificial sequence
<220> FEATURE:
<223> OTHER INFORMATION: primer

<400> SEQUENCE: 21
agctcagatg tcttccttgg atgc 24

<210> SEQ ID NO 22
<211> LENGTH: 810
<212> TYPE: DNA
<213> ORGANISM: Zea mays

<400> SEQUENCE: 22
atgtcgccgc ccctcgagcc ccacgactac atcggcctct ccgccgcggc cgcggccgcg 60
ccgccgaccc cgaccccgac ctcctcctcc tcttcgtcct cctcgccggc cccgcgcctc 120
acccttcgcc tcggcctgcc gggctccgag tcccccgacc gcgaccggga ctgctgcgag 180
gacgtcgccg ccacgctctc cctcggcccg ctgccggcgg ccgctgccgt ctccgccaag 240
cgcgccttcc cggaccccgc ccagcgcccc ggcgcttcca aggctagcga cgccaagcag 300
caggcttccc ccgccgcgcc gccggccgcc aaagcgcagg tggttggatg gccgcccgtg 360
cgcaactacc ggaagaatac cctcgccgcc gcgaccgcct ccaggagcaa ggcgccggcg 420
gaggaggccg cgtccggagc tgggcccatg tacgtgaagg tgagcatgga tggcgcgccc 480
tacctcagga aggtggacat caagatgtac tccagctacg aggacctctc cctggcgctc 540
gagaagatgt tcagctgctt catcgctggt caaagtggtc tgcataaatc atcgagcaaa 600
gacaggctca ctaatggctc aaaggtggat gccctcaaag accaggagta tgtccttaca 660
tatgaggata aggatgcaga ctggatgctt gtcggtgatc ttccctggga ttattttacc 720
tctatctgcc ggaagctcaa aatcatgagg ggctctgatg ctgttggaat agctccacga 780
accgtcgagc agacaggtca gaacaaataa 810

<210> SEQ ID NO 23
<211> LENGTH: 732
<212> TYPE: DNA
<213> ORGANISM: Zea mays

<400> SEQUENCE: 23
atgtcgccgc ccctcgagcc ccacgactac atcggcctct ccgccgcggc cgcggccgcg 60
ccgccgaccc cgacctcctc ctcctcttcc tcctcctcgc cggccccccg cctcaccctt 120
cgcctcggcc tgccgggctc cgagtccccc gaccgcgacc gggactgctg cgaggacgtc 180
gccgccacgc tctccctcgg cccgctgccg gcggcagccg ccgtctccgc caagcgcgcc 240
ttcccggacc ccgcccagcg ccccggcgct tccaaggcta gcgacgccaa gcagcaggct 300
tcccccgccg cgccgccggc cgccaagagc aaggcgccgg cggaggaggc cgcgtccgga 360
gctgggccca tgtacgtaaa ggtgagcatg gatggcgcgc cctacctcag gaaggtggac 420
atcaagatgt actccagcta cgaggacctc tccctggcgc tcgagaagat gttcagctgc 480
ttcatcgctg gtcaaagtgg tctgcataaa tcatcgagca aagacaggct gaccaatggc 540
tcaaaggtgg atgccctcaa agatcaggag tatgtcctta catatgagga taaggatgca 600
gactggatgc ttgtcggtga tcttccctgg gattatttta cctctatctg ccggaagctc 660
aaaatcatga ggggctctga tgctgttgga atagctccac gaaccgtcga gcagacaggt 720
cagaacaaat aa 732

<210> SEQ ID NO 24
<211> LENGTH: 269
<212> TYPE: PRT
<213> ORGANISM: Zea mays

<400> SEQUENCE: 24

Met Ser Pro Pro Leu Glu Pro His Asp Tyr Ile Gly Leu Ser Ala Ala
1 5 10 15

Ala Ala Ala Ala Pro Pro Thr Pro Thr Pro Thr Ser Ser Ser Ser Ser
20 25 30

Ser Ser Ser Pro Ala Pro Arg Leu Thr Leu Arg Leu Gly Leu Pro Gly
35 40 45

Ser Glu Ser Pro Asp Arg Asp Arg Asp Cys Cys Glu Asp Val Ala Ala
50 55 60

Thr Leu Ser Leu Gly Pro Leu Pro Ala Ala Ala Ala Val Ser Ala Lys
65 70 75 80

Arg Ala Phe Pro Asp Pro Ala Gln Arg Pro Gly Ala Ser Lys Ala Ser
85 90 95

Asp Ala Lys Gln Gln Ala Ser Pro Ala Ala Pro Pro Ala Ala Lys Ala
100 105 110

Gln Val Val Gly Trp Pro Pro Val Arg Asn Tyr Arg Lys Asn Thr Leu
115 120 125

Ala Ala Ala Thr Ala Ser Arg Ser Lys Ala Pro Ala Glu Glu Ala Ala

```
    130                 135                 140

Ser Gly Ala Gly Pro Met Tyr Val Lys Val Ser Met Asp Gly Ala Pro
145                 150                 155                 160

Tyr Leu Arg Lys Val Asp Ile Lys Met Tyr Ser Gly Tyr Glu Asp Leu
                165                 170                 175

Ser Leu Ala Leu Glu Lys Met Phe Ser Cys Phe Ile Ala Gly Gln Ser
            180                 185                 190

Gly Leu His Lys Ser Ser Ser Lys Asp Arg Leu Thr Asn Gly Ser Lys
        195                 200                 205

Val Asp Ala Leu Lys Asp Gln Glu Tyr Val Leu Thr Tyr Glu Asp Lys
    210                 215                 220

Asp Ala Asp Trp Met Leu Val Gly Asp Leu Pro Trp Asp Tyr Phe Thr
225                 230                 235                 240

Ser Ile Cys Arg Lys Leu Lys Ile Met Arg Gly Ser Asp Ala Val Gly
                245                 250                 255

Ile Ala Pro Arg Thr Val Glu Gln Thr Gly Gln Asn Lys
            260                 265


<210> SEQ ID NO 25
<211> LENGTH: 243
<212> TYPE: PRT
<213> ORGANISM: Zea mays

<400> SEQUENCE: 25

Met Ser Pro Pro Leu Glu Pro His Asp Tyr Ile Gly Leu Ser Ala Ala
1               5                   10                  15

Ala Ala Ala Ala Pro Pro Thr Pro Thr Ser Ser Ser Ser Ser Ser Ser
            20                  25                  30

Ser Pro Ala Pro Arg Leu Thr Leu Arg Leu Gly Leu Pro Gly Ser Glu
        35                  40                  45

Ser Pro Asp Arg Asp Arg Asp Cys Cys Glu Asp Val Ala Ala Thr Leu
    50                  55                  60

Ser Leu Gly Pro Leu Pro Ala Ala Ala Ala Val Ser Ala Lys Arg Ala
65                  70                  75                  80

Phe Pro Asp Pro Ala Gln Arg Pro Gly Ala Ser Lys Ala Ser Asp Ala
                85                  90                  95

Lys Gln Gln Ala Ser Pro Ala Ala Pro Pro Ala Ala Lys Ser Lys Ala
            100                 105                 110

Pro Ala Glu Glu Ala Ala Ser Gly Ala Gly Pro Met Tyr Val Lys Val
        115                 120                 125

Ser Met Asp Gly Ala Pro Tyr Leu Arg Lys Val Asp Ile Lys Met Tyr
    130                 135                 140

Ser Ser Tyr Glu Asp Leu Ser Leu Ala Leu Glu Lys Met Phe Ser Cys
145                 150                 155                 160

Phe Ile Ala Gly Gln Ser Gly Leu His Lys Ser Ser Ser Lys Asp Arg
                165                 170                 175

Leu Thr Asn Gly Ser Lys Val Asp Ala Leu Lys Asp Gln Glu Tyr Val
            180                 185                 190

Leu Thr Tyr Glu Asp Lys Asp Ala Asp Trp Met Leu Val Gly Asp Leu
        195                 200                 205

Pro Trp Asp Tyr Phe Thr Ser Ile Cys Arg Lys Leu Lys Ile Met Arg
    210                 215                 220

Gly Ser Asp Ala Val Gly Ile Ala Pro Arg Thr Val Glu Gln Thr Gly
225                 230                 235                 240

Gln Asn Lys
```

<210> SEQ ID NO 26
<211> LENGTH: 885
<212> TYPE: DNA
<213> ORGANISM: Zea mays

<400> SEQUENCE: 26

```
gcacgcggtc tgcgaggacg tcgccgccac gctctccctc ggcccgttgc cggcggccgc     60

cgccgtctcc gccaagcgcg ccttcccgga ccccgcccag cgccccggcg cttccaaggc    120

tagcgacgcc aagcagcagg cttcccccgc cgcgccgccg gccgccaaag cgcaggtggt    180

tggatggccg cccgtgcgca actaccggaa gaataccctc gccgccgcga ccgcctccag    240

gagcaaggcg ccggcggagg aggccgcgtc cggagctggg cccatgtacg tgaaggtgag    300

catggatggc gcgccctacc tcaggaaggt ggacatcaag atgtactcca gctacgagga    360

cctctccctg gcgctcgaga agatgttcag ctgcttcatc gctggtcaaa gtggtctgca    420

taaatcatcg agcaaagaca ggctcactaa tggctcaaag gtggatgctc tcaaagatca    480

ggagtatgtc cttacatatg aggataagga tgcagactgg atgcttgtcg gtgatcttcc    540

ctgggattat tttacctcta tctgccggaa gctcaaaatc atgaggggct ctgatgctgt    600

tggaatagct ccacgaaccg tcgagcagac aggtcagaac aaataagctt tggcctttgc    660

ctgcatccaa ggaagacatc tgagctagct gggagactat gttgaaggct gaagcctgaa    720

atagttgccg ggaatcgtca aaacccgtca agtgtttagt gtagttttca cgtgtccttg    780

agacatgtgc atttgtatgt ttgtgacgtg atccgttaga tcgtgcaatc gtaggttgct    840

gttcttgtgc cccttaaaaa aaaaaaaaaa aaaactcgag ggggg                    885
```

<210> SEQ ID NO 27
<211> LENGTH: 214
<212> TYPE: PRT
<213> ORGANISM: Arabidopsis thaliana

<400> SEQUENCE: 27

```
His Ala Val Cys Glu Asp Val Ala Ala Thr Leu Ser Leu Gly Pro Leu
1               5                   10                  15

Pro Ala Ala Ala Ala Val Ser Ala Lys Arg Ala Phe Pro Asp Pro Ala
            20                  25                  30

Gln Arg Pro Gly Ala Ser Lys Ala Ser Asp Ala Lys Gln Gln Ala Ser
        35                  40                  45

Pro Ala Ala Pro Pro Ala Ala Lys Ala Gln Val Val Gly Trp Pro Pro
    50                  55                  60

Val Arg Asn Tyr Arg Lys Asn Thr Leu Ala Ala Ala Thr Ala Ser Arg
65                  70                  75                  80

Ser Lys Ala Pro Ala Glu Glu Ala Ala Ser Gly Ala Gly Pro Met Tyr
                85                  90                  95

Val Lys Val Ser Met Asp Gly Ala Pro Tyr Leu Arg Lys Val Asp Ile
            100                 105                 110

Lys Met Tyr Ser Ser Tyr Glu Asp Leu Ser Leu Ala Leu Glu Lys Met
        115                 120                 125

Phe Ser Cys Phe Ile Ala Gly Gln Ser Gly Leu His Lys Ser Ser Ser
    130                 135                 140

Lys Asp Arg Leu Thr Asn Gly Ser Lys Val Asp Ala Leu Lys Asp Gln
145                 150                 155                 160

Glu Tyr Val Leu Thr Tyr Glu Asp Lys Asp Ala Asp Trp Met Leu Val
                165                 170                 175
```

```
Gly Asp Leu Pro Trp Asp Tyr Phe Thr Ser Ile Cys Arg Lys Leu Lys
            180                 185                 190

Ile Met Arg Gly Ser Asp Ala Val Gly Ile Ala Pro Arg Thr Val Glu
        195                 200                 205

Gln Thr Gly Gln Asn Lys
    210


<210> SEQ ID NO 28
<211> LENGTH: 810
<212> TYPE: DNA
<213> ORGANISM: Zea mays

<400> SEQUENCE: 28

atgtcgccgc ccctcgagcc ccacgactac atcggcctct ccgccgtggc cgcggccgcg      60

ccgccgaccc cgaccccgac ctcctcctcc tcttcgtcct cctcgccggc cccccgtctc     120

acccttcgcc tcggcctgcc gggctccgag tcccccgacc gcgaccggga ctgctgcgag     180

gacgtcgccg ccacgctctc cctcggcccg ctgccggcgg ccgccgccgt ctccgccaag     240

cgcgccttcc cggaccccgc ccagcgcccc ggcgcttcca aggctagcga cgccaagcag     300

caggcttccc ccgccgcgcc gccggccgcc aaggcgcagg tggttggatg gccgcccgtg     360

cgcaactacc ggaagaatac cctcgccgcc gcgaccgcct ccaggagcaa ggcgccggcg     420

gaggaggccg cgtccggagc tgggcccatg tacgtgaagg tgagcatgga tggcgcgccc     480

tacctcagga aggtggacat caagatgtac tccagctacg aggacctctc cctggcgctc     540

gagaagatgt tcagctgctt catcgctggt caaagtggtc tgcataaatc atcgagcaaa     600

gacaggctca ctaatggctc aaaggtggat gctctcaaag atcaggagta tgtccttaca     660

tatgaggata aggatgcaga ctggatgctt gtcggtgatc ttccctggga ttattttacc     720

tctatctgcc ggaagctcaa aatcatgagg ggctctgatg ctgttggaat agctccacga     780

accgtcgagc agacaggtca gaacaaataa                                      810


<210> SEQ ID NO 29
<211> LENGTH: 269
<212> TYPE: PRT
<213> ORGANISM: Zea mays

<400> SEQUENCE: 29

Met Ser Pro Pro Leu Glu Pro His Asp Tyr Ile Gly Leu Ser Ala Val
1               5                   10                  15

Ala Ala Ala Ala Pro Pro Thr Pro Thr Pro Thr Ser Ser Ser Ser Ser
            20                  25                  30

Ser Ser Ser Pro Ala Pro Arg Leu Thr Leu Arg Leu Gly Leu Pro Gly
        35                  40                  45

Ser Glu Ser Pro Asp Arg Asp Arg Asp Cys Cys Glu Asp Val Ala Ala
    50                  55                  60

Thr Leu Ser Leu Gly Pro Leu Pro Ala Ala Ala Ala Val Ser Ala Lys
65                  70                  75                  80

Arg Ala Phe Pro Asp Pro Ala Gln Arg Pro Gly Ala Ser Lys Ala Ser
                85                  90                  95

Asp Ala Lys Gln Gln Ala Ser Pro Ala Ala Pro Pro Ala Ala Lys Ala
            100                 105                 110

Gln Val Val Gly Trp Pro Pro Val Arg Asn Tyr Arg Lys Asn Thr Leu
        115                 120                 125

Ala Ala Ala Thr Ala Ser Arg Ser Lys Ala Pro Ala Glu Glu Ala Ala
    130                 135                 140
```

```
Ser Gly Ala Gly Pro Met Tyr Val Lys Val Ser Met Asp Gly Ala Pro
145                 150                 155                 160

Tyr Leu Arg Lys Val Asp Ile Lys Met Tyr Ser Ser Tyr Glu Asp Leu
                165                 170                 175

Ser Leu Ala Leu Glu Lys Met Phe Ser Cys Phe Ile Ala Gly Gln Ser
            180                 185                 190

Gly Leu His Lys Ser Ser Ser Lys Asp Arg Leu Thr Asn Gly Ser Lys
        195                 200                 205

Val Asp Ala Leu Lys Asp Gln Glu Tyr Val Leu Thr Tyr Glu Asp Lys
    210                 215                 220

Asp Ala Asp Trp Met Leu Val Gly Asp Leu Pro Trp Asp Tyr Phe Thr
225                 230                 235                 240

Ser Ile Cys Arg Lys Leu Lys Ile Met Arg Gly Ser Asp Ala Val Gly
                245                 250                 255

Ile Ala Pro Arg Thr Val Glu Gln Thr Gly Gln Asn Lys
            260                 265


<210> SEQ ID NO 30
<211> LENGTH: 321
<212> TYPE: PRT
<213> ORGANISM: Arabidopsis thaliana

<400> SEQUENCE: 30

Met Ser Tyr Arg Leu Leu Ser Val Asp Lys Asp Glu Leu Val Thr Ser
1               5                   10                  15

Pro Cys Leu Lys Glu Arg Asn Tyr Leu Gly Leu Ser Asp Cys Ser Ser
            20                  25                  30

Val Asp Ser Ser Thr Ile Pro Asn Val Val Gly Lys Ser Asn Leu Asn
        35                  40                  45

Phe Lys Ala Thr Glu Leu Arg Leu Gly Leu Pro Glu Ser Gln Ser Pro
    50                  55                  60

Glu Arg Glu Thr Asp Phe Gly Leu Leu Ser Pro Arg Thr Pro Asp Glu
65                  70                  75                  80

Lys Leu Leu Phe Pro Leu Leu Pro Ser Lys Asp Asn Gly Ser Ala Thr
                85                  90                  95

Thr Gly His Lys Asn Val Val Ser Gly Asn Lys Arg Gly Phe Ala Asp
            100                 105                 110

Thr Trp Asp Glu Phe Ser Gly Val Lys Gly Ser Val Arg Pro Gly Gly
        115                 120                 125

Gly Ile Asn Met Met Leu Ser Pro Lys Val Lys Asp Val Ser Lys Ser
    130                 135                 140

Ile Gln Glu Glu Arg Ser His Ala Lys Gly Gly Leu Asn Asn Ala Pro
145                 150                 155                 160

Ala Ala Lys Ala Gln Val Val Gly Trp Pro Pro Ile Arg Ser Tyr Arg
                165                 170                 175

Lys Asn Thr Met Ala Ser Ser Thr Ser Lys Asn Thr Asp Glu Val Asp
            180                 185                 190

Gly Lys Pro Gly Leu Gly Val Leu Phe Val Lys Val Ser Met Asp Gly
        195                 200                 205

Ala Pro Tyr Leu Arg Lys Val Asp Leu Arg Thr Tyr Thr Ser Tyr Gln
    210                 215                 220

Gln Leu Ser Ser Ala Leu Glu Lys Met Phe Ser Cys Phe Thr Leu Gly
225                 230                 235                 240

Gln Cys Gly Leu His Gly Ala Gln Gly Arg Glu Arg Met Ser Glu Ile
                245                 250                 255
```

Lys Leu Lys Asp Leu Leu His Gly Ser Glu Phe Val Leu Thr Tyr Glu
260 265 270

Asp Lys Asp Gly Asp Trp Met Leu Val Gly Asp Val Pro Trp Glu Ile
275 280 285

Phe Thr Glu Thr Cys Gln Lys Leu Lys Ile Met Lys Gly Ser Asp Ser
290 295 300

Ile Gly Leu Ala Pro Gly Ala Val Glu Lys Ser Lys Asn Lys Glu Arg
305 310 315 320

Val

<210> SEQ ID NO 31
<211> LENGTH: 228
<212> TYPE: PRT
<213> ORGANISM: Arabidopsis thaliana

<400> SEQUENCE: 31

Met Asn Leu Lys Glu Thr Glu Leu Cys Leu Gly Leu Pro Gly Gly Thr
1 5 10 15

Glu Thr Val Glu Ser Pro Ala Lys Ser Gly Val Gly Asn Lys Arg Gly
20 25 30

Phe Ser Glu Thr Val Asp Leu Lys Leu Asn Leu Gln Ser Asn Lys Gln
35 40 45

Gly His Val Asp Leu Asn Thr Asn Gly Ala Pro Lys Glu Lys Thr Phe
50 55 60

Leu Lys Asp Pro Ser Lys Pro Pro Ala Lys Ala Gln Val Val Gly Trp
65 70 75 80

Pro Pro Val Arg Asn Tyr Arg Lys Asn Val Met Ala Asn Gln Lys Ser
85 90 95

Gly Glu Ala Glu Glu Ala Met Ser Ser Gly Gly Gly Thr Val Ala Phe
100 105 110

Val Lys Val Ser Met Asp Gly Ala Pro Tyr Leu Arg Lys Val Asp Leu
115 120 125

Lys Met Tyr Thr Ser Tyr Lys Asp Leu Ser Asp Ala Leu Ala Lys Met
130 135 140

Phe Ser Ser Phe Thr Met Gly Ser Tyr Gly Ala Gln Gly Met Ile Asp
145 150 155 160

Phe Met Asn Glu Ser Lys Val Met Asp Leu Leu Asn Ser Ser Glu Tyr
165 170 175

Val Pro Ser Tyr Glu Asp Lys Asp Gly Asp Trp Met Leu Val Gly Asp
180 185 190

Val Pro Trp Pro Met Phe Val Glu Ser Cys Lys Arg Leu Arg Ile Met
195 200 205

Lys Gly Ser Glu Ala Ile Gly Leu Ala Pro Arg Ala Met Glu Lys Phe
210 215 220

Lys Asn Arg Ser
225

<210> SEQ ID NO 32
<211> LENGTH: 197
<212> TYPE: PRT
<213> ORGANISM: Arabidopsis thaliana

<400> SEQUENCE: 32

Met Glu Lys Glu Gly Leu Gly Leu Glu Ile Thr Glu Leu Arg Leu Gly
1 5 10 15

Leu Pro Gly Arg Asp Val Ala Glu Lys Met Met Lys Lys Arg Ala Phe
20 25 30

```
Thr Glu Met Asn Met Thr Ser Ser Gly Ser Asn Ser Asp Gln Cys Glu
        35                  40                  45

Ser Gly Val Val Ser Ser Gly Gly Asp Ala Glu Lys Val Asn Asp Ser
    50                  55                  60

Pro Ala Ala Lys Ser Gln Val Val Gly Trp Pro Pro Val Cys Ser Tyr
65                  70                  75                  80

Arg Lys Lys Asn Ser Cys Lys Glu Ala Ser Thr Thr Lys Val Gly Leu
                85                  90                  95

Gly Tyr Val Lys Val Ser Met Asp Gly Val Pro Tyr Leu Arg Lys Met
            100                 105                 110

Asp Leu Gly Ser Ser Gln Gly Tyr Asp Asp Leu Ala Phe Ala Leu Asp
        115                 120                 125

Lys Leu Phe Gly Phe Arg Gly Ile Gly Val Ala Leu Lys Asp Gly Asp
    130                 135                 140

Asn Cys Glu Tyr Val Thr Ile Tyr Glu Asp Lys Asp Gly Asp Trp Met
145                 150                 155                 160

Leu Ala Gly Asp Val Pro Trp Gly Met Phe Leu Glu Ser Cys Lys Arg
                165                 170                 175

Leu Arg Ile Met Lys Arg Ser Asp Ala Thr Gly Phe Gly Leu Gln Pro
            180                 185                 190

Arg Gly Val Asp Glu
        195
```

<210> SEQ ID NO 33
<211> LENGTH: 21
<212> TYPE: DNA
<213> ORGANISM: artificial sequence
<220> FEATURE:
<223> OTHER INFORMATION: primer

<400> SEQUENCE: 33
tccacttgtg agccggagta g 21

<210> SEQ ID NO 34
<211> LENGTH: 23
<212> TYPE: DNA
<213> ORGANISM: artificial sequence
<220> FEATURE:
<223> OTHER INFORMATION: primer

<400> SEQUENCE: 34
aggacgaaga ggaggaggag gtc 23

<210> SEQ ID NO 35
<211> LENGTH: 23
<212> TYPE: DNA
<213> ORGANISM: artificial sequence
<220> FEATURE:
<223> OTHER INFORMATION: primer

<400> SEQUENCE: 35
accagcactc tagcagcaag tcg 23

<210> SEQ ID NO 36
<211> LENGTH: 21
<212> TYPE: DNA
<213> ORGANISM: artificial sequence
<220> FEATURE:
<223> OTHER INFORMATION: primer

<400> SEQUENCE: 36
gagaggccga tgtagtcgtg g 21

<210> SEQ ID NO 37
<211> LENGTH: 32
<212> TYPE: DNA
<213> ORGANISM: artificial sequence
<220> FEATURE:
<223> OTHER INFORMATION: primer

<400> SEQUENCE: 37
agagaagcca acgccawcgc ctcyatttcg tc 32

<210> SEQ ID NO 38
<211> LENGTH: 819
<212> TYPE: DNA
<213> ORGANISM: Zea mays

<400> SEQUENCE: 38
atgtcgccgc ccctcgagcc ccacgactac atcggcctct ccgccgccgc cgccgcggcg 60
ccgccgacac cgacctcctc ctcgtcgtcc tcgtcctcgc cggcgccccg cctcaccctc 120
cgcctcggcc tgccgggctc cgagtccccc gaccgcgacc gcgaccggga ccgctgcgag 180
gacgtcgccg ccgcgctctc cctcggcccg ctgcctgcta cccccaaggc gcccgctgcc 240
gtctccgcca agcgcgcctt cccggacccc gcccagcgcc ccggcgctgc caaggctagc 300
gacgacaagc aggcgtcccc cgccgccccg ccggccgcca aggcgcaggt ggtgggatgg 360
ccgcccgtgc ggaactaccg gaagaacacc ctcgccgcga gcgcctccag gagcaaggcg 420
ccggcggcgg aggacgccgc gtctgcggcc cggcccatgt acgtgaaggt gagcatggat 480
ggcgcgccct acctcaggaa ggtggacatc aagatgtact ccagctacga ggacctctcc 540
gtggcgctcc agaagatgtt cagctgcttc atcgctggtc aaagtggcct gcataaatca 600
tcgagcaaag acaggctgac taatggctcg aaggtggatg ccctcaaaga ccaggagtat 660
gtacttacat atgaggataa ggatgcagac tggatgcttg tcggtgatct tccctgggat 720
tattttacct ctatctgccg gaagctcaaa atcatgaggg gctctgatgc tgttggaata 780
gctccaagaa ccatagagca gacaggtcag aacaaataa 819

<210> SEQ ID NO 39
<211> LENGTH: 272
<212> TYPE: PRT
<213> ORGANISM: Zea mays

<400> SEQUENCE: 39

Met Ser Pro Pro Leu Glu Pro His Asp Tyr Ile Gly Leu Ser Ala Ala
1 5 10 15

Ala Ala Ala Ala Pro Pro Thr Pro Thr Ser Ser Ser Ser Ser Ser Ser
20 25 30

Ser Pro Ala Pro Arg Leu Thr Leu Arg Leu Gly Leu Pro Gly Ser Glu
35 40 45

Ser Pro Asp Arg Asp Arg Asp Arg Asp Arg Cys Glu Asp Val Ala Ala
50 55 60

Ala Leu Ser Leu Gly Pro Leu Pro Ala Thr Pro Lys Ala Pro Ala Ala
65 70 75 80

Val Ser Ala Lys Arg Ala Phe Pro Asp Pro Ala Gln Arg Pro Gly Ala
85 90 95

Ala Lys Ala Ser Asp Asp Lys Gln Ala Ser Pro Ala Ala Pro Pro Ala
100 105 110

Ala Lys Ala Gln Val Val Gly Trp Pro Pro Val Arg Asn Tyr Arg Lys

```
        115                 120                 125

Asn Thr Leu Ala Ala Ser Ala Ser Arg Ser Lys Ala Pro Ala Ala Glu
    130                 135                 140

Asp Ala Ala Ser Ala Ala Arg Pro Met Tyr Val Lys Val Ser Met Asp
145                 150                 155                 160

Gly Ala Pro Tyr Leu Arg Lys Val Asp Ile Lys Met Tyr Ser Ser Tyr
                165                 170                 175

Glu Asp Leu Ser Val Ala Leu Gln Lys Met Phe Ser Cys Phe Ile Ala
            180                 185                 190

Gly Gln Ser Gly Leu His Lys Ser Ser Ser Lys Asp Arg Leu Thr Asn
        195                 200                 205

Gly Ser Lys Val Asp Ala Leu Lys Asp Gln Glu Tyr Val Leu Thr Tyr
    210                 215                 220

Glu Asp Lys Asp Ala Asp Trp Met Leu Val Gly Asp Leu Pro Trp Asp
225                 230                 235                 240

Tyr Phe Thr Ser Ile Cys Arg Lys Leu Lys Ile Met Arg Gly Ser Asp
                245                 250                 255

Ala Val Gly Ile Ala Pro Arg Thr Ile Glu Gln Thr Gly Gln Asn Lys
            260                 265                 270
```

<210> SEQ ID NO 40
<211> LENGTH: 24
<212> TYPE: DNA
<213> ORGANISM: artificial sequence
<220> FEATURE:
<223> OTHER INFORMATION: primer

<400> SEQUENCE: 40
gactcctgcc tcttctctct ctcg 24

<210> SEQ ID NO 41
<211> LENGTH: 23
<212> TYPE: DNA
<213> ORGANISM: artificial sequence
<220> FEATURE:
<223> OTHER INFORMATION: primer

<400> SEQUENCE: 41
agggcacaag aacagatctg acg 23

<210> SEQ ID NO 42
<211> LENGTH: 29
<212> TYPE: DNA
<213> ORGANISM: artificial sequence
<220> FEATURE:
<223> OTHER INFORMATION: primer

<400> SEQUENCE: 42
ggggacaagt ttgtacaaaa aagcaggct 29

<210> SEQ ID NO 43
<211> LENGTH: 29
<212> TYPE: DNA
<213> ORGANISM: artificial sequence
<220> FEATURE:
<223> OTHER INFORMATION: primer

<400> SEQUENCE: 43
ggggaccact ttgtacaaga aagctgggt 29

<210> SEQ ID NO 44
<211> LENGTH: 54

<212> TYPE: DNA
<213> ORGANISM: artificial sequence
<220> FEATURE:
<223> OTHER INFORMATION: primer

<400> SEQUENCE: 44
ttaaacaagt ttgtacaaaa aagcaggctg caattaaccc tcactaaagg gaac 54

<210> SEQ ID NO 45
<211> LENGTH: 53
<212> TYPE: DNA
<213> ORGANISM: artificial sequence
<220> FEATURE:
<223> OTHER INFORMATION: primer

<400> SEQUENCE: 45
ttaaaccact ttgtacaaga aagctgggtg cgtaatacga ctcactatag ggc 53

<210> SEQ ID NO 46
<211> LENGTH: 4291
<212> TYPE: DNA
<213> ORGANISM: artificial sequence
<220> FEATURE:
<223> OTHER INFORMATION: vector

<400> SEQUENCE: 46
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacacattg atgagcaatg cttttttata atgccaactt tgtacaaaaa 660
agctgaacga gaaacgtaaa atgatataaa tatcaatata ttaaattaga ttttgcataa 720
aaaacagact acataatact gtaaaacaca acatatccag tcactatgaa tcaactactt 780
agatggtatt agtgacctgt agtcgaccga cagccttcca aatgttcttc gggtgatgct 840
gccaacttag tcgaccgaca gccttccaaa tgttcttctc aaacggaatc gtcgtatcca 900
gcctactcgc tattgtcctc aatgccgtat taaatcataa aaagaaataa gaaaaagagg 960
tgcgagcctc ttttttgtgt gacaaaataa aaacatctac ctattcatat acgctagtgt 1020
catagtcctg aaaatcatct gcatcaagaa caatttcaca actcttatac ttttctctta 1080
caagtcgttc ggcttcatct ggattttcag cctctatact tactaaacgt gataaagttt 1140
ctgtaatttc tactgtatcg acctgcagac tggctgtgta taagggagcc tgacatttat 1200
attccccaga acatcaggtt aatggcgttt ttgatgtcat tttcgcggtg gctgagatca 1260
gccacttctt ccccgataac ggagaccggc acactggcca tatcggtggt catcatgcgc 1320
cagctttcat ccccgatatg caccaccggg taaagttcac gggagacttt atctgacagc 1380
agacgtgcac tggccagggg gatcaccatc cgtcgcccgg gcgtgtcaat aatatcactc 1440
tgtacatcca caaacagacg ataacggctc tctcttttat aggtgtaaac cttaaactgc 1500

-continued

```
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg gttgtgctta ccagaccgga gatattgaca tcatatatgc cttgagcaac   1680
tgatagctgt cgctgtcaac tgtcactgta atacgctgct tcatagcata cctcttttg    1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaaaataat atcatcatga tcagtcctgc   3120
tcctcggcca cgaagtgcac gcagttgccg gccgggtcgc gcagggcgaa ctcccgcccc   3180
cacggctgct cgccgatctc ggtcatggcc ggcccggagg cgtcccggaa gttcgtggac   3240
acgacctccg accactcggc gtacagctcg tccaggccgc gcacccacac ccaggccagg   3300
gtgttgtccg gcaccacctg gtcctggacc gcgctgatga acagggtcac gtcgtcccgg   3360
accacaccgg cgaagtcgtc ctccacgaag tcccgggaga acccgagccg gtcggtccag   3420
aactcgaccg ctccggcgac gtcgcgcgcg gtgagcaccg gaacggcact ggtcaacttg   3480
gccatggttt agttcctcac cttgtcgtat tatactatgc cgatatacta tgccgatgat   3540
taattgtcaa cacgtgctga tcatgaccaa aatcccttaa cgtgagttac gcgtcgttcc   3600
actgagcgtc agaccccgta gaaaagatca aaggatcttc ttgagatcct ttttttctgc   3660
gcgtaatctg ctgcttgcaa acaaaaaaac caccgctacc agcggtggtt tgtttgccgg   3720
atcaagagct accaactctt tttccgaagg taactggctt cagcagagcg cagataccaa   3780
atactgttct tctagtgtag ccgtagttag gccaccactt caagaactct gtagcaccgc   3840
ctacatacct cgctctgcta atcctgttac cagtggctgc tgccagtggc gataagtcgt   3900
```

gtcttaccgg gttggactca agacgatagt taccggataa ggcgcagcgg tcgggctgaa 3960 cgggggggttc gtgcacacag cccagcttgg agcgaacgac ctacaccgaa ctgagatacc 4020
tacagcgtga gctatgagaa agcgccacgc ttcccgaagg gagaaaggcg gacaggtatc 4080
cggtaagcgg cagggtcgga acaggagagc gcacgaggga gcttccaggg ggaaacgcct 4140
ggtatcttta tagtcctgtc gggtttcgcc acctctgact tgagcgtcga tttttgtgat 4200
gctcgtcagg ggggcggagc ctatggaaaa acgccagcaa cgcggccttt ttacggttcc 4260
tggccttttg ctggcctttt gctcacatgt t 4291

<210> SEQ ID NO 47
<211> LENGTH: 4762
<212> TYPE: DNA
<213> ORGANISM: artificial sequence
<220> FEATURE:
<223> OTHER INFORMATION: vector

<400> SEQUENCE: 47
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacacattg atgagcaatg cttttttata atgccaactt tgtacaaaaa 660
agctgaacga gaaacgtaaa atgatataaa tatcaatata ttaaattaga ttttgcataa 720
aaaacagact acataatact gtaaaacaca acatatccag tcactatgaa tcaactactt 780
agatggtatt agtgacctgt agtcgaccga cagccttcca aatgttcttc gggtgatgct 840
gccaacttag tcgaccgaca gccttccaaa tgttcttctc aaacggaatc gtcgtatcca 900
gcctactcgc tattgtcctc aatgccgtat taaatcataa aaagaaataa gaaaaagagg 960
tgcgagcctc ttttttgtgt gacaaaataa aaacatctac ctattcatat acgctagtgt 1020
catagtcctg aaaatcatct gcatcaagaa caatttcaca actcttatac ttttctctta 1080
caagtcgttc ggcttcatct ggattttcag cctctatact tactaaacgt gataaagttt 1140
ctgtaatttc tactgtatcg acctgcagac tggctgtgta taagggagcc tgacatttat 1200
attccccaga acatcaggtt aatggcgttt ttgatgtcat tttcgcggtg gctgagatca 1260
gccacttctt ccccgataac ggagaccggc acactggcca tatcggtggt catcatgcgc 1320
cagctttcat ccccgatatg caccaccggg taaagttcac gggagacttt atctgacagc 1380
agacgtgcac tggccagggg gatcaccatc cgtcgcccgg gcgtgtcaat aatatcactc 1440
tgtacatcca caaacagacg ataacggctc tctcttttat aggtgtaaac cttaaactgc 1500
atttcaccag cccctgttct cgtcagcaaa agagccgttc atttcaataa accgggcgac 1560
ctcagccatc ccttcctgat ttccgcttt ccagcgttcg gcacgcagac gacgggcttc 1620
attctgcatg gttgtgctta ccagaccgga gatattgaca tcatatatgc cttgagcaac 1680

```
tgatagctgt cgctgtcaac tgtcactgta atacgctgct tcatagcata cctctttttg   1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacggaa ttccggatga gcattcatca ggcgggcaag aatgtgaata aaggccggat   2340
aaaacttgtg cttatttttc tttacggtct ttaaaaaggc cgtaatatcc agctgaacgg   2400
tctggttata ggtacattga gcaactgact gaaatgcctc aaaatgttct ttacgatgcc   2460
attgggatat atcaacggtg gtatatccag tgattttttt ctccatttta gcttccttag   2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg tttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
ctcaaaatct ctgatgttac attgcacaag ataaaaataat atcatcatga acaataaaac   3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa aacagcattc caggtattag   3480
aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tatttttgac gaggggaaat   3780
taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
atggtattga taatcctgat atgaataaat tgcagtttca tttgatgctc gatgagtttt   3960
tctaatcaga attggttaat tggttgtaac actggcagag cattacgctg acttgacggg   4020
acggcgcaag ctcatgacca aaatccctta acgtgagtta cgcgtcgttc cactgagcgt   4080
```

```
cagaccccgt agaaaagatc aaaggatctt cttgagatcc tttttttctg cgcgtaatct   4140

gctgcttgca aacaaaaaaa ccaccgctac cagcggtggt ttgtttgccg gatcaagagc   4200

taccaactct ttttccgaag gtaactggct tcagcagagc gcagatacca aatactgttc   4260

ttctagtgta gccgtagtta ggccaccact tcaagaactc tgtagcaccg cctacatacc   4320

tcgctctgct aatcctgtta ccagtggctg ctgccagtgg cgataagtcg tgtcttaccg   4380

ggttggactc aagacgatag ttaccggata aggcgcagcg gtcgggctga acggggggtt   4440

cgtgcacaca gcccagcttg gagcgaacga cctacaccga actgagatac ctacagcgtg   4500

agctatgaga aagcgccacg cttcccgaag ggagaaaggc ggacaggtat ccggtaagcg   4560

gcagggtcgg aacaggagag cgcacgaggg agcttccagg gggaaacgcc tggtatcttt   4620

atagtcctgt cgggtttcgc cacctctgac ttgagcgtcg atttttgtga tgctcgtcag   4680

gggggcggag cctatggaaa aacgccagca acgcggcctt tttacggttc ctggcctttt   4740

gctggccttt tgctcacatg tt                                            4762
```

```
<210> SEQ ID NO 48
<211> LENGTH: 9142
<212> TYPE: DNA
<213> ORGANISM: artificial sequence
<220> FEATURE:
<223> OTHER INFORMATION: vector

<400> SEQUENCE: 48

ttatttgtct tctggttctg actctctttc tctcgtttca atgccaggtt gcctactccc     60

acaccactca caagaagatt ctactgttag tattaaatat tttttaatgt attaaatgat    120

gaatgctttt gtaaacagaa caagactatg tctaataagt gtcttgcaac atttttttaag    180

aaattaaaaa aaatatattt attatcaaaa tcaaatgtat gaaaaatcat gaataatata    240

attttataca tttttttaaa aaatctttta atttcttaat taatatctta aaaataatga    300

ttaatattta acccaaaata attagtatga ttggtaagga agatatccat gttatgtttg    360

gatgtgagtt tgatctagag caaagcttac tagagtcgac ctgcagcccc tccaccgcgg    420

tggcggccgc tctagagatc cgtcaacatg gtggagcacg acactctcgt ctactccaag    480

aatatcaaag atacagtctc agaagaccaa agggctattg agacttttca acaaagggta    540

atatcgggaa acctcctcgg attccattgc ccagctatct gtcacttcat caaaaggaca    600

gtagaaaagg aaggtggcac ctacaaatgc catcattgcg ataaaggaaa ggctatcgtt    660

caagatgcct ctgccgacag tggtcccaaa gatggacccc cacccacgag gagcatcgtg    720

gaaaaagaag acgttccaac cacgtcttca aagcaagtgg attgatgtga tgatcctatg    780

cgtatggtat gacgtgtgtt caagatgatg acttcaaacc tacctatgac gtatggtatg    840

acgtgtgtcg actgatgact tagatccact cgagcggcta taaatacgta cctacgcacc    900

ctgcgctacc atccctagag ctgcagctta tttttacaac aattaccaac aacaacaaac    960

aacaaacaac attacaatta ctatttacaa ttacagtcga cccatcaaca agtttgtaca   1020

aaaaagctga acgagaaacg taaaatgata taaatatcaa tatattaaat tagattttgc   1080

ataaaaaaca gactacataa tactgtaaaa cacaacatat ccagtcatat tggcggccgc   1140

attaggcacc ccaggcttta cactttatgc ttccggctcg tataatgtgt ggattttgag   1200

ttaggatccg tcgagatttt caggagctaa ggaagctaaa atggagaaaa aaatcactgg   1260

atataccacc gttgatatat cccaatggca tcgtaaagaa cattttgagg catttcagtc   1320

agttgctcaa tgtacctata accagaccgt tcagctggat attacggcct ttttaaagac   1380
```

```
cgtaaagaaa aataagcaca agttttatcc ggcctttatt cacattcttg cccgcctgat   1440
gaatgctcat ccggaattcc gtatggcaat gaaagacggt gagctggtga tatgggatag   1500
tgttcaccct tgttacaccg ttttccatga gcaaactgaa acgttttcat cgctctggag   1560
tgaataccac gacgatttcc ggcagtttct acacatatat tcgcaagatg tggcgtgtta   1620
cggtgaaaac ctggcctatt tccctaaagg gtttattgag aatatgtttt tcgtctcagc   1680
caatccctgg gtgagtttca ccagttttga tttaaacgtg gccaatatgg acaacttctt   1740
cgcccccgtt ttcaccatgg gcaaatatta tacgcaaggc gacaaggtgc tgatgccgct   1800
ggcgattcag gttcatcatg ccgtttgtga tggcttccat gtcggcagaa tgcttaatga   1860
attacaacag tactgcgatg agtggcaggg cggggcgtaa agatctggat ccggcttact   1920
aaaagccaga taacagtatg cgtatttgcg cgctgatttt tgcggtataa gaatatatac   1980
tgatatgtat acccgaagta tgtcaaaaag aggtatgcta tgaagcagcg tattacagtg   2040
acagttgaca gcgacagcta tcagttgctc aaggcatata tgatgtcaat atctccggtc   2100
tggtaagcac aaccatgcag aatgaagccc gtcgtctgcg tgccgaacgc tggaaagcgg   2160
aaaatcagga agggatggct gaggtcgccc ggtttattga aatgaacggc tcttttgctg   2220
acgagaacag gggctggtga aatgcagttt aaggtttaca cctataaaag agagagccgt   2280
tatcgtctgt ttgtggatgt acagagtgat attattgaca cgcccgggcg acggatggtg   2340
atccccctgg ccagtgcacg tctgctgtca gataaagtct cccgtgaact ttacccggtg   2400
gtgcatatcg gggatgaaag ctggcgcatg atgaccaccg atatggccag tgtgccggtc   2460
tccgttatcg gggaagaagt ggctgatctc agccaccgcg aaaatgacat caaaaacgcc   2520
attaacctga tgttctgggg aatataaatg tcaggctccc ttatacacag ccagtctgca   2580
ggtcgaccat agtgactgga tatgttgtgt tttacagtat tatgtagtct gtttttttatg   2640
caaaatctaa tttaatatat tgatatttat atcattttac gtttctcgtt cagctttctt   2700
gtacaaagtg gttgataacc tagacttgtc catcttctgg attggccaac ttaattaatg   2760
tatgaaataa aaggatgcac acatagtgac atgctaatca ctataatgtg ggcatcaaag   2820
ttgtgtgtta tgtgtaatta ctagttatct gaataaaaga gaaagagatc atccatattt   2880
cttatcctaa atgaatgtca cgtgtcttta taattctttg atgaaccaga tgcatttcat   2940
taaccaaatc catatacata taaatattaa tcatatataa ttaatatcaa ttgggttagc   3000
aaaacaaatc tagtctaggt gtgttttgcg aattcgatat caagcttgat gggtaccggc   3060
gcgcccgatc atccggatat agttcctcct ttcagcaaaa aacccctcaa gacccgttta   3120
gaggccccaa ggggttatgc tagttattgc tcagcggtgg cagcagccaa ctcagcttcc   3180
tttcgggctt tgttagcagc cggatcgatc caagctgtac ctcactattc ctttgccctc   3240
ggacgagtgc tggggcgtcg gtttccacta tcggcgagta cttctacaca gccatcggtc   3300
cagacggccg cgcttctgcg ggcgatttgt gtacgcccga cagtcccggc tccggatcgg   3360
acgattgcgt cgcatcgacc ctgcgcccaa gctgcatcat cgaaattgcc gtcaaccaag   3420
ctctgataga gttggtcaag accaatgcgg agcatatacg cccggagccg cggcgatcct   3480
gcaagctccg gatgcctccg ctcgaagtag cgcgtctgct gctccataca agccaaccac   3540
ggcctccaga agaagatgtt ggcgacctcg tattgggaat ccccgaacat cgcctcgctc   3600
cagtcaatga ccgctgttat gcggccattg tccgtcagga cattgttgga gccgaaatcc   3660
gcgtgcacga ggtgccggac ttcggggcag tcctcggccc aaagcatcag ctcatcgaga   3720
gcctgcgcga cggacgcact gacggtgtcg tccatcacag tttgccagtg atacacatgg   3780
```

-continued

```
ggatcagcaa tcgcgcatat gaaatcacgc catgtagtgt attgaccgat tccttgcggt   3840
ccgaatgggc cgaacccgct cgtctggcta agatcggccg cagcgatcgc atccatagcc   3900
tccgcgaccg gctgcagaac agcgggcagt tcggtttcag gcaggtcttg caacgtgaca   3960
ccctgtgcac ggcgggagat gcaataggtc aggctctcgc tgaattcccc aatgtcaagc   4020
acttccggaa tcgggagcgc ggccgatgca aagtgccgat aaacataacg atctttgtag   4080
aaaccatcgg cgcagctatt tacccgcagg acatatccac gccctcctac atcgaagctg   4140
aaagcacgag attcttcgcc ctccgagagc tgcatcaggt cggagacgct gtcgaacttt   4200
tcgatcagaa acttctcgac agacgtcgcg gtgagttcag gcttttccat gggtatatct   4260
ccttcttaaa gttaaacaaa attatttcta gagggaaacc gttgtggtct ccctatagtg   4320
agtcgtatta atttcgcggg atcgagatct gatcaacctg cattaatgaa tcggccaacg   4380
cgcggggaga ggcggtttgc gtattgggcg ctcttccgct tcctcgctca ctgactcgct   4440
gcgctcggtc gttcggctgc ggcgagcggt atcagctcac tcaaaggcgg taatacggtt   4500
atccacagaa tcaggggata acgcaggaaa gaacatgtga gcaaaaggcc agcaaaaggc   4560
caggaaccgt aaaaaggccg cgttgctggc gtttttccat aggctccgcc cccctgacga   4620
gcatcacaaa aatcgacgct caagtcagag gtggcgaaac ccgacaggac tataaagata   4680
ccaggcgttt ccccctggaa gctccctcgt gcgctctcct gttccgaccc tgccgcttac   4740
cggatacctg tccgcctttc tcccttcggg aagcgtggcg ctttctcaat gctcacgctg   4800
taggtatctc agttcggtgt aggtcgttcg ctccaagctg ggctgtgtgc acgaaccccc   4860
cgttcagccc gaccgctgcg ccttatccgg taactatcgt cttgagtcca acccggtaag   4920
acacgactta tcgccactgg cagcagccac tggtaacagg attagcagag cgaggtatgt   4980
aggcggtgct acagagttct tgaagtggtg gcctaactac ggctacacta gaaggacagt   5040
atttggtatc tgcgctctgc tgaagccagt taccttcgga aaaagagttg gtagctcttg   5100
atccggcaaa caaaccaccg ctggtagcgg tggttttttt gtttgcaagc agcagattac   5160
gcgcagaaaa aaaggatctc aagaagatcc tttgatcttt tctacggggt ctgacgctca   5220
gtggaacgaa aactcacgtt aagggatttt ggtcatgaca ttaacctata aaaataggcg   5280
tatcacgagg ccctttcgtc tcgcgcgttt cggtgatgac ggtgaaaacc tctgacacat   5340
gcagctcccg gagacggtca cagcttgtct gtaagcggat gccgggagca gacaagcccg   5400
tcagggcgcg tcagcgggtg ttggcgggtg tcggggctgg cttaactatg cggcatcaga   5460
gcagattgta ctgagagtgc accatatgga catattgtcg ttagaacgcg gctacaatta   5520
atacataacc ttatgtatca tacacatacg atttaggtga cactatagaa cggcgcgcca   5580
agctgggtct agaactagaa acgtgatgcc acttgttatt gaagtcgatt acagcatcta   5640
ttctgtttta ctatttataa ctttgccatt tctgactttt gaaaactatc tctggatttc   5700
ggtatcgctt tgtgaagatc gagcaaaaga gacgttttgt ggacgcaatg gtccaaatcc   5760
gttctacatg aacaaattgg tcacaatttc cactaaaagt aaataaatgg caagttaaaa   5820
aaggaatatg cattttactg attgcctagg tgagctccaa gagaagttga atctacacgt   5880
ctaccaaccg ctaaaaaaag aaaaacattg aatatgtaac ctgattccat tagcttttga   5940
cttcttcaac agattctcta cttagatttc taacagaaat attattacta gcacatcatt   6000
ttcagtctca ctacagcaaa aaatccaacg gcacaataca gacaacagga gatatcagac   6060
tacagagata gatagatgct actgcatgta gtaagttaaa taaaaggaaa ataaaatgtc   6120
ttgctaccaa aactactaca gactatgatg ctcaccacag gccaaatcct gcaactagga   6180
```

-continued

```
cagcattatc ttatatatat tgtacaaaac aagcatcaag gaacatttgg tctaggcaat   6240
cagtacctcg ttctaccatc accctcagtt atcacatcct tgaaggatcc attactggga   6300
atcatcggca acacatgctc ctgatggggc acaatgacat caagaaggta ggggccaggg   6360
gtgtccaaca ttctctgaat tgccgctcta agctcttcct tcttcgtcac tcgcgctgcc   6420
ggtatcccac aagcatcagc aaacttgagc atgtttggga atatctcgct ctcgctagac   6480
ggatctccaa gataggtgtg agctctattg gacttgtaga acctatcctc caactgaacc   6540
accataccca aatgctgatt gttcaacaac aatatcttaa ctgggagatt ctccactctt   6600
atagtggcca actcctgaac attcatgatg aaactaccat ccccatcaat gtcaaccaca   6660
acagccccag ggttagcaac agcagcacca atagccgcag gcaatccaaa acccatggct   6720
ccaagacccc ctgaggtcaa ccactgcctc ggtctcttgt acttgtaaaa ctgcgcagcc   6780
cacatttgat gctgcccaac cccagtacta acaatagcat ctccattagt caactcatca   6840
agaacctcga tagcatgctg cggagaaatc gcgtcctgga atgtcttgta acccaatgga   6900
aacttgtgtt tctgcacatt aatctcttct ctccaacctc caagatcaaa cttaccctcc   6960
actcctttct cctccaaaat catattaatt cccttcaagg ccaacttcaa atccgcgcaa   7020
accgacacgt gcgcctgctt gttcttccca atctcggcag aatcaatatc aatgtgaaca   7080
atcttagccc tactagcaaa agcctcaagc ttcccagtaa cacggtcatc aaaccttacc   7140
ccaaaggcaa gcaacaaatc actattgtca acagcatagt tagcataaac agtaccatgc   7200
atacccagca tctgaaggga atattcatca ccaataggaa aagttccaag acccattaaa   7260
gtgctagcaa cgggaatacc agtgagttca acaaagcgcc tcaattcagc actggaattc   7320
aaactgccac cgccgacgta gagaacgggc ttttgggcct ccatgatgag tctgacaatg   7380
tgttccaatt gggcctcggc ggggggcctg ggcagcctgg cgaggtaacc ggggaggtta   7440
acgggctcgt cccaattagg cacggcgagt tgctgctgaa cgtctttggg aatgtcgatg   7500
aggaccggac cggggcggcc ggaggtggcg acgaagaaag cctcggcgac gacgcggggg   7560
atgtcgtcga cgtcgaggat gaggtagttg tgcttcgtga tggatctgct cacctccacg   7620
atcggggttt cttggaaggc gtcggtgccg atcatccggc gggcgacctg gccggtgatg   7680
gcgacgactg ggacgctgtc cattaaagcg tcggcgaggc cgctcacgag gttggtggcg   7740
ccggggccgg aggtggcaat gcagacgccg gggaggccgg aggaacgcgc gtagccttcg   7800
gcggcgaaga cgccgccctg ctcgtggcgc gggagcacgt tgcggatggc ggcggagcgc   7860
gtgagcgcct ggtggatctc catcgacgca ccgccggggt acgcgaacac cgtcgtcacg   7920
ccctgcctct ccagcgcctc cacaaggatg tccgcgccct tgcgaggttc gccggaggcg   7980
aaccgtgaca cgaagggctc cgtggtcggc gcttccttgg tgaagggcgc cgccgtgggg   8040
ggtttggaga tggaacattt gattttgaga gcgtggttgg gtttggtgag ggtttgatga   8100
gagagaggga gggtggatct agtaatgcgt ttggggaagg tggggtgtga agaggaagaa   8160
gagaatcggg tggttctgga agcggtggcc gccattgtgt tgtgtggcat ggttatactt   8220
caaaaactgc acaacaagcc tagagttagt acctaaacag taaatttaca acagagagca   8280
aagacacatg caaaaatttc agccataaaa aaagttataa tagaatttaa agcaaaagtt   8340
tcatttttta aacatatata caaacaaact ggatttgaag gaagggatta attcccctgc   8400
tcaaagtttg aattcctatt gtgacctata ctcgaataaa attgaagcct aaggaatgta   8460
tgagaaacaa gaaaacaaaa caaaactaca gacaaacaag tacaattaca aaattcgcta   8520
aaattctgta atcaccaaac cccatctcag tcagcacaag gcccaaggtt tattttgaaa   8580
```

```
taaaaaaaaa gtgattttat ttctcataag ctaaaagaaa gaaaggcaat tatgaaatga   8640

tttcgactag atctgaaagt caaacgcgta ttccgcagat attaaagaaa gagtagagtt   8700

tcacatggat cctagatgga cccagttgag gaaaaagcaa ggcaaagcaa accagaagtg   8760

caagatccga aattgaacca cggaatctag gatttggtag agggagaaga aaagtacctt   8820

gagaggtaga agagaagaga agagcagaga gatatatgaa cgagtgtgtc ttggtctcaa   8880

ctctgaagcg atacgagttt agaggggagc attgagttcc aatttatagg gaaaccgggt   8940

ggcaggggtg agttaatgac ggaaaagccc ctaagtaacg agattggatt gtgggttaga   9000

ttcaaccgtt tgcatccgcg gcttagattg gggaagtcag agtgaatctc aaccgttgac   9060

tgagttgaaa attgaatgta gcaaccaatt gagccaaccc cagcctttgc cctttgattt   9120

tgatttgttt gttgcatact tt                                            9142
```

<210> SEQ ID NO 49
<211> LENGTH: 49911
<212> TYPE: DNA
<213> ORGANISM: artificial sequence
<220> FEATURE:
<223> OTHER INFORMATION: vector

<400> SEQUENCE: 49

```
gtgcagcgtg acccggtcgt gcccctctct agagataatg agcattgcat gtctaagtta     60

taaaaaatta ccacatattt tttttgtcac acttgtttga agtgcagttt atctatcttt    120

atacatatat ttaaacttta ctctacgaat aatataatct atagtactac aataatatca    180

gtgttttaga gaatcatata aatgaacagt tagacatggt ctaaaggaca attgagtatt    240

ttgacaacag gactctacag ttttatcttt ttagtgtgca tgtgttctcc tttttttttg    300

caaatagctt cacctatata atacttcatc cattttatta gtacatccat ttagggttta    360

gggttaatgg tttttataga ctaatttttt tagtacatct attttattct attttagcct    420

ctaaattaag aaaactaaaa ctctatttta gttttttat ttaataattt agatataaaa     480

tagaataaaa taaagtgact aaaaattaaa caaataccct ttaagaaatt aaaaaaaacta   540

aggaaacatt tttcttgttt cgagtagata atgccagcct gttaaacgcc gtcgacgagt    600

ctaacggaca ccaaccagcg aaccagcagc gtcgcgtcgg gccaagcgaa gcagacggca    660

cggcatctct gtcgctgcct ctggacccct ctcgagagtt ccgctccacc gttggacttg    720

ctccgctgtc ggcatccaga aattgcgtgg cggagcggca gacgtgagcc ggcacggcag    780

gcggcctcct cctcctctca cggcacggca gctacggggg attcctttcc caccgctcct    840

tcgctttccc ttcctcgccc gccgtaataa atagacaccc cctccacacc ctctttcccc    900

aacctcgtgt tgttcggagc gcacacacac acaaccagat ctcccccaaa tccacccgtc    960

ggcacctccg cttcaaggta cgccgctcgt cctccccccc ccccctctc taccttctct    1020

agatcggcgt tccggtccat ggttagggcc cggtagttct acttctgttc atgtttgtgt   1080

tagatccgtg tttgtgttag atccgtgctg ctagcgttcg tacacggatg cgacctgtac   1140

gtcagacacg ttctgattgc taacttgcca gtgtttctct ttggggaatc ctgggatggc   1200

tctagccgtt ccgcagacgg gatcgatttc atgatttttt ttgtttcgtt gcatagggtt   1260

tggtttgccc ttttccttta tttcaatata tgccgtgcac ttgtttgtcg ggtcatcttt   1320

tcatgctttt ttttgtcttg gttgtgatga tgtggtctgg ttgggcggtc gttctagatc   1380

ggagtagaat tctgtttcaa actacctggt ggatttatta attttggatc tgtatgtgtg   1440

tgccatacat attcatagtt acgaattgaa gatgatggat ggaaatatcg atctaggata   1500
```

```
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattattttg atcttgatat   1860
acttggatga tggcatatgc agcagctata tgtggatttt tttagccctg ccttcatacg   1920
ctatttattt gcttggtact gtttcttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
tccggcttac taaaagccag ataacagtat gcgtatttgc gcgctgattt ttgcggtata   2280
agaatatata ctgatatgta tacccgaagt atgtcaaaaa gaggtatgct atgaagcagc   2340
gtattacagt gacagttgac agcgacagct atcagttgct caaggcatat atgatgtcaa   2400
tatctccggt ctggtaagca caaccatgca gaatgaagcc cgtcgtctgc gtgccgaacg   2460
ctggaaagcg gaaaatcagg aagggatggc tgaggtcgcc cggtttattg aaatgaacgg   2520
ctcttttgct gacgagaaca ggggctggtg aaatgcagtt taaggtttac acctataaaa   2580
gagagagccg ttatcgtctg tttgtggatg tacagagtga tatcattgac acgcccggtc   2640
gacggatggt gatccccctg gccagtgcac gtctgctgtc agataaagtc tcccgtgaac   2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg gaatataaat gtcaggctcc cttatacaca   2880
gccagtctgc aggtcgacca tagtgactgg atatgttgtg ttttacagta ttatgtagtc   2940
tgtttttat gcaaaatcta atttaatata ttgatattta tatcatttta cgtttctcgt    3000
tcagctttct tgtacaaagt ggtgttaacc tagacttgtc catcttctgg attggccaac   3060
ttaattaatg tatgaaataa aaggatgcac acatagtgac atgctaatca ctataatgtg   3120
ggcatcaaag ttgtgtgtta tgtgtaatta ctagttatct gaataaaaga gaaagagatc   3180
atccatattt cttatcctaa atgaatgtca cgtgtcttta taattctttg atgaaccaga   3240
tgcatttcat taaccaaatc catatacata taaatattaa tcatatataa ttaatatcaa   3300
ttgggttagc aaaacaaatc tagtctaggt gtgttttgcg aattgcggcc gccaccgcgg   3360
tggagctcga attccggtcc gggtcacctt tgtccaccaa gatggaactg cggccgctca   3420
ttaattaagt caggcgcgcc tctagttgaa gacacgttca tgtcttcatc gtaagaagac   3480
actcagtagt cttcggccag aatggccatc tggattcagc aggcctagaa ggccatttaa   3540
atcctgagga tctggtcttc ctaaggaccc gggatatcgg accgattaaa ctttaattcg   3600
gtccgaagct tgcatgcctg cagtgcagcg tgacccggtc gtgcccctct ctagagataa   3660
tgagcattgc atgtctaagt tataaaaaat taccacatat ttttttgtc acacttgttt    3720
gaagtgcagt ttatctatct ttatacatat atttaaactt tactctacga ataatataat   3780
ctatagtact acaataatat cagtgtttta gagaatcata taaatgaaca gttagacatg   3840
gtctaaagga caattgagta ttttgacaac aggactctac agttttatct ttttagtgtg   3900
```

```
catgtgttct cctttttttt tgcaaatagc ttcacctata taatacttca tccattttat   3960

tagtacatcc atttagggtt tagggttaat ggtttttata gactaatttt tttagtacat   4020

ctattttatt ctattttagc ctctaaatta agaaaactaa aactctattt tagttttttt   4080

atttaataat ttagatataa aatagaataa aataaagtga ctaaaaatta aacaaatacc   4140

ctttaagaaa ttaaaaaaac taaggaaaca tttttcttgt ttcgagtaga taatgccagc   4200

ctgttaaacg ccgtcgacga gtctaacgga caccaaccag cgaaccagca gcgtcgcgtc   4260

gggccaagcg aagcagacgg cacggcatct ctgtcgctgc ctctggaccc ctctcgagag   4320

ttccgctcca ccgttggact tgctccgctg tcggcatcca gaaattgcgt ggcggagcgg   4380

cagacgtgag ccggcacggc aggcggcctc ctcctcctct cacggcaccg gcagctacgg   4440

gggattcctt tcccaccgct ccttcgcttt cccttcctcg cccgccgtaa taaatagaca   4500

ccccctccac accctctttc cccaacctcg tgttgttcgg agcgcacaca cacacaacca   4560

gatctccccc aaatccaccc gtcggcacct ccgcttcaag gtacgccgct cgtcctcccc   4620

cccccccctc tctaccttct ctagatcggc gttccggtcc atgcatggtt agggcccggt   4680

agttctactt ctgttcatgt ttgtgttaga tccgtgtttg tgttagatcc gtgctgctag   4740

cgttcgtaca cggatgcgac ctgtacgtca gacacgttct gattgctaac ttgccagtgt   4800

ttctctttgg ggaatcctgg gatggctcta gccgttccgc agacgggatc gatttcatga   4860

ttttttttgt ttcgttgcat agggtttggt ttgccctttt cctttatttc aatatatgcc   4920

gtgcacttgt ttgtcgggtc atcttttcat gctttttttt gtcttggttg tgatgatgtg   4980

gtctggttgg gcggtcgttc tagatcggag tagaattctg tttcaaacta cctggtggat   5040

ttattaattt tggatctgta tgtgtgtgcc atacatattc atagttacga attgaagatg   5100

atggatggaa atatcgatct aggataggta tacatgttga tgcgggtttt actgatgcat   5160

atacagagat gctttttgtt cgcttggttg tgatgatgtg gtgtggttgg gcggtcgttc   5220

attcgttcta gatcggagta gaatactgtt tcaaactacc tggtgtattt attaattttg   5280

gaactgtatg tgtgtgtcat acatcttcat agttacgagt ttaagatgga tggaaatatc   5340

gatctaggat aggtatacat gttgatgtgg gttttactga tgcatataca tgatggcata   5400

tgcagcatct attcatatgc tctaaccttg agtacctatc tattataata aacaagtatg   5460

ttttataatt attttgatct tgatatactt ggatgatggc atatgcagca gctatatgtg   5520

gattttttta gccctgcctt catacgctat ttatttgctt ggtactgttt cttttgtcga   5580

tgctcaccct gttgtttggt gttacttctg caggtcgact ttaacttagc ctaggatcca   5640

cacgacacca tgtcccccga gcgccgcccc gtcgagatcc gcccggccac cgccgccgac   5700

atggccgccg tgtgcgacat cgtgaaccac tacatcgaga cctccaccgt gaacttccgc   5760

accgagccgc agaccccgca ggagtggatc gacgacctgg agcgcctcca ggaccgctac   5820

ccgtggctcg tggccgaggt ggagggcgtg gtggccggca tcgcctacgc cggcccgtgg   5880

aaggcccgca acgcctacga ctggaccgtg gagtccaccg tgtacgtgtc ccaccgccac   5940

cagcgcctcg gcctcggctc caccctctac acccacctcc tcaagagcat ggaggcccag   6000

ggcttcaagt ccgtggtggc cgtgatcggc ctcccgaacg acccgtccgt gcgcctccac   6060

gaggccctcg gctacaccgc ccgcggcacc ctccgcgccg ccggctacaa gcacggcggc   6120

tggcacgacg tcggcttctg gcagcgcgac ttcgagctgc cggccccgcc gcgcccggtg   6180

cgcccggtga cgcagatctg agtcgaaacc tagacttgtc catcttctgg attggccaac   6240

ttaattaatg tatgaaataa aaggatgcac acatagtgac atgctaatca ctataatgtg   6300
```

-continued ggcatcaaag ttgtgtgtta tgtgtaatta ctagttatct gaataaaaga gaaagagatc 6360
atccatattt cttatcctaa atgaatgtca cgtgtcttta taattctttg atgaaccaga 6420
tgcatttcat taaccaaatc catatacata taaatattaa tcatatataa ttaatatcaa 6480
ttgggttagc aaaacaaatc tagtctaggt gtgttttgcg aattgcggcc gccaccgcgg 6540
tggagctcga attcattccg attaatcgtg gcctcttgct cttcaggatg aagagctatg 6600
tttaaacgtg caagcgctac tagacaattc agtacattaa aaacgtccgc aatgtgttat 6660
taagttgtct aagcgtcaat ttggtttaca ccacaatata tcctgccacc agccagccaa 6720
cagctccccg accggcagct cggcacaaaa tcaccactcg atacaggcag cccatcagtc 6780
cgggacggcg tcagcgggag agccgttgta aggcggcaga ctttgctcat gttaccgatg 6840
ctattcggaa gaacggcaac taagctgccg ggtttgaaac acggatgatc tcgcggaggg 6900
tagcatgttg attgtaacga tgacagagcg ttgctgcctg tgatcaaata tcatctccct 6960
cgcagagatc cgaattatca gccttcttat tcatttctcg cttaaccgtg acaggctgtc 7020
gatcttgaga actatgccga cataatagga aatcgctgga taaagccgct gaggaagctg 7080
agtggcgcta tttctttaga agtgaacgtt gacgatcgtc gaccgtaccc cgatgaatta 7140
attcggacgt acgttctgaa cacagctgga tacttacttg ggcgattgtc atacatgaca 7200
tcaacaatgt acccgtttgt gtaaccgtct cttggaggtt cgtatgacac tagtggttcc 7260
cctcagcttg cgactagatg ttgaggccta acattttatt agagagcagg ctagttgctt 7320
agatacatga tcttcaggcc gttatctgtc agggcaagcg aaaattggcc atttatgacg 7380
accaatgccc cgcagaagct cccatctttg ccgccataga cgccgcgccc ccccttttggg 7440
gtgtagaaca tccttttgcc agatgtggaa aagaagttcg ttgtcccatt gttggcaatg 7500
acgtagtagc cggcgaaagt gcgagaccca tttgcgctat atataagcct acgatttccg 7560
ttgcgactat tgtcgtaatt ggatgaacta ttatcgtagt tgctctcaga gttgtcgtaa 7620
tttgatggac tattgtcgta attgcttatg gagttgtcgt agttgcttgg agaaatgtcg 7680
tagttggatg gggagtagtc atagggaaga cgagcttcat ccactaaaac aattggcagg 7740
tcagcaagtg cctgccccga tgccatcgca agtacgaggc ttagaaccac cttcaacaga 7800
tcgcgcatag tcttccccag ctctctaacg cttgagttaa gccgcgccgc gaagcggcgt 7860
cggcttgaac gaattgttag acattatttg ccgactacct tggtgatctc gcctttcacg 7920
tagtgaacaa attcttccaa ctgatctgcg cgcgaggcca agcgatcttc ttgtccaaga 7980
taagcctgcc tagcttcaag tatgacgggc tgatactggg ccggcaggcg ctccattgcc 8040
cagtcggcag cgacatcctt cggcgcgatt ttgccggtta ctgcgctgta ccaaatgcgg 8100
gacaacgtaa gcactacatt tcgctcatcg ccagcccagt cgggcggcga gttccatagc 8160
gttaaggttt catttagcgc ctcaaataga tcctgttcag gaaccggatc aaagagttcc 8220
tccgccgctg gacctaccaa ggcaacgcta tgttctcttg cttttgtcag caagatagcc 8280
agatcaatgt cgatcgtggc tggctcgaag atacctgcaa gaatgtcatt gcgctgccat 8340
tctccaaatt gcagttcgcg cttagctgga taacgccacg gaatgatgtc gtcgtgcaca 8400
acaatggtga cttctacagc gcggagaatc tcgctctctc caggggaagc cgaagtttcc 8460
aaaaggtcgt tgatcaaagc tcgccgcgtt gtttcatcaa gccttacagt caccgtaacc 8520
agcaaatcaa tatcactgtg tggcttcagg ccgccatcca ctgcggagcc gtacaaatgt 8580
acggccagca acgtcggttc gagatggcgc tcgatgacgc caactacctc tgatagttga 8640
gtcgatactt cggcgatcac cgcttccctc atgatgttta actcctgaat taagccgcgc 8700

```
cgcgaagcgg tgtcggcttg aatgaattgt taggcgtcat cctgtgctcc cgagaaccag   8760
taccagtaca tcgctgtttc gttcgagact tgaggtctag ttttatacgt gaacaggtca   8820
atgccgccga gagtaaagcc acattttgcg tacaaattgc aggcaggtac attgttcgtt   8880
tgtgtctcta atcgtatgcc aaggagctgt ctgcttagtg cccacttttt cgcaaattcg   8940
atgagactgt gcgcgactcc tttgcctcgg tgcgtgtgcg acacaacaat gtgttcgata   9000
gaggctagat cgttccatgt tgagttgagt tcaatcttcc cgacaagctc ttggtcgatg   9060
aatgcgccat agcaagcaga gtcttcatca gagtcatcat ccgagatgta atccttccgg   9120
taggggctca cacttctggt agatagttca aagccttggt cggataggtg cacatcgaac   9180
acttcacgaa caatgaaatg gttctcagca tccaatgttt ccgccacctg ctcagggatc   9240
accgaaatct tcatatgacg cctaacgcct ggcacagcgg atcgcaaacc tggcgcggct   9300
tttggcacaa aaggcgtgac aggtttgcga atccgttgct gccacttgtt aacccttttg   9360
ccagatttgg taactataat ttatgttaga ggcgaagtct tgggtaaaaa ctggcctaaa   9420
attgctgggg atttcaggaa agtaaacatc accttccggc tcgatgtcta ttgtagatat   9480
atgtagtgta tctacttgat cgggggatct gctgcctcgc gcgtttcggt gatgacggtg   9540
aaaacctctg acacatgcag ctcccggaga cggtcacagc ttgtctgtaa gcggatgccg   9600
ggagcagaca agcccgtcag ggcgcgtcag cgggtgttgg cgggtgtcgg ggcgcagcca   9660
tgacccagtc acgtagcgat agcggagtgt atactggctt aactatgcgg catcagagca   9720
gattgtactg agagtgcacc atatgcggtg tgaaataccg cacagatgcg taaggagaaa   9780
ataccgcatc aggcgctctt ccgcttcctc gctcactgac tcgctgcgct cggtcgttcg   9840
gctgcggcga gcggtatcag ctcactcaaa ggcggtaata cggttatcca cagaatcagg   9900
ggataacgca ggaaagaaca tgtgagcaaa aggccagcaa aaggccagga accgtaaaaa   9960
ggccgcgttg ctggcgtttt tccataggct ccgcccccct gacgagcatc acaaaaatcg  10020
acgctcaagt cagaggtggc gaaacccgac aggactataa agataccagg cgtttccccc  10080
tggaagctcc ctcgtgcgct ctcctgttcc gaccctgccg cttaccggat acctgtccgc  10140
ctttctccct tcgggaagcg tggcgctttc tcatagctca cgctgtaggt atctcagttc  10200
ggtgtaggtc gttcgctcca agctgggctg tgtgcacgaa ccccccgttc agcccgaccg  10260
ctgcgcctta tccggtaact atcgtcttga gtccaacccg gtaagacacg acttatcgcc  10320
actggcagca gccactggta acaggattag cagagcgagg tatgtaggcg gtgctacaga  10380
gttcttgaag tggtggccta actacggcta cactagaagg acagtatttg gtatctgcgc  10440
tctgctgaag ccagttacct tcggaaaaag agttggtagc tcttgatccg gcaaacaaac  10500
caccgctggt agcggtggtt tttttgtttg caagcagcag attacgcgca gaaaaaaagg  10560
atctcaagaa gatcctttga tcttttctac ggggtctgac gctcagtgga acgaaaactc  10620
acgttaaggg attttggtca tgagattatc aaaaaggatc ttcacctaga tccttttaaa  10680
ttaaaaatga agttttaaat caatctaaag tatatatgag taaacttggt ctgacagtta  10740
ccaatgctta atcagtgagg cacctatctc agcgatctgt ctatttcgtt catccatagt  10800
tgcctgactc cccgtcgtgt agataactac gatacgggag ggcttaccat ctggccccag  10860
tgctgcaatg ataccgcgag acccacgctc accggctcca gatttatcag caataaacca  10920
gccagccgga agggccgagc gcagaagtgg tcctgcaact ttatccgcct ccatccagtc  10980
tattaattgt tgccgggaag ctagagtaag tagttcgcca gttaatagtt tgcgcaacgt  11040
tgttgccatt gctgcagggg gggggggggg gggggacttc cattgttcat tccacggaca  11100
```

```
aaaacagaga aaggaaacga cagaggccaa aaagcctcgc tttcagcacc tgtcgtttcc  11160
tttcttttca gagggtattt taaataaaaa cattaagtta tgacgaagaa gaacggaaac  11220
gccttaaacc ggaaaatttt cataaatagc gaaaacccgc gaggtcgccg ccccgtaacc  11280
tacctgtcgg atcaccggaa aggacccgta aagtgataat gattatcatc tacatatcac  11340
aacgtgcgtg gaggccatca aaccacgtca aataatcaat tatgacgcag gtatcgtatt  11400
aattgatctg catcaactta acgtaaaaac aacttcagac aatacaaatc agcgacactg  11460
aatacggggc aacctcatgt cccccccccc cccccccctg caggcatcgt ggtgtcacgc  11520
tcgtcgtttg gtatggcttc attcagctcc ggttcccaac gatcaaggcg agttacatga  11580
tcccccatgt tgtgcaaaaa agcggttagc tccttcggtc ctccgatcgt tgtcagaagt  11640
aagttggccg cagtgttatc actcatggtt atggcagcac tgcataattc tcttactgtc  11700
atgccatccg taagatgctt ttctgtgact ggtgagtact caaccaagtc attctgagaa  11760
tagtgtatgc ggcgaccgag ttgctcttgc ccggcgtcaa cacgggataa taccgcgcca  11820
catagcagaa ctttaaaagt gctcatcatt ggaaaacgtt cttcggggcg aaaactctca  11880
aggatcttac cgctgttgag atccagttcg atgtaaccca ctcgtgcacc caactgatct  11940
tcagcatctt ttactttcac cagcgtttct gggtgagcaa aaacaggaag gcaaaatgcc  12000
gcaaaaaagg gaataagggc gacacggaaa tgttgaatac tcatactctt cctttttcaa  12060
tattattgaa gcatttatca gggttattgt ctcatgagcg gatacatatt tgaatgtatt  12120
tagaaaaata aacaaatagg ggttccgcgc acatttcccc gaaaagtgcc acctgacgtc  12180
taagaaacca ttattatcat gacattaacc tataaaaata ggcgtatcac gaggcccttt  12240
cgtcttcaag aattcggagc ttttgccatt ctcaccggat tcagtcgtca ctcatggtga  12300
tttctcactt gataacctta tttttgacga ggggaaatta ataggttgta ttgatgttgg  12360
acgagtcgga atcgcagacc gataccagga tcttgccatc ctatggaact gcctcggtga  12420
gttttctcct tcattacaga aacggctttt tcaaaaatat ggtattgata atcctgatat  12480
gaataaattg cagtttcatt tgatgctcga tgagtttttc taatcagaat tggttaattg  12540
gttgtaacac tggcagagca ttacgctgac ttgacgggac ggcggctttg ttgaataaat  12600
cgaacttttg ctgagttgaa ggatcagatc acgcatcttc ccgacaacgc agaccgttcc  12660
gtggcaaagc aaaagttcaa aatcaccaac tggtccacct acaacaaagc tctcatcaac  12720
cgtggctccc tcactttctg gctggatgat ggggcgattc aggcctggta tgagtcagca  12780
acaccttctt cacgaggcag acctcagcgc cagaaggccg ccagagaggc cgagcgcggc  12840
cgtgaggctt ggacgctagg gcagggcatg aaaaagcccg tagcgggctg ctacgggcgt  12900
ctgacgcggt ggaaaggggg aggggatgtt gtctacatgg ctctgctgta gtgagtgggt  12960
tgcgctccgg cagcggtcct gatcaatcgt caccctttct cggtccttca acgttcctga  13020
caacgagcct ccttttcgcc aatccatcga caatcaccgc gagtccctgc tcgaacgctg  13080
cgtccggacc ggcttcgtcg aaggcgtcta tcgcggcccg caacagcggc gagagcggag  13140
cctgttcaac ggtgccgccg cgctcgccgg catcgctgtc gccggcctgc tcctcaagca  13200
cggccccaac agtgaagtag ctgattgtca tcagcgcatt gacggcgtcc ccggccgaaa  13260
aacccgcctc gcagaggaag cgaagctgcg cgtcggccgt ttccatctgc ggtgcgcccg  13320
gtcgcgtgcc ggcatggatg cgcgcgccat cgcggtaggc gagcagcgcc tgcctgaagc  13380
tgcgggcatt cccgatcaga aatgagcgcc agtcgtcgtc ggctctcggc accgaatgcg  13440
tatgattctc cgccagcatg gcttcggcca gtgcgtcgag cagcgcccgc ttgttcctga  13500
```

agtgccagta aagcgccggc tgctgaaccc ccaaccgttc cgccagtttg cgtgtcgtca 13560
gaccgtctac gccgacctcg ttcaacaggt ccagggcggc acggatcact gtattcggct 13620
gcaactttgt catgcttgac actttatcac tgataaacat aatatgtcca ccaacttatc 13680
agtgataaag aatccgcgcg ttcaatcgga ccagcggagg ctggtccgga ggccagacgt 13740
gaaacccaac ataccccctga tcgtaattct gagcactgtc gcgctcgacg ctgtcggcat 13800
cggcctgatt atgccggtgc tgccgggcct cctgcgcgat ctggttcact cgaacgacgt 13860
caccgcccac tatggcattc tgctggcgct gtatgcgttg gtgcaatttg cctgcgcacc 13920
tgtgctgggc gcgctgtcgg atcgtttcgg gcggcggcca atcttgctcg tctcgctggc 13980
cggcgccact gtcgactacg ccatcatggc gacagcgcct ttcctttggg ttctctatat 14040
cgggcggatc gtggccggca tcaccggggc gactggggcg gtagccggcg cttatattgc 14100
cgatatcact gatggcgatg agcgcgcgcg gcacttcggc ttcatgagcg cctgtttcgg 14160
gttcgggatg gtcgcgggac ctgtgctcgg tgggctgatg ggcggtttct ccccccacgc 14220
tccgttcttc gccgcggcag ccttgaacgg cctcaatttc ctgacgggct gtttcctttt 14280
gccggagtcg cacaaaggcg aacgccggcc gttacgccgg gaggctctca acccgctcgc 14340
ttcgttccgg tgggcccggg gcatgaccgt cgtcgccgcc ctgatggcgg tcttcttcat 14400
catgcaactt gtcggacagg tgccggccgc gctttgggtc attttcggcg aggatcgctt 14460
tcactgggac gcgaccacga tcggcatttc gcttgccgca tttggcattc tgcattcact 14520
cgcccaggca atgatcaccg gccctgtagc cgcccggctc ggcgaaaggc gggcactcat 14580
gctcggaatg attgccgacg gcacaggcta catcctgctt gccttcgcga cacggggatg 14640
gatggcgttc ccgatcatgg tcctgcttgc ttcgggtggc atcggaatgc cggcgctgca 14700
agcaatgttg tccaggcagg tggatgagga acgtcagggg cagctgcaag gctcactggc 14760
ggcgctcacc agcctgacct cgatcgtcgg acccctcctc ttcacggcga tctatgcggc 14820
ttctataaca acgtggaacg ggtgggcatg gattgcaggc gctgccctct acttgctctg 14880
cctgccggcg ctgcgtcgcg ggctttggag cggcgcaggg caacgagccg atcgctgatc 14940
gtggaaacga taggcctatg ccatgcgggt caaggcgact tccggcaagc tatacgcgcc 15000
ctaggagtgc ggttggaacg ttggcccagc cagatactcc cgatcacgag caggacgccg 15060
atgatttgaa gcgcactcag cgtctgatcc aagaacaacc atcctagcaa cacggcggtc 15120
cccgggctga gaaagcccag taaggaaaca actgtaggtt cgagtcgcga gatcccccgg 15180
aaccaaagga agtaggttaa acccgctccg atcaggccga gccacgccag gccgagaaca 15240
ttggttcctg taggcatcgg gattggcgga tcaaacacta aagctactgg aacgagcaga 15300
agtcctccgg ccgccagttg ccaggcggta aaggtgagca gaggcacggg aggttgccac 15360
ttgcgggtca gcacggttcc gaacgccatg gaaaccgccc ccgccaggcc cgctgcgacg 15420
ccgacaggat ctagcgctgc gtttggtgtc aacaccaaca gcgccacgcc cgcagttccg 15480
caaatagccc ccaggaccgc catcaatcgt atcgggctac ctagcagagc ggcagagatg 15540
aacacgacca tcagcggctg cacagcgcct accgtcgccg cgaccccgcc cggcaggcgg 15600
tagaccgaaa taaacaacaa gctccagaat agcgaaatat taagtgcgcc gaggatgaag 15660
atgcgcatcc accagattcc cgttggaatc tgtcggacga tcatcacgag caataaaccc 15720
gccggcaacg cccgcagcag cataccggcg acccctcggc ctcgctgttc gggctccacg 15780
aaaacgccgg acagatgcgc cttgtgagcg tccttggggc cgtcctcctg tttgaagacc 15840
gacagcccaa tgatctcgcc gtcgatgtag gcgccgaatg ccacggcatc tcgcaaccgt 15900

```
tcagcgaacg cctccatggg ctttttctcc tcgtgctcgt aaacggaccc gaacatctct  15960
ggagctttct tcagggccga caatcggatc tcgcggaaat cctgcacgtc ggccgctcca  16020
agccgtcgaa tctgagcctt aatcacaatt gtcaatttta atcctctgtt tatcggcagt  16080
tcgtagagcg cgccgtgcgt cccgagcgat actgagcgaa gcaagtgcgt cgagcagtgc  16140
ccgcttgttc ctgaaatgcc agtaaagcgc tggctgctga acccccagcc ggaactgacc  16200
ccacaaggcc ctagcgtttg caatgcacca ggtcatcatt gacccaggcg tgttccacca  16260
ggccgctgcc tcgcaactct tcgcaggctt cgccgacctg ctcgcgccac ttcttcacgc  16320
gggtggaatc cgatccgcac atgaggcgga aggtttccag cttgagcggg tacggctccc  16380
ggtgcgagct gaaatagtcg aacatccgtc gggccgtcgg cgacagcttg cggtacttct  16440
cccatatgaa tttcgtgtag tggtcgccag caaacagcac gacgatttcc tcgtcgatca  16500
ggacctggca acgggacgtt ttcttgccac ggtccaggac gcggaagcgg tgcagcagcg  16560
acaccgattc caggtgccca acgcggtcgg acgtgaagcc catcgccgtc gcctgtaggc  16620
gcgacaggca ttcctcggcc ttcgtgtaat accggccatt gatcgaccag cccaggtcct  16680
ggcaaagctc gtagaacgtg aaggtgatcg gctcgccgat aggggtgcgc ttcgcgtact  16740
ccaacacctg ctgccacacc agttcgtcat cgtcggcccg cagctcgacg ccggtgtagg  16800
tgatcttcac gtccttgttg acgtggaaaa tgaccttgtt ttgcagcgcc tcgcgcggga  16860
ttttcttgtt gcgcgtggtg aacagggcag agcgggccgt gtcgtttggc atcgctcgca  16920
tcgtgtccgg ccacggcgca atatcgaaca aggaaagctg catttccttg atctgctgct  16980
tcgtgtgttt cagcaacgcg gcctgcttgg cctcgctgac ctgttttgcc aggtcctcgc  17040
cggcggtttt tcgcttcttg gtcgtcatag ttcctcgcgt gtcgatggtc atcgacttcg  17100
ccaaacctgc cgcctcctgt tcgagacgac gcgaacgctc cacggcggcc gatggcgcgg  17160
gcagggcagg gggagccagt tgcacgctgt cgcgctcgat cttggccgta gcttgctgga  17220
ccatcgagcc gacggactgg aaggtttcgc ggggcgcacg catgacggtg cggcttgcga  17280
tggtttcggc atcctcggcg gaaaaccccg cgtcgatcag ttcttgcctg tatgccttcc  17340
ggtcaaacgt ccgattcatt caccctcctt gcgggattgc cccgactcac gccggggcaa  17400
tgtgccctta ttcctgattt gacccgcctg gtgccttggt gtccagataa tccaccttat  17460
cggcaatgaa gtcggtcccg tagaccgtct ggccgtcctt ctcgtacttg gtattccgaa  17520
tcttgccctg cacgaatacc agcgacccct tgcccaaata cttgccgtgg gcctcggcct  17580
gagagccaaa acacttgatg cggaagaagt cggtgcgctc ctgcttgtcg ccggcatcgt  17640
tgcgccactc ttcattaacc gctatatcga aaattgcttg cggcttgtta gaattgccat  17700
gacgtacctc ggtgtcacgg gtaagattac cgataaactg gaactgatta tggctcatat  17760
cgaaagtctc cttgagaaag gagactctag tttagctaaa cattggttcc gctgtcaaga  17820
actttagcgg ctaaaatttt gcgggccgcg accaaaggtg cgaggggcgg cttccgctgt  17880
gtacaaccag atatttttca ccaacatcct tcgtctgctc gatgagcggg gcatgacgaa  17940
acatgagctg tcggagaggg caggggtttc aatttcgttt ttatcagact taaccaacgg  18000
taaggccaac ccctcgttga aggtgatgga ggccattgcc gacgccctgg aaactcccct  18060
acctcttctc ctggagtcca ccgaccttga ccgcgaggca ctcgcggaga ttgcgggtca  18120
tcctttcaag agcagcgtgc cgcccggata cgaacgcatc agtgtggttt tgccgtcaca  18180
taaggcgttt atcgtaaaga aatggggcga cgacacccga aaaaagctgc gtggaaggct  18240
ctgacgccaa gggttagggc ttgcacttcc ttctttagcc gctaaaacgg ccccttctct  18300
```

-continued

```
gcgggccgtc ggctcgcgca tcatatcgac atcctcaacg gaagccgtgc cgcgaatggc  18360
atcgggcggg tgcgctttga cagttgtttt ctatcagaac ccctacgtcg tgcggttcga  18420
ttagctgttt gtcttgcagg ctaaacactt tcggtatatc gtttgcctgt gcgataatgt  18480
tgctaatgat ttgttgcgta ggggttactg aaaagtgagc gggaaagaag agtttcagac  18540
catcaaggag cgggccaagc gcaagctgga acgcgacatg ggtgcggacc tgttggccgc  18600
gctcaacgac ccgaaaaccg ttgaagtcat gctcaacgcg gacggcaagg tgtggcacga  18660
acgccttggc gagccgatgc ggtacatctg cgacatgcgg cccagccagt cgcaggcgat  18720
tatagaaacg gtggccggat tccacggcaa agaggtcacg cggcattcgc ccatcctgga  18780
aggcgagttc cccttggatg gcagccgctt tgccggccaa ttgccgccgg tcgtggccgc  18840
gccaaccttt gcgatccgca agcgcgcggt cgccatcttc acgctggaac agtacgtcga  18900
ggcgggcatc atgacccgcg agcaatacga ggtcattaaa agcgccgtcg cggcgcatcg  18960
aaacatcctc gtcattggcg gtactggctc gggcaagacc acgctcgtca acgcgatcat  19020
caatgaaatg gtcgccttca acccgtctga gcgcgtcgtc atcatcgagg acaccggcga  19080
aatccagtgc gccgcagaga acgccgtcca ataccacacc agcatcgacg tctcgatgac  19140
gctgctgctc aagacaacgc tgcgtatgcg ccccgaccgc atcctggtcg gtgaggtacg  19200
tggccccgaa gcccttgatc tgttgatggc ctggaacacc gggcatgaag gaggtgccgc  19260
caccctgcac gcaaacaacc ccaaagcggg cctgagccgg ctcgccatgc ttatcagcat  19320
gcacccggat tcaccgaaac ccattgagcc gctgattggc gaggcggttc atgtggtcgt  19380
ccatatcgcc aggaccccta gcggccgtcg agtgcaagaa attctcgaag ttcttggtta  19440
cgagaacggc cagtacatca ccaaaaccct gtaaggagta tttccaatga caacggctgt  19500
tccgttccgt ctgaccatga atcgcggcat tttgttctac cttgccgtgt tcttcgttct  19560
cgctctcgcg ttatccgcgc atccggcgat ggcctcggaa ggcaccggcg gcagcttgcc  19620
atatgagagc tggctgacga acctgcgcaa ctccgtaacc ggcccggtgg ccttcgcgct  19680
gtccatcatc ggcatcgtcg tcgccggcgg cgtgctgatc ttcggcggcg aactcaacgc  19740
cttcttccga accctgatct tcctggttct ggtgatggcg ctgctggtcg gcgcgcagaa  19800
cgtgatgagc accttcttcg gtcgtggtgc cgaaatcgcg gccctcggca acggggcgct  19860
gcaccaggtg caagtcgcgg cggcggatgc cgtgcgtgcg gtagcggctg gacggctcgc  19920
ctaatcatgg ctctgcgcac gatccccatc cgtcgcgcag gcaaccgaga aaacctgttc  19980
atgggtggtg atcgtgaact ggtgatgttc tcgggcctga tggcgtttgc gctgattttc  20040
agcgcccaag agctgcgggc caccgtggtc ggtctgatcc tgtggttcgg ggcgctctat  20100
gcgttccgaa tcatggcgaa ggccgatccg aagatgcggt tcgtgtacct gcgtcaccgc  20160
cggtacaagc cgtattaccc ggcccgctcg accccgttcc gcgagaacac caatagccaa  20220
gggaagcaat accgatgatc caagcaattg cgattgcaat cgcgggcctc ggcgcgcttc  20280
tgttgttcat cctctttgcc cgcatccgcg cggtcgatgc cgaactgaaa ctgaaaaagc  20340
atcgttccaa ggacgccggc ctggccgatc tgctcaacta cgccgctgtc gtcgatgacg  20400
gcgtaatcgt gggcaagaac ggcagcttta tggctgcctg gctgtacaag ggcgatgaca  20460
acgcaagcag caccgaccag cagcgcgaag tagtgtccgc ccgcatcaac caggccctcg  20520
cgggcctggg aagtgggtgg atgatccatg tggacgccgt gcggcgtcct gctccgaact  20580
acgcggagcg gggcctgtcg gcgttccctg accgtctgac ggcagcgatt gaagaagagc  20640
gctcggtctt gccttgctcg tcggtgatgt acttcaccag ctccgcgaag tcgctcttct  20700
```

-continued

```
tgatggagcg catggggacg tgcttggcaa tcacgcgcac cccccggccg ttttagcggc  20760
taaaaaagtc atggctctgc cctcgggcgg accacgccca tcatgacctt gccaagctcg  20820
tcctgcttct cttcgatctt cgccagcagg gcgaggatcg tggcatcacc gaaccgcgcc  20880
gtgcgcgggt cgtcggtgag ccagagtttc agcaggccgc ccaggcggcc caggtcgcca  20940
ttgatgcggg ccagctcgcg gacgtgctca tagtccacga cgcccgtgat tttgtagccc  21000
tggccgacgg ccagcaggta ggccgacagg ctcatgccgg ccgccgccgc cttttcctca  21060
atcgctcttc gttcgtctgg aaggcagtac accttgatag gtgggctgcc cttcctggtt  21120
ggcttggttt catcagccat ccgcttgccc tcatctgtta cgccggcggt agccggccag  21180
cctcgcagag caggattccc gttgagcacc gccaggtgcg aataagggac agtgaagaag  21240
gaacacccgc tcgcgggtgg gcctacttca cctatcctgc ccggctgacg ccgttggata  21300
caccaaggaa agtctacacg aaccctttgg caaaatcctg tatatcgtgc gaaaaaggat  21360
ggatataccg aaaaaatcgc tataatgacc ccgaagcagg gttatgcagc ggaaaagcgc  21420
tgcttccctg ctgttttgtg gaatatctac cgactggaaa caggcaaatg caggaaatta  21480
ctgaactgag gggacaggcg agagacgatg ccaaagagct acaccgacga gctggccgag  21540
tgggttgaat cccgcgcggc caagaagcgc cggcgtgatg aggctgcggt tgcgttcctg  21600
gcggtgaggg cggatgtcga ggcggcgtta gcgtccggct atgcgctcgt caccatttgg  21660
gagcacatgc gggaaacggg gaaggtcaag ttctcctacg agacgttccg ctcgcacgcc  21720
aggcggcaca tcaaggccaa gcccgccgat gtgcccgcac cgcaggccaa ggctgcggaa  21780
cccgcgccgg cacccaagac gccggagcca cggcggccga agcagggggg caaggctgaa  21840
aagccggccc ccgctgcggc cccgaccggc ttcaccttca acccaacacc ggacaaaaag  21900
gatctactgt aatggcgaaa attcacatgg ttttgcaggg caagggcggg gtcggcaagt  21960
cggccatcgc cgcgatcatt gcgcagtaca agatggacaa ggggcagaca cccttgtgca  22020
tcgacaccga cccggtgaac gcgacgttcg agggctacaa ggccctgaac gtccgccggc  22080
tgaacatcat ggccggcgac gaaattaact cgcgcaactt cgacaccctg gtcgagctga  22140
ttgcgccgac caaggatgac gtggtgatcg acaacggtgc cagctcgttc gtgcctctgt  22200
cgcattacct catcagcaac caggtgccgg ctctgctgca agaaatgggg catgagctgg  22260
tcatccatac cgtcgtcacc ggcggccagg ctctcctgga cacggtgagc ggcttcgccc  22320
agctcgccag ccagttcccg gccgaagcgc ttttcgtggt ctggctgaac ccgtattggg  22380
ggcctatcga gcatgagggc aagagctttg agcagatgaa ggcgtacacg gccaacaagg  22440
cccgcgtgtc gtccatcatc cagattccgg ccctcaagga agaaacctac ggccgcgatt  22500
tcagcgacat gctgcaagag cggctgacgt tcgaccaggc gctggccgat gaatcgctca  22560
cgatcatgac gcggcaacgc ctcaagatcg tgcggcgcgg cctgtttgaa cagctcgacg  22620
cggcggccgt gctatgagcg accagattga agagctgatc cgggagattg cggccaagca  22680
cggcatcgcc gtcggccgcg acgacccggt gctgatcctg cataccatca acgcccggct  22740
catggccgac agtgcggcca agcaagagga aatccttgcc gcgttcaagg aagagctgga  22800
agggatcgcc catcgttggg gcgaggacgc caaggccaaa gcggagcgga tgctgaacgc  22860
ggccctggcg gccagcaagg acgcaatggc gaaggtaatg aaggacagcg ccgcgcaggc  22920
ggccgaagcg atccgcaggg aaatcgacga cggccttggc cgccagctcg cggccaaggt  22980
cgcggacgcg cggcgcgtgg cgatgatgaa catgatcgcc ggcggcatgg tgttgttcgc  23040
ggccgccctg gtggtgtggg cctcgttatg aatcgcagag gcgcagatga aaaagcccgg  23100
```

```
cgttgccggg ctttgttttt gcgttagctg ggcttgtttg acaggcccaa gctctgactg  23160
cgcccgcgct cgcgctcctg ggcctgtttc ttctcctgct cctgcttgcg catcagggcc  23220
tggtgccgtc gggctgcttc acgcatcgaa tcccagtcgc cggccagctc gggatgctcc  23280
gcgcgcatct tgcgcgtcgc cagttcctcg atcttgggcg cgtgaatgcc catgccttcc  23340
ttgatttcgc gcaccatgtc cagccgcgtg tgcagggtct gcaagcgggc ttgctgttgg  23400
gcctgctgct gctgccaggc ggcctttgta cgcggcaggg acagcaagcc gggggcattg  23460
gactgtagct gctgcaaacg cgcctgctga cggtctacga gctgttctag gcggtcctcg  23520
atgcgctcca cctggtcatg ctttgcctgc acgtagagcg caagggtctg ctggtaggtc  23580
tgctcgatgg gcgcggattc taagagggcc tgctgttccg tctcggcctc ctgggccgcc  23640
tgtagcaaat cctcgccgct gttgccgctg gactgcttta ctgccgggga ctgctgttgc  23700
cctgctcgcg ccgtcgtcgc agttcggctt gcccccactc gattgactgc ttcatttcga  23760
gccgcagcga tgcgatctcg gattgcgtca acggacgggg cagcgcggag gtgtccggct  23820
tctccttggg tgagtcggtc gatgccatag ccaaaggttt ccttccaaaa tgcgtccatt  23880
gctggaccgt gtttctcatt gatgcccgca agcatcttcg gcttgaccgc caggtcaagc  23940
gcgccttcat gggcggtcat gacggacgcc gccatgacct tgccgccgtt gttctcgatg  24000
tagccgcgta atgaggcaat ggtgccgccc atcgtcagcg tgtcatcgac aacgatgtac  24060
ttctggccgg ggatcacctc cccctcgaaa gtcgggttga acgccaggcg atgatctgaa  24120
ccggctccgg ttcgggcgac cttctcccgc tgcacaatgt ccgtttcgac ctcaaggcca  24180
aggcggtcgg ccagaacgac cgccatcatg gccggaatct tgttgttccc cgccgcctcg  24240
acggcgagga ctggaacgat gcggggcttg tcgtcgccga tcagcgtctt gagctgggca  24300
acagtgtcgt ccgaaatcag gcgctcgacc aaattaagcg ccgcttccgc gtcgccctgc  24360
ttcgcagcct ggtattcagg ctcgttggtc aaagaaccaa ggtcgccgtt gcgaaccacc  24420
ttcgggaagt ctccccacgg tgcgcgctcg gctctgctgt agctgctcaa gacgcctccc  24480
tttttagccg ctaaaactct aacgagtgcg cccgcgactc aacttgacgc tttcggcact  24540
tacctgtgcc ttgccacttg cgtcataggt gatgcttttc gcactcccga tttcaggtac  24600
tttatcgaaa tctgaccggg cgtgcattac aaagttcttc cccacctgtt ggtaaatgct  24660
gccgctatct gcgtggacga tgctgccgtc gtggcgctgc gacttatcgg ccttttgggc  24720
catatagatg ttgtaaatgc caggtttcag ggccccggct ttatctacct tctggttcgt  24780
ccatgcgcct tggttctcgg tctggacaat tctttgccca ttcatgacca ggaggcggtg  24840
tttcattggg tgactcctga cggttgcctc tggtgttaaa cgtgtcctgg tcgcttgccg  24900
gctaaaaaaa agccgacctc ggcagttcga ggccggcttt ccctagagcc gggcgcgtca  24960
aggttgttcc atctatttta gtgaactgcg ttcgatttat cagttacttt cctcccgctt  25020
tgtgtttcct cccactcgtt tccgcgtcta gccgacccct caacatagcg gcctcttctt  25080
gggctgcctt tgcctcttgc cgcgcttcgt cacgctcggc ttgcaccgtc gtaaagcgct  25140
cggcctgcct ggccgcctct tgcgccgcca acttcctttg ctcctggtgg gcctcggcgt  25200
cggcctgcgc cttcgctttc accgctgcca actccgtgcg caaactctcc gcttcgcgcc  25260
tggtggcgtc gcgctcgccg cgaagcgcct gcatttcctg gttggccgcg tccagggtct  25320
tgcggctctc ttctttgaat gcgcgggcgt cctggtgagc gtagtccagc tcggcgcgca  25380
gctcctgcgc tcgacgctcc acctcgtcgg cccgctgcgt cgccagcgcg gcccgctgct  25440
cggctcctgc cagggcggtg cgtgcttcgg ccagggcttg ccgctggcgt gcggccagct  25500
```

cggccgcctc ggcggcctgc tgctctagca atgtaacgcg cgcctgggct tcttccagct 25560
cgcgggcctg cgcctcgaag gcgtcggcca gctccccgcg cacggcttcc aactcgttgc 25620
gctcacgatc ccagccggct tgcgctgcct gcaacgattc attggcaagg gcctgggcgg 25680
cttgccagag ggcggccacg gcctggttgc cggcctgctg caccgcgtcc ggcacctgga 25740
ctgccagcgg ggcggcctgc gccgtgcgct ggcgtcgcca ttcgcgcatg ccggcgctgg 25800
cgtcgttcat gttgacgcgg gcggccttac gcactgcatc cacggtcggg aagttctccc 25860
ggtcgccttg ctcgaacagc tcgtccgcag ccgcaaaaat gcggtcgcgc gtctctttgt 25920
tcagttccat gttggctccg gtaattggta agaataataa tactcttacc taccttatca 25980
gcgcaagagt ttagctgaac agttctcgac ttaacggcag gtttttttagc ggctgaaggg 26040
caggcaaaaa aagccccgca cggtcggcgg gggcaaaggg tcagcgggaa ggggattagc 26100
gggcgtcggg cttcttcatg cgtcggggcc gcgcttcttg ggatggagca cgacgaagcg 26160
cgcacgcgca tcgtcctcgg ccctatcggc ccgcgtcgcg gtcaggaact tgtcgcgcgc 26220
taggtcctcc ctggtgggca ccaggggcat gaactcggcc tgctcgatgt aggtccactc 26280
catgaccgca tcgcagtcga ggccgcgttc cttcaccgtc tcttgcaggt cgcggtacgc 26340
ccgctcgttg agcggctggt aacgggccaa ttggtcgtaa atggctgtcg gccatgagcg 26400
gcctttcctg ttgagccagc agccgacgac gaagccggca atgcaggccc ctggcacaac 26460
caggccgacg ccgggggcag gggatggcag cagctcgcca accaggaacc ccgccgcgat 26520
gatgccgatg ccggtcaacc agcccttgaa actatccggc cccgaaacac ccctgcgcat 26580
tgcctggatg ctgcgccgga tagcttgcaa catcaggagc cgtttctttt gttcgtcagt 26640
catggtccgc cctcaccagt tgttcgtatc ggtgtcggac gaactgaaat cgcaagagct 26700
gccggtatcg gtccagccgc tgtccgtgtc gctgctgccg aagcacggcg aggggtccgc 26760
gaacgccgca gacggcgtat ccggccgcag cgcatcgccc agcatggccc cggtcagcga 26820
gccgccggcc aggtagccca gcatggtgct gttggtcgcc ccggccacca gggccgacgt 26880
gacgaaatcg ccgtcattcc ctctggattg ttcgctgctc ggcggggcag tgcgccgcgc 26940
cggcggcgtc gtggatggct cgggttggct ggcctgcgac ggccggcgaa aggtgcgcag 27000
cagctcgtta tcgaccggct gcggcgtcgg ggccgccgcc ttgcgctgcg gtcggtgttc 27060
cttcttcggc tcgcgcagct tgaacagcat gatcgcggaa accagcagca acgccgcgcc 27120
tacgcctccc gcgatgtaga acagcatcgg attcattctt cggtcctcct tgtagcggaa 27180
ccgttgtctg tgcggcgcgg gtggcccgcg ccgctgtctt tggggatcag ccctcgatga 27240
gcgcgaccag tttcacgtcg gcaaggttcg cctcgaactc ctggccgtcg tcctcgtact 27300
tcaaccaggc atagccttcc gccggcggcc gacggttgag gataaggcgg gcagggcgct 27360
cgtcgtgctc gacctggacg atggcctttt tcagcttgtc cgggtccggc tccttcgcgc 27420
ccttttcctt ggcgtcctta ccgtcctggt cgccgtcctc gccgtcctgg ccgtcgccgg 27480
cctccgcgtc acgctcggca tcagtctggc cgttgaaggc atcgacggtg ttgggatcgc 27540
ggcccttctc gtccaggaac tcgcgcagca gcttgaccgt gccgcgcgtg atttcctggg 27600
tgtcgtcgtc aagccacgcc tcgacttcct ccgggcgctt cttgaaggcc gtcaccagct 27660
cgttcaccac ggtcacgtcg cgcacgcggc cggtgttgaa cgcatcggcg atcttctccg 27720
gcaggtccag cagcgtgacg tgctgggtga tgaacgccgg cgacttgccg atttccttgg 27780
cgatatcgcc tttcttcttg cccttcgcca gctcgcggcc aatgaagtcg gcaatttcgc 27840
gcggggtcag ctcgttgcgt tgcaggttct cgataacctg gtcggcttcg ttgtagtcgt 27900
tgtcgatgaa cgccgggatg gacttcttgc cggcccactt cgagccacgg tagcggcggg 27960
cgccgtgatt gatgatatag cggcccggct gctcctggtt ctcgcgcacc gaaatgggtg 28020
acttcacccc gcgctctttg atcgtggcac cgatttccgc gatgctctcc ggggaaaagc 28080
cggggttgtc ggccgtccgc ggctgatgcg gatcttcgtc gatcaggtcc aggtccagct 28140
cgatagggcc ggaaccgccc tgagacgccg caggagcgtc caggaggctc gacaggtcgc 28200
cgatgctatc caaccccagg ccggacggct gcgccgcgcc tgcggcttcc tgagcggccg 28260
cagcggtgtt tttcttggtg gtcttggctt gagccgcagt cattgggaaa tctccatctt 28320
cgtgaacacg taatcagcca gggcgcgaac ctctttcgat gccttgcgcg cggccgtttt 28380
cttgatcttc cagaccggca caccggatgc gagggcatcg gcgatgctgc tgcgcaggcc 28440
aacggtggcc ggaatcatca tcttggggta cgcggccagc agctcggctt ggtggcgcgc 28500
gtggcgcgga ttccgcgcat cgaccttgct gggcaccatg ccaaggaatt gcagcttggc 28560
gttcttctgg cgcacgttcg caatggtcgt gaccatcttc ttgatgccct ggatgctgta 28620
cgcctcaagc tcgatggggg acagcacata gtcggccgcg aagagggcgg ccgccaggcc 28680
gacgccaagg gtcggggccg tgtcgatcag gcacacgtcg aagccttggt tcgccagggc 28740
cttgatgttc gccccgaaca gctcgcgggc gtcgtccagc gacagccgtt cggcgttcgc 28800
cagtaccggg ttggactcga tgagggcgag gcgcgcggcc tggccgtcgc cggctgcggg 28860
tgcggtttcg gtccagccgc cggcagggac agcgccgaac agcttgcttg catgcaggcc 28920
ggtagcaaag tccttgagcg tgtaggacgc attgccctgg gggtccaggt cgatcacggc 28980
aacccgcaag ccgcgctcga aaaagtcgaa ggcaagatgc acaagggtcg aagtcttgcc 29040
gacgccgcct ttctggttgg ccgtgaccaa agttttcatc gtttggtttc ctgtttttc 29100
ttggcgtccg cttcccactt ccggacgatg tacgcctgat gttccggcag aaccgccgtt 29160
acccgcgcgt acccctcggg caagttcttg tcctcgaacg cggcccacac gcgatgcacc 29220
gcttgcgaca ctgcgcccct ggtcagtccc agcgacgttg cgaacgtcgc ctgtggcttc 29280
ccatcgacta agacgccccg cgctatctcg atggtctgct gccccacttc cagcccctgg 29340
atcgcctcct ggaactggct ttcggtaagc cgtttcttca tggataacac ccataatttg 29400
ctccgcgcct tggttgaaca tagcggtgac agccgccagc acatgagaga agtttagcta 29460
aacatttctc gcacgtcaac acctttagcc gctaaaactc gtccttggcg taacaaaaca 29520
aaagcccgga aaccgggctt tcgtctcttg ccgcttatgg ctctgcaccc ggctccatca 29580
ccaacaggtc gcgcacgcgc ttcactcggt tgcggatcga cactgccagc ccaacaaagc 29640
cggttgccgc cgccgccagg atcgcgccga tgatgccggc cacaccggcc atcgcccacc 29700
aggtcgccgc cttccggttc cattcctgct ggtactgctt cgcaatgctg gacctcggct 29760
caccataggc tgaccgctcg atggcgtatg ccgcttctcc ccttggcgta aaacccagcg 29820
ccgcaggcgg cattgccatg ctgcccgccg ctttcccgac cacgacgcgc gcaccaggct 29880
tgcggtccag accttcggcc acggcgagct gcgcaaggac ataatcagcc gccgacttgg 29940
ctccacgcgc ctcgatcagc tcttgcactc gcgcgaaatc cttggcctcc acggccgcca 30000
tgaatcgcgc acgcggcgaa ggctccgcag ggccggcgtc gtgatcgccg ccgagaatgc 30060
ccttcaccaa gttcgacgac acgaaaatca tgctgacggc tatcaccatc atgcagacgg 30120
atcgcacgaa cccgctgaat tgaacacgag cacggcaccc gcgaccacta tgccaagaat 30180
gcccaaggta aaaattgccg gccccgccat gaagtccgtg aatgccccga cggccgaagt 30240
gaagggcagg ccgccaccca ggccgccgcc ctcactgccc ggcacctggt cgctgaatgt 30300

-continued

```
cgatgccagc acctgcggca cgtcaatgct tccgggcgtc gcgctcgggc tgatcgccca  30360
tcccgttact gccccgatcc cggcaatggc aaggactgcc agcgctgcca tttttggggt  30420
gaggccgttc gcggccgagg ggcgcagccc ctggggggat gggaggcccg cgttagcggg  30480
ccgggagggt tcgagaaggg ggggcacccc ccttcggcgt gcgcggtcac gcgcacaggg  30540
cgcagccctg gttaaaaaca aggtttataa atattggttt aaaagcaggt taaaagacag  30600
gttagcggtg gccgaaaaac gggcggaaac ccttgcaaat gctggatttt ctgcctgtgg  30660
acagcccctc aaatgtcaat aggtgcgccc ctcatctgtc agcactctgc ccctcaagtg  30720
tcaaggatcg cgcccctcat ctgtcagtag tcgcgcccct caagtgtcaa taccgcaggg  30780
cacttatccc caggcttgtc cacatcatct gtgggaaact cgcgtaaaat caggcgtttt  30840
cgccgatttg cgaggctggc cagctccacg tcgccggccg aaatcgagcc tgcccctcat  30900
ctgtcaacgc cgcgccgggt gagtcggccc ctcaagtgtc aacgtccgcc cctcatctgt  30960
cagtgagggc caagttttcc gcgaggtatc cacaacgccg gcggccgcgg tgtctcgcac  31020
acggcttcga cggcgtttct ggcgcgtttg cagggccata gacggccgcc agcccagcgg  31080
cgagggcaac cagcccggtg agcgtcggaa aggcgctgga agccccgtag cgacgcggag  31140
aggggcgaga caagccaagg gcgcaggctc gatgcgcagc acgacatagc cggttctcgc  31200
aaggacgaga atttccctgc ggtgcccctc aagtgtcaat gaaagtttcc aacgcgagcc  31260
attcgcgaga gccttgagtc cacgctagat gagagctttg ttgtaggtgg accagttggt  31320
gattttgaac ttttgctttg ccacggaacg gtctgcgttg tcgggaagat gcgtgatctg  31380
atccttcaac tcagcaaaag ttcgatttat tcaacaaagc cacgttgtgt ctcaaaatct  31440
ctgatgttac attgcacaag ataaaaatat atcatcatga acaataaaac tgtctgctta  31500
cataaacagt aatacaaggg gtgttatgag ccatattcaa cgggaaacgt cttgctcgac  31560
tctagagctc gttcctcgag gaacggtacc tgcggggaag cttacaataa tgtgtgttgt  31620
taagtcttgt tgcctgtcat cgtctgactg actttcgtca taaatcccgg cctccgtaac  31680
ccagctttgg gcaagctcac ggatttgatc cggcggaacg ggaatatcga gatgccgggc  31740
tgaacgctgc agttccagct ttccctttcg ggacaggtac tccagctgat tgattatctg  31800
ctgaagggtc ttggttccac ctcctggcac aatgcgaatg attacttgag cgcgatcggg  31860
catccaattt tctcccgtca ggtgcgtggt caagtgctac aaggcacctt tcagtaacga  31920
gcgaccgtcg atccgtcgcc gggatacgga caaaatggag cgcagtagtc catcgagggc  31980
ggcgaaagcc tcgccaaaag caatacgttc atctcgcaca gcctccagat ccgatcgagg  32040
gtcttcggcg taggcagata gaagcatgga tacattgctt gagagtattc cgatggactg  32100
aagtatggct tccatctttt ctcgtgtgtc tgcatctatt tcgagaaagc cccgatgcg  32160
gcgcaccgca acgcgaattg ccatactatc cgaaagtccc agcaggcgcg cttgatagga  32220
aaaggtttca tactcggccg atcgcagacg ggcactcacg accttgaacc cttcaacttt  32280
cagggatcga tgctggttga tggtagtctc actcgacgtg gctctggtgt gttttgacat  32340
agcttcctcc aaagaaagcg gaaggtctgg atactccagc acgaaatgtg cccgggtaga  32400
cggatggaag tctagccctg ctcaatatga aatcaacagt acatttacag tcaatactga  32460
atatacttgc tacatttgca attgtcttat aacgaatgtg aaataaaaat agtgtaacaa  32520
cgcttttact catcgataat cacaaaaaca tttatacgaa caaaaataca aatgcactcc  32580
ggtttcacag gataggcggg atcagaatat gcaacttttg acgttttgtt ctttcaaagg  32640
gggtgctggc aaaaccaccg cactcatggg cctttgcgct gctttggcaa atgacggtaa  32700
```

```
acgagtggcc ctctttgatg ccgacgaaaa ccggcctctg acgcgatgga gagaaaacgc  32760
cttacaaagc agtactggga tcctcgctgt gaagtctatt ccgccgacga aatgcccctt  32820
cttgaagcag cctatgaaaa tgccgagctc gaaggatttg attatgcgtt ggccgatacg  32880
cgtggcggct cgagcgagct caacaacaca atcatcgcta gctcaaacct gcttctgatc  32940
cccaccatgc taacgccgct cgacatcgat gaggcactat ctacctaccg ctacgtcatc  33000
gagctgctgt tgagtgaaaa tttggcaatt cctacagctg ttttgcgcca acgcgtcccg  33060
gtcggccgat tgacaacatc gcaacgcagg atgtcagaga cgctagagag ccttccagtt  33120
gtaccgtctc ccatgcatga aagagatgca tttgccgcga tgaaagaacg cggcatgttg  33180
catcttacat tactaaacac gggaactgat ccgacgatgc gcctcataga gaggaatctt  33240
cggattgcga tggaggaagt cgtggtcatt tcgaaactga tcagcaaaat cttggaggct  33300
tgaagatggc aattcgcaag cccgcattgt cggtcggcga agcacggcgg cttgctggtg  33360
ctcgacccga gatccaccat cccaacccga cacttgttcc ccagaagctg gacctccagc  33420
acttgcctga aaaagccgac gagaaagacc agcaacgtga gcctctcgtc gccgatcaca  33480
tttacagtcc cgatcgacaa cttaagctaa ctgtggatgc ccttagtcca cctccgtccc  33540
cgaaaaagct ccaggttttt ctttcagcgc gaccgcccgc gcctcaagtg tcgaaaacat  33600
atgacaacct cgttcggcaa tacagtccct cgaagtcgct acaaatgatt ttaaggcgcg  33660
cgttggacga tttcgaaagc atgctggcag atggatcatt tcgcgtggcc ccgaaaagtt  33720
atccgatccc ttcaactaca gaaaaatccg ttctcgttca gacctcacgc atgttcccgg  33780
ttgcgttgct cgaggtcgct cgaagtcatt ttgatccgtt ggggttggag accgctcgag  33840
ctttcggcca caagctggct accgccgcgc tcgcgtcatt ctttgctgga gagaagccat  33900
cgagcaattg gtgaagaggg acctatcgga acccctcacc aaatattgag tgtaggtttg  33960
aggccgctgg ccgcgtcctc agtcaccttt tgagccagat aattaagagc caaatgcaat  34020
tggctcaggc tgccatcgtc cccccgtgcg aaacctgcac gtccgcgtca aagaaataac  34080
cggcacctct tgctgttttt atcagttgag ggcttgacgg atccgcctca agtttgcggc  34140
gcagccgcaa aatgagaaca tctatactcc tgtcgtaaac ctcctcgtcg cgtactcgac  34200
tggcaatgag aagttgctcg cgcgatagaa cgtcgcgggg tttctctaaa aacgcgagga  34260
gaagattgaa ctcacctgcc gtaagtttca cctcaccgcc agcttcggac atcaagcgac  34320
gttgcctgag attaagtgtc cagtcagtaa aacaaaaaga ccgtcggtct ttggagcgga  34380
caacgttggg gcgcacgcgc aaggcaaccc gaatgcgtgc aagaaactct ctcgtactaa  34440
acggcttagc gataaaatca cttgctccta gctcgagtgc aacaacttta tccgtctcct  34500
caaggcggtc gccactgata attatgattg gaatatcaga ctttgccgcc agatttcgaa  34560
cgatctcaag cccatcttca cgacctaaat ttagatcaac aaccacgaca tcgaccgtcg  34620
cggaagagag tactctagtg aactgggtgc tgtcggctac cgcggtcact ttgaaggcgt  34680
ggatcgtaag gtattcgata ataagatgcc gcatagcgac atcgtcatcg ataagaagaa  34740
cgtgtttcaa cggctcacct ttcaatctaa aatctgaacc cttgttcaca gcgcttgaga  34800
aattttcacg tgaaggatgt acaatcatct ccagctaaat gggcagttcg tcagaattgc  34860
ggctgaccgc ggatgacgaa aatgcgaacc aagtatttca attttatgac aaaagttctc  34920
aatcgttgtt acaagtgaaa cgcttcgagg ttacagctac tattgattaa ggagatcgcc  34980
tatggtctcg ccccggcgtc gtgcgtccgc cgcgagccag atctcgccta cttcataaac  35040
gtcctcatag gcacggaatg gaatgatgac atcgatcgcc gtagagagca tgtcaatcag  35100
```

```
tgtgcgatct tccaagctag caccttgggc gctacttttg acaagggaaa acagtttctt  35160
gaatccttgg attggattcg cgccgtgtat tgttgaaatc gatcccggat gtcccgagac  35220
gacttcactc agataagccc atgctgcatc gtcgcgcatc tcgccaagca atatccggtc  35280
cggccgcata cgcagacttg cttggagcaa gtgctcggcg ctcacagcac ccagcccagc  35340
accgttcttg gagtagagta gtctaacatg attatcgtgt ggaatgacga gttcgagcgt  35400
atcttctatg gtgattagcc tttcctgggg ggggatggcg ctgatcaagg tcttgctcat  35460
tgttgtcttg ccgcttccgg tagggccaca tagcaacatc gtcagtcggc tgacgacgca  35520
tgcgtgcaga aacgcttcca aatccccgtt gtcaaaatgc tgaaggatag cttcatcatc  35580
ctgattttgg cgtttccttc gtgtctgcca ctggttccac ctcgaagcat cataacggga  35640
ggagacttct ttaagaccag aaacacgcga gcttggccgt cgaatggtca agctgacggt  35700
gcccgaggga acggtcggcg gcagacagat ttgtagtcgt tcaccaccag gaagttcagt  35760
ggcgcagagg gggttacgtg gtccgacatc ctgctttctc agcgcgcccg ctaaaatagc  35820
gatatcttca agatcatcat aagagacggg caaaggcatc ttggtaaaaa tgccggcttg  35880
gcgcacaaat gcctctccag gtcgattgat cgcaatttct tcagtcttcg ggtcatcgag  35940
ccattccaaa atcggcttca gaagaaagcg tagttgcgga tccacttcca tttacaatgt  36000
atcctatctc taagcggaaa tttgaattca ttaagagcgg cggttcctcc cccgcgtggc  36060
gccgccagtc aggcggagct ggtaaacacc aaagaaatcg aggtcccgtg ctacgaaaat  36120
ggaaacggtg tcaccctgat tcttcttcag ggttggcggt atgttgatgg ttgccttaag  36180
ggctgtctca gttgtctgct caccgttatt ttgaaagctg ttgaagctca tcccgccacc  36240
cgagctgccg gcgtaggtgc tagctgcctg gaaggcgcct tgaacaacac tcaagagcat  36300
agctccgcta aaacgctgcc agaagtggct gtcgaccgag cccggcaatc ctgagcgacc  36360
gagttcgtcc gcgcttggcg atgttaacga gatcatcgca tggtcaggtg tctcggcgcg  36420
atcccacaac acaaaaacgc gcccatctcc ctgttgcaag ccacgctgta tttcgccaac  36480
aacggtggtg ccacgatcaa gaagcacgat attgttcgtt gttccacgaa tatcctgagg  36540
caagacacac tttacatagc ctgccaaatt tgtgtcgatt gcggtttgca agatgcacgg  36600
aattattgtc ccttgcgtta ccataaaatc ggggtgcggc aagagcgtgg cgctgctggg  36660
ctgcagctcg gtgggtttca tacgtatcga caaatcgttc tcgccggaca cttcgccatt  36720
cggcaaggag ttgtcgtcac gcttgccttc ttgtcttcgg cccgtgtcgc cctgaatggc  36780
gcgtttgctg accccttgat cgccgctgct atatgcaaaa atcggtgttt cttccggccg  36840
tggctcatgc cgctccggtt cgcccctcgg cggtagagga gcagcaggct gaacagcctc  36900
ttgaaccgct ggaggatccg gcggcacctc aatcggagct ggatgaaatg gcttggtgtt  36960
tgttgcgatc aaagttgacg gcgatgcgtt ctcattcacc ttcttttggc gcccacctag  37020
ccaaatgagg cttaatgata acgcgagaac gacacctccg acgatcaatt tctgagaccc  37080
cgaaagacgc cggcgatgtt tgtcggagac cagggatcca gatgcatcaa cctcatgtgc  37140
cgcttgctga ctatcgttat tcatcccttc gccccccttca ggacgcgttt cacatcgggc  37200
ctcaccgtgc ccgtttgcgg cctttggcca acgggatcgt aagcggtgtt ccagatacat  37260
agtactgtgt ggccatccct cagacgccaa cctcgggaaa ccgaagaaat ctcgacatcg  37320
ctccctttaa ctgaatagtt ggcaacagct tccttgccat caggattgat ggtgtagatg  37380
gagggtatgc gtacattgcc cggaaagtgg aataccgtcg taaatccatt gtcgaagact  37440
tcgagtggca acagcgaacg atcgccttgg gcgacgtagt gccaattact gtccgccgca  37500
```

ccaagggctg tgacaggctg atccaataaa ttctcagctt tccgttgata ttgtgcttcc 37560
gcgtgtagtc tgtccacaac agccttctgt tgtgcctccc ttcgccgagc cgccgcatcg 37620
tcggcggggt aggcgaattg gacgctgtaa tagagatcgg gctgctcttt atcgaggtgg 37680
gacagagtct tggaacttat actgaaaaca taacggcgca tcccggagtc gcttgcggtt 37740
agcacgatta ctggctgagg cgtgaggacc tggcttgcct tgaaaaatag ataatttccc 37800
cgcggtaggg ctgctagatc tttgctattt gaaacggcaa ccgctgtcac cgtttcgttc 37860
gtggcgaatg ttacgaccaa agtagctcca accgccgtcg agaggcgcac cacttgatcg 37920
ggattgtaag ccaaataacg catgcgcgga tctagcttgc ccgccattgg agtgtcttca 37980
gcctccgcac cagtcgcagc ggcaaataaa catgctaaaa tgaaaagtgc ttttctgatc 38040
atggttcgct gtggcctacg tttgaaacgg tatcttccga tgtctgatag gaggtgacaa 38100
ccagacctgc cgggttggtt agtctcaatc tgccgggcaa gctggtcacc ttttcgtagc 38160
gaactgtcgc ggtccacgta ctcaccacag gcattttgcc gtcaacgacg agggtccttt 38220
tatagcgaat ttgctgcgtg cttggagtta catcatttga agcgatgtgc tcgacctcca 38280
ccctgccgcg tttgccaaga atgacttgag gcgaactggg attgggatag ttgaagaatt 38340
gctggtaatc ctggcgcact gttggggcac tgaagttcga taccaggtcg taggcgtact 38400
gagcggtgtc ggcatcataa ctctcgcgca ggcgaacgta ctcccacaat gaggcgttaa 38460
cgacggcctc ctcttgagtt gcaggcaatc gcgagacaga cacctcgctg tcaacggtgc 38520
cgtccggccg tatccataga tatacgggca caagcctgct caacggcacc attgtggcta 38580
tagcgaacgc ttgagcaaca tttcccaaaa tcgcgatagc tgcgacagct gcaatgagtt 38640
tggagagacg tcgcgccgat ttcgctcgcg cggtttgaaa ggcttctact tccttatagt 38700
gctcggcaag gctttcgcgc gccactagca tggcatattc aggccccgtc atagcgtcca 38760
cccgaattgc cgagctgaag atctgacgga gtaggctgcc atcgccccac attcagcggg 38820
aagatcgggc ctttgcagct cgctaatgtg tcgtttgtct ggcagccgct caaagcgaca 38880
actaggcaca gcaggcaata cttcatagaa ttctccattg aggcgaattt ttgcgcgacc 38940
tagcctcgct caacctgagc gaagcgacgg tacaagctgc tggcagattg ggttgcgccg 39000
ctccagtaac tgcctccaat gttgccggcg atcgccggca aagcgacaat gagcgcatcc 39060
cctgtcagaa aaaacatatc gagttcgtaa agaccaatga tcttggccgc ggtcgtaccg 39120
gcgaaggtga ttacaccaag cataagggtg agcgcagtcg cttcggttag gatgacgatc 39180
gttgccacga ggtttaagag gagaagcaag agaccgtagg tgataagttg cccgatccac 39240
ttagctgcga tgtcccgcgt gcgatcaaaa atatatccga cgaggatcag aggcccgatc 39300
gcgagaagca ctttcgtgag aattccaacg gcgtcgtaaa ctccgaaggc agaccagagc 39360
gtgccgtaaa ggacccactg tgccccttgg aaagcaagga tgtcctggtc gttcatcgga 39420
ccgatttcgg atgcgatttt ctgaaaaacg gcctgggtca cggcgaacat tgtatccaac 39480
tgtgccggaa cagtctgcag aggcaagccg gttacactaa actgctgaac aaagtttggg 39540
accgtctttt cgaagatgga aaccacatag tcttggtagt tagcctgccc aacaattaga 39600
gcaacaacga tggtgaccgt gatcacccga gtgataccgc tacgggtatc gacttcgccg 39660
cgtatgacta aaataccctg aacaataatc caaagagtga cacaggcgat caatggcgca 39720
ctcaccgcct cctggatagt ctcaagcatc gagtccaagc ctgtcgtgaa ggctacatcg 39780
aagatcgtat gaatggccgt aaacggcgcc ggaatcgtga aattcatcga ttggacctga 39840
acttgactgg tttgtcgcat aatgttggat aaaatgagct cgcattcggc gaggatgcgg 39900

```
gcggatgaac aaatcgccca gccttagggg agggcaccaa agatgacagc ggtcttttga  39960
tgctccttgc gttgagcggc cgcctcttcc gcctcgtgaa ggccggcctg cgcggtagtc  40020
atcgttaata ggcttgtcgc ctgtacattt tgaatcattg cgtcatggat ctgcttgaga  40080
agcaaaccat tggtcacggt tgcctgcatg atattgcgag atcgggaaag ctgagcagac  40140
gtatcagcat tcgccgtcaa gcgtttgtcc atcgtttcca gattgtcagc cgcaatgcca  40200
gcgctgtttg cggaaccggt gatctgcgat cgcaacaggt ccgcttcagc atcactaccc  40260
acgactgcac gatctgtatc gctggtgatc gcacgtgccg tggtcgacat tggcattcgc  40320
ggcgaaaaca tttcattgtc taggtccttc gtcgaaggat actgattttt ctggttgagc  40380
gaagtcagta gtccagtaac gccgtaggcc gacgtcaaca tcgtaaccat cgctatagtc  40440
tgagtgagat tctccgcagt cgcgagcgca gtcgcgagcg tctcagcctc cgttgccggg  40500
tcgctaacaa caaactgcgc ccgcgcgggc tgaatatata gaaagctgca ggtcaaaact  40560
gttgcaataa gttgcgtcgt cttcatcgtt tcctacctta tcaatcttct gcctcgtggt  40620
gacgggccat gaattcgctg agccagccag atgagttgcc ttcttgtgcc tcgcgtagtc  40680
gagttgcaaa gcgcaccgtg ttggcacgcc ccgaaagcac ggcgacatat tcacgcatat  40740
cccgcagatc aaattcgcag atgacgcttc cactttctcg tttaagaaga aacttacggc  40800
tgccgaccgt catgtcttca cggatcgcct gaaattcctt ttcggtacat ttcagtccat  40860
cgacataagc cgatcgatct gcggttggtg atggatagaa aatcttcgtc atacattgcg  40920
caaccaagct ggctcctagc ggcgattcca gaacatgctc tggttgctgc gttgccagta  40980
ttagcatccc gttgtttttt cgaacggtca ggaggaattt gtcgacgaca gtcgaaaatt  41040
tagggtttaa caaataggcg cgaaactcat cgcagctcat cacaaaacgg cggccgtcga  41100
tcatggctcc aatccgatgc aggagatatg ctgcagcggg agcgcatact tcctcgtatt  41160
cgagaagatg cgtcatgtcg aagccggtaa tcgacggatc taactttact tcgtcaactt  41220
cgccgtcaaa tgcccagcca agcgcatggc cccggcacca gcgttggagc cgcgctcctg  41280
cgccttcggc gggcccatgc aacaaaaatt cacgtaaccc cgcgattgaa cgcatttgtg  41340
gatcaaacga gagctgacga tggataccac ggaccagacg gcggttctct tccggagaaa  41400
tcccaccccg accatcactc tcgatgagag ccacgatcca ttcgcgcaga aaatcgtgtg  41460
aggctgctgt gttttctagg ccacgcaacg gcgccaaccc gctgggtgtg cctctgtgaa  41520
gtgccaaata tgttcctcct gtggcgcgaa ccagcaattc gccaccccgg tccttgtcaa  41580
agaacacgac cgtacctgca cggtcgacca tgctctgttc gagcatggct agaacaaaca  41640
tcatgagcgt cgtcttaccc ctcccgatag gcccgaatat tgccgtcatg ccaacatcgt  41700
gctcatgcgg gatatagtcg aaaggcgttc cgccattggt acgaaatcgg gcaatcgcgt  41760
tgccccagtg gcctgagctg gcgccctctg gaaagttttc gaaagagaca aaccctgcga  41820
aattgcgtga agtgattgcg ccagggcgtg tgcgccactt aaaattcccc ggcaattggg  41880
accaataggc cgcttccata ccaatacctt cttggacaac cacggcacct gcatccgcca  41940
ttcgtgtccg agcccgcgcg cccctgtccc caagactatt gagatcgtct gcatagacgc  42000
aaaggctcaa atgatgtgag cccataacga attcgttgct cgcaagtgcg tcctcagcct  42060
cggataattt gccgatttga gtcacggctt tatcgccgga actcagcatc tggctcgatt  42120
tgaggctaag tttcgcgtgc gcttgcgggc gagtcaggaa cgaaaaactc tgcgtgagaa  42180
caagtggaaa atcgagggat agcagcgcgt tgagcatgcc cggccgtgtt tttgcagggt  42240
attcgcgaaa cgaatagatg gatccaacgt aactgtcttt tggcgttctg atctcgagtc  42300
```

```
ctcgcttgcc gcaaatgact ctgtcggtat aaatcgaagc gccgagtgag ccgctgacga  42360
ccggaaccgg tgtgaaccga ccagtcatga tcaaccgtag cgcttcgcca atttcggtga  42420
agagcacacc ctgcttctcg cggatgccaa gacgatgcag gccatacgct ttaagagagc  42480
cagcgacaac atgccaaaga tcttccatgt tcctgatctg gcccgtgaga tcgttttccc  42540
tttttccgct tagcttggtg aacctcctct ttaccttccc taaagccgcc tgtgggtaga  42600
caatcaacgt aaggaagtgt tcattgcgga ggagttggcc ggagagcacg cgctgttcaa  42660
aagcttcgtt caggctagcg gcgaaaacac tacggaagtg tcgcggcgcc gatgatggca  42720
cgtcggcatg acgtacgagg tgagcatata ttgacacatg atcatcagcg atattgcgca  42780
acagcgtgtt gaacgcacga caacgcgcat tgcgcatttc agtttcctca agctcgaatg  42840
caacgccatc aattctcgca atggtcatga tcgatccgtc ttcaagaagg acgatatggt  42900
cgctgaggtg gccaatataa gggagataga tctcaccgga tctttcggtc gttccactcg  42960
cgccgagcat cacaccattc ctctccctcg tgggggaacc ctaattggat ttgggctaac  43020
agtagcgccc ccccaaactg cactatcaat gcttcttccc gcggtccgca aaaatagcag  43080
gacgacgctc gccgcattgt agtctcgctc cacgatgagc cgggctgcaa accataacgg  43140
cacgagaacg acttcgtaga gcgggttctg aacgataacg atgacaaagc cggcgaacat  43200
catgaataac cctgccaatg tcagtggcac cccaagaaac aatgcgggcc gtgtggctgc  43260
gaggtaaagg gtcgattctt ccaaacgatc agccatcaac taccgccagt gagcgtttgg  43320
ccgaggaagc tcgccccaaa catgataaca atgccgccga cgacgccggc aaccagccca  43380
agcgaagccc gcccgaacat ccaggagatc ccgatagcga caatgccgag aacagcgagt  43440
gactggccga acggaccaag gataaacgtg catatattgt taaccattgt ggcggggtca  43500
gtgccgccac ccgcagattg cgctgcggcg ggtccggatg aggaaatgct ccatgcaatt  43560
gcaccgcaca agcttggggc gcagctcgat atcacgcgca tcatcgcatt cgagagcgag  43620
aggcgattta gatgtaaacg gtatctctca aagcatcgca tcaatgcgca cctccttagt  43680
ataagtcgaa taagacttga ttgtcgtctg cggatttgcc gttgtcctgg tgtggcggtg  43740
gcggagcgat taaaccgcca gcgccatcct cctgcgagcg gcgctgatat gacccccaaa  43800
catcccacgt ctcttcggat tttagcgcct cgtgatcgtc ttttggaggc tcgattaacg  43860
cgggcaccag cgattgagca gctgtttcaa cttttcgcac gtagccgttt gcaaaaccgc  43920
cgatgaaatt accggtgttg taagcggaga tcgcccgacg aagcgcaaat tgcttctcgt  43980
caatcgtttc gccgcctgca taacgacttt tcagcatgtt tgcagcggca gataatgatg  44040
tgcacgcctg gagcgcaccg tcaggtgtca gaccgagcat agaaaaattt cgagagttta  44100
tttgcatgag gccaacatcc agcgaatgcc gtgcatcgag acggtgcctg acgacttggg  44160
ttgcttggct gtgatcttgc cagtgaagcg tttcgccggt cgtgttgtca tgaatcgcta  44220
aaggatcaaa gcgactctcc accttagcta tcgccgcaag cgtagatgtc gcaactgatg  44280
gggcacactt gcgagcaaca tggtcaaact cagcagatga gagtggcgtg gcaaggctcg  44340
acgaacagaa ggagaccatc aaggcaagag aaagcgaccc cgatctctta agcatacctt  44400
atctccttag ctcgcaacta acaccgcctc tcccgttgga agaagtgcgt tgttttatgt  44460
tgaagattat cgggagggtc ggttactcga aaattttcaa ttgcttcttt atgatttcaa  44520
ttgaagcgag aaacctcgcc cggcgtcttg gaacgcaaca tggaccgaga accgcgcatc  44580
catgactaag caaccggatc gacctattca ggccgcagtt ggtcaggtca ggctcagaac  44640
gaaaatgctc ggcgaggtta cgctgtctgt aaacccattc gatgaacggg aagcttcctt  44700
```

ccgattgctc ttggcaggaa tattggccca tgcctgcttg cgctttgcaa atgctcttat 44760
cgcgttggta tcatatgcct tgtccgccag cagaaacgca ctctaagcga ttatttgtaa 44820
aaatgtttcg gtcatgcggc ggtcatgggc ttgacccgct gtcagcgcaa gacggatcgg 44880
tcaaccgtcg gcatcgacaa cagcgtgaat cttggtggtc aaaccgccac gggaacgtcc 44940
catacagcca tcgtcttgat cccgctgttt cccgtcgccg catgttggtg gacgcggaca 45000
caggaactgt caatcatgac gacattctat cgaaagcctt ggaaatcaca ctcagaatat 45060
gatcccagac gtctgcctca cgccatcgta caaagcgatt gtagcaggtt gtacaggaac 45120
cgtatcgatc aggaacgtct gcccagggcg ggcccgtccg gaagcgccac aagatgacat 45180
tgatcacccg cgtcaacgcg cggcacgcga cgcggcttat ttgggaacaa aggactgaac 45240
aacagtccat tcgaaatcgg tgacatcaaa gcggggacgg gttatcagtg gcctccaagt 45300
caagcctcaa tgaatcaaaa tcagaccgat ttgcaaacct gatttatgag tgtgcggcct 45360
aaatgatgaa atcgtccttc tagatcgcct ccgtggtgta gcaacacctc gcagtatcgc 45420
cgtgctgacc ttggccaggg aattgactgg caagggtgct ttcacatgac cgctcttttg 45480
gccgcgatag atgatttcgt tgctgctttg ggcacgtaga aggagagaag tcatatcgga 45540
gaaattcctc ctggcgcgag agcctgctct atcgcgacgg catcccactg tcgggaacag 45600
accggatcat tcacgaggcg aaagtcgtca acacatgcgt tataggcatc ttcccttgaa 45660
ggatgatctt gttgctgcca atctggaggt gcggcagccg caggcagatg cgatctcagc 45720
gcaacttgcg gcaaaacatc tcactcacct gaaaaccact agcgagtctc gcgatcagac 45780
gaaggccttt tacttaacga cacaatatcc gatgtctgca tcacaggcgt cgctatccca 45840
gtcaatacta aagcggtgca ggaactaaag attactgatg acttaggcgt gccacgaggc 45900
ctgagacgac gcgcgtagac agttttttga aatcattatc aaagtgatgg cctccgctga 45960
agcctatcac ctctgcgccg gtctgtcgga gagatgggca agcattatta cggtcttcgc 46020
gcccgtacat gcattggacg attgcagggt caatggatct gagatcatcc agaggattgc 46080
cgcccttacc ttccgtttcg agttggagcc agcccctaaa tgagacgaca tagtcgactt 46140
gatgtgacaa tgccaagaga gagatttgct taacccgatt tttttgctca agcgtaagcc 46200
tattgaagct tgccggcatg acgtccgcgc cgaaagaata tcctacaagt aaaacattct 46260
gcacaccgaa atgcttggtg tagacatcga ttatgtgacc aagatcctta gcagtttcgc 46320
ttggggaccg ctccgaccag aaataccgaa gtgaactgac gccaatgaca ggaatccctt 46380
ccgtctgcag ataggtacca tcgatagatc tgctgcctcg cgcgtttcgg tgatgacggt 46440
gaaaacctct gacacatgca gctcccggag acggtcacag cttgtctgta agcggatgcc 46500
gggagcagac aagcccgtca gggcgcgtca gcgggtgttg gcgggtgtcg gggcgcagcc 46560
atgacccagt cacgtagcga tagcggagtg tatactggct taactatgcg gcatcagagc 46620
agattgtact gagagtgcac catatgcggt gtgaaatacc gcacagatgc gtaaggagaa 46680
aataccgcat caggcgctct tccgcttcct cgctcactga ctcgctgcgc tcggtcgttc 46740
ggctgcggcg agcggtatca gctcactcaa aggcggtaat acggttatcc acagaatcag 46800
gggataacgc aggaaagaac atgtgagcaa aaggccagca aaaggccagg aaccgtaaaa 46860
aggccgcgtt gctggcgttt ttccataggc tccgcccccc tgacgagcat cacaaaaatc 46920
gacgctcaag tcagaggtgg cgaaacccga caggactata aagataccag gcgtttcccc 46980
ctggaagctc cctcgtgcgc tctcctgttc cgaccctgcc gcttaccgga tacctgtccg 47040
cctttctccc ttcgggaagc gtggcgcttt ctcatagctc acgctgtagg tatctcagtt 47100

```
cggtgtaggt cgttcgctcc aagctgggct gtgtgcacga accccccgtt cagcccgacc  47160
gctgcgcctt atccggtaac tatcgtcttg agtccaaccc ggtaagacac gacttatcgc  47220
cactggcagc agccactggt aacaggatta gcagagcgag gtatgtaggc ggtgctacag  47280
agttcttgaa gtggtggcct aactacggct acactagaag gacagtattt ggtatctgcg  47340
ctctgctgaa gccagttacc ttcggaaaaa gagttggtag ctcttgatcc ggcaaacaaa  47400
ccaccgctgg tagcggtggt ttttttgttt gcaagcagca gattacgcgc agaaaaaaag  47460
gatctcaaga agatcctttg atcttttcta cggggtctga cgctcagtgg aacgaaaact  47520
cacgttaagg gattttggtc atgagattat caaaaaggat cttcacctag atccttttaa  47580
attaaaaatg aagttttaaa tcaatctaaa gtatatatga gtaaacttgg tctgacagtt  47640
accaatgctt aatcagtgag gcacctatct cagcgatctg tctatttcgt tcatccatag  47700
ttgcctgact ccccgtcgtg tagataacta cgatacggga gggcttacca tctggcccca  47760
gtgctgcaat gataccgcga gacccacgct caccggctcc agatttatca gcaataaacc  47820
agccagccgg aagggccgag cgcagaagtg gtcctgcaac tttatccgcc tccatccagt  47880
ctattaattg ttgccgggaa gctagagtaa gtagttcgcc agttaatagt ttgcgcaacg  47940
ttgttgccat tgctgcaggg gggggggggg ggggggactt ccattgttca ttccacggac  48000
aaaaacagag aaaggaaacg acagaggcca aaaagcctcg ctttcagcac ctgtcgtttc  48060
ctttcttttc agagggtatt ttaaataaaa acattaagtt atgacgaaga agaacggaaa  48120
cgccttaaac cggaaaattt tcataaatag cgaaaacccg cgaggtcgcc gccccgtagt  48180
cggatcaccg gaaaggaccc gtaaagtgat aatgattatc atctacatat cacaacgtgc  48240
gtggaggcca tcaaaccacg tcaaataatc aattatgacg caggtatcgt attaattgat  48300
ctgcatcaac ttaacgtaaa aacaacttca gacaatacaa atcagcgaca ctgaatacgg  48360
ggcaacctca tgtccccccc cccccccccc ctgcaggcat cgtggtgtca cgctcgtcgt  48420
ttggtatggc ttcattcagc tccggttccc aacgatcaag gcgagttaca tgatccccca  48480
tgttgtgcaa aaaagcggtt agctccttcg gtcctccgat cgttgtcaga agtaagttgg  48540
ccgcagtgtt atcactcatg gttatggcag cactgcataa ttctcttact gtcatgccat  48600
ccgtaagatg cttttctgtg actggtgagt actcaaccaa gtcattctga gaatagtgta  48660
tgcggcgacc gagttgctct tgcccggcgt caacacggga taataccgcg ccacatagca  48720
gaactttaaa agtgctcatc attggaaaac gttcttcggg gcgaaaactc tcaaggatct  48780
taccgctgtt gagatccagt tcgatgtaac ccactcgtgc acccaactga tcttcagcat  48840
cttttacttt caccagcgtt tctgggtgag caaaaacagg aaggcaaaat gccgcaaaaa  48900
agggaataag ggcgacacgg aaatgttgaa tactcatact cttccttttt caatattatt  48960
gaagcattta tcagggttat tgtctcatga gcggatacat atttgaatgt atttagaaaa  49020
ataaacaaat aggggttccg cgcacatttc cccgaaaagt gccacctgac gtctaagaaa  49080
ccattattat catgacatta acctataaaa ataggcgtat cacgaggccc tttcgtcttc  49140
aagaattggt cgacgatctt gctgcgttcg gatattttcg tggagttccc gccacagacc  49200
cggattgaag gcgagatcca gcaactcgcg ccagatcatc ctgtgacgga actttggcgc  49260
gtgatgactg gccaggacgt cggccgaaag agcgacaagc agatcacgct tttcgacagc  49320
gtcggatttg cgatcgagga tttttcggcg ctgcgctacg tccgcgaccg cgttgaggga  49380
tcaagccaca gcagcccact cgaccttcta gccgacccag acgagccaag ggatcttttt  49440
ggaatgctgc tccgtcgtca ggctttccga cgtttgggtg gttgaacaga agtcattatc  49500
```

```
gtacggaatg ccaagcactc ccgaggggaa ccctgtggtt ggcatgcaca tacaaatgga  49560

cgaacggata aacctttca cgccctttta aatatccgtt attctaataa acgctctttt  49620

ctcttaggtt tacccgccaa tatatcctgt caaacactga tagtttaaac tgaaggcggg  49680

aaacgacaat ctgatcatga gcggagaatt aagggagtca cgttatgacc cccgccgatg  49740

acgcgggaca agccgtttta cgtttggaac tgacagaacc gcaacgttga aggagccact  49800

cagcaagctg gtacgattgt aatacgactc actatagggc gaattgagcg ctgtttaaac  49860

gctcttcaac tggaagagcg gttacccgga ccgaagcttg catgcctgca g           49911
```

```
<210> SEQ ID NO 50
<211> LENGTH: 36909
<212> TYPE: DNA
<213> ORGANISM: artificial sequence
<220> FEATURE:
<223> OTHER INFORMATION: vector

<400> SEQUENCE: 50

tctagagctc gttcctcgag gcctcgaggc ctcgaggaac ggtacctgcg gggaagctta    60

caataatgtg tgttgttaag tcttgttgcc tgtcatcgtc tgactgactt tcgtcataaa   120

tcccggcctc cgtaacccag ctttgggcaa gctcacggat ttgatccggc ggaacgggaa   180

tatcgagatg ccgggctgaa cgctgcagtt ccagctttcc ctttcgggac aggtactcca   240

gctgattgat tatctgctga agggtcttgg ttccacctcc tggcacaatg cgaatgatta   300

cttgagcgcg atcgggcatc caattttctc ccgtcaggtg cgtggtcaag tgctacaagg   360

cacctttcag taacgagcga ccgtcgatcc gtcgccggga tacggacaaa atggagcgca   420

gtagtccatc gagggcggcg aaagcctcgc caaaagcaat acgttcatct cgcacagcct   480

ccagatccga tcgagggtct tcggcgtagg cagatagaag catggataca ttgcttgaga   540

gtattccgat ggactgaagt atggcttcca tcttttctcg tgtgtctgca tctatttcga   600

gaaagccccc gatgcggcgc accgcaacgc gaattgccat actatccgaa agtcccagca   660

ggcgcgcttg ataggaaaag gtttcatact cggccgatcg cagacgggca ctcacgacct   720

tgaacccttc aactttcagg gatcgatgct ggttgatggt agtctcactc gacgtggctc   780

tggtgtgttt tgacatagct tcctccaaag aaagcggaag gtctggatac tccagcacga   840

aatgtgcccg ggtagacgga tggaagtcta gccctgctca atatgaaatc aacagtacat   900

ttacagtcaa tactgaatat acttgctaca tttgcaattg tcttataacg aatgtgaaat   960

aaaaatagtg taacaacgct tttactcatc gataatcaca aaaacattta tacgaacaaa  1020

aatacaaatg cactccggtt tcacaggata ggcgggatca gaatatgcaa cttttgacgt  1080

tttgttcttt caaagggggt gctggcaaaa ccaccgcact catgggcctt tgcgctgctt  1140

tggcaaatga cggtaaacga gtggccctct ttgatgccga cgaaaaccgg cctctgacgc  1200

gatggagaga aaacgcctta caaagcagta ctgggatcct cgctgtgaag tctattccgc  1260

cgacgaaatg ccccttcttg aagcagccta tgaaaatgcc gagctcgaag gatttgatta  1320

tgcgttggcc gatacgcgtg gcggctcgag cgagctcaac aacacaatca tcgctagctc  1380

aaacctgctt ctgatcccca ccatgctaac gccgctcgac atcgatgagg cactatctac  1440

ctaccgctac gtcatcgagc tgctgttgag tgaaaatttg gcaattccta cagctgtttt  1500

gcgccaacgc gtcccggtcg gccgattgac aacatcgcaa cgcaggatgt cagagacgct  1560

agagagcctt ccagttgtac cgtctcccat gcatgaaaga gatgcatttg ccgcgatgaa  1620

agaacgcggc atgttgcatc ttacattact aaacacggga actgatccga cgatgcgcct  1680
```

```
catagagagg aatcttcgga ttgcgatgga ggaagtcgtg gtcatttcga aactgatcag   1740
caaaatcttg gaggcttgaa gatggcaatt cgcaagcccg cattgtcggt cggcgaagca   1800
cggcggcttg ctggtgctcg acccgagatc caccatccca acccgacact tgttccccag   1860
aagctggacc tccagcactt gcctgaaaaa gccgacgaga aagaccagca acgtgagcct   1920
ctcgtcgccg atcacattta cagtcccgat cgacaactta agctaactgt ggatgccctt   1980
agtccacctc cgtccccgaa aaagctccag gtttttcttt cagcgcgacc gcccgcgcct   2040
caagtgtcga aaacatatga caacctcgtt cggcaataca gtccctcgaa gtcgctacaa   2100
atgattttaa ggcgcgcgtt ggacgatttc gaaagcatgc tggcagatgg atcatttcgc   2160
gtggccccga aaagttatcc gatcccttca actacagaaa aatccgttct cgttcagacc   2220
tcacgcatgt tcccggttgc gttgctcgag gtcgctcgaa gtcattttga tccgttgggg   2280
ttggagaccg ctcgagcttt cggccacaag ctggctaccg ccgcgctcgc gtcattcttt   2340
gctggagaga agccatcgag caattggtga agagggacct atcggaaccc ctcaccaaat   2400
attgagtgta ggtttgaggc cgctggccgc gtcctcagtc accttttgag ccagataatt   2460
aagagccaaa tgcaattggc tcaggctgcc atcgtccccc cgtgcgaaac ctgcacgtcc   2520
gcgtcaaaga aataaccggc acctcttgct gtttttatca gttgagggct tgacggatcc   2580
gcctcaagtt tgcggcgcag ccgcaaaatg agaacatcta tactcctgtc gtaaacctcc   2640
tcgtcgcgta ctcgactggc aatgagaagt tgctcgcgcg atagaacgtc gcggggtttc   2700
tctaaaaacg cgaggagaag attgaactca cctgccgtaa gtttcacctc accgccagct   2760
tcggacatca agcgacgttg cctgagatta agtgtccagt cagtaaaaca aaaagaccgt   2820
cggtctttgg agcggacaac gttggggcgc acgcgcaagg caacccgaat gcgtgcaaga   2880
aactctctcg tactaaacgg cttagcgata aaatcacttg ctcctagctc gagtgcaaca   2940
actttatccg tctcctcaag gcggtcgcca ctgataatta tgattggaat atcagacttt   3000
gccgccagat ttcgaacgat ctcaagccca tcttcacgac ctaaatttag atcaacaacc   3060
acgacatcga ccgtcgcgga agagagtact ctagtgaact gggtgctgtc ggctaccgcg   3120
gtcactttga aggcgtggat cgtaaggtat tcgataataa gatgccgcat agcgacatcg   3180
tcatcgataa gaagaacgtg tttcaacggc tcacctttca atctaaaatc tgaacccttg   3240
ttcacagcgc ttgagaaatt ttcacgtgaa ggatgtacaa tcatctccag ctaaatgggc   3300
agttcgtcag aattgcggct gaccgcggat gacgaaaatg cgaaccaagt atttcaattt   3360
tatgacaaaa gttctcaatc gttgttacaa gtgaaacgct tcgaggttac agctactatt   3420
gattaaggag atcgcctatg gtctcgcccc ggcgtcgtgc gtccgccgcg agccagatct   3480
cgcctacttc ataaacgtcc tcataggcac ggaatggaat gatgacatcg atcgccgtag   3540
agagcatgtc aatcagtgtg cgatcttcca agctagcacc ttgggcgcta cttttgacaa   3600
gggaaaacag tttcttgaat ccttggattg gattcgcgcc gtgtattgtt gaaatcgatc   3660
ccggatgtcc cgagacgact tcactcagat aagcccatgc tgcatcgtcg cgcatctcgc   3720
caagcaatat ccggtccggc cgcatacgca gacttgcttg gagcaagtgc tcggcgctca   3780
cagcacccag cccagcaccg ttcttggagt agagtagtct aacatgatta tcgtgtggaa   3840
tgacgagttc gagcgtatct tctatggtga ttagcctttc ctgggggggg atggcgctga   3900
tcaaggtctt gctcattgtt gtcttgccgc ttccggtagg gccacatagc aacatcgtca   3960
gtcggctgac gacgcatgcg tgcagaaacg cttccaaatc cccgttgtca aaatgctgaa   4020
ggatagcttc atcatcctga ttttggcgtt tccttcgtgt ctgccactgg ttccacctcg   4080
```

```
aagcatcata acgggaggag acttctttaa gaccagaaac acgcgagctt ggccgtcgaa   4140
tggtcaagct gacggtgccc gagggaacgg tcggcggcag acagatttgt agtcgttcac   4200
caccaggaag ttcagtggcg cagagggggt tacgtggtcc gacatcctgc tttctcagcg   4260
cgcccgctaa aatagcgata tcttcaagat catcataaga gacgggcaaa ggcatcttgg   4320
taaaaatgcc ggcttggcgc acaaatgcct ctccaggtcg attgatcgca atttcttcag   4380
tcttcgggtc atcgagccat tccaaaatcg gcttcagaag aaagcgtagt tgcggatcca   4440
cttccattta caatgtatcc tatctctaag cggaaatttg aattcattaa gagcggcggt   4500
tcctcccccg cgtggcgccg ccagtcaggc ggagctggta aacaccaaag aaatcgaggt   4560
cccgtgctac gaaaatggaa acggtgtcac cctgattctt cttcagggtt ggcggtatgt   4620
tgatggttgc cttaagggct gtctcagttg tctgctcacc gttattttga aagctgttga   4680
agctcatccc gccacccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacacttta catagcctgc caaatttgtg tcgattgcgg   5040
tttgcaagat gcacggaatt attgtccctt gcgttaccat aaaatcgggg tgcggcaaga   5100
gcgtggcgct gctgggctgc agctcggtgg gtttcatacg tatcgacaaa tcgttctcgc   5160
cggacacttc gccattcggc aaggagttgt cgtcacgctt gccttcttgt cttcggcccg   5220
tgtcgccctg aatggcgcgt ttgctgaccc cttgatcgcc gctgctatat gcaaaaatcg   5280
gtgtttcttc cggccgtggc tcatgccgct ccggttcgcc cctcggcggt agaggagcag   5340
caggctgaac agcctcttga accgctggag gatccggcgg cacctcaatc ggagctggat   5400
gaaatggctt ggtgtttgtt gcgatcaaag ttgacggcga tgcgttctca ttcaccttct   5460
tttggcgccc acctagccaa atgaggctta atgataacgc gagaacgaca cctccgacga   5520
tcaatttctg agaccccgaa agacgccggc gatgtttgtc ggagaccagg gatccagatg   5580
catcaacctc atgtgccgct tgctgactat cgttattcat cccttcgccc ccttcaggac   5640
gcgtttcaca tcgggcctca ccgtgcccgt ttgcggcctt tggccaacgg gatcgtaagc   5700
ggtgttccag atacatagta ctgtgtggcc atccctcaga cgccaacctc gggaaaccga   5760
agaaatctcg acatcgctcc ctttaactga atagttggca acagcttcct tgccatcagg   5820
attgatggtg tagatggagg gtatgcgtac attgcccgga aagtggaata ccgtcgtaaa   5880
tccattgtcg aagacttcga gtggcaacag cgaacgatcg ccttgggcga cgtagtgcca   5940
attactgtcc gccgcaccaa gggctgtgac aggctgatcc aataaattct cagctttccg   6000
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
```

```
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcacctttt cgtagcgaac tgtcgcggtc cacgtactca ccacaggcat tttgccgtca   6660
acgacgaggg tccttttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
cccgtcatag cgtccacccg aattgccgag ctgaagatct gacggagtag gctgccatcg   7260
ccccacattc agcgggaaga tcgggccttt gcagctcgct aatgtgtcgt ttgtctggca   7320
gccgctcaaa gcgacaacta ggcacagcag gcaatacttc atagaattct ccattgaggc   7380
gaatttttgc gcgacctagc ctcgctcaac ctgagcgaag cgacggtaca agctgctggc   7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaaatat atccgacgag   7740
gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tcttttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatg ttggataaaa tgagctcgca   8340
ttcggcgagg atgcgggcgg atgaacaaat cgcccagcct taggggaggg caccaaagat   8400
gacagcggtc ttttgatgct ccttgcgttg agcggccgcc tcttccgcct cgtgaaggcc   8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
ggaaagctga gcagacgtat cagcattcgc cgtcaagcgt ttgtccatcg tttccagatt   8640
gtcagccgca atgccagcgc tgtttgcgga accggtgatc tgcgatcgca acaggtccgc   8700
ttcagcatca ctacccacga ctgcacgatc tgtatcgctg gtgatcgcac gtgccgtggt   8760
cgacattggc attcgcggcg aaaacatttc attgtctagg tccttcgtcg aaggatactg   8820
atttttctgg ttgagcgaag tcagtagtcc agtaacgccg taggccgacg tcaacatcgt   8880
```

```
aaccatcgct atagtctgag tgagattctc cgcagtcgcg agcgcagtcg cgagcgtctc   8940
agcctccgtt gccgggtcgc taacaacaaa ctgcgcccgc gcgggctgaa tatatagaaa   9000
gctgcaggtc aaaactgttg caataagttg cgtcgtcttc atcgtttcct accttatcaa   9060
tcttctgcct cgtggtgacg ggccatgaat tcgctgagcc agccagatga gttgccttct   9120
tgtgcctcgc gtagtcgagt tgcaaagcgc accgtgttgg cacgccccga aagcacggcg   9180
acatattcac gcatatcccg cagatcaaat tcgcagatga cgcttccact ttctcgttta   9240
agaagaaact tacggctgcc gaccgtcatg tcttcacgga tcgcctgaaa ttccttttcg   9300
gtacatttca gtccatcgac ataagccgat cgatctgcgg ttggtgatgg atagaaaatc   9360
ttcgtcatac attgcgcaac caagctggct cctagcggcg attccagaac atgctctggt   9420
tgctgcgttg ccagtattag catcccgttg tttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
catacttcct cgtattcgag aagatgcgtc atgtcgaagc cggtaatcga cggatctaac   9660
tttacttcgt caacttcgcc gtcaaatgcc cagccaagcg catggccccg gcaccagcgt   9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680
cgtgtttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttccctttt tccgcttagc ttggtgaacc tcctctttac cttccctaaa  11040
gccgcctgtg ggtagacaat caacgtaagg aagtgttcat tgcggaggag ttggccggag  11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
```

-continued tcctcaagct cgaatgcaac gccatcaatt ctcgcaatgg tcatgatcga tccgtcttca 11340
agaaggacga tatggtcgct gaggtggcca atataaggga gatagatctc accggatctt 11400
tcggtcgttc cactcgcgcc gagcatcaca ccattcctct ccctcgtggg ggaaccctaa 11460
ttggatttgg gctaacagta gcgccccccc aaactgcact atcaatgctt cttcccgcgg 11520
tccgcaaaaa tagcaggacg acgctcgccg cattgtagtc tcgctccacg atgagccggg 11580
ctgcaaacca taacggcacg agaacgactt cgtagagcgg gttctgaacg ataacgatga 11640
caaagccggc gaacatcatg aataaccctg ccaatgtcag tggcacccca agaaacaatg 11700
cgggccgtgt ggctgcgagg taaagggtcg attcttccaa acgatcagcc atcaactacc 11760
gccagtgagc gtttggccga ggaagctcgc cccaaacatg ataacaatgc cgccgacgac 11820
gccggcaacc agcccaagcg aagcccgccc gaacatccag gagatcccga tagcgacaat 11880
gccgagaaca gcgagtgact ggccgaacgg accaaggata aacgtgcata tattgttaac 11940
cattgtggcg gggtcagtgc cgccacccgc agattgcgct gcggcgggtc cggatgagga 12000
aatgctccat gcaattgcac cgcacaagct tggggcgcag ctcgatatca cgcgcatcat 12060
cgcattcgag agcgagaggc gatttagatg taaacggtat ctctcaaagc atcgcatcaa 12120
tgcgcacctc cttagtataa gtcgaataag acttgattgt cgtctgcgga tttgccgttg 12180
tcctggtgtg gcggtggcgg agcgattaaa ccgccagcgc catcctcctg cgagcggcgc 12240
tgatatgacc cccaaacatc ccacgtctct tcggatttta gcgcctcgtg atcgtctttt 12300
ggaggctcga ttaacgcggg caccagcgat tgagcagctg tttcaacttt tcgcacgtag 12360
ccgtttgcaa aaccgccgat gaaattaccg gtgttgtaag cggagatcgc ccgacgaagc 12420
gcaaattgct tctcgtcaat cgtttcgccg cctgcataac gacttttcag catgtttgca 12480
gcggcagata atgatgtgca cgcctggagc gcaccgtcag gtgtcagacc gagcatagaa 12540
aaatttcgag agtttatttg catgaggcca acatccagcg aatgccgtgc atcgagacgg 12600
tgcctgacga cttgggttgc ttggctgtga tcttgccagt gaagcgtttc gccggtcgtg 12660
ttgtcatgaa tcgctaaagg atcaaagcga ctctccacct tagctatcgc cgcaagcgta 12720
gatgtcgcaa ctgatggggc acacttgcga gcaacatggt caaactcagc agatgagagt 12780
ggcgtggcaa ggctcgacga acagaaggag accatcaagg caagagaaag cgaccccgat 12840
ctcttaagca taccttatct ccttagctcg caactaacac cgcctctccc gttggaagaa 12900
gtgcgttgtt ttatgttgaa gattatcggg agggtcggtt actcgaaaat tttcaattgc 12960
ttctttatga tttcaattga agcgagaaac ctcgcccggc gtcttggaac gcaacatgga 13020
ccgagaaccg cgcatccatg actaagcaac cggatcgacc tattcaggcc gcagttggtc 13080
aggtcaggct cagaacgaaa atgctcggcg aggttacgct gtctgtaaac ccattcgatg 13140
aacgggaagc ttccttccga ttgctcttgg caggaatatt ggcccatgcc tgcttgcgct 13200
ttgcaaatgc tcttatcgcg ttggtatcat atgccttgtc cgccagcaga aacgcactct 13260
aagcgattat ttgtaaaaat gtttcggtca tgcggcggtc atgggcttga cccgctgtca 13320
gcgcaagacg gatcggtcaa ccgtcggcat cgacaacagc gtgaatcttg gtggtcaaac 13380
cgccacggga acgtcccata cagccatcgt cttgatcccg ctgtttcccg tcgccgcatg 13440
ttggtggacg cggacacagg aactgtcaat catgacgaca ttctatcgaa agccttggaa 13500
atcacactca gaatatgatc ccagacgtct gcctcacgcc atcgtacaaa gcgattgtag 13560
caggttgtac aggaaccgta tcgatcagga acgtctgccc agggcgggcc cgtccggaag 13620
cgccacaaga tgacattgat cacccgcgtc aacgcgcggc acgcgacgcg gcttatttgg 13680

-continued

```
gaacaaagga ctgaacaaca gtccattcga aatcggtgac atcaaagcgg ggacgggtta  13740
tcagtggcct ccaagtcaag cctcaatgaa tcaaaatcag accgatttgc aaacctgatt  13800
tatgagtgtg cggcctaaat gatgaaatcg tccttctaga tcgcctccgt ggtgtagcaa  13860
cacctcgcag tatcgccgtg ctgaccttgg ccagggaatt gactggcaag ggtgctttca  13920
catgaccgct cttttggccg cgatagatga tttcgttgct gctttgggca cgtagaagga  13980
gagaagtcat atcggagaaa ttcctcctgg cgcgagagcc tgctctatcg cgacggcatc  14040
ccactgtcgg gaacagaccg gatcattcac gaggcgaaag tcgtcaacac atgcgttata  14100
ggcatcttcc cttgaaggat gatcttgttg ctgccaatct ggaggtgcgg cagccgcagg  14160
cagatgcgat ctcagcgcaa cttgcggcaa aacatctcac tcacctgaaa accactagcg  14220
agtctcgcga tcagacgaag gccttttact taacgacaca atatccgatg tctgcatcac  14280
aggcgtcgct atcccagtca atactaaagc ggtgcaggaa ctaaagatta ctgatgactt  14340
aggcgtgcca cgaggcctga gacgacgcgc gtagacagtt ttttgaaatc attatcaaag  14400
tgatggcctc cgctgaagcc tatcacctct gcgccggtct gtcggagaga tgggcaagca  14460
ttattacggt cttcgcgccc gtacatgcat tggacgattg cagggtcaat ggatctgaga  14520
tcatccagag gattgccgcc cttaccttcc gtttcgagtt ggagccagcc cctaaatgag  14580
acgacatagt cgacttgatg tgacaatgcc aagagagaga tttgcttaac ccgatttttt  14640
tgctcaagcg taagcctatt gaagcttgcc ggcatgacgt ccgcgccgaa agaatatcct  14700
acaagtaaaa cattctgcac accgaaatgc ttggtgtaga catcgattat gtgaccaaga  14760
tccttagcag tttcgcttgg ggaccgctcc gaccagaaat accgaagtga actgacgcca  14820
atgacaggaa tcccttccgt ctgcagatag gtaccatcga tagatctgct gcctcgcgcg  14880
tttcggtgat gacggtgaaa acctctgaca catgcagctc ccggagacgg tcacagcttg  14940
tctgtaagcg gatgccggga gcagacaagc ccgtcagggc gcgtcagcgg gtgttggcgg  15000
gtgtcggggc gcagccatga cccagtcacg tagcgatagc ggagtgtata ctggcttaac  15060
tatgcggcat cagagcagat tgtactgaga gtgcaccata tgcggtgtga aataccgcac  15120
agatgcgtaa ggagaaaata ccgcatcagg cgctcttccg cttcctcgct cactgactcg  15180
ctgcgctcgg tcgttcggct gcggcgagcg gtatcagctc actcaaaggc ggtaatacgg  15240
ttatccacag aatcagggga taacgcagga aagaacatgt gagcaaaagg ccagcaaaag  15300
gccaggaacc gtaaaaaggc cgcgttgctg gcgtttttcc ataggctccg cccccctgac  15360
gagcatcaca aaaatcgacg ctcaagtcag aggtggcgaa acccgacagg actataaaga  15420
taccaggcgt ttccccctgg aagctccctc gtgcgctctc ctgttccgac cctgccgctt  15480
accggatacc tgtccgcctt tctcccttcg ggaagcgtgg cgctttctca tagctcacgc  15540
tgtaggtatc tcagttcggt gtaggtcgtt cgctccaagc tgggctgtgt gcacgaaccc  15600
cccgttcagc ccgaccgctg cgccttatcc ggtaactatc gtcttgagtc caacccggta  15660
agacacgact tatcgccact ggcagcagcc actggtaaca ggattagcag agcgaggtat  15720
gtaggcggtg ctacagagtt cttgaagtgg tggcctaact acggctacac tagaaggaca  15780
gtatttggta tctgcgctct gctgaagcca gttaccttcg gaaaaagagt tggtagctct  15840
tgatccggca aacaaaccac cgctggtagc ggtggttttt ttgtttgcaa gcagcagatt  15900
acgcgcagaa aaaaaggatc tcaagaagat cctttgatct tttctacggg gtctgacgct  15960
cagtggaacg aaaactcacg ttaagggatt ttggtcatga gattatcaaa aaggatcttc  16020
acctagatcc ttttaaatta aaaatgaagt tttaaatcaa tctaaagtat atatgagtaa  16080
```

acttggtctg acagttacca atgcttaatc agtgaggcac ctatctcagc gatctgtcta 16140
tttcgttcat ccatagttgc ctgactcccc gtcgtgtaga taactacgat acgggagggc 16200
ttaccatctg gccccagtgc tgcaatgata ccgcgagacc cacgctcacc ggctccagat 16260
ttatcagcaa taaaccagcc agccggaagg gccgagcgca gaagtggtcc tgcaacttta 16320
tccgcctcca tccagtctat taattgttgc cgggaagcta gagtaagtag ttcgccagtt 16380
aatagtttgc gcaacgttgt tgccattgct gcaggggggg gggggggggg gttccattgt 16440
tcattccacg gacaaaaaca gagaaaggaa acgacagagg ccaaaaagct cgctttcagc 16500
acctgtcgtt tcctttcttt tcagagggta ttttaaataa aaacattaag ttatgacgaa 16560
gaagaacgga aacgccttaa accggaaaat tttcataaat agcgaaaacc cgcgaggtcg 16620
ccgccccgta acctgtcgga tcaccggaaa ggacccgtaa agtgataatg attatcatct 16680
acatatcaca acgtgcgtgg aggccatcaa accacgtcaa ataatcaatt atgacgcagg 16740
tatcgtatta attgatctgc atcaacttaa cgtaaaaaca acttcagaca atacaaatca 16800
gcgacactga atacggggca acctcatgtc cccccccccc ccccccctgc aggcatcgtg 16860
gtgtcacgct cgtcgtttgg tatggcttca ttcagctccg gttcccaacg atcaaggcga 16920
gttacatgat cccccatgtt gtgcaaaaaa gcggttagct ccttcggtcc tccgatcgtt 16980
gtcagaagta agttggccgc agtgttatca ctcatggtta tggcagcact gcataattct 17040
cttactgtca tgccatccgt aagatgcttt tctgtgactg gtgagtactc aaccaagtca 17100
ttctgagaat agtgtatgcg gcgaccgagt tgctcttgcc cggcgtcaac acgggataat 17160
accgcgccac atagcagaac tttaaaagtg ctcatcattg gaaaacgttc ttcggggcga 17220
aaactctcaa ggatcttacc gctgttgaga tccagttcga tgtaacccac tcgtgcaccc 17280
aactgatctt cagcatcttt tactttcacc agcgtttctg ggtgagcaaa aacaggaagg 17340
caaaatgccg caaaaaaggg aataagggcg acacggaaat gttgaatact catactcttc 17400
ctttttcaat attattgaag catttatcag ggttattgtc tcatgagcgg atacatattt 17460
gaatgtattt agaaaaataa acaaataggg gttccgcgca catttccccg aaaagtgcca 17520
cctgacgtct aagaaaccat tattatcatg acattaacct ataaaaatag gcgtatcacg 17580
aggccctttc gtcttcaaga attcggagct tttgccattc tcaccggatt cagtcgtcac 17640
tcatggtgat ttctcacttg ataaccttat ttttgacgag gggaaattaa taggttgtat 17700
tgatgttgga cgagtcggaa tcgcagaccg ataccaggat cttgccatcc tatggaactg 17760
cctcggtgag ttttctcctt cattacagaa acggcttttt caaaaatatg gtattgataa 17820
tcctgatatg aataaattgc agtttcattt gatgctcgat gagtttttct aatcagaatt 17880
ggttaattgg ttgtaacact ggcagagcat tacgctgact tgacgggacg gcggctttgt 17940
tgaataaatc gaacttttgc tgagttgaag gatcagatca cgcatcttcc cgacaacgca 18000
gaccgttccg tggcaaagca aaagttcaaa atcaccaact ggtccaccta caacaaagct 18060
ctcatcaacc gtggctccct cactttctgg ctggatgatg gggcgattca ggcctggtat 18120
gagtcagcaa caccttcttc acgaggcaga cctcagcgcc agaaggccgc cagagaggcc 18180
gagcgcggcc gtgaggcttg gacgctaggg cagggcatga aaaagcccgt agcgggctgc 18240
tacgggcgtc tgacgcggtg gaaaggggga ggggatgttg tctacatggc tctgctgtag 18300
tgagtgggtt gcgctccggc agcggtcctg atcaatcgtc accctttctc ggtccttcaa 18360
cgttcctgac aacgagcctc cttttcgcca atccatcgac aatcaccgcg agtccctgct 18420
cgaacgctgc gtccggaccg gcttcgtcga aggcgtctat cgcggcccgc aacagcggcg 18480

```
agagcggagc ctgttcaacg gtgccgccgc gctcgccggc atcgctgtcg ccggcctgct  18540
cctcaagcac ggccccaaca gtgaagtagc tgattgtcat cagcgcattg acggcgtccc  18600
cggccgaaaa acccgcctcg cagaggaagc gaagctgcgc gtcggccgtt tccatctgcg  18660
gtgcgcccgg tcgcgtgccg gcatggatgc gcgcgccatc gcggtaggcg agcagcgcct  18720
gcctgaagct gcgggcattc ccgatcagaa atgagcgcca gtcgtcgtcg gctctcggca  18780
ccgaatgcgt atgattctcc gccagcatgg cttcggccag tgcgtcgagc agcgcccgct  18840
tgttcctgaa gtgccagtaa agcgccggct gctgaacccc caaccgttcc gccagtttgc  18900
gtgtcgtcag accgtctacg ccgacctcgt tcaacaggtc cagggcggca cggatcactg  18960
tattcggctg caactttgtc atgcttgaca ctttatcact gataaacata atatgtccac  19020
caacttatca gtgataaaga atccgcgcgt tcaatcggac cagcggaggc tggtccggag  19080
gccagacgtg aaacccaaca taccccctgat cgtaattctg agcactgtcg cgctcgacgc  19140
tgtcggcatc ggcctgatta tgccggtgct gccgggcctc ctgcgcgatc tggttcactc  19200
gaacgacgtc accgcccact atggcattct gctggcgctg tatgcgttgg tgcaatttgc  19260
ctgcgcacct gtgctgggcg cgctgtcgga tcgtttcggg cggcggccaa tcttgctcgt  19320
ctcgctggcc ggcgccactg tcgactacgc catcatggcg acagcgcctt tcctttgggt  19380
tctctatatc gggcggatcg tggccggcat caccggggcg actggggcgg tagccggcgc  19440
ttatattgcc gatatcactg atggcgatga gcgcgcgcgg cacttcggct tcatgagcgc  19500
ctgtttcggg ttcgggatgg tcgcgggacc tgtgctcggt gggctgatgg gcggtttctc  19560
cccccacgct ccgttcttcg ccgcggcagc cttgaacggc ctcaatttcc tgacgggctg  19620
tttccttttg ccggagtcgc acaaaggcga acgccggccg ttacgccggg aggctctcaa  19680
cccgctcgct tcgttccggt gggcccgggg catgaccgtc gtcgccgccc tgatggcggt  19740
cttcttcatc atgcaacttg tcggacaggt gccggccgcg ctttgggtca ttttcggcga  19800
ggatcgcttt cactgggacg cgaccacgat cggcatttcg cttgccgcat ttggcattct  19860
gcattcactc gcccaggcaa tgatcaccgg ccctgtagcc gcccggctcg gcgaaaggcg  19920
ggcactcatg ctcggaatga ttgccgacgg cacaggctac atcctgcttg ccttcgcgac  19980
acggggatgg atggcgttcc cgatcatggt cctgcttgct tcgggtggca tcggaatgcc  20040
ggcgctgcaa gcaatgttgt ccaggcaggt ggatgaggaa cgtcaggggc agctgcaagg  20100
ctcactggcg gcgctcacca gcctgacctc gatcgtcgga cccctcctct tcacggcgat  20160
ctatgcggct tctataacaa cgtggaacgg gtgggcatgg attgcaggcg ctgccctcta  20220
cttgctctgc ctgccggcgc tgcgtcgcgg gctttggagc ggcgcagggc aacgagccga  20280
tcgctgatcg tggaaacgat aggcctatgc catgcgggtc aaggcgactt ccggcaagct  20340
atacgcgccc taggagtgcg gttggaacgt tggcccagcc agatactccc gatcacgagc  20400
aggacgccga tgatttgaag cgcactcagc gtctgatcca agaacaacca tcctagcaac  20460
acggcggtcc ccgggctgag aaagcccagt aaggaaacaa ctgtaggttc gagtcgcgag  20520
atcccccgga accaaaggaa gtaggttaaa cccgctccga tcaggccgag ccacgccagg  20580
ccgagaacat tggttcctgt aggcatcggg attggcggat caaacactaa agctactgga  20640
acgagcagaa gtcctccggc cgccagttgc caggcggtaa aggtgagcag aggcacggga  20700
ggttgccact tgcgggtcag cacggttccg aacgccatgg aaaccgcccc cgccaggccc  20760
gctgcgacgc cgacaggatc tagcgctgcg tttggtgtca acaccaacag cgccacgccc  20820
gcagttccgc aaatagcccc caggaccgcc atcaatcgta tcgggctacc tagcagagcg  20880
```

gcagagatga acacgaccat cagcggctgc acagcgccta ccgtcgccgc gaccccgccc 20940
ggcaggcggt agaccgaaat aaacaacaag ctccagaata gcgaaatatt aagtgcgccg 21000
aggatgaaga tgcgcatcca ccagattccc gttggaatct gtcggacgat catcacgagc 21060
aataaacccg ccggcaacgc ccgcagcagc ataccggcga cccctcggcc tcgctgttcg 21120
ggctccacga aaacgccgga cagatgcgcc ttgtgagcgt ccttggggcc gtcctcctgt 21180
ttgaagaccg acagcccaat gatctcgccg tcgatgtagg cgccgaatgc cacggcatct 21240
cgcaaccgtt cagcgaacgc ctccatgggc tttttctcct cgtgctcgta aacggacccg 21300
aacatctctg gagctttctt cagggccgac aatcggatct cgcggaaatc ctgcacgtcg 21360
gccgctccaa gccgtcgaat ctgagcctta atcacaattg tcaattttaa tcctctgttt 21420
atcggcagtt cgtagagcgc gccgtgcgtc ccgagcgata ctgagcgaag caagtgcgtc 21480
gagcagtgcc cgcttgttcc tgaaatgcca gtaaagcgct ggctgctgaa cccccagccg 21540
gaactgaccc cacaaggccc tagcgtttgc aatgcaccag gtcatcattg acccaggcgt 21600
gttccaccag gccgctgcct cgcaactctt cgcaggcttc gccgacctgc tcgcgccact 21660
tcttcacgcg ggtggaatcc gatccgcaca tgaggcggaa ggtttccagc ttgagcgggt 21720
acggctcccg gtgcgagctg aaatagtcga acatccgtcg ggccgtcggc gacagcttgc 21780
ggtacttctc ccatatgaat ttcgtgtagt ggtcgccagc aaacagcacg acgatttcct 21840
cgtcgatcag gacctggcaa cgggacgttt tcttgccacg gtccaggacg cggaagcggt 21900
gcagcagcga caccgattcc aggtgcccaa cgcggtcgga cgtgaagccc atcgccgtcg 21960
cctgtaggcg cgacaggcat tcctcggcct tcgtgtaata ccggccattg atcgaccagc 22020
ccaggtcctg gcaaagctcg tagaacgtga aggtgatcgg ctcgccgata ggggtgcgct 22080
tcgcgtactc caacacctgc tgccacacca gttcgtcatc gtcggcccgc agctcgacgc 22140
cggtgtaggt gatcttcacg tccttgttga cgtggaaaat gaccttgttt tgcagcgcct 22200
cgcgcgggat tttcttgttg cgcgtggtga acagggcaga gcgggccgtg tcgtttggca 22260
tcgctcgcat cgtgtccggc cacggcgcaa tatcgaacaa ggaaagctgc atttccttga 22320
tctgctgctt cgtgtgtttc agcaacgcgg cctgcttggc ctcgctgacc tgttttgcca 22380
ggtcctcgcc ggcggttttt cgcttcttgg tcgtcatagt tcctcgcgtg tcgatggtca 22440
tcgacttcgc caaacctgcc gcctcctgtt cgagacgacg cgaacgctcc acggcggccg 22500
atggcgcggg cagggcaggg ggagccagtt gcacgctgtc gcgctcgatc ttggccgtag 22560
cttgctggac catcgagccg acggactgga aggtttcgcg gggcgcacgc atgacggtgc 22620
ggcttgcgat ggtttcggca tcctcggcgg aaaaccccgc gtcgatcagt tcttgcctgt 22680
atgccttccg gtcaaacgtc cgattcattc accctccttg cgggattgcc ccgactcacg 22740
ccggggcaat gtgcccttat tcctgatttg acccgcctgg tgccttggtg tccagataat 22800
ccaccttatc ggcaatgaag tcggtcccgt agaccgtctg gccgtccttc tcgtacttgg 22860
tattccgaat cttgccctgc acgaatacca gcgacccctt gcccaaatac ttgccgtggg 22920
cctcggcctg agagccaaaa cacttgatgc ggaagaagtc ggtgcgctcc tgcttgtcgc 22980
cggcatcgtt gcgccactct tcattaaccg ctatatcgaa aattgcttgc ggcttgttag 23040
aattgccatg acgtacctcg gtgtcacggg taagattacc gataaactgg aactgattat 23100
ggctcatatc gaaagtctcc ttgagaaagg agactctagt ttagctaaac attggttccg 23160
ctgtcaagaa ctttagcggc taaaattttg cgggccgcga ccaaaggtgc gaggggcggc 23220
ttccgctgtg tacaaccaga tatttttcac caacatcctt cgtctgctcg atgagcgggg 23280
catgacgaaa catgagctgt cggagagggc aggggtttca atttcgtttt tatcagactt 23340
aaccaacggt aaggccaacc cctcgttgaa ggtgatggag gccattgccg acgccctgga 23400
aactccccta cctcttctcc tggagtccac cgaccttgac cgcgaggcac tcgcggagat 23460
tgcgggtcat cctttcaaga gcagcgtgcc gcccggatac gaacgcatca gtgtggtttt 23520
gccgtcacat aaggcgttta tcgtaaagaa atggggcgac gacacccgaa aaaagctgcg 23580
tggaaggctc tgacgccaag ggttagggct tgcacttcct tctttagccg ctaaaacggc 23640
cccttctctg cgggccgtcg gctcgcgcat catatcgaca tcctcaacgg aagccgtgcc 23700
gcgaatggca tcgggcgggt gcgctttgac agttgttttc tatcagaacc cctacgtcgt 23760
gcggttcgat tagctgtttg tcttgcaggc taaacacttt cggtatatcg tttgcctgtg 23820
cgataatgtt gctaatgatt tgttgcgtag gggttactga aaagtgagcg ggaaagaaga 23880
gtttcagacc atcaaggagc gggccaagcg caagctggaa cgcgacatgg gtgcggacct 23940
gttggccgcg ctcaacgacc cgaaaaccgt tgaagtcatg ctcaacgcgg acggcaaggt 24000
gtggcacgaa cgccttggcg agccgatgcg gtacatctgc gacatgcggc ccagccagtc 24060
gcaggcgatt atagaaacgg tggccggatt ccacggcaaa gaggtcacgc ggcattcgcc 24120
catcctggaa ggcgagttcc ccttggatgg cagccgcttt gccggccaat tgccgccggt 24180
cgtggccgcg ccaacctttg cgatccgcaa gcgcgcggtc gccatcttca cgctggaaca 24240
gtacgtcgag gcgggcatca tgacccgcga gcaatacgag gtcattaaaa gcgccgtcgc 24300
ggcgcatcga aacatcctcg tcattggcgg tactggctcg ggcaagacca cgctcgtcaa 24360
cgcgatcatc aatgaaatgg tcgccttcaa cccgtctgag cgcgtcgtca tcatcgagga 24420
caccggcgaa atccagtgcg ccgcagagaa cgccgtccaa taccacacca gcatcgacgt 24480
ctcgatgacg ctgctgctca agacaacgct gcgtatgcgc cccgaccgca tcctggtcgg 24540
tgaggtacgt ggccccgaag cccttgatct gttgatggcc tggaacaccg ggcatgaagg 24600
aggtgccgcc accctgcacg caaacaaccc caaagcgggc ctgagccggc tcgccatgct 24660
tatcagcatg cacccggatt caccgaaacc cattgagccg ctgattggcg aggcggttca 24720
tgtggtcgtc catatcgcca ggacccctag cggccgtcga gtgcaagaaa ttctcgaagt 24780
tcttggttac gagaacggcc agtacatcac caaaaccctg taaggagtat ttccaatgac 24840
aacggctgtt ccgttccgtc tgaccatgaa tcgcggcatt ttgttctacc ttgccgtgtt 24900
cttcgttctc gctctcgcgt tatccgcgca tccggcgatg gcctcggaag gcaccggcgg 24960
cagcttgcca tatgagagct ggctgacgaa cctgcgcaac tccgtaaccg gcccggtggc 25020
cttcgcgctg tccatcatcg gcatcgtcgt cgccggcggc gtgctgatct tcggcggcga 25080
actcaacgcc ttcttccgaa ccctgatctt cctggttctg gtgatggcgc tgctggtcgg 25140
cgcgcagaac gtgatgagca ccttcttcgg tcgtggtgcc gaaatcgcgg ccctcggcaa 25200
cggggcgctg caccaggtgc aagtcgcggc ggcggatgcc gtgcgtgcgg tagcggctgg 25260
acggctcgcc taatcatggc tctgcgcacg atccccatcc gtcgcgcagg caaccgagaa 25320
aacctgttca tgggtggtga tcgtgaactg gtgatgttct cgggcctgat ggcgtttgcg 25380
ctgattttca gcgcccaaga gctgcgggcc accgtggtcg gtctgatcct gtggttcggg 25440
gcgctctatg cgttccgaat catggcgaag gccgatccga agatgcggtt cgtgtacctg 25500
cgtcaccgcc ggtacaagcc gtattacccg gcccgctcga ccccgttccg cgagaacacc 25560
aatagccaag ggaagcaata ccgatgatcc aagcaattgc gattgcaatc gcgggcctcg 25620
gcgcgcttct gttgttcatc ctctttgccc gcatccgcgc ggtcgatgcc gaactgaaac 25680

```
tgaaaaagca tcgttccaag gacgccggcc tggccgatct gctcaactac gccgctgtcg  25740
tcgatgacgg cgtaatcgtg ggcaagaacg gcagctttat ggctgcctgg ctgtacaagg  25800
gcgatgacaa cgcaagcagc accgaccagc agcgcgaagt agtgtccgcc cgcatcaacc  25860
aggccctcgc gggcctggga agtgggtgga tgatccatgt ggacgccgtg cggcgtcctg  25920
ctccgaacta cgcggagcgg ggcctgtcgg cgttccctga ccgtctgacg gcagcgattg  25980
aagaagagcg ctcggtcttg ccttgctcgt cggtgatgta cttcaccagc tccgcgaagt  26040
cgctcttctt gatggagcgc atggggacgt gcttggcaat cacgcgcacc ccccggccgt  26100
tttagcggct aaaaaagtca tggctctgcc ctcgggcgga ccacgcccat catgaccttg  26160
ccaagctcgt cctgcttctc ttcgatcttc gccagcaggg cgaggatcgt ggcatcaccg  26220
aaccgcgccg tgcgcgggtc gtcggtgagc cagagtttca gcaggccgcc caggcggccc  26280
aggtcgccat tgatgcgggc cagctcgcgg acgtgctcat agtccacgac gcccgtgatt  26340
ttgtagccct ggccgacggc cagcaggtag gccgacaggc tcatgccggc cgccgccgcc  26400
ttttcctcaa tcgctcttcg ttcgtctgga aggcagtaca ccttgatagg tgggctgccc  26460
ttcctggttg gcttggtttc atcagccatc cgcttgccct catctgttac gccggcggta  26520
gccggccagc ctcgcagagc aggattcccg ttgagcaccg ccaggtgcga ataagggaca  26580
gtgaagaagg aacacccgct cgcgggtggg cctacttcac ctatcctgcc cggctgacgc  26640
cgttggatac accaaggaaa gtctacacga accctttggc aaaatcctgt atatcgtgcg  26700
aaaaaggatg gatataccga aaaaatcgct ataatgaccc cgaagcaggg ttatgcagcg  26760
gaaaagcgct gcttccctgc tgttttgtgg aatatctacc gactggaaac aggcaaatgc  26820
aggaaattac tgaactgagg ggacaggcga gagacgatgc caaagagcta caccgacgag  26880
ctggccgagt gggttgaatc ccgcgcggcc aagaagcgcc ggcgtgatga ggctgcggtt  26940
gcgttcctgg cggtgagggc ggatgtcgag gcggcgttag cgtccggcta tgcgctcgtc  27000
accatttggg agcacatgcg ggaaacgggg aaggtcaagt tctcctacga gacgttccgc  27060
tcgcacgcca ggcggcacat caaggccaag cccgccgatg tgcccgcacc gcaggccaag  27120
gctgcggaac ccgcgccggc acccaagacg ccggagccac ggcggccgaa gcaggggggc  27180
aaggctgaaa agccggcccc cgctgcggcc ccgaccggct tcaccttcaa cccaacaccg  27240
gacaaaaagg atctactgta atggcgaaaa ttcacatggt tttgcagggc aagggcgggg  27300
tcggcaagtc ggccatcgcc gcgatcattg cgcagtacaa gatggacaag gggcagacac  27360
ccttgtgcat cgacaccgac ccggtgaacg cgacgttcga gggctacaag gccctgaacg  27420
tccgccggct gaacatcatg gccggcgacg aaattaactc gcgcaacttc gacaccctgg  27480
tcgagctgat tgcgccgacc aaggatgacg tggtgatcga caacggtgcc agctcgttcg  27540
tgcctctgtc gcattacctc atcagcaacc aggtgccggc tctgctgcaa gaaatggggc  27600
atgagctggt catccatacc gtcgtcaccg gcggccaggc tctcctggac acggtgagcg  27660
gcttcgccca gctcgccagc cagttcccgg ccgaagcgct tttcgtggtc tggctgaacc  27720
cgtattgggg gcctatcgag catgagggca agagctttga gcagatgaag gcgtacacgg  27780
ccaacaaggc ccgcgtgtcg tccatcatcc agattccggc cctcaaggaa gaaacctacg  27840
gccgcgattt cagcgacatg ctgcaagagc ggctgacgtt cgaccaggcg ctggccgatg  27900
aatcgctcac gatcatgacg cggcaacgcc tcaagatcgt gcggcgcggc ctgtttgaac  27960
agctcgacgc ggcggccgtg ctatgagcga ccagattgaa gagctgatcc gggagattgc  28020
ggccaagcac ggcatcgccg tcggccgcga cgacccggtg ctgatcctgc ataccatcaa  28080
```

-continued

```
cgcccggctc atggccgaca gtgcggccaa gcaagaggaa atccttgccg cgttcaagga  28140
agagctggaa gggatcgccc atcgttgggg cgaggacgcc aaggccaaag cggagcggat  28200
gctgaacgcg gccctggcgg ccagcaagga cgcaatggcg aaggtaatga aggacagcgc  28260
cgcgcaggcg gccgaagcga tccgcaggga aatcgacgac ggccttggcc gccagctcgc  28320
ggccaaggtc gcggacgcgc ggcgcgtggc gatgatgaac atgatcgccg gcggcatggt  28380
gttgttcgcg gccgccctgg tggtgtgggc ctcgttatga atcgcagagg cgcagatgaa  28440
aaagcccggc gttgccgggc tttgtttttg cgttagctgg gcttgtttga caggcccaag  28500
ctctgactgc gcccgcgctc gcgctcctgg gcctgtttct tctcctgctc ctgcttgcgc  28560
atcagggcct ggtgccgtcg ggctgcttca cgcatcgaat cccagtcgcc ggccagctcg  28620
ggatgctccg cgcgcatctt gcgcgtcgcc agttcctcga tcttgggcgc gtgaatgccc  28680
atgccttcct tgatttcgcg caccatgtcc agccgcgtgt gcagggtctg caagcgggct  28740
tgctgttggg cctgctgctg ctgccaggcg gcctttgtac gcggcaggga cagcaagccg  28800
ggggcattgg actgtagctg ctgcaaacgc gcctgctgac ggtctacgag ctgttctagg  28860
cggtcctcga tgcgctccac ctggtcatgc tttgcctgca cgtagagcgc aagggtctgc  28920
tggtaggtct gctcgatggg cgcggattct aagagggcct gctgttccgt ctcggcctcc  28980
tgggccgcct gtagcaaatc ctcgccgctg ttgccgctgg actgctttac tgccggggac  29040
tgctgttgcc ctgctcgcgc cgtcgtcgca gttcggcttg cccccactcg attgactgct  29100
tcatttcgag ccgcagcgat gcgatctcgg attgcgtcaa cggacggggc agcgcggagg  29160
tgtccggctt ctccttgggt gagtcggtcg atgccatagc caaaggtttc cttccaaaat  29220
gcgtccattg ctggaccgtg tttctcattg atgcccgcaa gcatcttcgg cttgaccgcc  29280
aggtcaagcg cgccttcatg ggcggtcatg acggacgccg ccatgacctt gccgccgttg  29340
ttctcgatgt agccgcgtaa tgaggcaatg gtgccgccca tcgtcagcgt gtcatcgaca  29400
acgatgtact tctggccggg gatcacctcc ccctcgaaag tcgggttgaa cgccaggcga  29460
tgatctgaac cggctccggt tcgggcgacc ttctcccgct gcacaatgtc cgtttcgacc  29520
tcaaggccaa ggcggtcggc cagaacgacc gccatcatgg ccggaatctt gttgttcccc  29580
gccgcctcga cggcgaggac tggaacgatg cggggcttgt cgtcgccgat cagcgtcttg  29640
agctgggcaa cagtgtcgtc cgaaatcagg cgctcgacca aattaagcgc cgcttccgcg  29700
tcgccctgct tcgcagcctg gtattcaggc tcgttggtca aagaaccaag gtcgccgttg  29760
cgaaccacct tcgggaagtc tccccacggt gcgcgctcgg ctctgctgta gctgctcaag  29820
acgcctccct ttttagccgc taaaactcta acgagtgcgc ccgcgactca acttgacgct  29880
ttcggcactt acctgtgcct tgccacttgc gtcataggtg atgcttttcg cactcccgat  29940
ttcaggtact ttatcgaaat ctgaccgggc gtgcattaca aagttcttcc ccacctgttg  30000
gtaaatgctg ccgctatctg cgtggacgat gctgccgtcg tggcgctgcg acttatcggc  30060
cttttgggcc atatagatgt tgtaaatgcc aggtttcagg gccccggctt tatctacctt  30120
ctggttcgtc catgcgcctt ggttctcggt ctggacaatt ctttgcccat tcatgaccag  30180
gaggcggtgt ttcattgggt gactcctgac ggttgcctct ggtgttaaac gtgtcctggt  30240
cgcttgccgg ctaaaaaaaa gccgacctcg gcagttcgag gccggctttc cctagagccg  30300
ggcgcgtcaa ggttgttcca tctattttag tgaactgcgt tcgatttatc agttactttc  30360
ctcccgcttt gtgtttcctc ccactcgttt ccgcgtctag ccgacccctc aacatagcgg  30420
cctcttcttg ggctgccttt gcctcttgcc gcgcttcgtc acgctcggct tgcaccgtcg  30480
```

taaagcgctc ggcctgcctg gccgcctctt gcgccgccaa cttcctttgc tcctggtggg 30540
cctcggcgtc ggcctgcgcc ttcgctttca ccgctgccaa ctccgtgcgc aaactctccg 30600
cttcgcgcct ggtggcgtcg cgctcgccgc gaagcgcctg catttcctgg ttggccgcgt 30660
ccagggtctt gcggctctct tctttgaatg cgcgggcgtc ctggtgagcg tagtccagct 30720
cggcgcgcag ctcctgcgct cgacgctcca cctcgtcggc ccgctgcgtc gccagcgcgg 30780
cccgctgctc ggctcctgcc agggcggtgc gtgcttcggc cagggcttgc cgctggcgtg 30840
cggccagctc ggccgcctcg gcggcctgct gctctagcaa tgtaacgcgc gcctgggctt 30900
cttccagctc gcgggcctgc gcctcgaagg cgtcggccag ctccccgcgc acggcttcca 30960
actcgttgcg ctcacgatcc cagccggctt gcgctgcctg caacgattca ttggcaaggg 31020
cctgggcggc ttgccagagg gcggccacgg cctggttgcc ggcctgctgc accgcgtccg 31080
gcacctggac tgccagcggg gcggcctgcg ccgtgcgctg gcgtcgccat tcgcgcatgc 31140
cggcgctggc gtcgttcatg ttgacgcggg cggccttacg cactgcatcc acggtcggga 31200
agttctcccg gtcgccttgc tcgaacagct cgtccgcagc cgcaaaaatg cggtcgcgcg 31260
tctctttgtt cagttccatg ttggctccgg taattggtaa gaataataat actcttacct 31320
accttatcag cgcaagagtt tagctgaaca gttctcgact taacggcagg ttttttagcg 31380
gctgaagggc aggcaaaaaa agccccgcac ggtcggcggg ggcaaagggt cagcgggaag 31440
gggattagcg ggcgtcgggc ttcttcatgc gtcggggccg cgcttcttgg gatggagcac 31500
gacgaagcgc gcacgcgcat cgtcctcggc cctatcggcc cgcgtcgcgg tcaggaactt 31560
gtcgcgcgct aggtcctccc tggtgggcac caggggcatg aactcggcct gctcgatgta 31620
ggtccactcc atgaccgcat cgcagtcgag gccgcgttcc ttcaccgtct cttgcaggtc 31680
gcggtacgcc cgctcgttga gcggctggta acgggccaat tggtcgtaaa tggctgtcgg 31740
ccatgagcgg cctttcctgt tgagccagca gccgacgacg aagccggcaa tgcaggcccc 31800
tggcacaacc aggccgacgc cgggggcagg ggatggcagc agctcgccaa ccaggaaccc 31860
cgccgcgatg atgccgatgc cggtcaacca gcccttgaaa ctatccggcc ccgaaacacc 31920
cctgcgcatt gcctggatgc tgcgccggat agcttgcaac atcaggagcc gtttcttttg 31980
ttcgtcagtc atggtccgcc ctcaccagtt gttcgtatcg gtgtcggacg aactgaaatc 32040
gcaagagctg ccggtatcgg tccagccgct gtccgtgtcg ctgctgccga agcacggcga 32100
ggggtccgcg aacgccgcag acggcgtatc cggccgcagc gcatcgccca gcatggcccc 32160
ggtcagcgag ccgccggcca ggtagcccag catggtgctg ttggtcgccc cggccaccag 32220
ggccgacgtg acgaaatcgc cgtcattccc tctggattgt tcgctgctcg gcggggcagt 32280
gcgccgcgcc ggcggcgtcg tggatggctc gggttggctg gcctgcgacg gccggcgaaa 32340
ggtgcgcagc agctcgttat cgaccggctg cggcgtcggg gccgccgcct tgcgctgcgg 32400
tcggtgttcc ttcttcggct cgcgcagctt gaacagcatg atcgcggaaa ccagcagcaa 32460
cgccgcgcct acgcctcccg cgatgtagaa cagcatcgga ttcattcttc ggtcctcctt 32520
gtagcggaac cgttgtctgt gcggcgcggg tggcccgcgc cgctgtcttt ggggatcagc 32580
cctcgatgag cgcgaccagt ttcacgtcgg caaggttcgc ctcgaactcc tggccgtcgt 32640
cctcgtactt caaccaggca tagccttccg ccggcggccg acggttgagg ataaggcggg 32700
cagggcgctc gtcgtgctcg acctggacga tggccttttt cagcttgtcc gggtccggct 32760
ccttcgcgcc cttttccttg gcgtccttac cgtcctggtc gccgtcctcg ccgtcctggc 32820
cgtcgccggc ctccgcgtca cgctcggcat cagtctggcc gttgaaggca tcgacggtgt 32880
tgggatcgcg gcccttctcg tccaggaact cgcgcagcag cttgaccgtg ccgcgcgtga 32940
tttcctgggt gtcgtcgtca agccacgcct cgacttcctc cgggcgcttc ttgaaggccg 33000
tcaccagctc gttcaccacg gtcacgtcgc gcacgcggcc ggtgttgaac gcatcggcga 33060
tcttctccgg caggtccagc agcgtgacgt gctgggtgat gaacgccggc gacttgccga 33120
tttccttggc gatatcgcct ttcttcttgc ccttcgccag ctcgcggcca atgaagtcgg 33180
caatttcgcg cggggtcagc tcgttgcgtt gcaggttctc gataacctgg tcggcttcgt 33240
tgtagtcgtt gtcgatgaac gccgggatgg acttcttgcc ggcccacttc gagccacggt 33300
agcggcgggc gccgtgattg atgatatagc ggcccggctg ctcctggttc tcgcgcaccg 33360
aaatgggtga cttcaccccg cgctctttga tcgtggcacc gatttccgcg atgctctccg 33420
gggaaaagcc ggggttgtcg gccgtccgcg gctgatgcgg atcttcgtcg atcaggtcca 33480
ggtccagctc gatagggccg gaaccgccct gagacgccgc aggagcgtcc aggaggctcg 33540
acaggtcgcc gatgctatcc aaccccaggc cggacggctg cgccgcgcct gcggcttcct 33600
gagcggccgc agcggtgttt ttcttggtgg tcttggcttg agccgcagtc attgggaaat 33660
ctccatcttc gtgaacacgt aatcagccag ggcgcgaacc tctttcgatg ccttgcgcgc 33720
ggccgttttc ttgatcttcc agaccggcac accggatgcg agggcatcgg cgatgctgct 33780
gcgcaggcca acggtggccg gaatcatcat cttggggtac gcggccagca gctcggcttg 33840
gtggcgcgcg tggcgcggat tccgcgcatc gaccttgctg ggcaccatgc caaggaattg 33900
cagcttggcg ttcttctggc gcacgttcgc aatggtcgtg accatcttct tgatgccctg 33960
gatgctgtac gcctcaagct cgatggggga cagcacatag tcggccgcga agagggcggc 34020
cgccaggccg acgccaaggg tcggggccgt gtcgatcagg cacacgtcga agccttggtt 34080
cgccagggcc ttgatgttcg ccccgaacag ctcgcgggcg tcgtccagcg acagccgttc 34140
ggcgttcgcc agtaccgggt tggactcgat gagggcgagg cgcgcggcct ggccgtcgcc 34200
ggctgcgggt gcggtttcgg tccagccgcc ggcagggaca gcgccgaaca gcttgcttgc 34260
atgcaggccg gtagcaaagt ccttgagcgt gtaggacgca ttgccctggg ggtccaggtc 34320
gatcacggca acccgcaagc cgcgctcgaa aaagtcgaag gcaagatgca caagggtcga 34380
agtcttgccg acgccgcctt tctggttggc cgtgaccaaa gttttcatcg tttggtttcc 34440
tgtttttttct tggcgtccgc ttcccacttc cggacgatgt acgcctgatg ttccggcaga 34500
accgccgtta cccgcgcgta cccctcgggc aagttcttgt cctcgaacgc ggcccacacg 34560
cgatgcaccg cttgcgacac tgcgcccctg gtcagtccca gcgacgttgc gaacgtcgcc 34620
tgtggcttcc catcgactaa gacgccccgc gctatctcga tggtctgctg ccccacttcc 34680
agcccctgga tcgcctcctg gaactggctt tcggtaagcc gtttcttcat ggataacacc 34740
cataatttgc tccgcgcctt ggttgaacat agcggtgaca gccgccagca catgagagaa 34800
gtttagctaa acatttctcg cacgtcaaca cctttagccg ctaaaactcg tccttggcgt 34860
aacaaaacaa aagcccggaa accgggcttt cgtctcttgc cgcttatggc tctgcacccg 34920
gctccatcac caacaggtcg cgcacgcgct tcactcggtt gcggatcgac actgccagcc 34980
caacaaagcc ggttgccgcc gccgccagga tcgcgccgat gatgccggcc acaccggcca 35040
tcgcccacca ggtcgccgcc ttccggttcc attcctgctg gtactgcttc gcaatgctgg 35100
acctcggctc accataggct gaccgctcga tggcgtatgc cgcttctccc cttggcgtaa 35160
aacccagcgc cgcaggcggc attgccatgc tgcccgccgc tttcccgacc acgacgcgcg 35220
caccaggctt gcggtccaga ccttcggcca cggcgagctg cgcaaggaca taatcagccg 35280
ccgacttggc tccacgcgcc tcgatcagct cttgcactcg cgcgaaatcc ttggcctcca 35340
cggccgccat gaatcgcgca cgcggcgaag gctccgcagg gccggcgtcg tgatcgccgc 35400
cgagaatgcc cttcaccaag ttcgacgaca cgaaaatcat gctgacggct atcaccatca 35460
tgcagacgga tcgcacgaac ccgctgaatt gaacacgagc acggcacccg cgaccactat 35520
gccaagaatg cccaaggtaa aaattgccgg ccccgccatg aagtccgtga atgccccgac 35580
ggccgaagtg aagggcaggc cgccacccag gccgccgccc tcactgcccg gcacctggtc 35640
gctgaatgtc gatgccagca cctgcggcac gtcaatgctt ccgggcgtcg cgctcgggct 35700
gatcgcccat cccgttactg ccccgatccc ggcaatggca aggactgcca gcgctgccat 35760
ttttggggtg aggccgttcg cggccgaggg gcgcagcccc tggggggatg ggaggcccgc 35820
gttagcgggc cgggagggtt cgagaagggg gggcaccccc cttcggcgtg cgcggtcacg 35880
cgcacagggc gcagccctgg ttaaaaacaa ggtttataaa tattggttta aaagcaggtt 35940
aaaagacagg ttagcggtgg ccgaaaaacg ggcggaaacc cttgcaaatg ctggattttc 36000
tgcctgtgga cagcccctca aatgtcaata ggtgcgcccc tcatctgtca gcactctgcc 36060
cctcaagtgt caaggatcgc gcccctcatc tgtcagtagt cgcgcccctc aagtgtcaat 36120
accgcagggc acttatcccc aggcttgtcc acatcatctg tgggaaactc gcgtaaaatc 36180
aggcgttttc gccgatttgc gaggctggcc agctccacgt cgccggccga aatcgagcct 36240
gcccctcatc tgtcaacgcc gcgccgggtg agtcggcccc tcaagtgtca acgtccgccc 36300
ctcatctgtc agtgagggcc aagttttccg cgaggtatcc acaacgccgg cggccgcggt 36360
gtctcgcaca cggcttcgac ggcgtttctg gcgcgtttgc agggccatag acggccgcca 36420
gcccagcggc gagggcaacc agcccggtga gcgtcggaaa ggcgctggaa gccccgtagc 36480
gacgcggaga ggggcgagac aagccaaggg cgcaggctcg atgcgcagca cgacatagcc 36540
ggttctcgca aggacgagaa tttccctgcg gtgcccctca agtgtcaatg aaagtttcca 36600
acgcgagcca ttcgcgagag ccttgagtcc acgctagatg agagctttgt tgtaggtgga 36660
ccagttggtg attttgaact tttgctttgc cacggaacgg tctgcgttgt cgggaagatg 36720
cgtgatctga tccttcaact cagcaaaagt tcgatttatt caacaaagcc acgttgtgtc 36780
tcaaaatctc tgatgttaca ttgcacaaga taaaaatata tcatcatgaa caataaaact 36840
gtctgcttac ataaacagta atacaagggg tgttatgagc catattcaac gggaaacgtc 36900
ttgctcgac 36909

<210> SEQ ID NO 51
<211> LENGTH: 825
<212> TYPE: DNA
<213> ORGANISM: Zea mays

<400> SEQUENCE: 51
aaatccttac agaattgctg tagtttcata gtgctagatg tggacagcaa agcgccgctg 60
tatgcttctg cttttctttt ttggtgtgtg tagccacatc ctttgttcct gcccggcgcc 120
atcccacttg gttgtttttt tttatgattg aaagccttca tgcttcctcg gtcaatcacc 180
ggtgcgcact gggagcatcg ccggaaaaaa aattcttcgg ctaagagtaa cttctttctc 240
cttttcttct ctgatctcgc gagcagtgct gataacgtgt tgtaatctac ttagcggtaa 300
cgagattgag agagacaaaa tgacagaact attgtcttta ttgcagagtg tcatgtattt 360
atacagggga tacaaagtct cccaaggggt gtgtcccttg ggagtaactg ccagttgatc 420
acaggacaat attttgtaac aaaacgtaca catcgtcaaa atagcgaggc atgaaactgg 480
ccttggccat ggacgcgtga agcgcgccat gcgttggata tgtggtcaat aagtatatac 540
aatacaatgt ttaacagagc tgatagtact gctttggcac atttttgtcc acgcttcatg 600
agagataaaa cacctgcacg taaattcaca tgctgcactg aaggcccgat cactgaggag 660
cgaactgccg taactccctt ctatatatac ccccagtccc tgtttcagtt ttcgtcaagc 720
tagcagcacc aagttgtcga tcacttgcct gctcttgagc tcgattaagc tatcatcagc 780
tacagcatcc gatcccaaac tgcaactgta gcagcgacaa ctgcc 825

<210> SEQ ID NO 52
<211> LENGTH: 860
<212> TYPE: DNA
<213> ORGANISM: Zea mays

<400> SEQUENCE: 52
ctggtaatta ttggctgtag gattctaaac agagcctaaa tagctggaat agctctagcc 60
ctcaatccaa actaatgata tctatactta tgcaactcta aatttttatt ctaaaagtaa 120
tatttcattt ttgtcaacga gattctctac tctattccac aatcttttga agcaatattt 180
accttaaatc tgtactctat accaataatc atatattcta ttatttattt ttatctctct 240
cctaaggagc atccccctat gtctgcatgg cccccgcctc gggtcccaat ctcttgctct 300
gctagtagca cagaagaaaa cactagaaat gacttgcttg acttagagta tcagataaac 360
atcatgttta cttaacttta atttgtatcg gtttctacta tttttataat atttttgtct 420
ctatagatac tacgtgcaac agtataatca acctagttta atccagagcg aaggattttt 480
tactaagtac gtgactccat atgcacagcg ttccttttat ggttcctcac tgggcacagc 540
ataaacgaac cctgtccaat gttttcagcg cgaacaaaca gaaattccat cagcgaacaa 600
acaacataca tgcgagatga aaataaataa taaaaaaagc tccgtctcga taggccggca 660
cgaatcgaga gcctccatag ccagtttttt ccatcggaac ggcggttcgc gcacctaatt 720
atatgcacca cacgcctata aagccaacca acccgtcgga ggggcgcaag ccagacagaa 780
gacagcccgt cagcccctct cgtttttcat ccgccttcgc ctccaaccgc gtgcgctcca 840
cgcctcctcc aggaaagcga 860

<210> SEQ ID NO 53
<211> LENGTH: 896
<212> TYPE: DNA
<213> ORGANISM: Zea mays

<400> SEQUENCE: 53
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc ttttttttg 300 caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctt 896

<210> SEQ ID NO 54
<211> LENGTH: 318
<212> TYPE: DNA
<213> ORGANISM: Solanum tuberosum

<400> SEQUENCE: 54
agacttgtcc atcttctgga ttggccaact taattaatgt atgaaataaa aggatgcaca 60
catagtgaca tgctaatcac tataatgtgg gcatcaaagt tgtgtgttat gtgtaattac 120
tagttatctg aataaaagag aaagagatca tccatatttc ttatcctaaa tgaatgtcac 180
gtgtctttat aattctttga tgaaccagat gcatttcatt aaccaaatcc atatacatat 240
aaatattaat catatataat taatatcaat tgggttagca aaacaaatct agtctaggtg 300
tgttttgcga attgcggc 318

<210> SEQ ID NO 55
<211> LENGTH: 4678
<212> TYPE: DNA
<213> ORGANISM: artificial sequence
<220> FEATURE:
<223> OTHER INFORMATION: vector

<400> SEQUENCE: 55
gaaaggccca gtcttccgac tgagcctttc gttttatttg atgcctggca gttccctact 60
ctcgcgttaa cgctagcatg gatgttttcc cagtcacgac gttgtaaaac gacggccagt 120
cttaagctcg ggcccgcgtt aacgctacca tggagctcca aataatgatt ttattttgac 180
tgatagtgac ctgttcgttg caacaaattg ataagcaatg ctttttttata atgccaactt 240 tgtatagaaa agttgggccg aattcgagct cggtacggcc agaatggccc ggaccgggtt 300
accgaattcg agctcggtac cctgggatcc ctggtaatta ttggctgtag gattctaaac 360
agagcctaaa tagctggaat agctctagcc ctcaatccaa actaatgata tctatactta 420
tgcaactcta aatttttatt ctaaaagtaa tatttcattt ttgtcaacga gattctctac 480
tctattccac aatcttttga agcaatattt accttaaatc tgtactctat accaataatc 540
atatattcta ttatttattt ttatctctct cctaaggagc atccccctat gtctgcatgg 600
cccccgcctc gggtcccaat ctcttgctct gctagtagca cagaagaaaa cactagaaat 660
gacttgcttg acttagagta tcagataaac atcatgttta cttaacttta atttgtatcg 720
gtttctacta tttttataat atttttgtct ctatagatac tacgtgcaac agtataatca 780
acctagttta atccagagcg aaggattttt tactaagtac gtgactccat atgcacagcg 840
ttccttttat ggttcctcac tgggcacagc ataaacgaac cctgtccaat gttttcagcg 900
cgaacaaaca gaaattccat cagcgaacaa acaacataca tgcgagatga aaataaataa 960
taaaaaaagc tccgtctcga taggccggca cgaatcgaga gcctccatag ccagtttttt 1020
ccatcggaac ggcggttcgc gcacctaatt atatgcacca cacgcctata aagccaacca 1080
acccgtcgga ggggcgcaag ccagacagaa gacagcccgt cagcccctct cgtttttcat 1140
ccgccttcgc ctccaaccgc gtgcgctcca cgcctcctcc aggaaagcga ggatctcccc 1200
caaatccacc cgtcggcacc tccgcttcaa ggtacgccgc tcgtcctccc cccccccccc 1260

-continued

```
tctctacctt ctctagatcg gcgttccggt ccatggttag ggcccggtag ttctacttct   1320
gttcatgttt gtgttagatc cgtgtttgtg ttagatccgt gctgctagcg ttcgtacacg   1380
gatgcgacct gtacgtcaga cacgttctga ttgctaactt gccagtgttt ctctttgggg   1440
aatcctggga tggctctagc cgttccgcag acgggatcga tttcatgatt ttttttgttt   1500
cgttgcatag ggtttggttt gcccttttcc tttatttcaa tatatgccgt gcacttgttt   1560
gtcgggtcat cttttcatgc ttttttttgt cttggttgtg atgatgtggt ctggttgggc   1620
ggtcgttcta gatcggagta gaattctgtt tcaaactacc tggtggattt attaattttg   1680
gatctgtatg tgtgtgccat acatattcat agttacgaat tgaagatgat ggatggaaat   1740
atcgatctag gataggtata catgttgatg cgggttttac tgatgcatat acagagatgc   1800
tttttgttcg cttggttgtg atgatgtggt gtggttgggc ggtcgttcat tcgttctaga   1860
tcggagtaga atactgtttc aaactacctg gtgtatttat taattttgga actgtatgtg   1920
tgtgtcatac atcttcatag ttacgagttt aagatggatg gaaatatcga tctaggatag   1980
gtatacatgt tgatgtgggt tttactgatg catatacatg atggcatatg cagcatctat   2040
tcatatgctc taaccttgag tacctatcta ttataataaa caagtatgtt ttataattat   2100
tttgatcttg atatacttgg atgatggcat atgcagcagc tatatgtgga tttttttagc   2160
cctgccttca tacgctattt atttgcttgg tactgtttct tttgtcgatg ctcaccctgt   2220
tgtttggtgt tacttctgca ggtcgactct agaagcttgg tcacccggtc cgggcctaga   2280
aggccagctt caagtttgta caaaaaagtt gaacgagaaa cgtaaaatga tataaatatc   2340
aatatattaa attagatttt gcataaaaaa cagactacat aatactgtaa aacacaacat   2400
atgcagtcac tatgaatcaa ctacttagat ggtattagtg acctgtagaa ttcgagctct   2460
agagctgcag ggcggccgcg atatccccta tagtgagtcg tattacatgg tcatagctgt   2520
ttcctggcag ctctggcccg tgtctcaaaa tctctgatgt tacattgcac aagataaaaa   2580
tatatcatca tgaacaataa aactgtctgc ttacataaac agtaatacaa ggggtgttat   2640
gagccatatt caacgggaaa cgtcgaggcc gcgattaaat tccaacatgg atgctgattt   2700
atatgggtat aaatgggctc gcgataatgt cgggcaatca ggtgcgacaa tctatcgctt   2760
gtatgggaag cccgatgcgc cagagttgtt tctgaaacat ggcaaaggta gcgttgccaa   2820
tgatgttaca gatgagatgg tcagactaaa ctggctgacg gaatttatgc ctcttccgac   2880
catcaagcat tttatccgta ctcctgatga tgcatggtta ctcaccactg cgatccccgg   2940
aaaaacagca ttccaggtat tagaagaata tcctgattca ggtgaaaata ttgttgatgc   3000
gctggcagtg ttcctgcgcc ggttgcattc gattcctgtt tgtaattgtc cttttaacag   3060
cgatcgcgta tttcgtctcg ctcaggcgca atcacgaatg aataacggtt tggttgatgc   3120
gagtgatttt gatgacgagc gtaatggctg gcctgttgaa caagtctgga aagaaatgca   3180
taaacttttg ccattctcac cggattcagt cgtcactcat ggtgatttct cacttgataa   3240
ccttattttt gacgagggga aattaatagg ttgtattgat gttggacgag tcggaatcgc   3300
agaccgatac caggatcttg ccatcctatg gaactgcctc ggtgagtttt ctccttcatt   3360
acagaaacgg ctttttcaaa aatatggtat tgataatcct gatatgaata aattgcagtt   3420
tcatttgatg ctcgatgagt ttttctaatc agaattggtt aattggttgt aacactggca   3480
gagcattacg ctgacttgac gggacggcgc aagctcatga ccaaaatccc ttaacgtgag   3540
ttacgcgtcg ttccactgag cgtcagaccc cgtagaaaag atcaaaggat cttcttgaga   3600
tccttttttt ctgcgcgtaa tctgctgctt gcaaacaaaa aaaccaccgc taccagcggt   3660
```

ggtttgtttg ccggatcaag agctaccaac tctttttccg aaggtaactg gcttcagcag 3720
agcgcagata ccaaatactg tccttctagt gtagccgtag ttaggccacc acttcaagaa 3780
ctctgtagca ccgcctacat acctcgctct gctaatcctg ttaccagtgg ctgctgccag 3840
tggcgataag tcgtgtctta ccgggttgga ctcaagacga tagttaccgg ataaggcgca 3900
gcggtcgggc tgaacggggg gttcgtgcac acagcccagc ttggagcgaa cgacctacac 3960
cgaactgaga tacctacagc gtgagcattg agaaagcgcc acgcttcccg aagggagaaa 4020
ggcggacagg tatccggtaa gcggcagggt cggaacagga gagcgcacga gggagcttcc 4080
agggggaaac gcctggtatc tttatagtcc tgtcgggttt cgccacctct gacttgagcg 4140
tcgatttttg tgatgctcgt caggggggcg gagcctatgg aaaaacgcca gcaacgcggc 4200
ctttttacgg ttcctggcct tttgctggcc ttttgctcac atgttctttc ctgcgttatc 4260
ccctgattct gtggataacc gtattaccgc ctttgagtga gctgataccg ctcgccgcag 4320
ccgaacgacc gagcgcagcg agtcagtgag cgaggaagcg gaagagcgcc caatacgcaa 4380
accgcctctc cccgcgcgtt ggccgattca ttaatgcagc tggcacgaca ggtttcccga 4440
ctggaaagcg ggcagtgagc gcaacgcaat taatacgcgt accgctagcc aggaagagtt 4500
tgtagaaacg caaaaaggcc atccgtcagg atggccttct gcttagtttg atgcctggca 4560
gtttatggcg ggcgtcctgc ccgccaccct ccgggccgtt gcttcacaac gttcaaatcc 4620
gctcccggcg gatttgtcct actcaggaga gcgttcaccg acaaacaaca gataaaac 4678

<210> SEQ ID NO 56
<211> LENGTH: 2991
<212> TYPE: DNA
<213> ORGANISM: artificial sequence
<220> FEATURE:
<223> OTHER INFORMATION: vector

<400> SEQUENCE: 56
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggccctg cagctctaga gctcgaattc tacaggtcac 600
taataccatc taagtagttg gttcatagtg actgcatatg ttgtgtttta cagtattatg 660
tagtctgttt tttatgcaaa atctaattta atatattgat atttatatca ttttacgttt 720
ctcgttcaac tttcttgtac aaagtggccg ttaacggatc cagacttgtc catcttctgg 780
attggccaac ttaattaatg tatgaaataa aaggatgcac acatagtgac atgctaatca 840
ctataatgtg ggcatcaaag ttgtgtgtta tgtgtaatta ctagttatct gaataaaaga 900
gaaagagatc atccatattt cttatcctaa atgaatgtca cgtgtcttta taattctttg 960
atgaaccaga tgcatttcat taaccaaatc catatacata taaatattaa tcatatataa 1020
ttaatatcaa ttgggttagc aaaacaaatc tagtctaggt gtgttttgcg aattgcggca 1080

-continued

```
agcttgcggc cgccccgggc aactttatta tacaaagttg gcattataaa aaagcattgc   1140
ttatcaattt gttgcaacga acaggtcact atcagtcaaa ataaaatcat tatttggagc   1200
tccatggtag cgttaacgcg gccgcgatat cccctatagt gagtcgtatt acatggtcat   1260
agctgtttcc tggcagctct ggcccgtgtc tcaaaatctc tgatgttaca ttgcacaaga   1320
taaaaatata tcatcatgaa caataaaact gtctgcttac ataaacagta atacaagggg   1380
tgttatgagc catattcaac gggaaacgtc gaggccgcga ttaaattcca acatggatgc   1440
tgatttatat gggtataaat gggctcgcga taatgtcggg caatcaggtg cgacaatcta   1500
tcgcttgtat gggaagcccg atgcgccaga gttgtttctg aaacatggca aaggtagcgt   1560
tgccaatgat gttacagatg agatggtcag actaaactgg ctgacggaat ttatgcctct   1620
tccgaccatc aagcatttta tccgtactcc tgatgatgca tggttactca ccactgcgat   1680
ccccggaaaa acagcattcc aggtattaga agaatatcct gattcaggtg aaaatattgt   1740
tgatgcgctg gcagtgttcc tgcgccggtt gcattcgatt cctgtttgta attgtccttt   1800
taacagcgat cgcgtatttc gtctcgctca ggcgcaatca cgaatgaata acggtttggt   1860
tgatgcgagt gattttgatg acgagcgtaa tggctggcct gttgaacaag tctggaaaga   1920
aatgcataaa cttttgccat tctcaccgga ttcagtcgtc actcatggtg atttctcact   1980
tgataacctt atttttgacg aggggaaatt aataggttgt attgatgttg gacgagtcgg   2040
aatcgcagac cgataccagg atcttgccat cctatggaac tgcctcggtg agttttctcc   2100
ttcattacag aaacggcttt ttcaaaaata tggtattgat aatcctgata tgaataaatt   2160
gcagtttcat ttgatgctcg atgagttttt ctaatcagaa ttggttaatt ggttgtaaca   2220
ctggcagagc attacgctga cttgacggga cggcgcaagc tcatgaccaa aatcccttaa   2280
cgtgagttac gcgtcgttcc actgagcgtc agaccccgta gaaaagatca aaggatcttc   2340
ttgagatcct ttttttctgc gcgtaatctg ctgcttgcaa acaaaaaaac caccgctacc   2400
agcggtggtt tgtttgccgg atcaagagct accaactctt tttccgaagg taactggctt   2460
cagcagagcg cagataccaa atactgtcct tctagtgtag ccgtagttag gccaccactt   2520
caagaactct gtagcaccgc ctacatacct cgctctgcta atcctgttac cagtggctgc   2580
tgccagtggc gataagtcgt gtcttaccgg gttggactca agacgatagt taccggataa   2640
ggcgcagcgg tcgggctgaa cggggggttc gtgcacacag cccagcttgg agcgaacgac   2700
ctacaccgaa ctgagatacc tacagcgtga gcattgagaa agcgccacgc ttcccgaagg   2760
gagaaaggcg gacaggtatc cggtaagcgg cagggtcgga acaggagagc gcacgaggga   2820
gcttccaggg ggaaacgcct ggtatcttta tagtcctgtc gggtttcgcc acctctgact   2880
tgagcgtcga tttttgtgat gctcgtcagg ggggcggagc ctatggaaaa acgccagcaa   2940
cgcggccttt ttacggttcc tggccttttg ctggcctttt gctcacatgt t            2991
```

<210> SEQ ID NO 57
<211> LENGTH: 13807
<212> TYPE: DNA
<213> ORGANISM: artificial sequence
<220> FEATURE:
<223> OTHER INFORMATION: vector

<400> SEQUENCE: 57

```
aagctggtac gattgtaata cgactcacta tagggcgaat tgagcgctgt ttaaacgctc     60
ttcaactgga agagcggtta ccagagctgg tcacctttgt ccaccaagat ggaactgcgg    120
ccgctcatta attaagtcag gcgcgcctct agttgaagac acgttcatgt cttcatcgta    180
```

```
agaagacact cagtagtctt cggccagaat ggccgtaggt gaattaagag gagagaggag    240
gtaaacattt tcttctattt tttcatattt tcaggataaa ttattgtaaa agtttacaag    300
atttccattt gactagtgta aatgaggaat attctctagt aagatcatta tttcatctac    360
ttcttttatc ttctaccagt agaggaataa acaatattta gctcctttgt aaatacaaat    420
taattttcgt tcttgacatc attcaatttt aattttacgt ataaaataaa agatcatacc    480
tattagaacg attaaggaga aatacaattc gaatgagaag gatgtgccgt ttgttataat    540
aaacagccac acgacgtaaa cgtaaaatga ccacatgatg ggccaataga catggaccga    600
ctactaataa tagtaagtta cattttagga tggaataaat atcataccga catcagtttg    660
aaagaaaagg gaaaaaaaga aaaaataaat aaaagatata ctaccgacat gagttccaaa    720
aagcaaaaaa aaagatcaag ccgacacaga cacgcgtaga gagcaaaatg actttgacgt    780
cacaccacga aaacagacgc ttcatacgtg tccctttatc tctctcagtc tctctataaa    840
cttagtgaga ccctcctctg ttttactcag gatccccggg taccgagctc gaattcaccg    900
gtcgccacca tggcccacag caagcacggc ctgaaggagg agatgaccat gaagtaccac    960
atggagggct gcgtgaacgg ccacaagttc gtgatcaccg gcgagggcat cggctacccc   1020
ttcaagggca agcagaccat caacctgtgc gtgatcgagg gcggccccct gcccttcagc   1080
gaggacatcc tgagcgccgg cttcaagtac ggcgaccgga tcttcaccga gtacccccag   1140
gacatcgtgg actacttcaa gaacagctgc cccgccggct acacctgggg ccggagcttc   1200
ctgttcgagg acggcgccgt gtgcatctgt aacgtggaca tcaccgtgag cgtgaaggag   1260
aactgcatct accacaagag catcttcaac ggcgtgaact tccccgccga cggccccgtg   1320
atgaagaaga tgaccaccaa ctgggaggcc agctgcgaga agatcatgcc cgtgcctaag   1380
cagggcatcc tgaagggcga cgtgagcatg tacctgctgc tgaaggacgg cggccggtac   1440
cggtgccagt tcgacaccgt gtacaaggcc aagagcgtgc ccagcaagat gcccgagtgg   1500
cacttcatcc agcacaagct gctgcgggag gaccggagcg acgccaagaa ccagaagtgg   1560
cagctgaccg agcacgccat cgccttcccc agcgccctgg cctgaagcgg cccatggata   1620
ttcgaacgcg taggtaccac atggttaacc tagacttgtc catcttctgg attggccaac   1680
ttaattaatg tatgaaataa aaggatgcac acatagtgac atgctaatca ctataatgtg   1740
ggcatcaaag ttgtgtgtta tgtgtaatta ctagttatct gaataaaaga gaaagagatc   1800
atccatattt cttatcctaa atgaatgtca cgtgtcttta taattctttg atgaaccaga   1860
tgcatttcat taaccaaatc catatacata taaatattaa tcatatataa ttaatatcaa   1920
ttgggttagc aaaacaaatc tagtctaggt gtgttttgcg aatgcggcca ttggcctaga   1980
aggccattta aatcctgagg atctggtctt cctaaggacc cgggatatcg ctatcaactt   2040
tgtatagaaa agttgaacga gaaacgtaaa atgatataaa tatcaatata ttaaattaga   2100
ttttgcataa aaaacagact acataaatact gtaaaacaca acatatccag tcactatggt   2160
cgacctgcag actggctgtg tataagggag cctgacattt atattcccca gaacatcagg   2220
ttaatggcgt ttttgatgtc attttcgcgg tggctgagat cagccacttc ttccccgata   2280
acggagaccg gcacactggc catatcggtg gtcatcatgc gccagctttc atccccgata   2340
tgcaccaccg ggtaaagttc acgggggact ttatctgaca gcagacgtgc actggccagg   2400
gggatcacca tccgtcgccc gggcgtgtca ataatatcac tctgtacatc cacaaacaga   2460
cgataacggc tctctctttt ataggtgtaa accttaaact gcatttcacc agcccctgtt   2520
ctcgtcggca aaagagccgt tcatttcaat aaaccgggcg acctcagcca tcccttcctg   2580
```

```
atttccgct ttccagcgtt cggcacgcag acgacgggct tcattctgca tggttgtgct   2640
taccgaaccg gagatattga catcatatat gccttgagca actgatagct gtcgctgtca   2700
actgtcactg taatacgctg cttcatagca tacctctttt tgacatactt cgggtataca   2760
tatcagtata tattcttata ccgcaaaaat cagcgcgcaa atacgcatac tgttatctgg   2820
cttttagtaa gccggatcct ctagattacg ccccgcctgc cactcatcgc agtactgttg   2880
taattcatta agcattctgc cgacatggaa gccatcacaa acggcatgat gaacctgaat   2940
cgccagcggc atcagcacct tgtcgccttg cgtataatat ttgcccatgg tgaaaacggg   3000
ggcgaagaag ttgtccatat tggccacgtt taaatcaaaa ctggtgaaac tcacccaggg   3060
attggctgag acgaaaaaca tattctcaat aaacccttta gggaaatagg ccaggttttc   3120
accgtaacac gccacatctt gcgaatatat gtgtagaaac tgccggaaat cgtcgtggta   3180
ttcactccag agcgatgaaa acgtttcagt ttgctcatgg aaaacggtgt aacaagggtg   3240
aacactatcc catatcacca gctcaccgtc tttcattgcc atacggaatt ccggatgagc   3300
attcatcagg cgggcaagaa tgtgaataaa ggccggataa aacttgtgct tatttttctt   3360
tacggtcttt aaaaaggccg taatatccag ctgaacggtc tggttatagg tacattgagc   3420
aactgactga aatgcctcaa aatgttcttt acgatgccat tgggatatat caacggtggt   3480
atatccagtg atttttttct ccattttagc ttccttagct cctgaaaatc tcgacggatc   3540
ctaactcaaa atccacacat tatacgagcc ggaagcataa agtgtaaagc ctggggtgcc   3600
ctaatgcggc cgccatagtg actggatatg ttgtgtttta cagtattatg tagtctgttt   3660
tttatgcaaa atctaattta atatattgat atttatatca ttttacgttt ctcgttcaac   3720
tttattatac aaagttgata gatatcggac cgattaaact ttaattcggt ccgaagcttg   3780
catgcctgca gtgcagcgtg acccggtcgt gcccctctct agagataatg agcattgcat   3840
gtctaagtta taaaaaatta ccacatattt tttttgtcac acttgtttga agtgcagttt   3900
atctatcttt atacatatat ttaaacttta ctctacgaat aatataatct atagtactac   3960
aataatatca gtgttttaga gaatcatata aatgaacagt tagacatggt ctaaaggaca   4020
attgagtatt ttgacaacag gactctacag ttttatcttt ttagtgtgca tgtgttctcc   4080
tttttttttg caaatagctt cacctatata atacttcatc cattttatta gtacatccat   4140
ttagggttta gggttaatgg tttttataga ctaatttttt tagtacatct attttattct   4200
attttagcct ctaaattaag aaaactaaaa ctctatttta gtttttttat ttaataattt   4260
agatataaaa tagaataaaa taaagtgact aaaaattaaa caaataccct ttaagaaatt   4320
aaaaaaacta aggaaacatt tttcttgttt cgagtagata atgccagcct gttaaacgcc   4380
gtcgacgagt ctaacggaca ccaaccagcg aaccagcagc gtcgcgtcgg gccaagcgaa   4440
gcagacggca cggcatctct gtcgctgcct ctggacccct ctcgagagtt ccgctccacc   4500
gttggacttg ctccgctgtc ggcatccaga aattgcgtgg cggagcggca gacgtgagcc   4560
ggcacggcag gcggcctcct cctcctctca cggcaccggc agctacgggg gattcctttc   4620
ccaccgctcc ttcgctttcc cttcctcgcc cgcccgtaata aatagacacc ccctccacac   4680
cctctttccc caacctcgtg ttgttcggag cgcacacaca cacaaccaga tctcccccaa   4740
atccacccgt cggcacctcc gcttcaaggt acgccgctcg tcctcccccc cccccctctc   4800
taccttctct agatcggcgt tccggtccat gcatggttag ggcccggtag ttctacttct   4860
gttcatgttt gtgttagatc cgtgtttgtg ttagatccgt gctgctagcg ttcgtacacg   4920
gatgcgacct gtacgtcaga cacgttctga ttgctaactt gccagtgttt ctctttgggg   4980
```

-continued aatcctggga tggctctagc cgttccgcag acgggatcga tttcatgatt ttttttgttt 5040
cgttgcatag ggtttggttt gcccttttcc tttatttcaa tatatgccgt gcacttgttt 5100
gtcgggtcat cttttcatgc ttttttttgt cttggttgtg atgatgtggt ctggttgggc 5160
ggtcgttcta gatcggagta gaattctgtt tcaaactacc tggtggattt attaattttg 5220
gatctgtatg tgtgtgccat acatattcat agttacgaat tgaagatgat ggatggaaat 5280
atcgatctag gataggtata catgttgatg cgggttttac tgatgcatat acagagatgc 5340
tttttgttcg cttggttgtg atgatgtggt gtggttgggc ggtcgttcat tcgttctaga 5400
tcggagtaga atactgtttc aaactacctg gtgtatttat taattttgga actgtatgtg 5460
tgtgtcatac atcttcatag ttacgagttt aagatggatg gaaatatcga tctaggatag 5520
gtatacatgt tgatgtgggt tttactgatg catatacatg atggcatatg cagcatctat 5580
tcatatgctc taaccttgag tacctatcta ttataataaa caagtatgtt ttataattat 5640
tttgatcttg atatacttgg atgatggcat atgcagcagc tatatgtgga tttttttagc 5700
cctgccttca tacgctattt atttgcttgg tactgtttct tttgtcgatg ctcaccctgt 5760
tgtttggtgt tacttctgca ggtcgacttt aacttagcct aggatccaca cgacaccatg 5820
tcccccgagc gccgccccgt cgagatccgc ccggccaccg ccgccgacat ggccgccgtg 5880
tgcgacatcg tgaaccacta catcgagacc tccaccgtga acttccgcac cgagccgcag 5940
accccgcagg agtggatcga cgacctggag cgcctccagg accgctaccc gtggctcgtg 6000
gccgaggtgg agggcgtggt ggccggcatc gcctacgccg gcccgtggaa ggcccgcaac 6060
gcctacgact ggaccgtgga gtccaccgtg tacgtgtccc accgccacca gcgcctcggc 6120
ctcggctcca ccctctacac ccacctcctc aagagcatgg aggcccaggg cttcaagtcc 6180
gtggtggccg tgatcggcct cccgaacgac ccgtccgtgc gcctccacga ggccctcggc 6240
tacaccgccc gcggcaccct ccgcgccgcc ggctacaagc acggcggctg gcacgacgtc 6300
ggcttctggc agcgcgactt cgagctgccg gccccgccgc gcccggtgcg cccggtgacg 6360
cagatctccg gtggaggcgg cagcggtggc ggaggctccg gaggcggtgg ctccatggcc 6420
tcctccgagg acgtcatcaa ggagttcatg cgcttcaagg tgcgcatgga gggctccgtg 6480
aacggccacg agttcgagat cgagggcgag ggcgagggcc gcccctacga gggcacccag 6540
accgccaagc tgaaggtgac caagggcggc cccctgccct tcgcctggga catcctgtcc 6600
ccccagttcc agtacggctc caaggtgtac gtgaagcacc ccgccgacat ccccgactac 6660
aagaagctgt ccttccccga gggcttcaag tgggagcgcg tgatgaactt cgaggacggc 6720
ggcgtggtga ccgtgaccca ggactcctcc ctgcaggacg gctccttcat ctacaaggtg 6780
aagttcatcg gcgtgaactt cccctccgac ggccccgtaa tgcagaagaa gactatgggc 6840
tgggaggcct ccaccgagcg cctgtacccc cgcgacggcg tgctgaaggg cgagatccac 6900
aaggccctga agctgaagga cggcggccac tacctggtgg agttcaagtc catctacatg 6960
gccaagaagc ccgtgcagct gcccggctac tactacgtgg actccaagct ggacatcacc 7020
tcccacaacg aggactacac catcgtggag cagtacgagc gcgccgaggg ccgccaccac 7080
ctgttcctgt agtcaggatc tgagtcgaaa cctagacttg tccatcttct ggattggcca 7140
acttaattaa tgtatgaaat aaaaggatgc acacatagtg acatgctaat cactataatg 7200
tgggcatcaa agttgtgtgt tatgtgtaat tactagttat ctgaataaaa gagaaagaga 7260
tcatccatat ttcttatcct aaatgaatgt cacgtgtctt tataattctt tgatgaacca 7320
gatgcatttc attaaccaaa tccatataca tataaatatt aatcatatat aattaatatc 7380

```
aattgggtta gcaaaacaaa tctagtctag gtgtgttttg cgaatgcggc cgccaccgcg   7440
gtggagctcg aattcattcc gattaatcgt ggcctcttgc tcttcaggat gaagagctat   7500
gtttaaacgt gcaagcgcta ctagacaatt cagtacatta aaaacgtccg caatgtgtta   7560
ttaagttgtc taagcgtcaa tttgtttaca ccacaatata tcctgccacc agccagccaa   7620
cagctccccg accggcagct cggcacaaaa tcaccactcg atacaggcag cccatcagtc   7680
cgggacggcg tcagcgggag agccgttgta aggcggcaga ctttgctcat gttaccgatg   7740
ctattcggaa gaacggcaac taagctgccg ggtttgaaac acggatgatc tcgcggaggg   7800
tagcatgttg attgtaacga tgacagagcg ttgctgcctg tgatcaaata tcatctccct   7860
cgcagagatc cgaattatca gccttcttat tcatttctcg cttaaccgtg acaggctgtc   7920
gatcttgaga actatgccga cataatagga aatcgctgga taaagccgct gaggaagctg   7980
agtggcgcta tttctttaga agtgaacgtt gacgatcgtc gaccgtaccc cgatgaatta   8040
attcggacgt acgttctgaa cacagctgga tacttacttg ggcgattgtc atacatgaca   8100
tcaacaatgt acccgtttgt gtaaccgtct cttggaggtt cgtatgacac tagtggttcc   8160
cctcagcttg cgactagatg ttgaggccta acattttatt agagagcagg ctagttgctt   8220
agatacatga tcttcaggcc gttatctgtc agggcaagcg aaaattggcc atttatgacg   8280
accaatgccc cgcagaagct cccatctttg ccgccataga cgccgcgccc ccccttttggg   8340
gtgtagaaca tccttttgcc agatgtggaa aagaagttcg ttgtcccatt gttggcaatg   8400
acgtagtagc cggcgaaagt gcgagaccca tttgcgctat atataagcct acgatttccg   8460
ttgcgactat tgtcgtaatt ggatgaacta ttatcgtagt tgctctcaga gttgtcgtaa   8520
tttgatggac tattgtcgta attgcttatg gagttgtcgt agttgcttgg agaaatgtcg   8580
tagttggatg gggagtagtc atagggaaga cgagcttcat ccactaaaac aattggcagg   8640
tcagcaagtg cctgccccga tgccatcgca agtacgaggc ttagaaccac cttcaacaga   8700
tcgcgcatag tcttccccag ctctctaacg cttgagttaa gccgcgccgc gaagcggcgt   8760
cggcttgaac gaattgttag acattatttg ccgactacct tggtgatctc gcctttcacg   8820
tagtgaacaa attcttccaa ctgatctgcg cgcgaggcca agcgatcttc ttgtccaaga   8880
taagcctgcc tagcttcaag tatgacgggc tgatactggg ccggcaggcg ctccattgcc   8940
cagtcggcag cgacatcctt cggcgcgatt ttgccggtta ctgcgctgta ccaaatgcgg   9000
gacaacgtaa gcactacatt tcgctcatcg ccagcccagt cgggcggcga gttccatagc   9060
gttaaggttt catttagcgc ctcaaataga tcctgttcag gaaccggatc aaagagttcc   9120
tccgccgctg gacctaccaa ggcaacgcta tgttctcttg cttttgtcag caagatagcc   9180
agatcaatgt cgatcgtggc tggctcgaag atacctgcaa gaatgtcatt gcgctgccat   9240
tctccaaatt gcagttcgcg cttagctgga taacgccacg gaatgatgtc gtcgtgcaca   9300
acaatggtga cttctacagc gcggagaatc tcgctctctc caggggaagc cgaagtttcc   9360
aaaaggtcgt tgatcaaagc tcgccgcgtt gtttcatcaa gccttacagt caccgtaacc   9420
agcaaatcaa tatcactgtg tggcttcagg ccgccatcca ctgcggagcc gtacaaatgt   9480
acggccagca acgtcggttc gagatggcgc tcgatgacgc caactacctc tgatagttga   9540
gtcgatactt cggcgatcac cgcttccctc atgatgttta actcctgaat taagccgcgc   9600
cgcgaagcgg tgtcggcttg aatgaattgt taggcgtcat cctgtgctcc cgagaaccag   9660
taccagtaca tcgctgtttc gttcgagact tgaggtctag ttttatacgt gaacaggtca   9720
atgccgccga gagtaaagcc acattttgcg tacaaattgc aggcaggtac attgttcgtt   9780
```

-continued

```
tgtgtctcta atcgtatgcc aaggagctgt ctgcttagtg cccacttttt cgcaaattcg   9840
atgagactgt gcgcgactcc tttgcctcgg tgcgtgtgcg acacaacaat gtgttcgata   9900
gaggctagat cgttccatgt tgagttgagt tcaatcttcc cgacaagctc ttggtcgatg   9960
aatgcgccat agcaagcaga gtcttcatca gagtcatcat ccgagatgta atccttccgg  10020
taggggctca cacttctggt agatagttca aagccttggt cggataggtg cacatcgaac  10080
acttcacgaa caatgaaatg gttctcagca tccaatgttt ccgccacctg ctcagggatc  10140
accgaaatct tcatatgacg cctaacgcct ggcacagcgg atcgcaaacc tggcgcggct  10200
tttggcacaa aaggcgtgac aggtttgcga atccgttgct gccacttgtt aacccttttg  10260
ccagatttgg taactataat ttatgttaga ggcgaagtct tgggtaaaaa ctggcctaaa  10320
attgctgggg atttcaggaa agtaaacatc accttccggc tcgatgtcta ttgtagatat  10380
atgtagtgta tctacttgat cgggggatct gctgcctcgc gcgtttcggt gatgacggtg  10440
aaaacctctg acacatgcag ctcccggaga cggtcacagc ttgtctgtaa gcggatgccg  10500
ggagcagaca agcccgtcag ggcgcgtcag cgggtgttgg cgggtgtcgg ggcgcagcca  10560
tgacccagtc acgtagcgat agcggagtgt atactggctt aactatgcgg catcagagca  10620
gattgtactg agagtgcacc atatgcggtg tgaaataccg cacagatgcg taaggagaaa  10680
ataccgcatc aggcgctctt ccgcttcctc gctcactgac tcgctgcgct cggtcgttcg  10740
gctgcggcga gcggtatcag ctcactcaaa ggcggtaata cggttatcca cagaatcagg  10800
ggataacgca ggaaagaaca tgtgagcaaa aggccagcaa aaggccagga accgtaaaaa  10860
ggccgcgttg ctggcgtttt tccataggct ccgcccccct gacgagcatc acaaaaatcg  10920
acgctcaagt cagaggtggc gaaacccgac aggactataa agataccagg cgtttccccc  10980
tggaagctcc ctcgtgcgct ctcctgttcc gaccctgccg cttaccggat acctgtccgc  11040
ctttctccct tcgggaagcg tggcgctttc tcatagctca cgctgtaggt atctcagttc  11100
ggtgtaggtc gttcgctcca agctgggctg tgtgcacgaa ccccccgttc agcccgaccg  11160
ctgcgcctta tccggtaact atcgtcttga gtccaacccg gtaagacacg acttatcgcc  11220
actggcagca gccactggta acaggattag cagagcgagg tatgtaggcg gtgctacaga  11280
gttcttgaag tggtggccta actacggcta cactagaagg acagtatttg gtatctgcgc  11340
tctgctgaag ccagttacct tcggaaaaag agttggtagc tcttgatccg gcaaacaaac  11400
caccgctggt agcggtggtt tttttgtttg caagcagcag attacgcgca gaaaaaaagg  11460
atctcaagaa gatcctttga tcttttctac ggggtctgac gctcagtgga acgaaaactc  11520
acgttaaggg attttggtca tgagattatc aaaaaggatc ttcacctaga tccttttaaa  11580
ttaaaaatga agttttaaat caatctaaag tatatatgag taaacttggt ctgacagtta  11640
ccaatgctta atcagtgagg cacctatctc agcgatctgt ctatttcgtt catccatagt  11700
tgcctgactc cccgtcgtgt agataactac gatacgggag ggcttaccat ctggccccag  11760
tgctgcaatg ataccgcgag acccacgctc accggctcca gatttatcag caataaacca  11820
gccagccgga agggccgagc gcagaagtgg tcctgcaact ttatccgcct ccatccagtc  11880
tattaattgt tgccgggaag ctagagtaag tagttcgcca gttaatagtt tgcgcaacgt  11940
tgttgccatt gctgcagggg gggggggggg gggggacttc cattgttcat tccacggaca  12000
aaaacagaga aaggaaacga cagaggccaa aaagcctcgc tttcagcacc tgtcgtttcc  12060
tttcttttca gagggtattt taaataaaaa cattaagtta tgacgaagaa gaacggaaac  12120
gccttaaacc ggaaaatttt cataaatagc gaaaacccgc gaggtcgccg ccccgtaacc  12180
```

```
tgtcggatca ccggaaagga cccgtaaagt gataatgatt atcatctaca tatcacaacg  12240
tgcgtggagg ccatcaaacc acgtcaaata atcaattatg acgcaggtat cgtattaatt  12300
gatctgcatc aacttaacgt aaaaacaact tcagacaata caaatcagcg acactgaata  12360
cggggcaacc tcatgtcccc cccccccccc cccctgcagg catcgtggtg tcacgctcgt  12420
cgtttggtat ggcttcattc agctccggtt cccaacgatc aaggcgagtt acatgatccc  12480
ccatgttgtg caaaaaagcg gttagctcct tcggtcctcc gatcgttgtc agaagtaagt  12540
tggccgcagt gttatcactc atggttatgg cagcactgca taattctctt actgtcatgc  12600
catccgtaag atgcttttct gtgactggtg agtactcaac caagtcattc tgagaatagt  12660
gtatgcggcg accgagttgc tcttgcccgg cgtcaacacg ggataatacc gcgccacata  12720
gcagaacttt aaaagtgctc atcattggaa aacgttcttc ggggcgaaaa ctctcaagga  12780
tcttaccgct gttgagatcc agttcgatgt aacccactcg tgcacccaac tgatcttcag  12840
catcttttac tttcaccagc gtttctgggt gagcaaaaac aggaaggcaa aatgccgcaa  12900
aaaagggaat aagggcgaca cggaaatgtt gaatactcat actcttcctt tttcaatatt  12960
attgaagcat ttatcagggt tattgtctca tgagcggata catatttgaa tgtatttaga  13020
aaaataaaca aataggggtt ccgcgcacat ttccccgaaa agtgccacct gacgtctaag  13080
aaaccattat tatcatgaca ttaacctata aaaataggcg tatcacgagg ccctttcgtc  13140
ttcaagaatt ggtcgacgat cttgctgcgt tcggatattt tcgtggagtt cccgccacag  13200
acccggattg aaggcgagat ccagcaactc gcgccagatc atcctgtgac ggaactttgg  13260
cgcgtgatga ctggccagga cgtcggccga aagagcgaca agcagatcac gcttttcgac  13320
agcgtcggat ttgcgatcga ggatttttcg gcgctgcgct acgtccgcga ccgcgttgag  13380
ggatcaagcc acagcagccc actcgacctt ctagccgacc cagacgagcc aagggatctt  13440
tttggaatgc tgctccgtcg tcaggctttc cgacgtttgg gtggttgaac agaagtcatt  13500
atcgtacgga atgccaagca ctcccgaggg gaaccctgtg gttggcatgc acatacaaat  13560
ggacgaacgg ataaaccttt tcacgccctt ttaaatatcc gttattctaa taaacgctct  13620
tttctcttag gtttacccgc caatatatcc tgtcaaacac tgatagttta aactgaaggc  13680
gggaaacgac aatctgatca tgagcggaga attaagggag tcacgttatg acccccgccg  13740
atgacgcggg acaagccgtt ttacgtttgg aactgacaga accgcaacgt tgaaggagcc  13800
actcagc                                                            13807
```

<210> SEQ ID NO 58
<211> LENGTH: 3505
<212> TYPE: DNA
<213> ORGANISM: artificial sequence
<220> FEATURE:
<223> OTHER INFORMATION: vector

<400> SEQUENCE: 58

```
gatccccggg taccgagctc gaattcggcc caagtttgta caaaaaagtt gaacgagaaa     60
cgtaaaatga tataaatatc aatatattaa attagatttt gcataaaaaa cagactacat    120
aatactgtaa aacacaacat atgcagtcac tatgaatcaa ctacttagat ggtattagtg    180
acctgtagaa ttcgagctct agagctgcag ggcggccgcg atatccccta tagtgagtcg    240
tattacatgg tcatagctgt ttcctggcag ctctggcccg tgtctcaaaa tctctgatgt    300
tacattgcac aagataaaaa tatatcatca tgaacaataa aactgtctgc ttacataaac    360
agtaatacaa ggggtgttat gagccatatt caacgggaaa cgtcgaggcc gcgattaaat    420
```

-continued

```
tccaacatgg atgctgattt atatgggtat aaatgggctc gcgataatgt cgggcaatca    480
ggtgcgacaa tctatcgctt gtatgggaag cccgatgcgc cagagttgtt tctgaaacat    540
ggcaaaggta gcgttgccaa tgatgttaca gatgagatgg tcagactaaa ctggctgacg    600
gaatttatgc ctcttccgac catcaagcat tttatccgta ctcctgatga tgcatggtta    660
ctcaccactg cgatccccgg aaaaacagca ttccaggtat tagaagaata tcctgattca    720
ggtgaaaata ttgttgatgc gctggcagtg ttcctgcgcc ggttgcattc gattcctgtt    780
tgtaattgtc cttttaacag cgatcgcgta tttcgtctcg ctcaggcgca atcacgaatg    840
aataacggtt tggttgatgc gagtgatttt gatgacgagc gtaatggctg gcctgttgaa    900
caagtctgga aagaaatgca taaacttttg ccattctcac cggattcagt cgtcactcat    960
ggtgatttct cacttgataa ccttattttt gacgagggga aattaatagg ttgtattgat   1020
gttggacgag tcggaatcgc agaccgatac caggatcttg ccatcctatg gaactgcctc   1080
ggtgagtttt ctccttcatt acagaaacgg ctttttcaaa aatatggtat tgataatcct   1140
gatatgaata aattgcagtt tcatttgatg ctcgatgagt ttttctaatc agaattggtt   1200
aattggttgt aacactggca gagcattacg ctgacttgac gggacggcgc aagctcatga   1260
ccaaaatccc ttaacgtgag ttacgcgtcg ttccactgag cgtcagaccc cgtagaaaag   1320
atcaaaggat cttcttgaga tccttttttt ctgcgcgtaa tctgctgctt gcaaacaaaa   1380
aaaccaccgc taccagcggt ggtttgtttg ccggatcaag agctaccaac tctttttccg   1440
aaggtaactg gcttcagcag agcgcagata ccaaatactg tccttctagt gtagccgtag   1500
ttaggccacc acttcaagaa ctctgtagca ccgcctacat acctcgctct gctaatcctg   1560
ttaccagtgg ctgctgccag tggcgataag tcgtgtctta ccgggttgga ctcaagacga   1620
tagttaccgg ataaggcgca gcggtcgggc tgaacggggg gttcgtgcac acagcccagc   1680
ttggagcgaa cgacctacac cgaactgaga tacctacagc gtgagcattg agaaagcgcc   1740
acgcttcccg aagggagaaa ggcggacagg tatccggtaa gcggcagggt cggaacagga   1800
gagcgcacga gggagcttcc agggggaaac gcctggtatc tttatagtcc tgtcgggttt   1860
cgccacctct gacttgagcg tcgatttttg tgatgctcgt caggggggcg gagcctatgg   1920
aaaaacgcca gcaacgcggc ctttttacgg ttcctggcct tttgctggcc ttttgctcac   1980
atgttctttc ctgcgttatc ccctgattct gtggataacc gtattaccgc ctttgagtga   2040
gctgataccg ctcgccgcag ccgaacgacc gagcgcagcg agtcagtgag cgaggaagcg   2100
gaagagcgcc caatacgcaa accgcctctc cccgcgcgtt ggccgattca ttaatgcagc   2160
tggcacgaca ggtttcccga ctggaaagcg ggcagtgagc gcaacgcaat taatacgcgt   2220
accgctagcc aggaagagtt tgtagaaacg caaaaaggcc atccgtcagg atggccttct   2280
gcttagtttg atgcctggca gtttatggcg ggcgtcctgc ccgccaccct ccgggccgtt   2340
gcttcacaac gttcaaatcc gctcccggcg gatttgtcct actcaggaga gcgttcaccg   2400
acaaacaaca gataaaacga aaggcccagt cttccgactg agcctttcgt tttatttgat   2460
gcctggcagt tccctactct cgcgttaacg ctagcatgga tgttttccca gtcacgacgt   2520
tgtaaaacga cggccagtct taagctcggg cccgcgttaa cgctaccatg gagctccaaa   2580
taatgatttt attttgactg atagtgacct gttcgttgca acaaattgat aagcaatgct   2640
tttttataat gccaactttg tatagaaaag ttgaagctta aatccttaca gaattgctgt   2700
agtttcatag tgctagatgt ggacagcaaa gcgccgctgt atgcttctgc ttttcttttt   2760
tggtgtgtgt agccacatcc tttgttcctg cccggcgcca tcccacttgg ttgttttttt   2820
```

ttatgattga aagccttcat gcttcctcgg tcaatcaccg gtgcgcactg ggagcatcgc 2880
cggaaaaaaa attcttcggc taagagtaac ttctttctcc ttttcttctc tgatctcgcg 2940
agcagtgctg ataacgtgtt gtaatctact tagcggtaac gagattgaga gagacaaaat 3000
gacagaacta ttgtctttat tgcagagtgt catgtattta tacaggggat acaaagtctc 3060
ccaaggggtg tgtcccttgg gagtaactgc cagttgatca caggacaata ttttgtaaca 3120
aaacgtacac atcgtcaaaa tagcgaggca tgaaactggc cttggccatg gacgcgtgaa 3180
gcgcgccatg cgttggatat gtggtcaata agtatataca atacaatgtt taacagagct 3240
gatagtactg ctttggcaca tttttgtcca cgcttcatga gagataaaac acctgcacgt 3300
aaattcacat gctgcactga aggcccgatc actgaggagc gaactgccgt aactcccttc 3360
tatatatacc cccagtccct gtttcagttt tcgtcaagct agcagcacca agttgtcgat 3420
cacttgcctg ctcttgagct cgattaagct atcatcagct acagcatccg atcccaaact 3480
gcaactgtag cagcgacaac tgccg 3505

<210> SEQ ID NO 59
<211> LENGTH: 4778
<212> TYPE: DNA
<213> ORGANISM: artificial sequence
<220> FEATURE:
<223> OTHER INFORMATION: plasmid

<400> SEQUENCE: 59
tggctgacgg aatttatgcc tcttccgacc atcaagcatt ttatccgtac tcctgatgat 60
gcatggttac tcaccactgc gatccccgga aaaacagcat tccaggtatt agaagaatat 120
cctgattcag gtgaaaatat tgttgatgcg ctggcagtgt tcctgcgccg gttgcattcg 180
attcctgttt gtaattgtcc ttttaacagc gatcgcgtat ttcgtctcgc tcaggcgcaa 240
tcacgaatga ataacggttt ggttgatgcg agtgattttg atgacgagcg taatggctgg 300
cctgttgaac aagtctggaa agaaatgcat aaacttttgc cattctcacc ggattcagtc 360
gtcactcatg gtgatttctc acttgataac cttatttttg acgaggggaa attaataggt 420
tgtattgatg ttggacgagt cggaatcgca gaccgatacc aggatcttgc catcctatgg 480
aactgcctcg gtgagttttc tccttcatta cagaaacggc tttttcaaaa atatggtatt 540
gataatcctg atatgaataa attgcagttt catttgatgc tcgatgagtt tttctaatca 600
gaattggtta attggttgta acactggcag agcattacgc tgacttgacg ggacggcgca 660
agctcatgac caaaatccct taacgtgagt tacgcgtcgt tccactgagc gtcagacccc 720
gtagaaaaga tcaaaggatc ttcttgagat cctttttttc tgcgcgtaat ctgctgcttg 780
caaacaaaaa aaccaccgct accagcggtg gtttgtttgc cggatcaaga gctaccaact 840
ctttttccga aggtaactgg cttcagcaga gcgcagatac caaatactgt ccttctagtg 900
tagccgtagt taggccacca cttcaagaac tctgtagcac cgcctacata cctcgctctg 960
ctaatcctgt taccagtggc tgctgccagt ggcgataagt cgtgtcttac cgggttggac 1020
tcaagacgat agttaccgga taaggcgcag cggtcgggct gaacgggggg ttcgtgcaca 1080
cagcccagct tggagcgaac gacctacacc gaactgagat acctacagcg tgagcattga 1140
gaaagcgcca cgcttcccga agggagaaag gcggacaggt atccggtaag cggcagggtc 1200
ggaacaggag agcgcacgag ggagcttcca gggggaaacg cctggtatct ttatagtcct 1260
gtcgggtttc gccacctctg acttgagcgt cgatttttgt gatgctcgtc aggggggcgg 1320
agcctatgga aaaacgccag caacgcggcc tttttacggt tcctggcctt ttgctggcct 1380

-continued

```
tttgctcaca tgttctttcc tgcgttatcc cctgattctg tggataaccg tattaccgcc   1440
tttgagtgag ctgataccgc tcgccgcagc cgaacgaccg agcgcagcga gtcagtgagc   1500
gaggaagcgg aagagcgccc aatacgcaaa ccgcctctcc ccgcgcgttg gccgattcat   1560
taatgcagct ggcacgacag gtttcccgac tggaaagcgg gcagtgagcg caacgcaatt   1620
aatacgcgta ccgctagcca ggaagagttt gtagaaacgc aaaaaggcca tccgtcagga   1680
tggccttctg cttagtttga tgcctggcag tttatggcgg gcgtcctgcc cgccaccctc   1740
cgggccgttg cttcacaacg ttcaaatccg ctcccggcgg atttgtccta ctcaggagag   1800
cgttcaccga caaacaacag ataaaacgaa aggcccagtc ttccgactga gcctttcgtt   1860
ttatttgatg cctggcagtt ccctactctc gcgttaacgc tagcatggat gttttcccag   1920
tcacgacgtt gtaaaacgac ggccagtctt aagctcgggc ccgcgttaac gctaccatgg   1980
agctccaaat aatgatttta ttttgactga tagtgacctg ttcgttgcaa caaattgata   2040
agcaatgctt ttttataatg ccaactttgt atagaaaagt tgggccgaat tcgagctcgg   2100
tacggccaga atggcccgga ccgggttacc gaattcgagc tcggtaccct gggatcagct   2160
tgcatgcctg cagtgcagcg tgacccggtc gtgcccctct ctagagataa tgagcattgc   2220
atgtctaagt tataaaaaat taccacatat ttttttgtc acacttgttt gaagtgcagt   2280
ttatctatct ttatacatat atttaaactt tactctacga ataatataat ctatagtact   2340
acaataatat cagtgtttta gagaatcata taaatgaaca gttagacatg gtctaaagga   2400
caattgagta ttttgacaac aggactctac agttttatct ttttagtgtg catgtgttct   2460
cctttttttt tgcaaatagc ttcacctata taatacttca tccattttat tagtacatcc   2520
atttagggtt tagggttaat ggtttttata gactaatttt tttagtacat ctattttatt   2580
ctattttagc ctctaaatta agaaaactaa aactctattt tagttttttt atttaataat   2640
ttagatataa aatagaataa aataaagtga ctaaaaatta aacaaatacc ctttaagaaa   2700
ttaaaaaaac taaggaaaca tttttcttgt ttcgagtaga taatgccagc ctgttaaacg   2760
ccgtcgacga gtctaacgga caccaaccag cgaaccagca gcgtcgcgtc gggccaagcg   2820
aagcagacgg cacggcatct ctgtcgctgc ctctggaccc ctctcgagag ttccgctcca   2880
ccgttggact tgctccgctg tcggcatcca gaaattgcgt ggcggagcgg cagacgtgag   2940
ccggcacggc aggcggcctc ctcctcctct cacggcaccg gcagctacgg gggattcctt   3000
tcccaccgct ccttcgcttt cccttcctcg cccgccgtaa taaatagaca ccccctccac   3060
accctctttc cccaacctcg tgttgttcgg agcgcacaca cacacaacca gatctccccc   3120
aaatccaccc gtcggcacct ccgcttcaag gtacgccgct cgtcctcccc cccccccctc   3180
tctaccttct ctagatcggc gttccggtcc atgcatggtt agggcccggt agttctactt   3240
ctgttcatgt ttgtgttaga tccgtgtttg tgttagatcc gtgctgctag cgttcgtaca   3300
cggatgcgac ctgtacgtca gacacgttct gattgctaac ttgccagtgt ttctctttgg   3360
ggaatcctgg gatggctcta gccgttccgc agacgggatc gatttcatga ttttttttgt   3420
ttcgttgcat agggtttggt ttgccctttt cctttatttc aatatatgcc gtgcacttgt   3480
ttgtcgggtc atcttttcat gctttttttt gtcttggttg tgatgatgtg gtctggttgg   3540
gcggtcgttc tagatcggag tagaattctg tttcaaacta cctggtggat ttattaattt   3600
tggatctgta tgtgtgtgcc atacatattc atagttacga attgaagatg atggatggaa   3660
atatcgatct aggataggta tacatgttga tgcgggtttt actgatgcat atacagagat   3720
gctttttgtt cgcttggttg tgatgatgtg gtgtggttgg gcggtcgttc attcgttcta   3780
```

gatcggagta gaatactgtt tcaaactacc tggtgtattt attaattttg gaactgtatg 3840
tgtgtgtcat acatcttcat agttacgagt ttaagatgga tggaaatatc gatctaggat 3900
aggtatacat gttgatgtgg gttttactga tgcatataca tgatggcata tgcagcatct 3960
attcatatgc tctaaccttg agtacctatc tattataata aacaagtatg ttttataatt 4020
attttgatct tgatatactt ggatgatggc atatgcagca gctatatgtg gattttttta 4080
gccctgcctt catacgctat ttatttgctt ggtactgttt cttttgtcga tgctcaccct 4140
gttgtttggt gttacttctg caggtcgact ctagaggatc agcttggtca cccggtccgg 4200
gcctagaagg ccagcttcaa gtttgtacaa aaaagttgaa cgagaaacgt aaaatgatat 4260
aaatatcaat atattaaatt agattttgca taaaaaacag actacataat actgtaaaac 4320
acaacatatg cagtcactat gaatcaacta cttagatggt attagtgacc tgtagaattc 4380
gagctctaga gctgcagggc ggccgcgata tcccctatag tgagtcgtat tacatggtca 4440
tagctgtttc ctggcagctc tggcccgtgt ctcaaaatct ctgatgttac attgcacaag 4500
ataaaaatat atcatcatga acaataaaac tgtctgctta cataaacagt aatacaaggg 4560
gtgttatgag ccatattcaa cgggaaacgt cgaggccgcg attaaattcc aacatggatg 4620
ctgatttata tgggtataaa tgggctcgcg ataatgtcgg gcaatcaggt gcgacaatct 4680
atcgcttgta tgggaagccc gatgcgccag agttgtttct gaaacatggc aaaggtagcg 4740
ttgccaatga tgttacagat gagatggtca gactaaac 4778

<210> SEQ ID NO 60
<211> LENGTH: 13019
<212> TYPE: DNA
<213> ORGANISM: artificial sequence
<220> FEATURE:
<223> OTHER INFORMATION: vector

<400> SEQUENCE: 60
gttacccgga ccgaagctta gcccgggcat gcctgcagtg cagcgtgacc cggtcgtgcc 60
cctctctaga gataatgagc attgcatgtc taagttataa aaaattacca catatttttt 120
ttgtcacact tgtttgaagt gcagtttatc tatctttata catatattta aactttactc 180
tacgaataat ataatctata gtactacaat aatatcagtg ttttagagaa tcatataaat 240
gaacagttag acatggtcta aaggacaatt gagtattttg acaacaggac tctacagttt 300
tatcttttta gtgtgcatgt gttctccttt ttttttgcaa atagcttcac ctatataata 360
cttcatccat tttattagta catccattta gggtttaggg ttaatggttt ttatagacta 420
atttttttag tacatctatt ttattctatt ttagcctcta aattaagaaa actaaaactc 480
tattttagtt tttttattta ataatttaga tataaaatag aataaaataa agtgactaaa 540
aattaaacaa ataccctta agaaattaaa aaaactaagg aaacattttt cttgtttcga 600
gtagataatg ccagcctgtt aaacgccgtc gacgagtcta acggacacca accagcgaac 660
cagcagcgtc gcgtcgggcc aagcgaagca gacggcacgg catctctgtc gctgcctctg 720
gacccctctc gagagttccg ctccaccgtt ggacttgctc cgctgtcggc atccagaaat 780
tgcgtggcgg agcggcagac gtgagccggc acggcaggcg gcctcctcct cctctcacgg 840
cacggcagct acgggggatt cctttcccac cgctccttcg ctttcccttc ctcgcccgcc 900
gtaataaata gacacccct ccacaccctc tttccccaac ctcgtgttgt tcggagcgca 960
cacacacaca accagatctc ccccaaatcc acccgtcggc acctccgctt caaggtacgc 1020
cgctcgtcct cccccccccc ccctctctac cttctctaga tcggcgttcc ggtccatggt 1080

```
tagggcccgg tagttctact tctgttcatg tttgtgttag atccgtgttt gtgttagatc   1140
cgtgctgcta gcgttcgtac acggatgcga cctgtacgtc agacacgttc tgattgctaa   1200
cttgccagtg tttctctttg gggaatcctg ggatggctct agccgttccg cagacgggat   1260
cgatttcatg attttttttg tttcgttgca tagggtttgg tttgcccttt tcctttattt   1320
caatatatgc cgtgcacttg tttgtcgggt catcttttca tgcttttttt tgtcttggtt   1380
gtgatgatgt ggtctggttg ggcggtcgtt ctagatcgga gtagaattct gtttcaaact   1440
acctggtgga tttattaatt ttggatctgt atgtgtgtgc catacatatt catagttacg   1500
aattgaagat gatggatgga aatatcgatc taggataggt atacatgttg atgcgggttt   1560
tactgatgca tatacagaga tgctttttgt tcgcttggtt gtgatgatgt ggtgtggttg   1620
ggcggtcgtt cattcgttct agatcggagt agaatactgt ttcaaactac ctggtgtatt   1680
tattaatttt ggaactgtat gtgtgtgtca tacatcttca tagttacgag tttaagatgg   1740
atggaaatat cgatctagga taggtataca tgttgatgtg ggttttactg atgcatatac   1800
atgatggcat atgcagcatc tattcatatg ctctaacctt gagtacctat ctattataat   1860
aaacaagtat gttttataat tattttgatc ttgatatact tggatgatgg catatgcagc   1920
agctatatgt ggattttttt agccctgcct tcatacgcta tttatttgct tggtactgtt   1980
tcttttgtcg atgctcaccc tgttgtttgg tgttacttct gcaggtcgac tctagaggat   2040
ccacaagttt gtacaaaaaa gctgaacgag aaacgtaaaa tgatataaat atcaatatat   2100
taaattagat tttgcataaa aaacagacta cataatactg taaaacacaa catatccagt   2160
cactatggcg gccgcattag gcaccccagg ctttacactt tatgcttccg gctcgtataa   2220
tgtgtggatt ttgagttagg atttaaatac gcgttgatcc ggcttactaa aagccagata   2280
acagtatgcg tatttgcgcg ctgatttttg cggtataaga atatatactg atatgtatac   2340
ccgaagtatg tcaaaaagag gtatgctatg aagcagcgta ttacagtgac agttgacagc   2400
gacagctatc agttgctcaa ggcatatatg atgtcaatat ctccggtctg gtaagcacaa   2460
ccatgcagaa tgaagcccgt cgtctgcgtg ccgaacgctg gaaagcggaa aatcaggaag   2520
ggatggctga ggtcgcccgg tttattgaaa tgaacggctc ttttgctgac gagaacaggg   2580
gctggtgaaa tgcagtttaa ggtttacacc tataaaagag agagccgtta tcgtctgttt   2640
gtggatgtac agagtgatat cattgacacg cccggtcgac ggatggtgat ccccctggcc   2700
agtgcacgtc tgctgtcaga taaagtctcc cgtgaacttt acccggtggt gcatatcggg   2760
gatgaaagct ggcgcatgat gaccaccgat atggccagtg tgccggtctc cgttatcggg   2820
gaagaagtgg ctgatctcag ccaccgcgaa aatgacatca aaaacgccat taacctgatg   2880
ttctggggaa tataaatgtc aggctccctt atacacagcc agtctgcagg tcgaccatag   2940
tgactggata tgttgtgttt tacagtatta tgtagtctgt tttttatgca aaatctaatt   3000
taatatattg atatttatat cattttacgt ttctcgttca gctttcttgt acaaagtggt   3060
gttaacctag acttgtccat cttctggatt ggccaactta attaatgtat gaaataaaag   3120
gatgcacaca tagtgacatg ctaatcacta taatgtgggc atcaaagttg tgtgttatgt   3180
gtaattacta gttatctgaa taaaagagaa agagatcatc catatttctt atcctaaatg   3240
aatgtcacgt gtctttataa ttctttgatg aaccagatgc atttcattaa ccaaatccat   3300
atacatataa atattaatca tatataatta atatcaattg ggttagcaaa acaaatctag   3360
tctaggtgtg ttttgcgaat tgcggccgcc accgcggtgg agctcgaatt ccggtccggg   3420
tcacctttgt ccaccaagat ggaactgcgg ccgctcatta attaagtcag gcgcgcctct   3480
```

-continued

```
agttgaagac acgttcatgt cttcatcgta agaagacact cagtagtctt cggccagaat   3540
ggccatctgg attcagcagg cctagaaggc catttaaatc ctgaggatct ggtcttccta   3600
aggacccggg atatcggacc gattaaactt taattcggtc cgaagcttgc atgcctgcag   3660
tgcagcgtga cccggtcgtg cccctctcta gagataatga gcattgcatg tctaagttat   3720
aaaaaattac cacatatttt ttttgtcaca cttgtttgaa gtgcagttta tctatcttta   3780
tacatatatt taaactttac tctacgaata atataatcta tagtactaca ataatatcag   3840
tgttttagag aatcatataa atgaacagtt agacatggtc taaaggacaa ttgagtattt   3900
tgacaacagg actctacagt tttatctttt tagtgtgcat gtgttctcct ttttttttgc   3960
aaatagcttc acctatataa tacttcatcc attttattag tacatccatt tagggtttag   4020
ggttaatggt ttttatagac taattttttt agtacatcta ttttattcta ttttagcctc   4080
taaattaaga aaactaaaac tctattttag tttttttatt taataattta gatataaaat   4140
agaataaaat aaagtgacta aaaattaaac aaataccctt taagaaatta aaaaaactaa   4200
ggaaacattt ttcttgtttc gagtagataa tgccagcctg ttaaacgccg tcgacgagtc   4260
taacggacac caaccagcga accagcagcg tcgcgtcggg ccaagcgaag cagacggcac   4320
ggcatctctg tcgctgcctc tggacccctc tcgagagttc cgctccaccg ttggacttgc   4380
tccgctgtcg gcatccagaa attgcgtggc ggagcggcag acgtgagccg gcacggcagg   4440
cggcctcctc ctcctctcac ggcaccggca gctacggggg attcctttcc caccgctcct   4500
tcgctttccc ttcctcgccc gccgtaataa atagacaccc cctccacacc ctctttcccc   4560
aacctcgtgt tgttcggagc gcacacacac acaaccagat ctcccccaaa tccacccgtc   4620
ggcacctccg cttcaaggta cgccgctcgt cctccccccc cccccctctct accttctcta   4680
gatcggcgtt ccggtccatg catggttagg gcccggtagt tctacttctg ttcatgtttg   4740
tgttagatcc gtgtttgtgt tagatccgtg ctgctagcgt tcgtacacgg atgcgacctg   4800
tacgtcagac acgttctgat tgctaacttg ccagtgtttc tctttgggga atcctgggat   4860
ggctctagcc gttccgcaga cgggatcgat ttcatgattt tttttgtttc gttgcatagg   4920
gtttggtttg cccttttcct ttatttcaat atatgccgtg cacttgtttg tcgggtcatc   4980
ttttcatgct ttttttgtc ttggttgtga tgatgtggtc tggttgggcg gtcgttctag   5040
atcggagtag aattctgttt caaactacct ggtggattta ttaattttgg atctgtatgt   5100
gtgtgccata catattcata gttacgaatt gaagatgatg gatggaaata tcgatctagg   5160
ataggtatac atgttgatgc gggttttact gatgcatata cagagatgct tttgttcgc   5220
ttggttgtga tgatgtggtg tggttgggcg gtcgttcatt cgttctagat cggagtagaa   5280
tactgtttca aactacctgg tgtatttatt aattttggaa ctgtatgtgt gtgtcataca   5340
tcttcatagt tacgagttta agatggatgg aaatatcgat ctaggatagg tatacatgtt   5400
gatgtgggtt ttactgatgc atatacatga tggcatatgc agcatctatt catatgctct   5460
aaccttgagt acctatctat tataataaac aagtatgttt tataattatt ttgatcttga   5520
tatacttgga tgatggcata tgcagcagct atatgtggat ttttttagcc ctgccttcat   5580
acgctattta tttgcttggt actgtttctt ttgtcgatgc tcaccctgtt gtttggtgtt   5640
acttctgcag gtcgacttta acttagccta ggatccacac gacaccatgt cccccgagcg   5700
ccgccccgtc gagatccgcc cggccaccgc cgccgacatg gccgccgtgt gcgacatcgt   5760
gaaccactac atcgagacct ccaccgtgaa cttccgcacc gagccgcaga ccccgcagga   5820
gtggatcgac gacctggagc gcctccagga ccgctacccg tggctcgtgg ccgaggtgga   5880
```

```
gggcgtggtg gccggcatcg cctacgccgg cccgtggaag gcccgcaacg cctacgactg   5940
gaccgtggag tccaccgtgt acgtgtccca ccgccaccag cgcctcggcc tcggctccac   6000
cctctacacc cacctcctca agagcatgga ggcccagggc ttcaagtccg tggtggccgt   6060
gatcggcctc ccgaacgacc cgtccgtgcg cctccacgag gccctcggct acaccgcccg   6120
cggcaccctc cgcgccgccg gctacaagca cggcggctgg cacgacgtcg gcttctggca   6180
gcgcgacttc gagctgccgg ccccgccgcg cccggtgcgc ccggtgacgc agatctgagt   6240
cgaaacctag acttgtccat cttctggatt ggccaactta attaatgtat gaaataaaag   6300
gatgcacaca tagtgacatg ctaatcacta taatgtgggc atcaaagttg tgtgttatgt   6360
gtaattacta gttatctgaa taaaagagaa agagatcatc catatttctt atcctaaatg   6420
aatgtcacgt gtctttataa ttctttgatg aaccagatgc atttcattaa ccaaatccat   6480
atacatataa atattaatca tatataatta atatcaattg ggttagcaaa acaaatctag   6540
tctaggtgtg ttttgcgaat tgcggccgcc accgcggtgg agctcgaatt cattccgatt   6600
aatcgtggcc tcttgctctt caggatgaag agctatgttt aaacgtgcaa gcgctactag   6660
acaattcagt acattaaaaa cgtccgcaat gtgttattaa gttgtctaag cgtcaatttg   6720
tttacaccac aatatatcct gccaccagcc agccaacagc tccccgaccg gcagctcggc   6780
acaaaatcac cactcgatac aggcagccca tcagtccggg acggcgtcag cgggagagcc   6840
gttgtaaggc ggcagacttt gctcatgtta ccgatgctat tcggaagaac ggcaactaag   6900
ctgccgggtt tgaaacacgg atgatctcgc ggagggtagc atgttgattg taacgatgac   6960
agagcgttgc tgcctgtgat caaatatcat ctccctcgca gagatccgaa ttatcagcct   7020
tcttattcat ttctcgctta accgtgacag gctgtcgatc ttgagaacta tgccgacata   7080
ataggaaatc gctggataaa gccgctgagg aagctgagtg gcgctatttc tttagaagtg   7140
aacgttgacg atcgtcgacc gtaccccgat gaattaattc ggacgtacgt tctgaacaca   7200
gctggatact tacttgggcg attgtcatac atgacatcaa caatgtaccc gtttgtgtaa   7260
ccgtctcttg gaggttcgta tgacactagt ggttcccctc agcttgcgac tagatgttga   7320
ggcctaacat tttattagag agcaggctag ttgcttagat acatgatctt caggccgtta   7380
tctgtcaggg caagcgaaaa ttggccattt atgacgacca atgccccgca gaagctccca   7440
tctttgccgc catagacgcc gcgccccct tttggggtgt agaacatcct tttgccagat   7500
gtggaaaaga agttcgttgt cccattgttg gcaatgacgt agtagccggc gaaagtgcga   7560
gacccatttg cgctatatat aagcctacga tttccgttgc gactattgtc gtaattggat   7620
gaactattat cgtagttgct ctcagagttg tcgtaatttg atggactatt gtcgtaattg   7680
cttatggagt tgtcgtagtt gcttggagaa atgtcgtagt tggatgggga gtagtcatag   7740
ggaagacgag cttcatccac taaaacaatt ggcaggtcag caagtgcctg ccccgatgcc   7800
atcgcaagta cgaggcttag aaccaccttc aacagatcgc gcatagtctt ccccagctct   7860
ctaacgcttg agttaagccg cgccgcgaag cggcgtcggc ttgaacgaat tgttagacat   7920
tatttgccga ctaccttggt gatctcgcct ttcacgtagt gaacaaattc ttccaactga   7980
tctgcgcgcg aggccaagcg atcttcttgt ccaagataag cctgcctagc ttcaagtatg   8040
acgggctgat actgggccgg caggcgctcc attgcccagt cggcagcgac atccttcggc   8100
gcgattttgc cggttactgc gctgtaccaa atgcgggaca acgtaagcac tacatttcgc   8160
tcatcgccag cccagtcggg cggcgagttc catagcgtta aggtttcatt tagcgcctca   8220
aatagatcct gttcaggaac cggatcaaag agttcctccg ccgctggacc taccaaggca   8280
```

```
acgctatgtt ctcttgcttt tgtcagcaag atagccagat caatgtcgat cgtggctggc   8340
tcgaagatac ctgcaagaat gtcattgcgc tgccattctc caaattgcag ttcgcgctta   8400
gctggataac gccacggaat gatgtcgtcg tgcacaacaa tggtgacttc tacagcgcgg   8460
agaatctcgc tctctccagg ggaagccgaa gtttccaaaa ggtcgttgat caaagctcgc   8520
cgcgttgttt catcaagcct tacagtcacc gtaaccagca aatcaatatc actgtgtggc   8580
ttcaggccgc catccactgc ggagccgtac aaatgtacgg ccagcaacgt cggttcgaga   8640
tggcgctcga tgacgccaac tacctctgat agttgagtcg atacttcggc gatcaccgct   8700
tccctcatga tgtttaactc ctgaattaag ccgcgccgcg aagcggtgtc ggcttgaatg   8760
aattgttagg cgtcatcctg tgctcccgag aaccagtacc agtacatcgc tgtttcgttc   8820
gagacttgag gtctagtttt atacgtgaac aggtcaatgc cgccgagagt aaagccacat   8880
tttgcgtaca aattgcaggc aggtacattg ttcgtttgtg tctctaatcg tatgccaagg   8940
agctgtctgc ttagtgccca ctttttcgca aattcgatga gactgtgcgc gactcctttg   9000
cctcggtgcg tgtgcgacac aacaatgtgt tcgatagagg ctagatcgtt ccatgttgag   9060
ttgagttcaa tcttcccgac aagctcttgg tcgatgaatg cgccatagca agcagagtct   9120
tcatcagagt catcatccga gatgtaatcc ttccggtagg ggctcacact tctggtagat   9180
agttcaaagc cttggtcgga taggtgcaca tcgaacactt cacgaacaat gaaatggttc   9240
tcagcatcca atgtttccgc cacctgctca gggatcaccg aaatcttcat atgacgccta   9300
acgcctggca cagcggatcg caaacctggc gcggcttttg gcacaaaagg cgtgacaggt   9360
ttgcgaatcc gttgctgcca cttgttaacc cttttgccag atttggtaac tataatttat   9420
gttagaggcg aagtcttggg taaaaactgg cctaaaattg ctggggattt caggaaagta   9480
aacatcacct tccggctcga tgtctattgt agatatatgt agtgtatcta cttgatcggg   9540
ggatctgctg cctcgcgcgt ttcggtgatg acggtgaaaa cctctgacac atgcagctcc   9600
cggagacggt cacagcttgt ctgtaagcgg atgccgggag cagacaagcc cgtcagggcg   9660
cgtcagcggg tgttggcggg tgtcggggcg cagccatgac ccagtcacgt agcgatagcg   9720
gagtgtatac tggcttaact atgcggcatc agagcagatt gtactgagag tgcaccatat   9780
gcggtgtgaa ataccgcaca gatgcgtaag gagaaaatac cgcatcaggc gctcttccgc   9840
ttcctcgctc actgactcgc tgcgctcggt cgttcggctg cggcgagcgg tatcagctca   9900
ctcaaaggcg gtaatacggt tatccacaga atcaggggat aacgcaggaa agaacatgtg   9960
agcaaaaggc cagcaaaagg ccaggaaccg taaaaaggcc gcgttgctgg cgtttttcca  10020
taggctccgc ccccctgacg agcatcacaa aaatcgacgc tcaagtcaga ggtggcgaaa  10080
cccgacagga ctataaagat accaggcgtt tccccctgga agctccctcg tgcgctctcc  10140
tgttccgacc ctgccgctta ccggatacct gtccgccttt ctcccttcgg gaagcgtggc  10200
gctttctcat agctcacgct gtaggtatct cagttcggtg taggtcgttc gctccaagct  10260
gggctgtgtg cacgaacccc ccgttcagcc cgaccgctgc gccttatccg gtaactatcg  10320
tcttgagtcc aacccggtaa gacacgactt atcgccactg gcagcagcca ctggtaacag  10380
gattagcaga gcgaggtatg taggcggtgc tacagagttc ttgaagtggt ggcctaacta  10440
cggctacact agaaggacag tatttggtat ctgcgctctg ctgaagccag ttaccttcgg  10500
aaaaagagtt ggtagctctt gatccggcaa acaaaccacc gctggtagcg gtggtttttt  10560
tgtttgcaag cagcagatta cgcgcagaaa aaaaggatct caagaagatc ctttgatctt  10620
ttctacgggg tctgacgctc agtggaacga aaactcacgt taagggattt tggtcatgag  10680
```

-continued

```
attatcaaaa aggatcttca cctagatcct tttaaattaa aaatgaagtt ttaaatcaat  10740
ctaaagtata tatgagtaaa cttggtctga cagttaccaa tgcttaatca gtgaggcacc  10800
tatctcagcg atctgtctat ttcgttcatc catagttgcc tgactccccg tcgtgtagat  10860
aactacgata cgggagggct taccatctgg ccccagtgct gcaatgatac cgcgagaccc  10920
acgctcaccg gctccagatt tatcagcaat aaaccagcca gccggaaggg ccgagcgcag  10980
aagtggtcct gcaactttat ccgcctccat ccagtctatt aattgttgcc gggaagctag  11040
agtaagtagt tcgccagtta atagtttgcg caacgttgtt gccattgctg cagggggggg  11100
gggggggggg gacttccatt gttcattcca cggacaaaaa cagagaaagg aaacgacaga  11160
ggccaaaaag cctcgctttc agcacctgtc gtttcctttc ttttcagagg gtattttaaa  11220
taaaaacatt aagttatgac gaagaagaac ggaaacgcct taaaccggaa aattttcata  11280
aatagcgaaa acccgcgagg tcgccgcccc gtaacctgtc ggatcaccgg aaaggacccg  11340
taaagtgata atgattatca tctacatatc acaacgtgcg tggaggccat caaaccacgt  11400
caaataatca attatgacgc aggtatcgta ttaattgatc tgcatcaact taacgtaaaa  11460
acaacttcag acaatacaaa tcagcgacac tgaatacggg gcaacctcat gtcccccccc  11520
cccccccccc tgcaggcatc gtggtgtcac gctcgtcgtt tggtatggct tcattcagct  11580
ccggttccca acgatcaagg cgagttacat gatcccccat gttgtgcaaa aaagcggtta  11640
gctccttcgg tcctccgatc gttgtcagaa gtaagttggc cgcagtgtta tcactcatgg  11700
ttatggcagc actgcataat tctcttactg tcatgccatc cgtaagatgc ttttctgtga  11760
ctggtgagta ctcaaccaag tcattctgag aatagtgtat gcggcgaccg agttgctctt  11820
gcccggcgtc aacacgggat aataccgcgc cacatagcag aactttaaaa gtgctcatca  11880
ttggaaaacg ttcttcgggg cgaaaactct caaggatctt accgctgttg agatccagtt  11940
cgatgtaacc cactcgtgca cccaactgat cttcagcatc ttttactttc accagcgttt  12000
ctgggtgagc aaaaacagga aggcaaaatg ccgcaaaaaa gggaataagg gcgacacgga  12060
aatgttgaat actcatactc ttcctttttc aatattattg aagcatttat cagggttatt  12120
gtctcatgag cggatacata tttgaatgta tttagaaaaa taaacaaata ggggttccgc  12180
gcacatttcc ccgaaaagtg ccacctgacg tctaagaaac cattattatc atgacattaa  12240
cctataaaaa taggcgtatc acgaggccct ttcgtcttca agaattggtc gacgatcttg  12300
ctgcgttcgg atattttcgt ggagttcccg ccacagaccc ggattgaagg cgagatccag  12360
caactcgcgc cagatcatcc tgtgacggaa ctttggcgcg tgatgactgg ccaggacgtc  12420
ggccgaaaga gcgacaagca gatcacgctt ttcgacagcg tcggatttgc gatcgaggat  12480
ttttcggcgc tgcgctacgt ccgcgaccgc gttgagggat caagccacag cagcccactc  12540
gaccttctag ccgacccaga cgagccaagg gatctttttg gaatgctgct ccgtcgtcag  12600
gctttccgac gtttgggtgg ttgaacagaa gtcattatcg tacggaatgc caagcactcc  12660
cgaggggaac cctgtggttg gcatgcacat acaaatggac gaacggataa accttttcac  12720
gcccttttaa atatccgtta ttctaataaa cgctcttttc tcttaggttt acccgccaat  12780
atatcctgtc aaacactgat agtttaaact gaaggcggga aacgacaatc tgatcatgag  12840
cggagaatta agggagtcac gttatgaccc ccgccgatga cgcgggacaa gccgttttac  12900
gtttggaact gacagaaccg caacgttgaa ggagccactc agcaagctgg tacgattgta  12960
atacgactca ctatagggcg aattgagcgc tgtttaaacg ctcttcaact ggaagagcg   13019
```

<210> SEQ ID NO 61
<211> LENGTH: 49765
<212> TYPE: DNA
<213> ORGANISM: artificial sequence
<220> FEATURE:
<223> OTHER INFORMATION: vector

<400> SEQUENCE: 61
gggggggggg ggggggggtt ccattgttca ttccacggac aaaaacagag aaaggaaacg 60
acagaggcca aaaagctcgc tttcagcacc tgtcgtttcc tttcttttca gagggtattt 120
taaataaaaa cattaagtta tgacgaagaa gaacggaaac gccttaaacc ggaaaatttt 180
cataaatagc gaaaacccgc gaggtcgccg ccccgtaacc tgtcggatca ccggaaagga 240
cccgtaaagt gataatgatt atcatctaca tatcacaacg tgcgtggagg ccatcaaacc 300
acgtcaaata atcaattatg acgcaggtat cgtattaatt gatctgcatc aacttaacgt 360
aaaaacaact tcagacaata caaatcagcg acactgaata cggggcaacc tcatgtcccc 420
cccccccccc cccctgcagg catcgtggtg tcacgctcgt cgtttggtat ggcttcattc 480
agctccggtt cccaacgatc aaggcgagtt acatgatccc ccatgttgtg caaaaaagcg 540
gttagctcct tcggtcctcc gatcgttgtc agaagtaagt tggccgcagt gttatcactc 600
atggttatgg cagcactgca taattctctt actgtcatgc catccgtaag atgcttttct 660
gtgactggtg agtactcaac caagtcattc tgagaatagt gtatgcggcg accgagttgc 720
tcttgcccgg cgtcaacacg ggataatacc gcgccacata gcagaacttt aaaagtgctc 780
atcattggaa aacgttcttc ggggcgaaaa ctctcaagga tcttaccgct gttgagatcc 840
agttcgatgt aacccactcg tgcacccaac tgatcttcag catcttttac tttcaccagc 900
gtttctgggt gagcaaaaac aggaaggcaa aatgccgcaa aaaagggaat aagggcgaca 960
cggaaatgtt gaatactcat actcttcctt tttcaatatt attgaagcat ttatcagggt 1020
tattgtctca tgagcggata catatttgaa tgtatttaga aaaataaaca aataggggtt 1080
ccgcgcacat ttccccgaaa agtgccacct gacgtctaag aaaccattat tatcatgaca 1140
ttaacctata aaaataggcg tatcacgagg ccctttcgtc ttcaagaatt cggagctttt 1200
gccattctca ccggattcag tcgtcactca tggtgatttc tcacttgata accttatttt 1260
tgacgagggg aaattaatag gttgtattga tgttggacga gtcggaatcg cagaccgata 1320
ccaggatctt gccatcctat ggaactgcct cggtgagttt tctccttcat tacagaaacg 1380
gctttttcaa aaatatggta ttgataatcc tgatatgaat aaattgcagt ttcatttgat 1440
gctcgatgag tttttctaat cagaattggt taattggttg taacactggc agagcattac 1500
gctgacttga cgggacggcg gctttgttga ataaatcgaa cttttgctga gttgaaggat 1560
cagatcacgc atcttcccga caacgcagac cgttccgtgg caaagcaaaa gttcaaaatc 1620
accaactggt ccacctacaa caaagctctc atcaaccgtg gctccctcac tttctggctg 1680
gatgatgggg cgattcaggc ctggtatgag tcagcaacac cttcttcacg aggcagacct 1740
cagcgccaga aggccgccag agaggccgag cgcggccgtg aggcttggac gctagggcag 1800
ggcatgaaaa agcccgtagc gggctgctac gggcgtctga cgcggtggaa agggggaggg 1860
gatgttgtct acatggctct gctgtagtga gtgggttgcg ctccggcagc ggtcctgatc 1920
aatcgtcacc ctttctcggt ccttcaacgt tcctgacaac gagcctcctt ttcgccaatc 1980
catcgacaat caccgcgagt ccctgctcga acgctgcgtc cggaccggct tcgtcgaagg 2040
cgtctatcgc ggcccgcaac agcggcgaga gcggagcctg ttcaacggtg ccgccgcgct 2100
cgccggcatc gctgtcgccg gcctgctcct caagcacggc cccaacagtg aagtagctga 2160

```
ttgtcatcag cgcattgacg gcgtccccgg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaacccccaa ccgttccgcc agtttgcgtg tcgtcagacc gtctacgccg acctcgttca   2520
acaggtccag ggcggcacgg atcactgtat tcggctgcaa ctttgtcatg cttgacactt   2580
tatcactgat aaacataata tgtccaccaa cttatcagtg ataaagaatc cgcgcgttca   2640
atcggaccag cggaggctgg tccggaggcc agacgtgaaa cccaacatac ccctgatcgt   2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880
tttcgggcgg cggccaatct tgctcgtctc gctggccggc gccactgtcg actacgccat   2940
catggcgaca gcgcctttcc tttgggttct ctatatcggg cggatcgtgg ccggcatcac   3000
cggggcgact ggggcggtag ccggcgctta tattgccgat atcactgatg gcgatgagcg   3060
cgcgcggcac ttcggcttca tgagcgcctg tttcgggttc gggatggtcg cgggacctgt   3120
gctcggtggg ctgatgggcg gtttctcccc ccacgctccg ttcttcgccg cggcagcctt   3180
gaacggcctc aatttcctga cgggctgttt ccttttgccg gagtcgcaca aaggcgaacg   3240
ccggccgtta cgccgggagg ctctcaaccc gctcgcttcg ttccggtggg cccggggcat   3300
gaccgtcgtc gccgccctga tggcggtctt cttcatcatg caacttgtcg gacaggtgcc   3360
ggccgcgctt tgggtcattt tcggcgagga tcgctttcac tgggacgcga ccacgatcgg   3420
catttcgctt gccgcatttg gcattctgca ttcactcgcc caggcaatga tcaccggccc   3480
tgtagccgcc cggctcggcg aaaggcgggc actcatgctc ggaatgattg ccgacggcac   3540
aggctacatc ctgcttgcct tcgcgacacg gggatggatg gcgttcccga tcatggtcct   3600
gcttgcttcg ggtggcatcg gaatgccggc gctgcaagca atgttgtcca ggcaggtgga   3660
tgaggaacgt caggggcagc tgcaaggctc actggcggcg ctcaccagcc tgacctcgat   3720
cgtcggaccc ctcctcttca cggcgatcta tgcggcttct ataacaacgt ggaacgggtg   3780
ggcatggatt gcaggcgctg ccctctactt gctctgcctg ccggcgctgc gtcgcgggct   3840
ttggagcggc gcagggcaac gagccgatcg ctgatcgtgg aaacgatagg cctatgccat   3900
gcgggtcaag gcgacttccg gcaagctata cgcgccctag gagtgcggtt ggaacgttgg   3960
cccagccaga tactcccgat cacgagcagg acgccgatga tttgaagcgc actcagcgtc   4020
tgatccaaga acaaccatcc tagcaacacg gcggtccccg ggctgagaaa gcccagtaag   4080
gaaacaactg taggttcgag tcgcgagatc cccggaacc aaaggaagta ggttaaaccc   4140
gctccgatca ggccgagcca cgccaggccg agaacattgg ttcctgtagg catcgggatt   4200
ggcggatcaa acactaaagc tactggaacg agcagaagtc ctccggccgc cagttgccag   4260
gcggtaaagg tgagcagagg cacgggaggt tgccacttgc gggtcagcac ggttccgaac   4320
gccatggaaa ccgcccccgc caggcccgct gcgacgccga caggatctag cgctgcgttt   4380
ggtgtcaaca ccaacagcgc cacgcccgca gttccgcaaa tagcccccag gaccgccatc   4440
aatcgtatcg ggctacctag cagagcggca gagatgaaca cgaccatcag cggctgcaca   4500
gcgcctaccg tcgccgcgac ccgcccggc aggcggtaga ccgaaataaa caacaagctc   4560
```

-continued

```
cagaatagcg aaatattaag tgcgccgagg atgaagatgc gcatccacca gattcccgtt   4620
ggaatctgtc ggacgatcat cacgagcaat aaacccgccg gcaacgcccg cagcagcata   4680
ccggcgaccc ctcggcctcg ctgttcgggc tccacgaaaa cgccggacag atgcgccttg   4740
tgagcgtcct tggggccgtc ctcctgtttg aagaccgaca gcccaatgat ctcgccgtcg   4800
atgtaggcgc cgaatgccac ggcatctcgc aaccgttcag cgaacgcctc catgggcttt   4860
ttctcctcgt gctcgtaaac ggacccgaac atctctggag ctttcttcag ggccgacaat   4920
cggatctcgc ggaaatcctg cacgtcggcc gctccaagcc gtcgaatctg agccttaatc   4980
acaattgtca attttaatcc tctgtttatc ggcagttcgt agagcgcgcc gtgcgtcccg   5040
agcgatactg agcgaagcaa gtgcgtcgag cagtgcccgc ttgttcctga aatgccagta   5100
aagcgctggc tgctgaaccc ccagccggaa ctgaccccac aaggccctag cgtttgcaat   5160
gcaccaggtc atcattgacc caggcgtgtt ccaccaggcc gctgcctcgc aactcttcgc   5220
aggcttcgcc gacctgctcg cgccacttct tcacgcgggt ggaatccgat ccgcacatga   5280
ggcggaaggt ttccagcttg agcgggtacg gctcccggtg cgagctgaaa tagtcgaaca   5340
tccgtcgggc cgtcggcgac agcttgcggt acttctccca tatgaatttc gtgtagtggt   5400
cgccagcaaa cagcacgacg atttcctcgt cgatcaggac ctggcaacgg gacgttttct   5460
tgccacggtc caggacgcgg aagcggtgca gcagcgacac cgattccagg tgcccaacgc   5520
ggtcggacgt gaagcccatc gccgtcgcct gtaggcgcga caggcattcc tcggccttcg   5580
tgtaataccg gccattgatc gaccagccca ggtcctggca aagctcgtag aacgtgaagg   5640
tgatcggctc gccgataggg gtgcgcttcg cgtactccaa cacctgctgc cacaccagtt   5700
cgtcatcgtc ggcccgcagc tcgacgccgg tgtaggtgat cttcacgtcc ttgttgacgt   5760
ggaaaatgac cttgttttgc agcgcctcgc gcgggatttt cttgttgcgc gtggtgaaca   5820
gggcagagcg ggccgtgtcg tttggcatcg ctcgcatcgt gtccggccac ggcgcaatat   5880
cgaacaagga aagctgcatt tccttgatct gctgcttcgt gtgtttcagc aacgcggcct   5940
gcttggcctc gctgacctgt tttgccaggt cctcgccggc ggtttttcgc ttcttggtcg   6000
tcatagttcc tcgcgtgtcg atggtcatcg acttcgccaa acctgccgcc tcctgttcga   6060
gacgacgcga acgctccacg gcggccgatg gcgcgggcag ggcaggggga gccagttgca   6120
cgctgtcgcg ctcgatcttg gccgtagctt gctggaccat cgagccgacg gactggaagg   6180
tttcgcgggg cgcacgcatg acggtgcggc ttgcgatggt ttcggcatcc tcggcggaaa   6240
accccgcgtc gatcagttct tgcctgtatg ccttccggtc aaacgtccga ttcattcacc   6300
ctccttgcgg gattgccccg actcacgccg gggcaatgtg cccttattcc tgatttgacc   6360
cgcctggtgc cttggtgtcc agataatcca ccttatcggc aatgaagtcg gtcccgtaga   6420
ccgtctggcc gtccttctcg tacttggtat tccgaatctt gccctgcacg aataccagcg   6480
accccttgcc caaatacttg ccgtgggcct cggcctgaga gccaaaacac ttgatgcgga   6540
agaagtcggt gcgctcctgc ttgtcgccgg catcgttgcg ccactcttca ttaaccgcta   6600
tatcgaaaat tgcttgcggc ttgttagaat tgccatgacg tacctcggtg tcacgggtaa   6660
gattaccgat aaactggaac tgattatggc tcatatcgaa agtctccttg agaaaggaga   6720
ctctagttta gctaaacatt ggttccgctg tcaagaactt tagcggctaa aattttgcgg   6780
gccgcgacca aaggtgcgag gggcggcttc cgctgtgtac aaccagatat ttttcaccaa   6840
catccttcgt ctgctcgatg agcggggcat gacgaaacat gagctgtcgg agagggcagg   6900
ggtttcaatt tcgtttttat cagacttaac caacggtaag gccaacccct cgttgaaggt   6960
```

gatggaggcc attgccgacg ccctggaaac tcccctacct cttctcctgg agtccaccga 7020
ccttgaccgc gaggcactcg cggagattgc gggtcatcct ttcaagagca gcgtgccgcc 7080
cggatacgaa cgcatcagtg tggttttgcc gtcacataag gcgtttatcg taaagaaatg 7140
gggcgacgac acccgaaaaa agctgcgtgg aaggctctga cgccaagggt tagggcttgc 7200
acttccttct ttagccgcta aaacggcccc ttctctgcgg gccgtcggct cgcgcatcat 7260
atcgacatcc tcaacggaag ccgtgccgcg aatggcatcg ggcgggtgcg ctttgacagt 7320
tgttttctat cagaacccct acgtcgtgcg gttcgattag ctgtttgtct tgcaggctaa 7380
acactttcgg tatatcgttt gcctgtgcga taatgttgct aatgatttgt tgcgtagggg 7440
ttactgaaaa gtgagcggga aagaagagtt tcagaccatc aaggagcggg ccaagcgcaa 7500
gctggaacgc gacatgggtg cggacctgtt ggccgcgctc aacgacccga aaaccgttga 7560
agtcatgctc aacgcggacg gcaaggtgtg gcacgaacgc cttggcgagc cgatgcggta 7620
catctgcgac atgcggccca gccagtcgca ggcgattata gaaacggtgg ccggattcca 7680
cggcaaagag gtcacgcggc attcgcccat cctggaaggc gagttcccct tggatggcag 7740
ccgctttgcc ggccaattgc cgccggtcgt ggccgcgcca acctttgcga tccgcaagcg 7800
cgcggtcgcc atcttcacgc tggaacagta cgtcgaggcg ggcatcatga cccgcgagca 7860
atacgaggtc attaaaagcg ccgtcgcggc gcatcgaaac atcctcgtca ttggcggtac 7920
tggctcgggc aagaccacgc tcgtcaacgc gatcatcaat gaaatggtcg ccttcaaccc 7980
gtctgagcgc gtcgtcatca tcgaggacac cggcgaaatc cagtgcgccg cagagaacgc 8040
cgtccaatac cacaccagca tcgacgtctc gatgacgctg ctgctcaaga caacgctgcg 8100
tatgcgcccc gaccgcatcc tggtcggtga ggtacgtggc cccgaagccc ttgatctgtt 8160
gatggcctgg aacaccgggc atgaaggagg tgccgccacc ctgcacgcaa acaaccccaa 8220
agcgggcctg agccggctcg ccatgcttat cagcatgcac ccggattcac cgaaacccat 8280
tgagccgctg attggcgagg cggttcatgt ggtcgtccat atcgccagga cccctagcgg 8340
ccgtcgagtg caagaaattc tcgaagttct tggttacgag aacggccagt acatcaccaa 8400
aaccctgtaa ggagtatttc caatgacaac ggctgttccg ttccgtctga ccatgaatcg 8460
cggcattttg ttctaccttg ccgtgttctt cgttctcgct ctcgcgttat ccgcgcatcc 8520
ggcgatggcc tcggaaggca ccggcggcag cttgccatat gagagctggc tgacgaacct 8580
gcgcaactcc gtaaccggcc cggtggcctt cgcgctgtcc atcatcggca tcgtcgtcgc 8640
cggcggcgtg ctgatcttcg gcggcgaact caacgccttc ttccgaaccc tgatcttcct 8700
ggttctggtg atggcgctgc tggtcggcgc gcagaacgtg atgagcacct tcttcggtcg 8760
tggtgccgaa atcgcggccc tcggcaacgg ggcgctgcac caggtgcaag tcgcggcggc 8820
ggatgccgtg cgtgcggtag cggctggacg gctcgcctaa tcatggctct gcgcacgatc 8880
cccatccgtc gcgcaggcaa ccgagaaaac ctgttcatgg gtggtgatcg tgaactggtg 8940
atgttctcgg gcctgatggc gtttgcgctg attttcagcg cccaagagct gcgggccacc 9000
gtggtcggtc tgatcctgtg gttcggggcg ctctatgcgt tccgaatcat ggcgaaggcc 9060
gatccgaaga tgcggttcgt gtacctgcgt caccgccggt acaagccgta ttacccggcc 9120
cgctcgaccc cgttccgcga gaacaccaat agccaaggga agcaataccg atgatccaag 9180
caattgcgat tgcaatcgcg ggcctcggcg cgcttctgtt gttcatcctc tttgcccgca 9240
tccgcgcggt cgatgccgaa ctgaaactga aaaagcatcg ttccaaggac gccggcctgg 9300
ccgatctgct caactacgcc gctgtcgtcg atgacggcgt aatcgtgggc aagaacggca 9360
gctttatggc tgcctggctg tacaagggcg atgacaacgc aagcagcacc gaccagcagc 9420
gcgaagtagt gtccgcccgc atcaaccagg ccctcgcggg cctgggaagt gggtggatga 9480
tccatgtgga cgccgtgcgg cgtcctgctc cgaactacgc ggagcggggc ctgtcggcgt 9540
tccctgaccg tctgacggca gcgattgaag aagagcgctc ggtcttgcct tgctcgtcgg 9600
tgatgtactt caccagctcc gcgaagtcgc tcttcttgat ggagcgcatg gggacgtgct 9660
tggcaatcac gcgcaccccc cggccgtttt agcggctaaa aaagtcatgg ctctgccctc 9720
gggcggacca cgcccatcat gaccttgcca agctcgtcct gcttctcttc gatcttcgcc 9780
agcagggcga ggatcgtggc atcaccgaac cgcgccgtgc gcgggtcgtc ggtgagccag 9840
agtttcagca ggccgcccag gcggcccagg tcgccattga tgcgggccag ctcgcggacg 9900
tgctcatagt ccacgacgcc cgtgattttg tagccctggc cgacggccag caggtaggcc 9960
gacaggctca tgccggccgc cgccgccttt tcctcaatcg ctcttcgttc gtctggaagg 10020
cagtacacct tgataggtgg gctgcccttc ctggttggct tggtttcatc agccatccgc 10080
ttgccctcat ctgttacgcc ggcggtagcc ggccagcctc gcagagcagg attcccgttg 10140
agcaccgcca ggtgcgaata agggacagtg aagaaggaac acccgctcgc gggtgggcct 10200
acttcaccta tcctgcccgg ctgacgccgt tggatacacc aaggaaagtc tacacgaacc 10260
ctttggcaaa atcctgtata tcgtgcgaaa aaggatggat ataccgaaaa aatcgctata 10320
atgaccccga agcagggtta tgcagcggaa aagcgctgct tccctgctgt tttgtggaat 10380
atctaccgac tggaaacagg caaatgcagg aaattactga actgagggga caggcgagag 10440
acgatgccaa agagctacac cgacgagctg gccgagtggg ttgaatcccg cgcggccaag 10500
aagcgccggc gtgatgaggc tgcggttgcg ttcctggcgg tgagggcgga tgtcgaggcg 10560
gcgttagcgt ccggctatgc gctcgtcacc atttgggagc acatgcggga aacggggaag 10620
gtcaagttct cctacgagac gttccgctcg cacgccaggc ggcacatcaa ggccaagccc 10680
gccgatgtgc ccgcaccgca ggccaaggct gcggaacccg cgccggcacc caagacgccg 10740
gagccacggc ggccgaagca ggggggcaag gctgaaaagc cggcccccgc tgcggccccg 10800
accggcttca ccttcaaccc aacaccggac aaaaaggatc tactgtaatg gcgaaaattc 10860
acatggtttt gcagggcaag ggcggggtcg gcaagtcggc catcgccgcg atcattgcgc 10920
agtacaagat ggacaagggg cagacaccct tgtgcatcga caccgacccg gtgaacgcga 10980
cgttcgaggg ctacaaggcc ctgaacgtcc gccggctgaa catcatggcc ggcgacgaaa 11040
ttaactcgcg caacttcgac accctggtcg agctgattgc gccgaccaag gatgacgtgg 11100
tgatcgacaa cggtgccagc tcgttcgtgc ctctgtcgca ttacctcatc agcaaccagg 11160
tgccggctct gctgcaagaa atggggcatg agctggtcat ccataccgtc gtcaccggcg 11220
gccaggctct cctggacacg gtgagcggct tcgcccagct cgccagccag ttcccggccg 11280
aagcgctttt cgtggtctgg ctgaacccgt attgggggcc tatcgagcat gagggcaaga 11340
gctttgagca gatgaaggcg tacacggcca acaaggcccg cgtgtcgtcc atcatccaga 11400
ttccggccct caaggaagaa acctacggcc gcgatttcag cgacatgctg caagagcggc 11460
tgacgttcga ccaggcgctg gccgatgaat cgctcacgat catgacgcgg caacgcctca 11520
agatcgtgcg gcgcggcctg tttgaacagc tcgacgcggc ggccgtgcta tgagcgacca 11580
gattgaagag ctgatccggg agattgcggc caagcacggc atcgccgtcg gccgcgacga 11640
cccggtgctg atcctgcata ccatcaacgc ccggctcatg gccgacagtg cggccaagca 11700
agaggaaatc cttgccgcgt tcaaggaaga gctggaaggg atcgcccatc gttggggcga 11760
ggacgccaag gccaaagcgg agcggatgct gaacgcggcc ctggcggcca gcaaggacgc 11820
aatggcgaag gtaatgaagg acagcgccgc gcaggcggcc gaagcgatcc gcagggaaat 11880
cgacgacggc cttggccgcc agctcgcggc caaggtcgcg gacgcgcggc gcgtggcgat 11940
gatgaacatg atcgccggcg gcatggtgtt gttcgcggcc gccctggtgg tgtgggcctc 12000
gttatgaatc gcagaggcgc agatgaaaaa gcccggcgtt gccgggcttt gtttttgcgt 12060
tagctgggct tgtttgacag gcccaagctc tgactgcgcc cgcgctcgcg ctcctgggcc 12120
tgtttcttct cctgctcctg cttgcgcatc agggcctggt gccgtcgggc tgcttcacgc 12180
atcgaatccc agtcgccggc cagctcggga tgctccgcgc gcatcttgcg cgtcgccagt 12240
tcctcgatct tgggcgcgtg aatgcccatg ccttccttga tttcgcgcac catgtccagc 12300
cgcgtgtgca gggtctgcaa gcgggcttgc tgttgggcct gctgctgctg ccaggcggcc 12360
tttgtacgcg gcagggacag caagccgggg gcattggact gtagctgctg caaacgcgcc 12420
tgctgacggt ctacgagctg ttctaggcgg tcctcgatgc gctccacctg gtcatgcttt 12480
gcctgcacgt agagcgcaag ggtctgctgg taggtctgct cgatgggcgc ggattctaag 12540
agggcctgct gttccgtctc ggcctcctgg gccgcctgta gcaaatcctc gccgctgttg 12600
ccgctggact gctttactgc cggggactgc tgttgccctg ctcgcgccgt cgtcgcagtt 12660
cggcttgccc ccactcgatt gactgcttca tttcgagccg cagcgatgcg atctcggatt 12720
gcgtcaacgg acggggcagc gcggaggtgt ccggcttctc cttgggtgag tcggtcgatg 12780
ccatagccaa aggtttcctt ccaaaatgcg tccattgctg gaccgtgttt ctcattgatg 12840
cccgcaagca tcttcggctt gaccgccagg tcaagcgcgc cttcatgggc ggtcatgacg 12900
gacgccgcca tgaccttgcc gccgttgttc tcgatgtagc cgcgtaatga ggcaatggtg 12960
ccgcccatcg tcagcgtgtc atcgacaacg atgtacttct ggccggggat cacctccccc 13020
tcgaaagtcg ggttgaacgc caggcgatga tctgaaccgg ctccggttcg ggcgaccttc 13080
tcccgctgca caatgtccgt ttcgacctca aggccaaggc ggtcggccag aacgaccgcc 13140
atcatggccg gaatcttgtt gttccccgcc gcctcgacgg cgaggactgg aacgatgcgg 13200
ggcttgtcgt cgccgatcag cgtcttgagc tgggcaacag tgtcgtccga aatcaggcgc 13260
tcgaccaaat taagcgccgc ttccgcgtcg ccctgcttcg cagcctggta ttcaggctcg 13320
ttggtcaaag aaccaaggtc gccgttgcga accaccttcg ggaagtctcc ccacggtgcg 13380
cgctcggctc tgctgtagct gctcaagacg cctccctttt tagccgctaa aactctaacg 13440
agtgcgcccg cgactcaact tgacgctttc ggcacttacc tgtgccttgc cacttgcgtc 13500
ataggtgatg cttttcgcac tcccgatttc aggtacttta tcgaaatctg accgggcgtg 13560
cattacaaag ttcttcccca cctgttggta aatgctgccg ctatctgcgt ggacgatgct 13620
gccgtcgtgg cgctgcgact tatcggcctt ttgggccata tagatgttgt aaatgccagg 13680
tttcagggcc ccggctttat ctaccttctg gttcgtccat gcgccttggt tctcggtctg 13740
gacaattctt tgcccattca tgaccaggag gcggtgtttc attgggtgac tcctgacggt 13800
tgcctctggt gttaaacgtg tcctggtcgc ttgccggcta aaaaaaagcc gacctcggca 13860
gttcgaggcc ggctttccct agagccgggc gcgtcaaggt tgttccatct attttagtga 13920
actgcgttcg atttatcagt tactttcctc ccgctttgtg tttcctccca ctcgtttccg 13980
cgtctagccg acccctcaac atagcggcct cttcttgggc tgcctttgcc tcttgccgcg 14040
cttcgtcacg ctcggcttgc accgtcgtaa agcgctcggc ctgcctggcc gcctcttgcg 14100
ccgccaactt cctttgctcc tggtgggcct cggcgtcggc ctgcgccttc gctttcaccg 14160
ctgccaactc cgtgcgcaaa ctctccgctt cgcgcctggt ggcgtcgcgc tcgccgcgaa 14220
gcgcctgcat ttcctggttg gccgcgtcca gggtcttgcg gctctcttct ttgaatgcgc 14280
gggcgtcctg gtgagcgtag tccagctcgg cgcgcagctc ctgcgctcga cgctccacct 14340
cgtcggcccg ctgcgtcgcc agcgcggccc gctgctcggc tcctgccagg gcggtgcgtg 14400
cttcggccag ggcttgccgc tggcgtgcgg ccagctcggc cgcctcggcg gcctgctgct 14460
ctagcaatgt aacgcgcgcc tgggcttctt ccagctcgcg ggcctgcgcc tcgaaggcgt 14520
cggccagctc cccgcgcacg gcttccaact cgttgcgctc acgatcccag ccggcttgcg 14580
ctgcctgcaa cgattcattg gcaagggcct gggcggcttg ccagagggcg gccacggcct 14640
ggttgccggc ctgctgcacc gcgtccggca cctggactgc cagcggggcg gcctgcgccg 14700
tgcgctggcg tcgccattcg cgcatgccgg cgctggcgtc gttcatgttg acgcgggcgg 14760
ccttacgcac tgcatccacg gtcgggaagt tctcccggtc gccttgctcg aacagctcgt 14820
ccgcagccgc aaaaatgcgg tcgcgcgtct ctttgttcag ttccatgttg gctccggtaa 14880
ttggtaagaa taataatact cttacctacc ttatcagcgc aagagtttag ctgaacagtt 14940
ctcgacttaa cggcaggttt tttagcggct gaagggcagg caaaaaaagc cccgcacggt 15000
cggcgggggc aaagggtcag cgggaagggg attagcgggc gtcgggcttc ttcatgcgtc 15060
ggggccgcgc ttcttgggat ggagcacgac gaagcgcgca cgcgcatcgt cctcggccct 15120
atcggcccgc gtcgcggtca ggaacttgtc gcgcgctagg tcctccctgg tgggcaccag 15180
gggcatgaac tcggcctgct cgatgtaggt ccactccatg accgcatcgc agtcgaggcc 15240
gcgttccttc accgtctctt gcaggtcgcg gtacgcccgc tcgttgagcg gctggtaacg 15300
ggccaattgg tcgtaaatgg ctgtcggcca tgagcggcct ttcctgttga gccagcagcc 15360
gacgacgaag ccggcaatgc aggcccctgg cacaaccagg ccgacgccgg gggcagggga 15420
tggcagcagc tcgccaacca ggaaccccgc cgcgatgatg ccgatgccgg tcaaccagcc 15480
cttgaaacta tccggccccg aaacacccct gcgcattgcc tggatgctgc gccggatagc 15540
ttgcaacatc aggagccgtt tcttttgttc gtcagtcatg gtccgccctc accagttgtt 15600
cgtatcggtg tcggacgaac tgaaatcgca agagctgccg gtatcggtcc agccgctgtc 15660
cgtgtcgctg ctgccgaagc acggcgaggg gtccgcgaac gccgcagacg gcgtatccgg 15720
ccgcagcgca tcgcccagca tggccccggt cagcgagccg ccggccaggt agcccagcat 15780
ggtgctgttg gtcgccccgg ccaccagggc cgacgtgacg aaatcgccgt cattccctct 15840
ggattgttcg ctgctcggcg gggcagtgcg ccgcgccggc ggcgtcgtgg atggctcggg 15900
ttggctggcc tgcgacggcc ggcgaaaggt gcgcagcagc tcgttatcga ccggctgcgg 15960
cgtcggggcc gccgccttgc gctgcggtcg gtgttccttc ttcggctcgc gcagcttgaa 16020
cagcatgatc gcggaaacca gcagcaacgc cgcgcctacg cctcccgcga tgtagaacag 16080
catcggattc attcttcggt cctccttgta gcggaaccgt tgtctgtgcg gcgcgggtgg 16140
cccgcgccgc tgtctttggg gatcagccct cgatgagcgc gaccagtttc acgtcggcaa 16200
ggttcgcctc gaactcctgg ccgtcgtcct cgtacttcaa ccaggcatag ccttccgccg 16260
gcggccgacg gttgaggata aggcgggcag ggcgctcgtc gtgctcgacc tggacgatgg 16320
cctttttcag cttgtccggg tccggctcct tcgcgccctt ttccttggcg tccttaccgt 16380
cctggtcgcc gtcctcgccg tcctggccgt cgccggcctc cgcgtcacgc tcggcatcag 16440
tctggccgtt gaaggcatcg acggtgttgg gatcgcggcc cttctcgtcc aggaactcgc 16500
gcagcagctt gaccgtgccg cgcgtgattt cctgggtgtc gtcgtcaagc cacgcctcga 16560
cttcctccgg gcgcttcttg aaggccgtca ccagctcgtt caccacggtc acgtcgcgca 16620
cgcggccggt gttgaacgca tcggcgatct tctccggcag gtccagcagc gtgacgtgct 16680
gggtgatgaa cgccggcgac ttgccgattt ccttggcgat atcgcctttc ttcttgccct 16740
tcgccagctc gcggccaatg aagtcggcaa tttcgcgcgg ggtcagctcg ttgcgttgca 16800
ggttctcgat aacctggtcg gcttcgttgt agtcgttgtc gatgaacgcc gggatggact 16860
tcttgccggc ccacttcgag ccacggtagc ggcgggcgcc gtgattgatg atatagcggc 16920
ccggctgctc ctggttctcg cgcaccgaaa tgggtgactt caccccgcgc tctttgatcg 16980
tggcaccgat ttccgcgatg ctctccgggg aaaagccggg gttgtcggcc gtccgcggct 17040
gatgcggatc ttcgtcgatc aggtccaggt ccagctcgat agggccggaa ccgccctgag 17100
acgccgcagg agcgtccagg aggctcgaca ggtcgccgat gctatccaac cccaggccgg 17160
acggctgcgc cgcgcctgcg gcttcctgag cggccgcagc ggtgtttttc ttggtggtct 17220
tggcttgagc cgcagtcatt gggaaatctc catcttcgtg aacacgtaat cagccagggc 17280
gcgaacctct ttcgatgcct tgcgcgcggc cgttttcttg atcttccaga ccggcacacc 17340
ggatgcgagg gcatcggcga tgctgctgcg caggccaacg gtggccggaa tcatcatctt 17400
ggggtacgcg gccagcagct cggcttggtg gcgcgcgtgg cgcggattcc gcgcatcgac 17460
cttgctgggc accatgccaa ggaattgcag cttggcgttc ttctggcgca cgttcgcaat 17520
ggtcgtgacc atcttcttga tgccctggat gctgtacgcc tcaagctcga tgggggacag 17580
cacatagtcg gccgcgaaga gggcggccgc caggccgacg ccaagggtcg gggccgtgtc 17640
gatcaggcac acgtcgaagc cttggttcgc cagggccttg atgttcgccc cgaacagctc 17700
gcgggcgtcg tccagcgaca gccgttcggc gttcgccagt accgggttgg actcgatgag 17760
ggcgaggcgc gcggcctggc cgtcgccggc tgcgggtgcg gtttcggtcc agccgccggc 17820
agggacagcg ccgaacagct tgcttgcatg caggccggta gcaaagtcct tgagcgtgta 17880
ggacgcattg ccctgggggt ccaggtcgat cacggcaacc cgcaagccgc gctcgaaaaa 17940
gtcgaaggca agatgcacaa gggtcgaagt cttgccgacg ccgcctttct ggttggccgt 18000
gaccaaagtt ttcatcgttt ggtttcctgt tttttcttgg cgtccgcttc ccacttccgg 18060
acgatgtacg cctgatgttc cggcagaacc gccgttaccc gcgcgtaccc ctcgggcaag 18120
ttcttgtcct cgaacgcggc ccacacgcga tgcaccgctt gcgacactgc gcccctggtc 18180
agtcccagcg acgttgcgaa cgtcgcctgt ggcttcccat cgactaagac gccccgcgct 18240
atctcgatgg tctgctgccc cacttccagc ccctggatcg cctcctggaa ctggctttcg 18300
gtaagccgtt tcttcatgga taacacccat aatttgctcc gcgccttggt tgaacatagc 18360
ggtgacagcc gccagcacat gagagaagtt tagctaaaca tttctcgcac gtcaacacct 18420
ttagccgcta aaactcgtcc ttggcgtaac aaaacaaaag cccggaaacc gggctttcgt 18480
ctcttgccgc ttatggctct gcacccggct ccatcaccaa caggtcgcgc acgcgcttca 18540
ctcggttgcg gatcgacact gccagcccaa caaagccggt tgccgccgcc gccaggatcg 18600
cgccgatgat gccggccaca ccggccatcg cccaccaggt cgccgccttc cggttccatt 18660
cctgctggta ctgcttcgca atgctggacc tcggctcacc ataggctgac cgctcgatgg 18720
cgtatgccgc ttctcccctt ggcgtaaaac ccagcgccgc aggcggcatt gccatgctgc 18780
ccgccgcttt cccgaccacg acgcgcgcac caggcttgcg gtccagacct tcggccacgg 18840
cgagctgcgc aaggacataa tcagccgccg acttggctcc acgcgcctcg atcagctctt 18900
gcactcgcgc gaaatccttg gcctccacgg ccgccatgaa tcgcgcacgc ggcgaaggct 18960

```
ccgcagggcc ggcgtcgtga tcgccgccga gaatgccctt caccaagttc gacgacacga  19020
aaatcatgct gacggctatc accatcatgc agacggatcg cacgaacccg ctgaattgaa  19080
cacgagcacg gcacccgcga ccactatgcc aagaatgccc aaggtaaaaa ttgccggccc  19140
cgccatgaag tccgtgaatg ccccgacggc cgaagtgaag ggcaggccgc cacccaggcc  19200
gccgccctca ctgcccggca cctggtcgct gaatgtcgat gccagcacct gcggcacgtc  19260
aatgcttccg ggcgtcgcgc tcgggctgat cgcccatccc gttactgccc cgatcccggc  19320
aatggcaagg actgccagcg ctgccatttt tggggtgagg ccgttcgcgg ccgaggggcg  19380
cagcccctgg ggggatggga ggcccgcgtt agcgggccgg gagggttcga gaaggggggg  19440
caccccccctt cggcgtgcgc ggtcacgcgc acagggcgca gccctggtta aaaacaaggt  19500
ttataaatat tggtttaaaa gcaggttaaa agacaggtta gcggtggccg aaaaacgggc  19560
ggaaaccctt gcaaatgctg gattttctgc ctgtggacag cccctcaaat gtcaataggt  19620
gcgcccctca tctgtcagca ctctgcccct caagtgtcaa ggatcgcgcc cctcatctgt  19680
cagtagtcgc gcccctcaag tgtcaatacc gcagggcact tatccccagg cttgtccaca  19740
tcatctgtgg gaaactcgcg taaaatcagg cgttttcgcc gatttgcgag gctggccagc  19800
tccacgtcgc cggccgaaat cgagcctgcc cctcatctgt caacgccgcg ccgggtgagt  19860
cggcccctca agtgtcaacg tccgcccctc atctgtcagt gagggccaag ttttccgcga  19920
ggtatccaca acgccggcgg ccgcggtgtc tcgcacacgg cttcgacggc gtttctggcg  19980
cgtttgcagg gccatagacg gccgccagcc cagcggcgag ggcaaccagc ccggtgagcg  20040
tcggaaaggc gctggaagcc ccgtagcgac gcggagaggg gcgagacaag ccaagggcgc  20100
aggctcgatg cgcagcacga catagccggt tctcgcaagg acgagaattt ccctgcggtg  20160
cccctcaagt gtcaatgaaa gtttccaacg cgagccattc gcgagagcct tgagtccacg  20220
ctagatgaga gctttgttgt aggtggacca gttggtgatt ttgaactttt gctttgccac  20280
ggaacggtct gcgttgtcgg gaagatgcgt gatctgatcc ttcaactcag caaaagttcg  20340
atttattcaa caaagccacg ttgtgtctca aaatctctga tgttacattg cacaagataa  20400
aaatatatca tcatgaacaa taaaactgtc tgcttacata aacagtaata caaggggtgt  20460
tatgagccat attcaacggg aaacgtcttg ctcgactcta gagctcgttc ctcgaggcct  20520
cgaggcctcg aggaacggta cctgcgggga agcttacaat aatgtgtgtt gttaagtctt  20580
gttgcctgtc atcgtctgac tgactttcgt cataaatccc ggcctccgta acccagcttt  20640
gggcaagctc acggatttga tccggcggaa cgggaatatc gagatgccgg gctgaacgct  20700
gcagttccag ctttcccttt cgggacaggt actccagctg attgattatc tgctgaaggg  20760
tcttggttcc acctcctggc acaatgcgaa tgattacttg agcgcgatcg ggcatccaat  20820
tttctcccgt caggtgcgtg gtcaagtgct acaaggcacc tttcagtaac gagcgaccgt  20880
cgatccgtcg ccgggatacg gacaaaatgg agcgcagtag tccatcgagg gcggcgaaag  20940
cctcgccaaa agcaatacgt tcatctcgca cagcctccag atccgatcga gggtcttcgg  21000
cgtaggcaga tagaagcatg gatacattgc ttgagagtat tccgatggac tgaagtatgg  21060
cttccatctt ttctcgtgtg tctgcatcta tttcgagaaa gcccccgatg cggcgcaccg  21120
caacgcgaat tgccatacta tccgaaagtc ccagcaggcg cgcttgatag gaaaaggttt  21180
catactcggc cgatcgcaga cgggcactca cgaccttgaa cccttcaact ttcagggatc  21240
gatgctggtt gatggtagtc tcactcgacg tggctctggt gtgttttgac atagcttcct  21300
ccaaagaaag cggaaggtct ggatactcca gcacgaaatg tgcccgggta gacggatgga  21360
```

agtctagccc tgctcaatat gaaatcaaca gtacatttac agtcaatact gaatatactt 21420
gctacatttg caattgtctt ataacgaatg tgaaataaaa atagtgtaac aacgctttta 21480
ctcatcgata atcacaaaaa catttatacg aacaaaaata caaatgcact ccggtttcac 21540
aggataggcg ggatcagaat atgcaacttt tgacgttttg ttctttcaaa gggggtgctg 21600
gcaaaaccac cgcactcatg ggcctttgcg ctgctttggc aaatgacggt aaacgagtgg 21660
ccctctttga tgccgacgaa aaccggcctc tgacgcgatg gagagaaaac gccttacaaa 21720
gcagtactgg gatcctcgct gtgaagtcta ttccgccgac gaaatgcccc ttcttgaagc 21780
agcctatgaa aatgccgagc tcgaaggatt tgattatgcg ttggccgata cgcgtggcgg 21840
ctcgagcgag ctcaacaaca caatcatcgc tagctcaaac ctgcttctga tccccaccat 21900
gctaacgccg ctcgacatcg atgaggcact atctacctac cgctacgtca tcgagctgct 21960
gttgagtgaa aatttggcaa ttcctacagc tgttttgcgc caacgcgtcc cggtcggccg 22020
attgacaaca tcgcaacgca ggatgtcaga gacgctagag agccttccag ttgtaccgtc 22080
tcccatgcat gaaagagatg catttgccgc gatgaaagaa cgcggcatgt tgcatcttac 22140
attactaaac acgggaactg atccgacgat gcgcctcata gagaggaatc ttcggattgc 22200
gatggaggaa gtcgtggtca tttcgaaact gatcagcaaa atcttggagg cttgaagatg 22260
gcaattcgca agcccgcatt gtcggtcggc gaagcacggc ggcttgctgg tgctcgaccc 22320
gagatccacc atcccaaccc gacacttgtt ccccagaagc tggacctcca gcacttgcct 22380
gaaaaagccg acgagaaaga ccagcaacgt gagcctctcg tcgccgatca catttacagt 22440
cccgatcgac aacttaagct aactgtggat gcccttagtc cacctccgtc cccgaaaaag 22500
ctccaggttt ttctttcagc gcgaccgccc gcgcctcaag tgtcgaaaac atatgacaac 22560
ctcgttcggc aatacagtcc ctcgaagtcg ctacaaatga ttttaaggcg cgcgttggac 22620
gatttcgaaa gcatgctggc agatggatca tttcgcgtgg ccccgaaaag ttatccgatc 22680
ccttcaacta cagaaaaatc cgttctcgtt cagacctcac gcatgttccc ggttgcgttg 22740
ctcgaggtcg ctcgaagtca ttttgatccg ttggggttgg agaccgctcg agctttcggc 22800
cacaagctgg ctaccgccgc gctcgcgtca ttctttgctg gagagaagcc atcgagcaat 22860
tggtgaagag ggacctatcg gaacccctca ccaaatattg agtgtaggtt tgaggccgct 22920
ggccgcgtcc tcagtcacct tttgagccag ataattaaga gccaaatgca attggctcag 22980
gctgccatcg tccccccgtg cgaaacctgc acgtccgcgt caaagaaata accggcacct 23040
cttgctgttt ttatcagttg agggcttgac ggatccgcct caagtttgcg gcgcagccgc 23100
aaaatgagaa catctatact cctgtcgtaa acctcctcgt cgcgtactcg actggcaatg 23160
agaagttgct cgcgcgatag aacgtcgcgg ggtttctcta aaaacgcgag gagaagattg 23220
aactcacctg ccgtaagttt cacctcaccg ccagcttcgg acatcaagcg acgttgcctg 23280
agattaagtg tccagtcagt aaaacaaaaa gaccgtcggt ctttggagcg gacaacgttg 23340
gggcgcacgc gcaaggcaac ccgaatgcgt gcaagaaact ctctcgtact aaacggctta 23400
gcgataaaat cacttgctcc tagctcgagt gcaacaactt tatccgtctc ctcaaggcgg 23460
tcgccactga taattatgat tggaatatca gactttgccg ccagatttcg aacgatctca 23520
agcccatctt cacgacctaa atttagatca acaaccacga catcgaccgt cgcggaagag 23580
agtactctag tgaactgggt gctgtcggct accgcggtca ctttgaaggc gtggatcgta 23640
aggtattcga taataagatg ccgcatagcg acatcgtcat cgataagaag aacgtgtttc 23700
aacggctcac ctttcaatct aaaatctgaa cccttgttca cagcgcttga gaaattttca 23760

```
cgtgaaggat gtacaatcat ctccagctaa atgggcagtt cgtcagaatt gcggctgacc  23820
gcggatgacg aaaatgcgaa ccaagtattt caattttatg acaaaagttc tcaatcgttg  23880
ttacaagtga aacgcttcga ggttacagct actattgatt aaggagatcg cctatggtct  23940
cgccccggcg tcgtgcgtcc gccgcgagcc agatctcgcc tacttcataa acgtcctcat  24000
aggcacggaa tggaatgatg acatcgatcg ccgtagagag catgtcaatc agtgtgcgat  24060
cttccaagct agcaccttgg gcgctacttt tgacaaggga aaacagtttc ttgaatcctt  24120
ggattggatt cgcgccgtgt attgttgaaa tcgatcccgg atgtcccgag acgacttcac  24180
tcagataagc ccatgctgca tcgtcgcgca tctcgccaag caatatccgg tccggccgca  24240
tacgcagact tgcttggagc aagtgctcgg cgctcacagc acccagccca gcaccgttct  24300
tggagtagag tagtctaaca tgattatcgt gtggaatgac gagttcgagc gtatcttcta  24360
tggtgattag cctttcctgg ggggggatgg cgctgatcaa ggtcttgctc attgttgtct  24420
tgccgcttcc ggtagggcca catagcaaca tcgtcagtcg gctgacgacg catgcgtgca  24480
gaaacgcttc caaatccccg ttgtcaaaat gctgaaggat agcttcatca tcctgatttt  24540
ggcgtttcct tcgtgtctgc cactggttcc acctcgaagc atcataacgg gaggagactt  24600
ctttaagacc agaaacacgc gagcttggcc gtcgaatggt caagctgacg gtgcccgagg  24660
gaacggtcgg cggcagacag atttgtagtc gttcaccacc aggaagttca gtggcgcaga  24720
gggggttacg tggtccgaca tcctgctttc tcagcgcgcc cgctaaaata gcgatatctt  24780
caagatcatc ataagagacg ggcaaaggca tcttggtaaa aatgccggct tggcgcacaa  24840
atgcctctcc aggtcgattg atcgcaattt cttcagtctt cgggtcatcg agccattcca  24900
aaatcggctt cagaagaaag cgtagttgcg gatccacttc catttacaat gtatcctatc  24960
tctaagcgga aatttgaatt cattaagagc ggcggttcct cccccgcgtg gcgccgccag  25020
tcaggcggag ctggtaaaca ccaaagaaat cgaggtcccg tgctacgaaa atggaaacgg  25080
tgtcaccctg attcttcttc agggttggcg gtatgttgat ggttgcctta agggctgtct  25140
cagttgtctg ctcaccgtta ttttgaaagc tgttgaagct catcccgcca cccgagctgc  25200
cggcgtaggt gctagctgcc tggaaggcgc cttgaacaac actcaagagc atagctccgc  25260
taaaacgctg ccagaagtgg ctgtcgaccg agcccggcaa tcctgagcga ccgagttcgt  25320
ccgcgcttgg cgatgttaac gagatcatcg catggtcagg tgtctcggcg cgatcccaca  25380
acacaaaaac gcgcccatct ccctgttgca agccacgctg tatttcgcca acaacggtgg  25440
tgccacgatc aagaagcacg atattgttcg ttgttccacg aatatcctga ggcaagacac  25500
actttacata gcctgccaaa tttgtgtcga ttgcggtttg caagatgcac ggaattattg  25560
tcccttgcgt taccataaaa tcggggtgcg gcaagagcgt ggcgctgctg ggctgcagct  25620
cggtgggttt catacgtatc gacaaatcgt tctcgccgga cacttcgcca ttcggcaagg  25680
agttgtcgtc acgcttgcct tcttgtcttc ggcccgtgtc gccctgaatg gcgcgtttgc  25740
tgaccccttg atcgccgctg ctatatgcaa aaatcggtgt ttcttccggc cgtggctcat  25800
gccgctccgg ttcgcccctc ggcggtagag gagcagcagg ctgaacagcc tcttgaaccg  25860
ctggaggatc cggcggcacc tcaatcggag ctggatgaaa tggcttggtg tttgttgcga  25920
tcaaagttga cggcgatgcg ttctcattca ccttcttttg gcgcccacct agccaaatga  25980
ggcttaatga taacgcgaga acgacacctc cgacgatcaa tttctgagac cccgaaagac  26040
gccggcgatg tttgtcggag accagggatc cagatgcatc aacctcatgt gccgcttgct  26100
gactatcgtt attcatccct tcgccccctt caggacgcgt ttcacatcgg gcctcaccgt  26160
```

gcccgtttgc ggcctttggc caacgggatc gtaagcggtg ttccagatac atagtactgt 26220
gtggccatcc ctcagacgcc aacctcggga aaccgaagaa atctcgacat cgctcccttt 26280
aactgaatag ttggcaacag cttccttgcc atcaggattg atggtgtaga tggagggtat 26340
gcgtacattg cccggaaagt ggaataccgt cgtaaatcca ttgtcgaaga cttcgagtgg 26400
caacagcgaa cgatcgcctt gggcgacgta gtgccaatta ctgtccgccg caccaagggc 26460
tgtgacaggc tgatccaata aattctcagc tttccgttga tattgtgctt ccgcgtgtag 26520
tctgtccaca acagccttct gttgtgcctc ccttcgccga gccgccgcat cgtcggcggg 26580
gtaggcgaat tggacgctgt aatagagatc gggctgctct ttatcgaggt gggacagagt 26640
cttggaactt atactgaaaa cataacggcg catcccggag tcgcttgcgg ttagcacgat 26700
tactggctga ggcgtgagga cctggcttgc cttgaaaaat agataatttc cccgcggtag 26760
ggctgctaga tctttgctat ttgaaacggc aaccgctgtc accgtttcgt tcgtggcgaa 26820
tgttacgacc aaagtagctc caaccgccgt cgagaggcgc accacttgat cgggattgta 26880
agccaaataa cgcatgcgcg gatctagctt gcccgccatt ggagtgtctt cagcctccgc 26940
accagtcgca gcggcaaata aacatgctaa aatgaaaagt gcttttctga tcatggttcg 27000
ctgtggccta cgtttgaaac ggtatcttcc gatgtctgat aggaggtgac aaccagacct 27060
gccgggttgg ttagtctcaa tctgccgggc aagctggtca ccttttcgta gcgaactgtc 27120
gcggtccacg tactcaccac aggcattttg ccgtcaacga cgagggtcct tttatagcga 27180
atttgctgcg tgcttggagt tacatcattt gaagcgatgt gctcgacctc caccctgccg 27240
cgtttgccaa gaatgacttg aggcgaactg ggattgggat agttgaagaa ttgctggtaa 27300
tcctggcgca ctgttggggc actgaagttc gataccaggt cgtaggcgta ctgagcggtg 27360
tcggcatcat aactctcgcg caggcgaacg tactcccaca atgaggcgtt aacgacggcc 27420
tcctcttgag ttgcaggcaa tcgcgagaca gacacctcgc tgtcaacggt gccgtccggc 27480
cgtatccata gatatacggg cacaagcctg ctcaacggca ccattgtggc tatagcgaac 27540
gcttgagcaa catttcccaa aatcgcgata gctgcgacag ctgcaatgag tttggagaga 27600
cgtcgcgccg atttcgctcg cgcggtttga aaggcttcta cttccttata gtgctcggca 27660
aggctttcgc gcgccactag catggcatat tcaggccccg tcatagcgtc cacccgaatt 27720
gccgagctga agatctgacg gagtaggctg ccatcgcccc acattcagcg ggaagatcgg 27780
gcctttgcag ctcgctaatg tgtcgtttgt ctggcagccg ctcaaagcga caactaggca 27840
cagcaggcaa tacttcatag aattctccat tgaggcgaat ttttgcgcga cctagcctcg 27900
ctcaacctga gcgaagcgac ggtacaagct gctggcagat tgggttgcgc cgctccagta 27960
actgcctcca atgttgccgg cgatcgccgg caaagcgaca atgagcgcat cccctgtcag 28020
aaaaaacata tcgagttcgt aaagaccaat gatcttggcc gcggtcgtac cggcgaaggt 28080
gattacacca agcataaggg tgagcgcagt cgcttcggtt aggatgacga tcgttgccac 28140
gaggtttaag aggagaagca agagaccgta ggtgataagt tgcccgatcc acttagctgc 28200
gatgtcccgc gtgcgatcaa aaatatatcc gacgaggatc agaggcccga tcgcgagaag 28260
cactttcgtg agaattccaa cggcgtcgta aactccgaag gcagaccaga gcgtgccgta 28320
aaggacccac tgtgcccctt ggaaagcaag gatgtcctgg tcgttcatcg gaccgatttc 28380
ggatgcgatt ttctgaaaaa cggcctgggt cacggcgaac attgtatcca actgtgccgg 28440
aacagtctgc agaggcaagc cggttacact aaactgctga acaaagtttg ggaccgtctt 28500
ttcgaagatg gaaaccacat agtcttggta gttagcctgc ccaacaatta gagcaacaac 28560

-continued

```
gatggtgacc gtgatcaccc gagtgatacc gctacgggta tcgacttcgc cgcgtatgac  28620
taaaataccc tgaacaataa tccaaagagt gacacaggcg atcaatggcg cactcaccgc  28680
ctcctggata gtctcaagca tcgagtccaa gcctgtcgtg aaggctacat cgaagatcgt  28740
atgaatggcc gtaaacggcg ccggaatcgt gaaattcatc gattggacct gaacttgact  28800
ggtttgtcgc ataatgttgg ataaaatgag ctcgcattcg gcgaggatgc gggcggatga  28860
acaaatcgcc cagccttagg ggagggcacc aaagatgaca gcggtctttt gatgctcctt  28920
gcgttgagcg gccgcctctt ccgcctcgtg aaggccggcc tgcgcggtag tcatcgttaa  28980
taggcttgtc gcctgtacat tttgaatcat tgcgtcatgg atctgcttga gaagcaaacc  29040
attggtcacg gttgcctgca tgatattgcg agatcgggaa agctgagcag acgtatcagc  29100
attcgccgtc aagcgtttgt ccatcgtttc cagattgtca gccgcaatgc cagcgctgtt  29160
tgcggaaccg gtgatctgcg atcgcaacag gtccgcttca gcatcactac ccacgactgc  29220
acgatctgta tcgctggtga tcgcacgtgc cgtggtcgac attggcattc gcggcgaaaa  29280
catttcattg tctaggtcct tcgtcgaagg atactgattt ttctggttga gcgaagtcag  29340
tagtccagta acgccgtagg ccgacgtcaa catcgtaacc atcgctatag tctgagtgag  29400
attctccgca gtcgcgagcg cagtcgcgag cgtctcagcc tccgttgccg ggtcgctaac  29460
aacaaactgc gcccgcgcgg gctgaatata tagaaagctg caggtcaaaa ctgttgcaat  29520
aagttgcgtc gtcttcatcg tttcctacct tatcaatctt ctgcctcgtg gtgacgggcc  29580
atgaattcgc tgagccagcc agatgagttg ccttcttgtg cctcgcgtag tcgagttgca  29640
aagcgcaccg tgttggcacg ccccgaaagc acggcgacat attcacgcat atcccgcaga  29700
tcaaattcgc agatgacgct tccactttct cgtttaagaa gaaacttacg gctgccgacc  29760
gtcatgtctt cacggatcgc ctgaaattcc ttttcggtac atttcagtcc atcgacataa  29820
gccgatcgat ctgcggttgg tgatggatag aaaatcttcg tcatacattg cgcaaccaag  29880
ctggctccta gcggcgattc cagaacatgc tctggttgct gcgttgccag tattagcatc  29940
ccgttgtttt ttcgaacggt caggaggaat ttgtcgacga cagtcgaaaa tttagggttt  30000
aacaaatagg cgcgaaactc atcgcagctc atcacaaaac ggcggccgtc gatcatggct  30060
ccaatccgat gcaggagata tgctgcagcg ggagcgcata cttcctcgta ttcgagaaga  30120
tgcgtcatgt cgaagccggt aatcgacgga tctaacttta cttcgtcaac ttcgccgtca  30180
aatgcccagc caagcgcatg gccccggcac cagcgttgga gccgcgctcc tgcgccttcg  30240
gcgggcccat gcaacaaaaa ttcacgtaac cccgcgattg aacgcatttg tggatcaaac  30300
gagagctgac gatggatacc acggaccaga cggcggttct cttccggaga aatcccaccc  30360
cgaccatcac tctcgatgag agccacgatc cattcgcgca gaaaatcgtg tgaggctgct  30420
gtgttttcta ggccacgcaa cggcgccaac ccgctgggtg tgcctctgtg aagtgccaaa  30480
tatgttcctc ctgtggcgcg aaccagcaat tcgccacccc ggtccttgtc aaagaacacg  30540
accgtacctg cacggtcgac catgctctgt tcgagcatgg ctagaacaaa catcatgagc  30600
gtcgtcttac ccctcccgat aggcccgaat attgccgtca tgccaacatc gtgctcatgc  30660
gggatatagt cgaaaggcgt tccgccattg gtacgaaatc gggcaatcgc gttgccccag  30720
tggcctgagc tggcgccctc tggaaagttt tcgaaagaga caaaccctgc gaaattgcgt  30780
gaagtgattg cgccagggcg tgtgcgccac ttaaaattcc ccggcaattg ggaccaatag  30840
gccgcttcca taccaatacc ttcttggaca accacggcac ctgcatccgc cattcgtgtc  30900
cgagcccgcg cgcccctgtc cccaagacta ttgagatcgt ctgcatagac gcaaaggctc  30960
```

aaatgatgtg agcccataac gaattcgttg ctcgcaagtg cgtcctcagc ctcggataat 31020
ttgccgattt gagtcacggc tttatcgccg gaactcagca tctggctcga tttgaggcta 31080
agtttcgcgt gcgcttgcgg gcgagtcagg aacgaaaaac tctgcgtgag aacaagtgga 31140
aaatcgaggg atagcagcgc gttgagcatg cccggccgtg tttttgcagg gtattcgcga 31200
aacgaataga tggatccaac gtaactgtct tttggcgttc tgatctcgag tcctcgcttg 31260
ccgcaaatga ctctgtcggt ataaatcgaa gcgccgagtg agccgctgac gaccggaacc 31320
ggtgtgaacc gaccagtcat gatcaaccgt agcgcttcgc caatttcggt gaagagcaca 31380
ccctgcttct cgcggatgcc aagacgatgc aggccatacg ctttaagaga gccagcgaca 31440
acatgccaaa gatcttccat gttcctgatc tggcccgtga gatcgttttc cctttttccg 31500
cttagcttgg tgaacctcct ctttaccttc cctaaagccg cctgtgggta gacaatcaac 31560
gtaaggaagt gttcattgcg gaggagttgg ccggagagca cgcgctgttc aaaagcttcg 31620
ttcaggctag cggcgaaaac actacggaag tgtcgcggcg ccgatgatgg cacgtcggca 31680
tgacgtacga ggtgagcata tattgacaca tgatcatcag cgatattgcg caacagcgtg 31740
ttgaacgcac gacaacgcgc attgcgcatt tcagtttcct caagctcgaa tgcaacgcca 31800
tcaattctcg caatggtcat gatcgatccg tcttcaagaa ggacgatatg gtcgctgagg 31860
tggccaatat aagggagata gatctcaccg gatctttcgg tcgttccact cgcgccgagc 31920
atcacaccat tcctctccct cgtgggggaa ccctaattgg atttgggcta acagtagcgc 31980
ccccccaaac tgcactatca atgcttcttc ccgcggtccg caaaaatagc aggacgacgc 32040
tcgccgcatt gtagtctcgc tccacgatga gccgggctgc aaaccataac ggcacgagaa 32100
cgacttcgta gagcgggttc tgaacgataa cgatgacaaa gccggcgaac atcatgaata 32160
accctgccaa tgtcagtggc accccaagaa acaatgcggg ccgtgtggct gcgaggtaaa 32220
gggtcgattc ttccaaacga tcagccatca actaccgcca gtgagcgttt ggccgaggaa 32280
gctcgcccca aacatgataa caatgccgcc gacgacgccg gcaaccagcc caagcgaagc 32340
ccgcccgaac atccaggaga tcccgatagc gacaatgccg agaacagcga gtgactggcc 32400
gaacggacca aggataaacg tgcatatatt gttaaccatt gtggcggggt cagtgccgcc 32460
acccgcagat tgcgctgcgg cgggtccgga tgaggaaatg ctccatgcaa ttgcaccgca 32520
caagcttggg gcgcagctcg atatcacgcg catcatcgca ttcgagagcg agaggcgatt 32580
tagatgtaaa cggtatctct caaagcatcg catcaatgcg cacctcctta gtataagtcg 32640
aataagactt gattgtcgtc tgcggatttg ccgttgtcct ggtgtggcgg tggcggagcg 32700
attaaaccgc cagcgccatc ctcctgcgag cggcgctgat atgaccccca aacatcccac 32760
gtctcttcgg attttagcgc ctcgtgatcg tcttttggag gctcgattaa cgcgggcacc 32820
agcgattgag cagctgtttc aacttttcgc acgtagccgt ttgcaaaacc gccgatgaaa 32880
ttaccggtgt tgtaagcgga gatcgcccga cgaagcgcaa attgcttctc gtcaatcgtt 32940
tcgccgcctg cataacgact tttcagcatg tttgcagcgg cagataatga tgtgcacgcc 33000
tggagcgcac cgtcaggtgt cagaccgagc atagaaaaat ttcgagagtt tatttgcatg 33060
aggccaacat ccagcgaatg ccgtgcatcg agacggtgcc tgacgacttg ggttgcttgg 33120
ctgtgatctt gccagtgaag cgtttcgccg gtcgtgttgt catgaatcgc taaaggatca 33180
aagcgactct ccaccttagc tatcgccgca agcgtagatg tcgcaactga tggggcacac 33240
ttgcgagcaa catggtcaaa ctcagcagat gagagtggcg tggcaaggct cgacgaacag 33300
aaggagacca tcaaggcaag agaaagcgac cccgatctct taagcatacc ttatctcctt 33360

-continued

```
agctcgcaac taacaccgcc tctcccgttg gaagaagtgc gttgttttat gttgaagatt  33420
atcgggaggg tcggttactc gaaaatttc aattgcttct ttatgatttc aattgaagcg  33480
agaaacctcg cccggcgtct tggaacgcaa catggaccga gaaccgcgca tccatgacta  33540
agcaaccgga tcgacctatt caggccgcag ttggtcaggt caggctcaga acgaaaatgc  33600
tcggcgaggt tacgctgtct gtaaacccat tcgatgaacg ggaagcttcc ttccgattgc  33660
tcttggcagg aatattggcc catgcctgct tgcgctttgc aaatgctctt atcgcgttgg  33720
tatcatatgc cttgtccgcc agcagaaacg cactctaagc gattatttgt aaaaatgttt  33780
cggtcatgcg gcggtcatgg gcttgacccg ctgtcagcgc aagacggatc ggtcaaccgt  33840
cggcatcgac aacagcgtga atcttggtgg tcaaaccgcc acgggaacgt cccatacagc  33900
catcgtcttg atcccgctgt ttcccgtcgc cgcatgttgg tggacgcgga cacaggaact  33960
gtcaatcatg acgacattct atcgaaagcc ttggaaatca cactcagaat atgatcccag  34020
acgtctgcct cacgccatcg tacaaagcga ttgtagcagg ttgtacagga accgtatcga  34080
tcaggaacgt ctgcccaggg cgggcccgtc cggaagcgcc acaagatgac attgatcacc  34140
cgcgtcaacg cgcggcacgc gacgcggctt atttgggaac aaaggactga acaacagtcc  34200
attcgaaatc ggtgacatca aagcggggac gggttatcag tggcctccaa gtcaagcctc  34260
aatgaatcaa aatcagaccg atttgcaaac ctgatttatg agtgtgcggc ctaaatgatg  34320
aaatcgtcct tctagatcgc ctccgtggtg tagcaacacc tcgcagtatc gccgtgctga  34380
ccttggccag ggaattgact ggcaagggtg ctttcacatg accgctcttt tggccgcgat  34440
agatgatttc gttgctgctt tgggcacgta gaaggagaga agtcatatcg gagaaattcc  34500
tcctggcgcg agagcctgct ctatcgcgac ggcatcccac tgtcgggaac agaccggatc  34560
attcacgagg cgaaagtcgt caacacatgc gttataggca tcttcccttg aaggatgatc  34620
ttgttgctgc caatctggag gtgcggcagc cgcaggcaga tgcgatctca gcgcaacttg  34680
cggcaaaaca tctcactcac ctgaaaacca ctagcgagtc tcgcgatcag acgaaggcct  34740
tttacttaac gacacaatat ccgatgtctg catcacaggc gtcgctatcc cagtcaatac  34800
taaagcggtg caggaactaa agattactga tgacttaggc gtgccacgag gcctgagacg  34860
acgcgcgtag acagtttttt gaaatcatta tcaaagtgat ggcctccgct gaagcctatc  34920
acctctgcgc cggtctgtcg gagagatggg caagcattat tacggtcttc gcgcccgtac  34980
atgcattgga cgattgcagg gtcaatggat ctgagatcat ccagaggatt gccgccctta  35040
ccttccgttt cgagttggag ccagccccta aatgagacga catagtcgac ttgatgtgac  35100
aatgccaaga gagagatttg cttaacccga tttttttgct caagcgtaag cctattgaag  35160
cttgccggca tgacgtccgc gccgaaagaa tatcctacaa gtaaaacatt ctgcacaccg  35220
aaatgcttgg tgtagacatc gattatgtga ccaagatcct tagcagtttc gcttggggac  35280
cgctccgacc agaaataccg aagtgaactg acgccaatga caggaatccc ttccgtctgc  35340
agataggtac catcgataga tctgctgcct cgcgcgtttc ggtgatgacg gtgaaaacct  35400
ctgacacatg cagctcccgg agacggtcac agcttgtctg taagcggatg ccgggagcag  35460
acaagcccgt cagggcgcgt cagcgggtgt tggcgggtgt cggggcgcag ccatgaccca  35520
gtcacgtagc gatagcggag tgtatactgg cttaactatg cggcatcaga gcagattgta  35580
ctgagagtgc accatatgcg gtgtgaaata ccgcacagat gcgtaaggag aaaataccgc  35640
atcaggcgct cttccgcttc ctcgctcact gactcgctgc gctcggtcgt tcggctgcgg  35700
cgagcggtat cagctcactc aaaggcggta atacggttat ccacagaatc aggggataac  35760
```

gcaggaaaga acatgtgagc aaaaggccag caaaaggcca ggaaccgtaa aaaggccgcg 35820
ttgctggcgt ttttccatag gctccgcccc cctgacgagc atcacaaaaa tcgacgctca 35880
agtcagaggt ggcgaaaccc gacaggacta taaagatacc aggcgtttcc ccctggaagc 35940
tccctcgtgc gctctcctgt tccgaccctg ccgcttaccg gatacctgtc cgcctttctc 36000
ccttcgggaa gcgtggcgct ttctcatagc tcacgctgta ggtatctcag ttcggtgtag 36060
gtcgttcgct ccaagctggg ctgtgtgcac gaaccccccg ttcagcccga ccgctgcgcc 36120
ttatccggta actatcgtct tgagtccaac ccggtaagac acgacttatc gccactggca 36180
gcagccactg gtaacaggat tagcagagcg aggtatgtag gcggtgctac agagttcttg 36240
aagtggtggc ctaactacgg ctacactaga aggacagtat ttggtatctg cgctctgctg 36300
aagccagtta ccttcggaaa aagagttggt agctcttgat ccggcaaaca aaccaccgct 36360
ggtagcggtg gtttttttgt ttgcaagcag cagattacgc gcagaaaaaa aggatctcaa 36420
gaagatcctt tgatcttttc tacggggtct gacgctcagt ggaacgaaaa ctcacgttaa 36480
gggattttgg tcatgagatt atcaaaaagg atcttcacct agatcctttt aaattaaaaa 36540
tgaagtttta aatcaatcta aagtatatat gagtaaactt ggtctgacag ttaccaatgc 36600
ttaatcagtg aggcacctat ctcagcgatc tgtctatttc gttcatccat agttgcctga 36660
ctccccgtcg tgtagataac tacgatacgg gagggcttac catctggccc cagtgctgca 36720
atgataccgc gagacccacg ctcaccggct ccagatttat cagcaataaa ccagccagcc 36780
ggaagggccg agcgcagaag tggtcctgca actttatccg cctccatcca gtctattaat 36840
tgttgccggg aagctagagt aagtagttcg ccagttaata gtttgcgcaa cgttgttgcc 36900
attgctgcag gggggggggg gggggggac ttccattgtt cattccacgg acaaaaacag 36960
agaaaggaaa cgacagaggc caaaaagcct cgctttcagc acctgtcgtt tcctttcttt 37020
tcagagggta ttttaaataa aaacattaag ttatgacgaa gaagaacgga aacgccttaa 37080
accggaaaat ttcataaat agcgaaaacc cgcgaggtcg ccgccccgta acctgtcgga 37140
tcaccggaaa ggacccgtaa agtgataatg attatcatct acatatcaca acgtgcgtgg 37200
aggccatcaa accacgtcaa ataatcaatt atgacgcagg tatcgtatta attgatctgc 37260
atcaacttaa cgtaaaaaca acttcagaca atacaaatca gcgacactga atacggggca 37320
acctcatgtc cccccccccc cccccctgc aggcatcgtg gtgtcacgct cgtcgtttgg 37380
tatggcttca ttcagctccg gttcccaacg atcaaggcga gttacatgat cccccatgtt 37440
gtgcaaaaaa gcggttagct ccttcggtcc tccgatcgtt gtcagaagta agttggccgc 37500
agtgttatca ctcatggtta tggcagcact gcataattct cttactgtca tgccatccgt 37560
aagatgcttt tctgtgactg gtgagtactc aaccaagtca ttctgagaat agtgtatgcg 37620
gcgaccgagt tgctcttgcc cggcgtcaac acgggataat accgcgccac atagcagaac 37680
tttaaaagtg ctcatcattg gaaaacgttc ttcggggcga aaactctcaa ggatcttacc 37740
gctgttgaga tccagttcga tgtaacccac tcgtgcaccc aactgatctt cagcatcttt 37800
tactttcacc agcgtttctg ggtgagcaaa aacaggaagg caaaatgccg caaaaaaggg 37860
aataagggcg acacggaaat gttgaatact catactcttc ctttttcaat attattgaag 37920
catttatcag ggttattgtc tcatgagcgg atacatattt gaatgtattt agaaaaataa 37980
acaaataggg gttccgcgca catttccccg aaaagtgcca cctgacgtct aagaaaccat 38040
tattatcatg acattaacct ataaaaatag gcgtatcacg aggccctttc gtcttcaaga 38100
attggtcgac gatcttgctg cgttcggata ttttcgtgga gttcccgcca cagacccgga 38160
ttgaaggcga gatccagcaa ctcgcgccag atcatcctgt gacggaactt tggcgcgtga 38220
tgactggcca ggacgtcggc cgaaagagcg acaagcagat cacgcttttc gacagcgtcg 38280
gatttgcgat cgaggatttt tcggcgctgc gctacgtccg cgaccgcgtt gagggatcaa 38340
gccacagcag cccactcgac cttctagccg acccagacga gccaagggat ctttttggaa 38400
tgctgctccg tcgtcaggct ttccgacgtt tgggtggttg aacagaagtc attatcgtac 38460
ggaatgccaa gcactcccga ggggaaccct gtggttggca tgcacataca aatggacgaa 38520
cggataaacc ttttcacgcc cttttaaata tccgttattc taataaacgc tcttttctct 38580
taggtttacc cgccaatata tcctgtcaaa cactgatagt ttaaactgaa ggcgggaaac 38640
gacaatctga tcatgagcgg agaattaagg gagtcacgtt atgacccccg ccgatgacgc 38700
gggacaagcc gttttacgtt tggaactgac agaaccgcaa cgttgaagga gccactcagc 38760
aagctggtac gattgtaata cgactcacta tagggcgaat tgagcgctgt ttaaacgctc 38820
ttcaactgga agagcggtta cccggaccga agcttgaagt tcctattccg aagttcctat 38880
tctctagaaa gtataggaac ttcagatctc gatgctcacc ctgttgtttg gtgttacttc 38940
tgcaggtcga ctctagagga tccaccatga gcccagaacg acgcccggcc gacatccgcc 39000
gtgccaccga ggcggacatg ccggcggtct gcaccatcgt caaccactac atcgagacaa 39060
gcacggtcaa cttccgtacc gagccgcagg aaccgcagga ctggacggac gacctcgtcc 39120
gtctgcggga gcgctatccc tggctcgtcg ccgaggtgga cggcgaggtc gccggcatcg 39180
cctacgcggg cccctggaag gcacgcaacg cctacgactg gacggccgag tcgaccgtgt 39240
acgtctcccc ccgccaccag cggacgggac tgggctccac gctctacacc cacctgctga 39300
agtccctgga ggcacagggc ttcaagagcg tggtcgctgt catcgggctg cccaacgacc 39360
cgagcgtgcg catgcacgag gcgctcggat atgccccccg cggcatgctg cgggcggccg 39420
gcttcaagca cgggaactgg catgacgtgg gtttctggca gctggacttc agcctgccgg 39480
taccgccccg tccggtcctg cccgtcaccg agatctgatc cgtcgaccaa cctagacttg 39540
tccatcttct ggattggcca acttaattaa tgtatgaaat aaaaggatgc acacatagtg 39600
acatgctaat cactataatg tgggcatcaa agttgtgtgt tatgtgtaat tactagttat 39660
ctgaataaaa gagaaagaga tcatccatat ttcttatcct aaatgaatgt cacgtgtctt 39720
tataattctt tgatgaacca gatgcatttc attaaccaaa tccatataca tataaatatt 39780
aatcatatat aattaatatc aattgggtta gcaaaacaaa tctagtctag gtgtgttttg 39840
cgaattgcgg ccgcgatctg gggaattccc atggacaccg gtaattccca tgatcttctc 39900
tccttcatca atggatgcca tgtttcataa caataacacc aaatgtttga tgagctacca 39960
acaattgcgc aaagactatg gctaagctcg agctcgctcg ctacaagttg ttgactttca 40020
aatacaagtt tgtttttgga acaccaaata ttctacatga tctttcacta agttgcgcac 40080
cactatcaaa agattatcta ggccattatt caagtaaaga gtgaacacgt ctaagaccca 40140
caaccacacc aaatagaata cgcatacatg caacatattg tgcaagaagt atccaactgg 40200
actcccatgt attctaaaac tattttcgta gagttaaagt tatgacaaac ttatcaaata 40260
aaaatttgaa cgctggacca aaactttcat ctttcaaatc caccatcgtc tatcctcata 40320
aattgttttg attataacac atctacgtaa atcatttgtt ttgaacaata ctaatttaat 40380
tttattaagt caaataacct gcttagaaaa taatccctcc acctcattta acaatttctt 40440
gtcaaacaca caccaagaaa aaaattaatg aaagagaaaa gaaatgaaaa ggacatggag 40500
ttgaatacta gcaaaattga ttgaaggaag attcacaatt gaaattgaaa ccatttaatt 40560

```
tattttcggg tccataataa taaattggta agaataaaaa cccgatcaag tccggtacag  40620
tacaattcca ctccaccaac tccttactta aacccctatt tatacccact ctcatcctca  40680
ctcttccttc acctctcaca ctctcttctc tctctcaaaa ccctcacaca aacgctgcgt  40740
ttagtgtaag aaattcaatc cggcgccttg gcgcgccgat catccacaag tttgtacaaa  40800
aaagctgaac gagaaacgta aaatgatata aatatcaata tattaaatta gattttgcat  40860
aaaaaacaga ctacataata ctgtaaaaca caacatatcc agtcactatg gcggccgcat  40920
taggcacccc aggctttaca ctttatgctt ccggctcgta taatgtgtgg attttgagtt  40980
aggatttaaa tacgcgttga tccggcttac taaaagccag ataacagtat gcgtatttgc  41040
gcgctgattt ttgcggtata agaatatata ctgatatgta tacccgaagt atgtcaaaaa  41100
gaggtatgct atgaagcagc gtattacagt gacagttgac agcgacagct atcagttgct  41160
caaggcatat atgatgtcaa tatctccggt ctggtaagca caaccatgca gaatgaagcc  41220
cgtcgtctgc gtgccgaacg ctggaaagcg gaaaatcagg aagggatggc tgaggtcgcc  41280
cggtttattg aaatgaacgg ctcttttgct gacgagaaca ggggctggtg aaatgcagtt  41340
taaggtttac acctataaaa gagagagccg ttatcgtctg tttgtggatg tacagagtga  41400
tatcattgac acgcccggtc gacggatggt gatccccctg gccagtgcac gtctgctgtc  41460
agataaagtc tcccgtgaac tttacccggt ggtgcatatc ggggatgaaa gctggcgcat  41520
gatgaccacc gatatggcca gtgtgccggt ctccgttatc ggggaagaag tggctgatct  41580
cagccaccgc gaaaatgaca tcaaaaacgc cattaacctg atgttctggg gaatataaat  41640
gtcaggctcc cttatacaca gccagtctgc aggtcgacca tagtgactgg atatgttgtg  41700
ttttacagta ttatgtagtc tgttttttat gcaaaatcta atttaatata ttgatattta  41760
tatcatttta cgtttctcgt tcagctttct tgtacaaagt ggtgttaacc tagacttgtc  41820
catcttctgg attggccaac ttaattaatg tatgaaataa aaggatgcac acatagtgac  41880
atgctaatca ctataatgtg ggcatcaaag ttgtgtgtta tgtgtaatta ctagttatct  41940
gaataaaaga gaaagagatc atccatattt cttatcctaa atgaatgtca cgtgtcttta  42000
taattctttg atgaaccaga tgcatttcat taaccaaatc catatacata taaatattaa  42060
tcatatataa ttaatatcaa ttgggttagc aaaacaaatc tagtctaggt gtgttttgcg  42120
aattgcggcc gccaccgcgg tggagctcga attccggtcc gggtcacctt tgtccaccaa  42180
gatggaactg cggccgctca ttaattaagt caggcgcgcc tctagttgaa gacacgttca  42240
tgtcttcatc gtaagaagac actcagtagt cttcggccag aatggccatc tggattcagc  42300
aggcctagaa ggccatttaa atcctgagga tctggtcttc ctaaggaccc gggatatcgg  42360
accgattaaa ctttaattcg gtccgaagct tgaagttcct attccgaagt tcctattctc  42420
cagaaagtat aggaacttcg catgcctgca gtgcagcgtg acccggtcgt gcccctctct  42480
agagataatg agcattgcat gtctaagtta taaaaaatta ccacatattt tttttgtcac  42540
acttgtttga agtgcagttt atctatcttt atacatatat ttaaacttta ctctacgaat  42600
aatataatct atagtactac aataatatca gtgttttaga gaatcatata aatgaacagt  42660
tagacatggt ctaaaggaca attgagtatt ttgacaacag gactctacag ttttatcttt  42720
ttagtgtgca tgtgttctcc tttttttttg caaatagctt cacctatata atacttcatc  42780
cattttatta gtacatccat ttagggttta gggttaatgg tttttataga ctaatttttt  42840
tagtacatct attttattct attttagcct ctaaattaag aaaactaaaa ctctatttta  42900
gtttttttat ttaataattt agatataaaa tagaataaaa taaagtgact aaaaattaaa  42960
```

-continued

```
caaatacccct ttaagaaatt aaaaaaacta aggaaacatt tttcttgttt cgagtagata  43020
atgccagcct gttaaacgcc gtcgacgagt ctaacggaca ccaaccagcg aaccagcagc  43080
gtcgcgtcgg gccaagcgaa gcagacggca cggcatctct gtcgctgcct ctggacccct  43140
ctcgagagtt ccgctccacc gttggacttg ctccgctgtc ggcatccaga aattgcgtgg  43200
cggagcggca gacgtgagcc ggcacggcag gcggcctcct cctcctctca cggcaccggc  43260
agctacgggg gattcctttc ccaccgctcc ttcgctttcc cttcctcgcc cgccgtaata  43320
aatagacacc ccctccacac cctctttccc caacctcgtg ttgttcggag cgcacacaca  43380
cacaaccaga tctcccccaa atccacccgt cggcacctcc gcttcaaggt acgccgctcg  43440
tcctccccccc cccccctctc taccttctct agatcggcgt tccggtccat gcatggttag  43500
ggcccggtag ttctacttct gttcatgttt gtgttagatc cgtgtttgtg ttagatccgt  43560
gctgctagcg ttcgtacacg gatgcgacct gtacgtcaga cacgttctga ttgctaactt  43620
gccagtgttt ctctttgggg aatcctggga tggctctagc cgttccgcag acgggatcga  43680
tttcatgatt ttttttgttt cgttgcatag ggtttggttt gccctttcc tttatttcaa  43740
tatatgccgt gcacttgttt gtcgggtcat cttttcatgc ttttttttgt cttggttgtg  43800
atgatgtggt ctggttgggc ggtcgttcta gatcggagta gaattctgtt tcaaactacc  43860
tggtggattt attaattttg gatctgtatg tgtgtgccat acatattcat agttacgaat  43920
tgaagatgat ggatggaaat atcgatctag gataggtata catgttgatg cgggttttac  43980
tgatgcatat acagagatgc tttttgttcg cttggttgtg atgatgtggt gtggttgggc  44040
ggtcgttcat tcgttctaga tcggagtaga atactgtttc aaactacctg gtgtatttat  44100
taattttgga actgtatgtg tgtgtcatac atcttcatag ttacgagttt aagatggatg  44160
gaaatatcga tctaggatag gtatacatgt tgatgtgggt tttactgatg catatacatg  44220
atggcatatg cagcatctat tcatatgctc taaccttgag tacctatcta ttataataaa  44280
caagtatgtt ttataattat tttgatcttg atatacttgg atgatggcat atgcagcagc  44340
tatatgtgga ttttttagc cctgccttca tacgctattt atttgcttgg tactgtttct  44400
tttgtcgatg ctcaccctgt tgtttggtgt tacttctgca ggtcgacttt aacttagcct  44460
aggatccaca cgacaccatg atagaggtga aaccgattaa cgcagaggat acctatgaac  44520
taaggcatag aatactcaga ccaaaccagc cgatagaagc gtgtatgttt gaaagcgatt  44580
tacttcgtgg tgcatttcac ttaggcggct attacggggg caaactgatt tccatagctt  44640
cattccacca ggccgagcac tcagaactcc aaggccagaa acagtaccag ctccgaggta  44700
tggctacctt ggaaggttat cgtgagcaga aggcgggatc gagtctaatt aaacacgctg  44760
aagaaattct tcgtaagagg ggggcggact tgctttggtg taatgcgcgg acatccgcct  44820
caggctacta caaaaagtta ggcttcagcg agcagggaga ggtattcgac acgccgccag  44880
taggacctca catcctgatg tataaaagga tcacataact agctagtcag ttaacctaga  44940
cttgtccatc ttctggattg gccaacttaa ttaatgtatg aaataaaagg atgcacacat  45000
agtgacatgc taatcactat aatgtgggca tcaaagttgt gtgttatgtg taattactag  45060
ttatctgaat aaaagagaaa gagatcatcc atatttctta tcctaaatga atgtcacgtg  45120
tctttataat tctttgatga accagatgca tttcattaac caaatccata tacatataaa  45180
tattaatcat atataattaa tatcaattgg gttagcaaaa caaatctagt ctaggtgtgt  45240
tttgcgaatt cagagctcga attcattccg attaatcgtg gcctcttgct cttcaggatg  45300
aagagctatg tttaaacgtg caagcgctac tagacaattc agtacattaa aaacgtccgc  45360
```

-continued

```
aatgtgttat taagttgtct aagcgtcaat ttgtttacac cacaatatat cctgccacca 45420
gccagccaac agctccccga ccggcagctc ggcacaaaat caccactcga tacaggcagc 45480
ccatcagtcc gggacggcgt cagcgggaga gccgttgtaa ggcggcagac tttgctcatg 45540
ttaccgatgc tattcggaag aacggcaact aagctgccgg gtttgaaaca cggatgatct 45600
cgcggagggt agcatgttga ttgtaacgat gacagagcgt tgctgcctgt gatcaaatat 45660
catctccctc gcagagatcc gaattatcag ccttcttatt catttctcgc ttaaccgtga 45720
caggctgtcg atcttgagaa ctatgccgac ataataggaa atcgctggat aaagccgctg 45780
aggaagctga gtggcgctat ttctttagaa gtgaacgttg acgatcgtcg accgtacccc 45840
gatgaattaa ttcggacgta cgttctgaac acagctggat acttacttgg gcgattgtca 45900
tacatgacat caacaatgta cccgtttgtg taaccgtctc ttggaggttc gtatgacact 45960
agtggttccc ctcagcttgc gactagatgt tgaggcctaa cattttatta gagagcaggc 46020
tagttgctta gatacatgat cttcaggccg ttatctgtca gggcaagcga aaattggcca 46080
tttatgacga ccaatgcccc gcagaagctc ccatctttgc cgccatagac gccgcgcccc 46140
ccttttgggg tgtagaacat ccttttgcca gatgtggaaa agaagttcgt tgtcccattg 46200
ttggcaatga cgtagtagcc ggcgaaagtg cgagacccat ttgcgctata tataagccta 46260
cgatttccgt tgcgactatt gtcgtaattg gatgaactat tatcgtagtt gctctcagag 46320
ttgtcgtaat ttgatggact attgtcgtaa ttgcttatgg agttgtcgta gttgcttgga 46380
gaaatgtcgt agttggatgg ggagtagtca tagggaagac gagcttcatc cactaaaaca 46440
attggcaggt cagcaagtgc ctgccccgat gccatcgcaa gtacgaggct tagaaccacc 46500
ttcaacagat cgcgcatagt cttccccagc tctctaacgc ttgagttaag ccgcgccgcg 46560
aagcggcgtc ggcttgaacg aattgttaga cattatttgc cgactacctt ggtgatctcg 46620
cctttcacgt agtgaacaaa ttcttccaac tgatctgcgc gcgaggccaa gcgatcttct 46680
tgtccaagat aagcctgcct agcttcaagt atgacgggct gatactgggc cggcaggcgc 46740
tccattgccc agtcggcagc gacatccttc ggcgcgattt tgccggttac tgcgctgtac 46800
caaatgcggg acaacgtaag cactacattt cgctcatcgc cagcccagtc gggcggcgag 46860
ttccatagcg ttaaggtttc atttagcgcc tcaaatagat cctgttcagg aaccggatca 46920
aagagttcct ccgccgctgg acctaccaag gcaacgctat gttctcttgc ttttgtcagc 46980
aagatagcca gatcaatgtc gatcgtggct ggctcgaaga tacctgcaag aatgtcattg 47040
cgctgccatt ctccaaattg cagttcgcgc ttagctggat aacgccacgg aatgatgtcg 47100
tcgtgcacaa caatggtgac ttctacagcg cggagaatct cgctctctcc aggggaagcc 47160
gaagtttcca aaaggtcgtt gatcaaagct cgccgcgttg tttcatcaag ccttacagtc 47220
accgtaacca gcaaatcaat atcactgtgt ggcttcaggc cgccatccac tgcggagccg 47280
tacaaatgta cggccagcaa cgtcggttcg agatggcgct cgatgacgcc aactacctct 47340
gatagttgag tcgatacttc ggcgatcacc gcttccctca tgatgtttaa ctcctgaatt 47400
aagccgcgcc gcgaagcggt gtcggcttga atgaattgtt aggcgtcatc ctgtgctccc 47460
gagaaccagt accagtacat cgctgtttcg ttcgagactt gaggtctagt tttatacgtg 47520
aacaggtcaa tgccgccgag agtaaagcca catttgcgt acaaattgca ggcaggtaca 47580
ttgttcgttt gtgtctctaa tcgtatgcca aggagctgtc tgcttagtgc ccactttttc 47640
gcaaattcga tgagactgtg cgcgactcct ttgcctcggt gcgtgtgcga cacaacaatg 47700
tgttcgatag aggctagatc gttccatgtt gagttgagtt caatcttccc gacaagctct 47760
```

tggtcgatga atgcgccata gcaagcagag tcttcatcag agtcatcatc cgagatgtaa 47820
tccttccggt aggggctcac acttctggta gatagttcaa agccttggtc ggataggtgc 47880
acatcgaaca cttcacgaac aatgaaatgg ttctcagcat ccaatgtttc cgccacctgc 47940
tcagggatca ccgaaatctt catatgacgc ctaacgcctg gcacagcgga tcgcaaacct 48000
ggcgcggctt ttggcacaaa aggcgtgaca ggtttgcgaa tccgttgctg ccacttgtta 48060
acccttttgc cagatttggt aactataatt tatgttagag gcgaagtctt gggtaaaaac 48120
tggcctaaaa ttgctgggga tttcaggaaa gtaaacatca ccttccggct cgatgtctat 48180
tgtagatata tgtagtgtat ctacttgatc gggggatctg ctgcctcgcg cgtttcggtg 48240
atgacggtga aaacctctga cacatgcagc tcccggagac ggtcacagct tgtctgtaag 48300
cggatgccgg gagcagacaa gcccgtcagg gcgcgtcagc gggtgttggc gggtgtcggg 48360
gcgcagccat gacccagtca cgtagcgata gcggagtgta tactggctta actatgcggc 48420
atcagagcag attgtactga gagtgcacca tatgcggtgt gaaataccgc acagatgcgt 48480
aaggagaaaa taccgcatca ggcgctcttc cgcttcctcg ctcactgact cgctgcgctc 48540
ggtcgttcgg ctgcggcgag cggtatcagc tcactcaaag gcggtaatac ggttatccac 48600
agaatcaggg gataacgcag gaaagaacat gtgagcaaaa ggccagcaaa aggccaggaa 48660
ccgtaaaaag gccgcgttgc tggcgttttt ccataggctc cgcccccctg acgagcatca 48720
caaaaatcga cgctcaagtc agaggtggcg aaacccgaca ggactataaa gataccaggc 48780
gtttccccct ggaagctccc tcgtgcgctc tcctgttccg accctgccgc ttaccggata 48840
cctgtccgcc tttctccctt cgggaagcgt ggcgctttct catagctcac gctgtaggta 48900
tctcagttcg gtgtaggtcg ttcgctccaa gctgggctgt gtgcacgaac cccccgttca 48960
gcccgaccgc tgcgccttat ccggtaacta tcgtcttgag tccaacccgg taagacacga 49020
cttatcgcca ctggcagcag ccactggtaa caggattagc agagcgaggt atgtaggcgg 49080
tgctacagag ttcttgaagt ggtggcctaa ctacggctac actagaagga cagtatttgg 49140
tatctgcgct ctgctgaagc cagttacctt cggaaaaaga gttggtagct cttgatccgg 49200
caaacaaacc accgctggta gcggtggttt ttttgtttgc aagcagcaga ttacgcgcag 49260
aaaaaaagga tctcaagaag atcctttgat cttttctacg gggtctgacg ctcagtggaa 49320
cgaaaactca cgttaaggga ttttggtcat gagattatca aaaaggatct tcacctagat 49380
ccttttaaat taaaaatgaa gttttaaatc aatctaaagt atatatgagt aaacttggtc 49440
tgacagttac caatgcttaa tcagtgaggc acctatctca gcgatctgtc tatttcgttc 49500
atccatagtt gcctgactcc ccgtcgtgta gataactacg atacgggagg gcttaccatc 49560
tggccccagt gctgcaatga taccgcgaga cccacgctca ccggctccag atttatcagc 49620
aataaaccag ccagccggaa gggccgagcg cagaagtggt cctgcaactt tatccgcctc 49680
catccagtct attaattgtt gccgggaagc tagagtaagt agttcgccag ttaatagttt 49740
gcgcaacgtt gttgccattg ctgca 49765

<210> SEQ ID NO 62
<211> LENGTH: 12856
<212> TYPE: DNA
<213> ORGANISM: artificial sequence
<220> FEATURE:
<223> OTHER INFORMATION: vector

<400> SEQUENCE: 62
cgccttggcg cgccgatcat ccacaagttt gtacaaaaaa gctgaacgag aaacgtaaaa 60

```
tgatataaat atcaatatat taaattagat tttgcataaa aaacagacta cataatactg    120
taaaacacaa catatccagt cactatggcg gccgcattag gcaccccagg ctttacactt    180
tatgcttccg gctcgtataa tgtgtggatt ttgagttagg atttaaatac gcgttgatcc    240
ggcttactaa aagccagata acagtatgcg tatttgcgcg ctgatttttg cggtataaga    300
atatatactg atatgtatac ccgaagtatg tcaaaaagag gtatgctatg aagcagcgta    360
ttacagtgac agttgacagc gacagctatc agttgctcaa ggcatatatg atgtcaatat    420
ctccggtctg gtaagcacaa ccatgcagaa tgaagcccgt cgtctgcgtg ccgaacgctg    480
gaaagcggaa aatcaggaag ggatggctga ggtcgcccgg tttattgaaa tgaacggctc    540
ttttgctgac gagaacaggg gctggtgaaa tgcagtttaa ggtttacacc tataaaagag    600
agagccgtta tcgtctgttt gtggatgtac agagtgatat cattgacacg cccggtcgac    660
ggatggtgat ccccctggcc agtgcacgtc tgctgtcaga taaagtctcc cgtgaacttt    720
acccggtggt gcatatcggg gatgaaagct ggcgcatgat gaccaccgat atggccagtg    780
tgccggtctc cgttatcggg gaagaagtgg ctgatctcag ccaccgcgaa aatgacatca    840
aaaacgccat taacctgatg ttctggggaa tataaatgtc aggctccctt atacacagcc    900
agtctgcagg tcgaccatag tgactggata tgttgtgttt tacagtatta tgtagtctgt    960
tttttatgca aaatctaatt taatatattg atatttatat cattttacgt ttctcgttca   1020
gctttcttgt acaaagtggt gttaacctag acttgtccat cttctggatt ggccaactta   1080
attaatgtat gaaataaaag gatgcacaca tagtgacatg ctaatcacta taatgtgggc   1140
atcaaagttg tgtgttatgt gtaattacta gttatctgaa taaaagagaa agagatcatc   1200
catatttctt atcctaaatg aatgtcacgt gtctttataa ttctttgatg aaccagatgc   1260
atttcattaa ccaaatccat atacatataa atattaatca tatataatta atatcaattg   1320
ggttagcaaa acaaatctag tctaggtgtg ttttgcgaat tgcggccgcc accgcggtgg   1380
agctcgaatt ccggtccggg tcacctttgt ccaccaagat ggaactgcgg ccgctcatta   1440
attaagtcag gcgcgcctct agttgaagac acgttcatgt cttcatcgta agaagacact   1500
cagtagtctt cggccagaat ggccatctgg attcagcagg cctagaaggc catttaaatc   1560
ctgaggatct ggtcttccta aggacccggg atatcggacc gattaaactt taattcggtc   1620
cgaagcttga agttcctatt ccgaagttcc tattctccag aaagtatagg aacttcgcat   1680
gcctgcagtg cagcgtgacc cggtcgtgcc cctctctaga gataatgagc attgcatgtc   1740
taagttataa aaaattacca catatttttt ttgtcacact tgtttgaagt gcagtttatc   1800
tatctttata catatattta aactttactc tacgaataat ataatctata gtactacaat   1860
aatatcagtg ttttagagaa tcatataaat gaacagttag acatggtcta aaggacaatt   1920
gagtattttg acaacaggac tctacagttt tatcttttta gtgtgcatgt gttctccttt   1980
tttttgcaa atagcttcac ctatataata cttcatccat tttattagta catccattta   2040
gggtttaggg ttaatggttt ttatagacta atttttttag tacatctatt ttattctatt   2100
ttagcctcta aattaagaaa actaaaactc tattttagtt tttttattta ataatttaga   2160
tataaaatag aataaaataa agtgactaaa aattaaacaa ataccctttta agaaattaaa   2220
aaaactaagg aaacattttt cttgtttcga gtagataatg ccagcctgtt aaacgccgtc   2280
gacgagtcta acggacacca accagcgaac cagcagcgtc gcgtcgggcc aagcgaagca   2340
gacggcacgg catctctgtc gctgcctctg gacccctctc gagagttccg ctccaccgtt   2400
ggacttgctc cgctgtcggc atccagaaat tgcgtggcgg agcggcagac gtgagccggc   2460
```

acggcaggcg gcctcctcct cctctcacgg caccggcagc tacgggggat tcctttccca 2520
ccgctccttc gctttccctt cctcgcccgc cgtaataaat agacaccccc tccacaccct 2580
ctttccccaa cctcgtgttg ttcggagcgc acacacacac aaccagatct cccccaaatc 2640
cacccgtcgg cacctccgct tcaaggtacg ccgctcgtcc tccccccccc ccctctctac 2700
cttctctaga tcggcgttcc ggtccatgca tggttagggc ccggtagttc tacttctgtt 2760
catgtttgtg ttagatccgt gtttgtgtta gatccgtgct gctagcgttc gtacacggat 2820
gcgacctgta cgtcagacac gttctgattg ctaacttgcc agtgtttctc tttggggaat 2880
cctgggatgg ctctagccgt tccgcagacg ggatcgattt catgattttt tttgtttcgt 2940
tgcatagggt ttggtttgcc cttttccttt atttcaatat atgccgtgca cttgtttgtc 3000
gggtcatctt ttcatgcttt tttttgtctt ggttgtgatg atgtggtctg gttgggcggt 3060
cgttctagat cggagtagaa ttctgtttca aactacctgg tggatttatt aattttggat 3120
ctgtatgtgt gtgccataca tattcatagt tacgaattga agatgatgga tggaaatatc 3180
gatctaggat aggtatacat gttgatgcgg gttttactga tgcatataca gagatgcttt 3240
ttgttcgctt ggttgtgatg atgtggtgtg gttgggcggt cgttcattcg ttctagatcg 3300
gagtagaata ctgtttcaaa ctacctggtg tatttattaa ttttggaact gtatgtgtgt 3360
gtcatacatc ttcatagtta cgagtttaag atggatggaa atatcgatct aggataggta 3420
tacatgttga tgtgggtttt actgatgcat atacatgatg gcatatgcag catctattca 3480
tatgctctaa ccttgagtac ctatctatta taataaacaa gtatgtttta taattatttt 3540
gatcttgata tacttggatg atggcatatg cagcagctat atgtggattt ttttagccct 3600
gccttcatac gctatttatt tgcttggtac tgtttctttt gtcgatgctc accctgttgt 3660
ttggtgttac ttctgcaggt cgactttaac ttagcctagg atccacacga caccatgata 3720
gaggtgaaac cgattaacgc agaggatacc tatgaactaa ggcatagaat actcagacca 3780
aaccagccga tagaagcgtg tatgtttgaa agcgatttac ttcgtggtgc atttcactta 3840
ggcggctatt acgggggcaa actgatttcc atagcttcat tccaccaggc cgagcactca 3900
gaactccaag gccagaaaca gtaccagctc cgaggtatgg ctaccttgga aggttatcgt 3960
gagcagaagg cgggatcgag tctaattaaa cacgctgaag aaattcttcg taagaggggg 4020
gcggacttgc tttggtgtaa tgcgcggaca tccgcctcag gctactacaa aaagttaggc 4080
ttcagcgagc agggagaggt attcgacacg ccgccagtag gacctcacat cctgatgtat 4140
aaaaggatca cataactagc tagtcagtta acctagactt gtccatcttc tggattggcc 4200
aacttaatta atgtatgaaa taaaaggatg cacacatagt gacatgctaa tcactataat 4260
gtgggcatca aagttgtgtg ttatgtgtaa ttactagtta tctgaataaa agagaaagag 4320
atcatccata tttcttatcc taaatgaatg tcacgtgtct ttataattct ttgatgaacc 4380
agatgcattt cattaaccaa atccatatac atataaatat taatcatata taattaatat 4440
caattgggtt agcaaaacaa atctagtcta ggtgtgtttt gcgaattcag agctcgaatt 4500
cattccgatt aatcgtggcc tcttgctctt caggatgaag agctatgttt aaacgtgcaa 4560
gcgctactag acaattcagt acattaaaaa cgtccgcaat gtgttattaa gttgtctaag 4620
cgtcaatttg tttacaccac aatatatcct gccaccagcc agccaacagc tccccgaccg 4680
gcagctcggc acaaaatcac cactcgatac aggcagccca tcagtccggg acggcgtcag 4740
cgggagagcc gttgtaaggc ggcagacttt gctcatgtta ccgatgctat tcggaagaac 4800
ggcaactaag ctgccgggtt tgaaacacgg atgatctcgc ggagggtagc atgttgattg 4860
taacgatgac agagcgttgc tgcctgtgat caaatatcat ctccctcgca gagatccgaa 4920
ttatcagcct tcttattcat ttctcgctta accgtgacag gctgtcgatc ttgagaacta 4980
tgccgacata ataggaaatc gctggataaa gccgctgagg aagctgagtg gcgctatttc 5040
tttagaagtg aacgttgacg atcgtcgacc gtaccccgat gaattaattc ggacgtacgt 5100
tctgaacaca gctggatact tacttgggcg attgtcatac atgacatcaa caatgtaccc 5160
gtttgtgtaa ccgtctcttg gaggttcgta tgacactagt ggttcccctc agcttgcgac 5220
tagatgttga ggcctaacat tttattagag agcaggctag ttgcttagat acatgatctt 5280
caggccgtta tctgtcaggg caagcgaaaa ttggccattt atgacgacca atgccccgca 5340
gaagctccca tctttgccgc catagacgcc gcgcccccct tttggggtgt agaacatcct 5400
tttgccagat gtggaaaaga agttcgttgt cccattgttg gcaatgacgt agtagccggc 5460
gaaagtgcga gacccatttg cgctatatat aagcctacga tttccgttgc gactattgtc 5520
gtaattggat gaactattat cgtagttgct ctcagagttg tcgtaatttg atggactatt 5580
gtcgtaattg cttatggagt tgtcgtagtt gcttggagaa atgtcgtagt tggatgggga 5640
gtagtcatag ggaagacgag cttcatccac taaaacaatt ggcaggtcag caagtgcctg 5700
ccccgatgcc atcgcaagta cgaggcttag aaccaccttc aacagatcgc gcatagtctt 5760
ccccagctct ctaacgcttg agttaagccg cgccgcgaag cggcgtcggc ttgaacgaat 5820
tgttagacat tatttgccga ctaccttggt gatctcgcct ttcacgtagt gaacaaattc 5880
ttccaactga tctgcgcgcg aggccaagcg atcttcttgt ccaagataag cctgcctagc 5940
ttcaagtatg acgggctgat actgggccgg caggcgctcc attgcccagt cggcagcgac 6000
atccttcggc gcgattttgc cggttactgc gctgtaccaa atgcgggaca acgtaagcac 6060
tacatttcgc tcatcgccag cccagtcggg cggcgagttc catagcgtta aggtttcatt 6120
tagcgcctca aatagatcct gttcaggaac cggatcaaag agttcctccg ccgctggacc 6180
taccaaggca acgctatgtt ctcttgcttt tgtcagcaag atagccagat caatgtcgat 6240
cgtggctggc tcgaagatac ctgcaagaat gtcattgcgc tgccattctc caaattgcag 6300
ttcgcgctta gctggataac gccacggaat gatgtcgtcg tgcacaacaa tggtgacttc 6360
tacagcgcgg agaatctcgc tctctccagg ggaagccgaa gtttccaaaa ggtcgttgat 6420
caaagctcgc cgcgttgttt catcaagcct tacagtcacc gtaaccagca aatcaatatc 6480
actgtgtggc ttcaggccgc catccactgc ggagccgtac aaatgtacgg ccagcaacgt 6540
cggttcgaga tggcgctcga tgacgccaac tacctctgat agttgagtcg atacttcggc 6600
gatcaccgct tccctcatga tgtttaactc ctgaattaag ccgcgccgcg aagcggtgtc 6660
ggcttgaatg aattgttagg cgtcatcctg tgctcccgag aaccagtacc agtacatcgc 6720
tgtttcgttc gagacttgag gtctagtttt atacgtgaac aggtcaatgc cgccgagagt 6780
aaagccacat tttgcgtaca aattgcaggc aggtacattg ttcgtttgtg tctctaatcg 6840
tatgccaagg agctgtctgc ttagtgccca ctttttcgca aattcgatga gactgtgcgc 6900
gactcctttg cctcggtgcg tgtgcgacac aacaatgtgt tcgatagagg ctagatcgtt 6960
ccatgttgag ttgagttcaa tcttcccgac aagctcttgg tcgatgaatg cgccatagca 7020
agcagagtct tcatcagagt catcatccga gatgtaatcc ttccggtagg ggctcacact 7080
tctggtagat agttcaaagc cttggtcgga taggtgcaca tcgaacactt cacgaacaat 7140
gaaatggttc tcagcatcca atgtttccgc cacctgctca gggatcaccg aaatcttcat 7200
atgacgccta acgcctggca cagcggatcg caaacctggc gcggcttttg gcacaaaagg 7260

```
cgtgacaggt ttgcgaatcc gttgctgcca cttgttaacc cttttgccag atttggtaac   7320
tataatttat gttagaggcg aagtcttggg taaaaactgg cctaaaattg ctggggattt   7380
caggaaagta aacatcacct tccggctcga tgtctattgt agatatatgt agtgtatcta   7440
cttgatcggg ggatctgctg cctcgcgcgt ttcggtgatg acggtgaaaa cctctgacac   7500
atgcagctcc cggagacggt cacagcttgt ctgtaagcgg atgccgggag cagacaagcc   7560
cgtcagggcg cgtcagcggg tgttggcggg tgtcggggcg cagccatgac ccagtcacgt   7620
agcgatagcg gagtgtatac tggcttaact atgcggcatc agagcagatt gtactgagag   7680
tgcaccatat gcggtgtgaa ataccgcaca gatgcgtaag gagaaaatac cgcatcaggc   7740
gctcttccgc ttcctcgctc actgactcgc tgcgctcggt cgttcggctg cggcgagcgg   7800
tatcagctca ctcaaaggcg gtaatacggt tatccacaga atcaggggat aacgcaggaa   7860
agaacatgtg agcaaaaggc cagcaaaagg ccaggaaccg taaaaaggcc gcgttgctgg   7920
cgtttttcca taggctccgc ccccctgacg agcatcacaa aaatcgacgc tcaagtcaga   7980
ggtggcgaaa cccgacagga ctataaagat accaggcgtt tccccctgga agctccctcg   8040
tgcgctctcc tgttccgacc ctgccgctta ccggatacct gtccgccttt ctcccttcgg   8100
gaagcgtggc gctttctcat agctcacgct gtaggtatct cagttcggtg taggtcgttc   8160
gctccaagct gggctgtgtg cacgaacccc ccgttcagcc cgaccgctgc gccttatccg   8220
gtaactatcg tcttgagtcc aacccggtaa gacacgactt atcgccactg gcagcagcca   8280
ctggtaacag gattagcaga gcgaggtatg taggcggtgc tacagagttc ttgaagtggt   8340
ggcctaacta cggctacact agaaggacag tatttggtat ctgcgctctg ctgaagccag   8400
ttaccttcgg aaaaagagtt ggtagctctt gatccggcaa acaaaccacc gctggtagcg   8460
gtggtttttt tgtttgcaag cagcagatta cgcgcagaaa aaaaggatct caagaagatc   8520
ctttgatctt ttctacgggg tctgacgctc agtggaacga aaactcacgt taagggattt   8580
tggtcatgag attatcaaaa aggatcttca cctagatcct tttaaattaa aaatgaagtt   8640
ttaaatcaat ctaaagtata tatgagtaaa cttggtctga cagttaccaa tgcttaatca   8700
gtgaggcacc tatctcagcg atctgtctat ttcgttcatc catagttgcc tgactccccg   8760
tcgtgtagat aactacgata cgggagggct taccatctgg ccccagtgct gcaatgatac   8820
cgcgagaccc acgctcaccg gctccagatt tatcagcaat aaaccagcca gccggaaggg   8880
ccgagcgcag aagtggtcct gcaactttat ccgcctccat ccagtctatt aattgttgcc   8940
gggaagctag agtaagtagt tcgccagtta atagtttgcg caacgttgtt gccattgctg   9000
caggggggggg ggggggggggg gacttccatt gttcattcca cggacaaaaa cagagaaagg   9060
aaacgacaga ggccaaaaag cctcgctttc agcacctgtc gtttcctttc ttttcagagg   9120
gtattttaaa taaaaacatt aagttatgac gaagaagaac ggaaacgcct taaaccggaa   9180
aattttcata aatagcgaaa acccgcgagg tcgccgcccc gtaacctgtc ggatcaccgg   9240
aaaggacccg taaagtgata atgattatca tctacatatc acaacgtgcg tggaggccat   9300
caaaccacgt caaataatca attatgacgc aggtatcgta ttaattgatc tgcatcaact   9360
taacgtaaaa acaacttcag acaatacaaa tcagcgacac tgaatacggg gcaacctcat   9420
gtcccccccc cccccccccc tgcaggcatc gtggtgtcac gctcgtcgtt tggtatggct   9480
tcattcagct ccggttccca acgatcaagg cgagttacat gatcccccat gttgtgcaaa   9540
aaagcggtta gctccttcgg tcctccgatc gttgtcagaa gtaagttggc cgcagtgtta   9600
tcactcatgg ttatggcagc actgcataat tctcttactg tcatgccatc cgtaagatgc   9660
```

-continued

```
ttttctgtga ctggtgagta ctcaaccaag tcattctgag aatagtgtat gcggcgaccg   9720
agttgctctt gcccggcgtc aacacgggat aataccgcgc cacatagcag aactttaaaa   9780
gtgctcatca ttggaaaacg ttcttcgggg cgaaaactct caaggatctt accgctgttg   9840
agatccagtt cgatgtaacc cactcgtgca cccaactgat cttcagcatc ttttactttc   9900
accagcgttt ctgggtgagc aaaaacagga aggcaaaatg ccgcaaaaaa gggaataagg   9960
gcgacacgga aatgttgaat actcatactc ttcctttttc aatattattg aagcatttat  10020
cagggttatt gtctcatgag cggatacata tttgaatgta tttagaaaaa taaacaaata  10080
ggggttccgc gcacatttcc ccgaaaagtg ccacctgacg tctaagaaac cattattatc  10140
atgacattaa cctataaaaa taggcgtatc acgaggccct ttcgtcttca agaattggtc  10200
gacgatcttg ctgcgttcgg atattttcgt ggagttcccg ccacagaccc ggattgaagg  10260
cgagatccag caactcgcgc cagatcatcc tgtgacggaa ctttggcgcg tgatgactgg  10320
ccaggacgtc ggccgaaaga gcgacaagca gatcacgctt ttcgacagcg tcggatttgc  10380
gatcgaggat tttcggcgc tgcgctacgt ccgcgaccgc gttgagggat caagccacag  10440
cagcccactc gaccttctag ccgacccaga cgagccaagg gatctttttg gaatgctgct  10500
ccgtcgtcag gctttccgac gtttgggtgg ttgaacagaa gtcattatcg tacggaatgc  10560
caagcactcc cgaggggaac cctgtggttg gcatgcacat acaaatggac gaacggataa  10620
accttttcac gcccttttaa atatccgtta ttctaataaa cgctcttttc tcttaggttt  10680
acccgccaat atatcctgtc aaacactgat agtttaaact gaaggcggga aacgacaatc  10740
tgatcatgag cggagaatta agggagtcac gttatgaccc ccgccgatga cgcgggacaa  10800
gccgttttac gtttggaact gacagaaccg caacgttgaa ggagccactc agcaagctgg  10860
tacgattgta atacgactca ctatagggcg aattgagcgc tgtttaaacg ctcttcaact  10920
ggaagagcgg ttacccggac cgaagcttga agttcctatt ccgaagttcc tattctctag  10980
aaagtatagg aacttcagat ctcgatgctc accctgttgt ttggtgttac ttctgcaggt  11040
cgactctaga ggatccacca tgagcccaga acgacgcccg gccgacatcc gccgtgccac  11100
cgaggcggac atgccggcgg tctgcaccat cgtcaaccac tacatcgaga caagcacggt  11160
caacttccgt accgagccgc aggaaccgca ggactggacg gacgacctcg tccgtctgcg  11220
ggagcgctat ccctggctcg tcgccgaggt ggacggcgag gtcgccggca tcgcctacgc  11280
gggcccctgg aaggcacgca acgcctacga ctggacggcc gagtcgaccg tgtacgtctc  11340
cccccgccac cagcggacgg gactgggctc cacgctctac acccacctgc tgaagtccct  11400
ggaggcacag ggcttcaaga gcgtggtcgc tgtcatcggg ctgcccaacg acccgagcgt  11460
gcgcatgcac gaggcgctcg gatatgcccc ccgcggcatg ctgcgggcgg ccggcttcaa  11520
gcacgggaac tggcatgacg tgggtttctg gcagctggac ttcagcctgc cggtaccgcc  11580
ccgtccggtc ctgcccgtca ccgagatctg atccgtcgac caacctagac ttgtccatct  11640
tctggattgg ccaacttaat taatgtatga aataaaagga tgcacacata gtgacatgct  11700
aatcactata atgtgggcat caaagttgtg tgttatgtgt aattactagt tatctgaata  11760
aaagagaaag agatcatcca tatttcttat cctaaatgaa tgtcacgtgt ctttataatt  11820
ctttgatgaa ccagatgcat ttcattaacc aaatccatat acatataaat attaatcata  11880
tataattaat atcaattggg ttagcaaaac aaatctagtc taggtgtgtt ttgcgaattg  11940
cggccgcgat ctggggaatt cccatggaca ccggtaattc ccatgatctt ctctccttca  12000
tcaatggatg ccatgtttca taacaataac accaaatgtt tgatgagcta ccaacaattg  12060
```

cgcaaagact atggctaagc tcgagctcgc tcgctacaag ttgttgactt tcaaatacaa 12120
gtttgttttt ggaacaccaa atattctaca tgatctttca ctaagttgcg caccactatc 12180
aaaagattat ctaggccatt attcaagtaa agagtgaaca cgtctaagac ccacaaccac 12240
accaaataga atacgcatac atgcaacata ttgtgcaaga agtatccaac tggactccca 12300
tgtattctaa aactattttc gtagagttaa agttatgaca aacttatcaa ataaaaattt 12360
gaacgctgga ccaaaacttt catctttcaa atccaccatc gtctatcctc ataaattgtt 12420
ttgattataa cacatctacg taaatcattt gttttgaaca atactaattt aattttatta 12480
agtcaaataa cctgcttaga aaataatccc tccacctcat ttaacaattt cttgtcaaac 12540
acacaccaag aaaaaaatta atgaaagaga aaagaaatga aaaggacatg gagttgaata 12600
ctagcaaaat tgattgaagg aagattcaca attgaaattg aaaccattta atttattttc 12660
gggtccataa taataaattg gtaagaataa aaacccgatc aagtccggta cagtacaatt 12720
ccactccacc aactccttac ttaaacccct atttataccc actctcatcc tcactcttcc 12780
ttcacctctc acactctctt ctctctctca aaaccctcac acaaacgctg cgtttagtgt 12840
aagaaattca atccgg 12856

<210> SEQ ID NO 63
<211> LENGTH: 879
<212> TYPE: DNA
<213> ORGANISM: Medicago sativa

<400> SEQUENCE: 63
aattcccatg atcttctctc cttcatcaat ggatgccatg tttcataaca ataacaccaa 60
atgtttgatg agctaccaac aattgcgcaa agactatggc taagctcgag ctcgctcgct 120
acaagttgtt gactttcaaa tacaagtttg tttttggaac accaaatatt ctacatgatc 180
tttcactaag ttgcgcacca ctatcaaaag attatctagg ccattattca agtaaagagt 240
gaacacgtct aagacccaca accacaccaa atagaatacg catacatgca acatattgtg 300
caagaagtat ccaactggac tcccatgtat tctaaaacta ttttcgtaga gttaaagtta 360
tgacaaactt atcaaataaa aatttgaacg ctggaccaaa actttcatct ttcaaatcca 420
ccatcgtcta tcctcataaa ttgttttgat tataacacat ctacgtaaat catttgtttt 480
gaacaatact aatttaattt tattaagtca aataacctgc ttagaaaata atccctccac 540
ctcatttaac aatttcttgt caaacacaca ccaagaaaaa aattaatgaa agagaaaaga 600
aatgaaaagg acatggagtt gaatactagc aaaattgatt gaaggaagat tcacaattga 660
aattgaaacc atttaattta ttttcgggtc cataataata aattggtaag aataaaaacc 720
cgatcaagtc cggtacagta caattccact ccaccaactc cttacttaaa cccctattta 780
tacccactct catcctcact cttccttcac ctctcacact ctcttctctc tctcaaaacc 840
ctcacacaaa cgctgcgttt agtgtaagaa attcaatcc 879

<210> SEQ ID NO 64
<211> LENGTH: 17
<212> TYPE: DNA
<213> ORGANISM: artificial sequence
<220> FEATURE:
<223> OTHER INFORMATION: DNA binding sequence

<400> SEQUENCE: 64
aggaagactc tcctccg 17

<210> SEQ ID NO 65
<211> LENGTH: 271
<212> TYPE: PRT
<213> ORGANISM: Oryza sativa

<400> SEQUENCE: 65

Met Ser Pro Pro Leu Glu Pro His Asp Tyr Ile Gly Leu Ser Ala Ala
1               5                   10                  15

Ala Ala Ser Pro Thr Pro Ser Ser Ser Ser Cys Ser Ser Ser Pro Asn
            20                  25                  30

Pro Gly Gly Glu Ala Arg Gly Pro Arg Leu Thr Leu Arg Leu Gly Leu
        35                  40                  45

Pro Gly Ser Glu Ser Pro Glu Arg Glu Val Val Ala Ala Gly Leu Thr
    50                  55                  60

Leu Gly Pro Leu Pro Pro Thr Thr Thr Lys Ala Ala Ser Lys Arg Ala
65                  70                  75                  80

Phe Pro Asp Ser Ser Pro Arg His Gly Ala Ser Ser Gly Ser Val Ala
                85                  90                  95

Ala Ala Ala Ala Cys Gln Asp Lys Ala Ala Pro Ala Ala Ala Pro Pro
            100                 105                 110

Ala Ala Lys Ala Gln Val Val Gly Trp Pro Pro Val Arg Asn Tyr Arg
        115                 120                 125

Lys Asn Thr Leu Ala Ala Ser Ala Ser Lys Gly Lys Gly Glu Asp Lys
    130                 135                 140

Gly Thr Ala Glu Gly Gly Pro Leu Tyr Val Lys Val Ser Met Asp Gly
145                 150                 155                 160

Ala Pro Tyr Leu Arg Lys Val Asp Leu Lys Met Tyr Ser Ser Tyr Glu
                165                 170                 175

Asp Leu Ser Met Ala Leu Glu Lys Met Phe Ser Cys Phe Ile Thr Gly
            180                 185                 190

Gln Ser Gly Leu Arg Lys Ser Ser Asn Arg Asp Arg Leu Thr Asn Gly
        195                 200                 205

Ser Lys Ala Asp Ala Leu Gln Asp Gln Glu Tyr Val Leu Thr Tyr Glu
    210                 215                 220

Asp Lys Asp Ala Asp Trp Met Leu Val Gly Asp Leu Pro Trp Asp Leu
225                 230                 235                 240

Phe Thr Thr Ile Cys Arg Lys Leu Lys Ile Met Arg Gly Ser Asp Ala
                245                 250                 255

Ala Gly Ile Ala Pro Arg Ser Ile Glu Gln Ser Gly Gln Ser Arg
            260                 265                 270

<210> SEQ ID NO 66
<211> LENGTH: 711
<212> TYPE: DNA
<213> ORGANISM: Brassica napus

<400> SEQUENCE: 66
atgattaatt ttgaggtaac ggagctgagg ttagggctgc cgggtgagaa tcacggagga 60
ggcatggctg cgaaaaacaa cggcaaaaga ggattctctg agaccgttga tctcaaattg 120
aatctttctt ctacggctat ggattcagtt tctgaacttg atttagtgaa tatgaaggag 180
aaggtcgtaa aaccaccggc caaggcacaa gttgtgggat ggccaccggt acgatctttc 240
cggaagaacg tcatgtcagg cccaaagcca accaccggag atgccttcca agcaactgaa 300
aagacttccg gcagcaacgg agccacctcc tctgcctcca ttggtgctac cgcagcttac 360
gtgaaggtta gcatggacgg tgcaccgtac ctaagaaaaa ttgatttgaa actctacaaa 420

-continued

```
acttaccaag atctctcgga tgcattaagc aaaatgttca gctcttttac cataggcagc    480

tatggaccgc aaggaatgaa agatattgtg aatgagggta aattgatcga tcttttgaac    540

ggatcagatt atgttccaac ttatgaagat aaagatggag actggatgct tgtaggagac    600

gtaccgtggg agatgtttgt tgattcatgc aaacgcataa gaattatgaa gggatcagaa    660

gcaatcggac ttgctccaag ggctttggaa aagtgcaaga acagaagatg a             711
```

<210> SEQ ID NO 67
<211> LENGTH: 236
<212> TYPE: PRT
<213> ORGANISM: Brassica napus

<400> SEQUENCE: 67

```
Met Ile Asn Phe Glu Val Thr Glu Leu Arg Leu Gly Leu Pro Gly Glu
1               5                   10                  15

Asn His Gly Gly Gly Met Ala Ala Lys Asn Asn Gly Lys Arg Gly Phe
            20                  25                  30

Ser Glu Thr Val Asp Leu Lys Leu Asn Leu Ser Ser Thr Ala Met Asp
        35                  40                  45

Ser Val Ser Glu Leu Asp Leu Val Asn Met Lys Glu Lys Val Val Lys
    50                  55                  60

Pro Pro Ala Lys Ala Gln Val Val Gly Trp Pro Pro Val Arg Ser Phe
65                  70                  75                  80

Arg Lys Asn Val Met Ser Gly Pro Lys Pro Thr Thr Gly Asp Ala Phe
                85                  90                  95

Gln Ala Thr Glu Lys Thr Ser Gly Ser Asn Gly Ala Thr Ser Ser Ala
            100                 105                 110

Ser Ile Gly Ala Thr Ala Ala Tyr Val Lys Val Ser Met Asp Gly Ala
        115                 120                 125

Pro Tyr Leu Arg Lys Ile Asp Leu Lys Leu Tyr Lys Thr Tyr Gln Asp
    130                 135                 140

Leu Ser Asp Ala Leu Ser Lys Met Phe Ser Ser Phe Thr Ile Gly Ser
145                 150                 155                 160

Tyr Gly Pro Gln Gly Met Lys Asp Ile Val Asn Glu Gly Lys Leu Ile
                165                 170                 175

Asp Leu Leu Asn Gly Ser Asp Tyr Val Pro Thr Tyr Glu Asp Lys Asp
            180                 185                 190

Gly Asp Trp Met Leu Val Gly Asp Val Pro Trp Glu Met Phe Val Asp
        195                 200                 205

Ser Cys Lys Arg Ile Arg Ile Met Lys Gly Ser Glu Ala Ile Gly Leu
    210                 215                 220

Ala Pro Arg Ala Leu Glu Lys Cys Lys Asn Arg Arg
225                 230                 235
```

<210> SEQ ID NO 68
<211> LENGTH: 1065
<212> TYPE: DNA
<213> ORGANISM: Glycine max

<400> SEQUENCE: 68

```
atgtcgccgc cgacgctggt aacggaggag gaggggcgga gcaccgtggc gtccgattct     60

tcgcaatcct tggactgttt ctctcagaat ggtgctggat tgaaagaacg gaattactta    120

gggttgtctg attgctcatc agtggatagc tgtgcctcta ctgtgccaag cttgtgtgat    180

gagaaaaagg agaacatgaa tttgaaggct acagagttga ggcttggtct tcccggattc    240

caatcgcctg aaagggaacc ggatcttttc tctttaagct caccaaagct tgatgagaag    300
```

```
ccactcttcc ctttgcttcc tactaaagac gggatttgct cgtcggggca gaaagctgtt    360

gtttctggca acaaaagagg ttttgctgat accatggatg ggttttctca ggggaagttt    420

gctggtaata cagggatgaa cgcggtgcta tcacctagac cttctggagc tcaaccttct    480

gctatgaaag aaacaccaag caaattgtca gaacgtcctt gctcaactaa taatggaacc    540

ggtcataacc atacaggtgc ttctatcagt ggcagcgcac cggcttctaa ggcacaggtt    600

gttggttggc ctcctattag atcatttagg aaaaactcaa tggctaccac cactaacaag    660

aacaatgatg aagtcgatgg aaaaccaggt gttggcgcac tctttgtgaa ggtcagcatg    720

gatggtgctc cgtatcttag gaaggtagat ctaagaagtt atacaacata tcaggaacta    780

tcttctgccc ttgagaagat gttcctaagc tgttttaccc taggtcagtg tggttcccat    840

ggagctccag gaagagaaat gttgagtgag agcaagctga gggatcttct gcatggttct    900

gagtatgttc tcacttatga agataaagat ggagattgga tgcttgtagg ggatgtgcca    960

tgggaaatgt tcattgagac ttgcaaaagg ctgaaaatta tgaagggttc tgatgccatt   1020

ggtttagctc ccagggccat ggaaaagtct aaaagcagga tttag                   1065
```

```
<210> SEQ ID NO 69
<211> LENGTH: 354
<212> TYPE: PRT
<213> ORGANISM: Glycine max

<400> SEQUENCE: 69

Met Ser Pro Pro Thr Leu Val Thr Glu Glu Glu Gly Arg Ser Thr Val
1               5                   10                  15

Ala Ser Asp Ser Ser Gln Ser Leu Asp Cys Phe Ser Gln Asn Gly Ala
            20                  25                  30

Gly Leu Lys Glu Arg Asn Tyr Leu Gly Leu Ser Asp Cys Ser Ser Val
        35                  40                  45

Asp Ser Cys Ala Ser Thr Val Pro Ser Leu Cys Asp Glu Lys Lys Glu
    50                  55                  60

Asn Met Asn Leu Lys Ala Thr Glu Leu Arg Leu Gly Leu Pro Gly Phe
65                  70                  75                  80

Gln Ser Pro Glu Arg Glu Pro Asp Leu Phe Ser Leu Ser Ser Pro Lys
                85                  90                  95

Leu Asp Glu Lys Pro Leu Phe Pro Leu Leu Pro Thr Lys Asp Gly Ile
            100                 105                 110

Cys Ser Ser Gly Gln Lys Ala Val Val Ser Gly Asn Lys Arg Gly Phe
        115                 120                 125

Ala Asp Thr Met Asp Gly Phe Ser Gln Gly Lys Phe Ala Gly Asn Thr
    130                 135                 140

Gly Met Asn Ala Val Leu Ser Pro Arg Pro Ser Gly Ala Gln Pro Ser
145                 150                 155                 160

Ala Met Lys Glu Thr Pro Ser Lys Leu Ser Glu Arg Pro Cys Ser Thr
                165                 170                 175

Asn Asn Gly Thr Gly His Asn His Thr Gly Ala Ser Ile Ser Gly Ser
            180                 185                 190

Ala Pro Ala Ser Lys Ala Gln Val Val Gly Trp Pro Pro Ile Arg Ser
        195                 200                 205

Phe Arg Lys Asn Ser Met Ala Thr Thr Thr Asn Lys Asn Asn Asp Glu
    210                 215                 220

Val Asp Gly Lys Pro Gly Val Gly Ala Leu Phe Val Lys Val Ser Met
225                 230                 235                 240
```

```
Asp Gly Ala Pro Tyr Leu Arg Lys Val Asp Leu Arg Ser Tyr Thr Thr
                245                 250                 255

Tyr Gln Glu Leu Ser Ser Ala Leu Glu Lys Met Phe Leu Ser Cys Phe
            260                 265                 270

Thr Leu Gly Gln Cys Gly Ser His Gly Ala Pro Gly Arg Glu Met Leu
        275                 280                 285

Ser Glu Ser Lys Leu Arg Asp Leu Leu His Gly Ser Glu Tyr Val Leu
    290                 295                 300

Thr Tyr Glu Asp Lys Asp Gly Asp Trp Met Leu Val Gly Asp Val Pro
305                 310                 315                 320

Trp Glu Met Phe Ile Glu Thr Cys Lys Arg Leu Lys Ile Met Lys Gly
                325                 330                 335

Ser Asp Ala Ile Gly Leu Ala Pro Arg Ala Met Glu Lys Ser Lys Ser
            340                 345                 350

Arg Ile


<210> SEQ ID NO 70
<211> LENGTH: 1080
<212> TYPE: DNA
<213> ORGANISM: Glycine max

<400> SEQUENCE: 70

atgatgtcgc cgccggcggt ggtaacggag gaggaggggc ggagcaacgt gtcgtcgacc      60

gtggcgtccg gttcttcgca atccttggac cgtttctctc agaatggggc tggattgaaa     120

gaacgaaatt acttagggtt atctgattgc tcatcagttg atagcagtgc ctctactgtg     180

ccaagcttgt gtgatgagaa aaaggagaac atgaatttga aggctacaga gttgaggctg     240

ggtcttcccg gatcccaatc gcctgaaagg gagccggatc ttttctcttt aagcccagca     300

aagcttgatg agaagccact gttccctttg cttcctacta aagacgggat ttgcttgtcg     360

gcgcaaaaaa ctgttgtttc tggcaacaaa agaggttttg ctgataccat ggatgggttt     420

tctcagggga agttcgctgg taatacaggg atgaacgcaa tgctatcacc taggccttct     480

ggagctcagc cttctgctat gaaagaaata ccaagcaagt tgcaagaaag gccctgttca     540

actaagaatg gaaccggtca taaccataca ggtgcttcca tcagtggcag cgcaccggct     600

tctaaggcac aggttgttgg ttggcctcct ataagatctt ttaggaaaaa ctcgatggcc     660

acgacaacta acaagaacaa tgatgaagtg gatgggaaac caggtgttgg cgcactcttt     720

gtgaaggtca gcatggatgg tgctccgtat cttaggaagg tagatctaag aagttataca     780

acttatcagg aactatcatc tgcgcttgag aagatgttcc taagctgttt taccctaggt     840

cagtgtggtt cccatggagc tccaggaaga gaaatgttga gtgagagcaa gttgagggat     900

cttctgcatg gttctgagta tgttctcact tatgaagata aagatggaga ttggatgctt     960

gtaggggatg taccatggga aatgttcatt gacacttgca aaaggctgaa aattatgaaa    1020

ggttctgatg ccattggttt agctcccagg gccatggaaa agtccaaaag caggagttag    1080


<210> SEQ ID NO 71
<211> LENGTH: 359
<212> TYPE: PRT
<213> ORGANISM: Glycine Max

<400> SEQUENCE: 71

Met Met Ser Pro Pro Ala Val Val Thr Glu Glu Glu Gly Arg Ser Asn
1               5                   10                  15

Val Ser Ser Thr Val Ala Ser Gly Ser Ser Gln Ser Leu Asp Arg Phe
            20                  25                  30
```

```
Ser Gln Asn Gly Ala Gly Leu Lys Glu Arg Asn Tyr Leu Gly Leu Ser
        35                  40                  45

Asp Cys Ser Ser Val Asp Ser Ser Ala Ser Thr Val Pro Ser Leu Cys
    50                  55                  60

Asp Glu Lys Lys Glu Asn Met Asn Leu Lys Ala Thr Glu Leu Arg Leu
65                  70                  75                  80

Gly Leu Pro Gly Ser Gln Ser Pro Glu Arg Glu Pro Asp Leu Phe Ser
                85                  90                  95

Leu Ser Pro Ala Lys Leu Asp Glu Lys Pro Leu Phe Pro Leu Leu Pro
            100                 105                 110

Thr Lys Asp Gly Ile Cys Leu Ser Ala Gln Lys Thr Val Val Ser Gly
        115                 120                 125

Asn Lys Arg Gly Phe Ala Asp Thr Met Asp Gly Phe Ser Gln Gly Lys
    130                 135                 140

Phe Ala Gly Asn Thr Gly Met Asn Ala Met Leu Ser Pro Arg Pro Ser
145                 150                 155                 160

Gly Ala Gln Pro Ser Ala Met Lys Glu Ile Pro Ser Lys Leu Gln Glu
                165                 170                 175

Arg Pro Cys Ser Thr Lys Asn Gly Thr Gly His Asn His Thr Gly Ala
            180                 185                 190

Ser Ile Ser Gly Ser Ala Pro Ala Ser Lys Ala Gln Val Val Gly Trp
        195                 200                 205

Pro Pro Ile Arg Ser Phe Arg Lys Asn Ser Met Ala Thr Thr Thr Asn
    210                 215                 220

Lys Asn Asn Asp Glu Val Asp Gly Lys Pro Gly Val Gly Ala Leu Phe
225                 230                 235                 240

Val Lys Val Ser Met Asp Gly Ala Pro Tyr Leu Arg Lys Val Asp Leu
                245                 250                 255

Arg Ser Tyr Thr Thr Tyr Gln Glu Leu Ser Ser Ala Leu Glu Lys Met
            260                 265                 270

Phe Leu Ser Cys Phe Thr Leu Gly Gln Cys Gly Ser His Gly Ala Pro
        275                 280                 285

Gly Arg Glu Met Leu Ser Glu Ser Lys Leu Arg Asp Leu Leu His Gly
    290                 295                 300

Ser Glu Tyr Val Leu Thr Tyr Glu Asp Lys Asp Gly Asp Trp Met Leu
305                 310                 315                 320

Val Gly Asp Val Pro Trp Glu Met Phe Ile Asp Thr Cys Lys Arg Leu
                325                 330                 335

Lys Ile Met Lys Gly Ser Asp Ala Ile Gly Leu Ala Pro Arg Ala Met
            340                 345                 350

Glu Lys Ser Lys Ser Arg Ser
        355
```

<210> SEQ ID NO 72
<211> LENGTH: 888
<212> TYPE: DNA
<213> ORGANISM: Triticum aestivum

<400> SEQUENCE: 72

```
atgccgccgc ccaatctcga agcgcgcgac tacatcggcc tcggcccctc tgcggcgccc      60

gcgcccgcct cctcctcctg ctcctcctcc gcctcgggcg acgccggccc gcacctcgcg     120

ctccgcctcg gcctgccggg ctgcggctcg ccgggacggg acgggccgga ggacgccgcc     180

gtcgacgccg cgctcacgct cgggccgtct ccagctaccg ctcatgcttc gcacaggggc     240
```

```
ggcgccaagc gcgggttcgc cgactcgctc gacggctccg ctgccagggc tgtcggggag    300

gaagacaaga agaagggtga ggccgccgcc gccgccggag ccggggctcc gccagctgcc    360

aaggcacaag ttgttgggtg gccgcctgtt cggagctacc ggaagaacac gctagccgcc    420

aatgccacaa agaccaaggc cgagaacgaa ggcagaagcg aggcagggtg ctgctatgtc    480

aaggtcagca tggatggagc accgtaccta aggaaggtcg atcttaagac ttactccagc    540

tatgacaacc tttccctgga gctggagaag atgttcagct gcttcatcac tggcaaaagc    600

agttcctgca aaacatcgac gagagacagg ctcactgatg gttctagggc tgatgctctt    660

caggaccaag agtatgtact cacctatgaa gacaaggatg ctgactggat gcttgttggt    720

gatcttcctt gggacttgtt taccactact tgtcggaaac tgagaatcat gagaggctct    780

gatgctgctg gaatgggtat ccccaagata gctggaaccg acgaccggcc agaacaaaca    840

ggcgcccgtc cgtcctggcc tctcctccgc ttcctgaagt ctgtctga                 888


<210> SEQ ID NO 73
<211> LENGTH: 295
<212> TYPE: PRT
<213> ORGANISM: Triticum aestivum

<400> SEQUENCE: 73

Met Pro Pro Pro Asn Leu Glu Ala Arg Asp Tyr Ile Gly Leu Gly Pro
1               5                   10                  15

Ser Ala Ala Pro Ala Pro Ala Ser Ser Ser Cys Ser Ser Ser Ala Ser
            20                  25                  30

Gly Asp Ala Gly Pro His Leu Ala Leu Arg Leu Gly Leu Pro Gly Cys
        35                  40                  45

Gly Ser Pro Gly Arg Asp Gly Pro Glu Asp Ala Ala Val Asp Ala Ala
    50                  55                  60

Leu Thr Leu Gly Pro Ser Pro Ala Thr Ala His Ala Ser His Arg Gly
65                  70                  75                  80

Gly Ala Lys Arg Gly Phe Ala Asp Ser Leu Asp Gly Ser Ala Ala Arg
                85                  90                  95

Ala Val Gly Glu Glu Asp Lys Lys Lys Gly Glu Ala Ala Ala Ala Ala
            100                 105                 110

Gly Ala Gly Ala Pro Pro Ala Ala Lys Ala Gln Val Val Gly Trp Pro
        115                 120                 125

Pro Val Arg Ser Tyr Arg Lys Asn Thr Leu Ala Ala Asn Ala Thr Lys
    130                 135                 140

Thr Lys Ala Glu Asn Glu Gly Arg Ser Glu Ala Gly Cys Cys Tyr Val
145                 150                 155                 160

Lys Val Ser Met Asp Gly Ala Pro Tyr Leu Arg Lys Val Asp Leu Lys
                165                 170                 175

Thr Tyr Ser Ser Tyr Asp Asn Leu Ser Leu Glu Leu Glu Lys Met Phe
            180                 185                 190

Ser Cys Phe Ile Thr Gly Lys Ser Ser Ser Cys Lys Thr Ser Thr Arg
        195                 200                 205

Asp Arg Leu Thr Asp Gly Ser Arg Ala Asp Ala Leu Gln Asp Gln Glu
    210                 215                 220

Tyr Val Leu Thr Tyr Glu Asp Lys Asp Ala Asp Trp Met Leu Val Gly
225                 230                 235                 240

Asp Leu Pro Trp Asp Leu Phe Thr Thr Thr Cys Arg Lys Leu Arg Ile
                245                 250                 255

Met Arg Gly Ser Asp Ala Ala Gly Met Gly Ile Pro Lys Ile Ala Gly
            260                 265                 270
```

Thr Asp Asp Arg Pro Glu Gln Thr Gly Ala Arg Pro Ser Trp Pro Leu
275 280 285

Leu Arg Phe Leu Lys Ser Val
290 295

<210> SEQ ID NO 74
<211> LENGTH: 236
<212> TYPE: PRT
<213> ORGANISM: Arabidopsis thaliana

<400> SEQUENCE: 74

Met Ile Asn Phe Glu Ala Thr Glu Leu Arg Leu Gly Leu Pro Gly Gly
1 5 10 15

Asn His Gly Gly Glu Met Ala Gly Lys Asn Asn Gly Lys Arg Gly Phe
20 25 30

Ser Glu Thr Val Asp Leu Lys Leu Asn Leu Ser Ser Thr Ala Met Asp
35 40 45

Ser Val Ser Lys Val Asp Leu Glu Asn Met Lys Glu Lys Val Val Lys
50 55 60

Pro Pro Ala Lys Ala Gln Val Val Gly Trp Pro Pro Val Arg Ser Phe
65 70 75 80

Arg Lys Asn Val Met Ser Gly Gln Lys Pro Thr Thr Gly Asp Ala Thr
85 90 95

Glu Gly Asn Asp Lys Thr Ser Gly Ser Ser Gly Ala Thr Ser Ser Ala
100 105 110

Ser Ala Cys Ala Thr Val Ala Tyr Val Lys Val Ser Met Asp Gly Ala
115 120 125

Pro Tyr Leu Arg Lys Ile Asp Leu Lys Leu Tyr Lys Thr Tyr Gln Asp
130 135 140

Leu Ser Asn Ala Leu Ser Lys Met Phe Ser Ser Phe Thr Ile Gly Asn
145 150 155 160

Tyr Gly Pro Gln Gly Met Lys Asp Phe Met Asn Glu Ser Lys Leu Ile
165 170 175

Asp Leu Leu Asn Gly Ser Asp Tyr Val Pro Thr Tyr Glu Asp Lys Asp
180 185 190

Gly Asp Trp Met Leu Val Gly Asp Val Pro Trp Glu Met Phe Val Asp
195 200 205

Ser Cys Lys Arg Ile Arg Ile Met Lys Gly Ser Glu Ala Ile Gly Leu
210 215 220

Ala Pro Arg Ala Leu Glu Lys Cys Lys Asn Arg Ser
225 230 235

<210> SEQ ID NO 75
<211> LENGTH: 339
<212> TYPE: PRT
<213> ORGANISM: Glycine max

<400> SEQUENCE: 75

Val Ala Ser Gly Ser Ser Gln Ser Leu Asp Arg Phe Ser Gln Asn Gly
1 5 10 15

Ala Gly Leu Lys Glu Arg Asn Tyr Leu Gly Leu Ser Asp Cys Ser Ser
20 25 30

Val Asp Ser Ser Ala Ser Thr Val Pro Ser Leu Cys Asp Glu Lys Lys
35 40 45

Glu Asn Met Asn Leu Lys Ala Thr Glu Leu Arg Leu Gly Leu Pro Gly
50 55 60

-continued

```
Ser Gln Ser Pro Glu Arg Glu Pro Asp Leu Phe Ser Leu Ser Pro Ala
65                  70                  75                  80

Lys Leu Asp Glu Lys Pro Leu Phe Pro Leu Leu Pro Thr Lys Asp Gly
                85                  90                  95

Ile Cys Leu Ser Ala Gln Lys Thr Val Val Ser Gly Asn Lys Arg Gly
            100                 105                 110

Phe Ala Asp Thr Met Asp Gly Phe Ser Gln Gly Lys Phe Ala Gly Asn
        115                 120                 125

Thr Gly Met Asn Ala Met Leu Ser Pro Arg Pro Ser Gly Ala Gln Pro
    130                 135                 140

Ser Ala Met Lys Glu Ile Pro Ser Lys Leu Gln Glu Arg Pro Cys Ser
145                 150                 155                 160

Thr Lys Asn Gly Thr Gly His Asn His Thr Gly Ala Ser Ile Ser Gly
                165                 170                 175

Ser Ala Pro Ala Ser Lys Ala Gln Val Val Gly Trp Pro Pro Ile Arg
            180                 185                 190

Ser Phe Arg Lys Asn Ser Met Ala Thr Thr Thr Asn Lys Asn Asn Asp
        195                 200                 205

Glu Val Asp Gly Lys Pro Gly Val Gly Ala Leu Phe Val Lys Val Ser
    210                 215                 220

Met Asp Gly Ala Pro Tyr Leu Arg Lys Val Asp Leu Arg Ser Tyr Thr
225                 230                 235                 240

Thr Tyr Gln Glu Leu Ser Ser Ala Leu Glu Lys Met Phe Leu Ser Cys
                245                 250                 255

Phe Thr Leu Gly Gln Cys Gly Ser His Gly Ala Pro Gly Arg Glu Met
            260                 265                 270

Leu Ser Glu Ser Lys Leu Arg Asp Leu Leu His Gly Ser Glu Tyr Val
        275                 280                 285

Leu Thr Tyr Glu Asp Lys Asp Gly Asp Trp Met Leu Val Gly Asp Val
    290                 295                 300

Pro Trp Glu Met Phe Ile Asp Thr Cys Lys Arg Leu Lys Ile Met Lys
305                 310                 315                 320

Gly Ser Asp Ala Ile Gly Leu Ala Pro Arg Ala Met Glu Lys Ser Lys
                325                 330                 335

Ser Arg Ser


<210> SEQ ID NO 76
<211> LENGTH: 346
<212> TYPE: PRT
<213> ORGANISM: Oryza sativa

<400> SEQUENCE: 76

Met Pro Pro Pro Leu Glu Ala Arg Asp Tyr Ile Gly Leu Gly Ala Thr
1               5                   10                  15

Pro Ala Ser Ser Ser Ser Ser Cys Cys Ala Ser Thr Pro Val Ala Glu
            20                  25                  30

Val Val Gly Ala His Leu Ala Leu Arg Leu Gly Leu Pro Gly Ser Glu
        35                  40                  45

Ser Pro Ala Arg Ala Glu Ala Glu Ala Val Val Val Asp Ala Ala Leu
    50                  55                  60

Thr Leu Gly Pro Ala Pro Pro Pro Arg Gly Gly Ala Lys Arg Gly Phe
65                  70                  75                  80

Val Asp Ser Leu Asp Arg Ser Glu Gly Arg Arg Ala Ala Ala Thr Ala
                85                  90                  95

Gly Asp Asp Glu Arg Gly Val Arg Glu Glu Glu Glu Glu Glu Glu Lys
```

```
            100                 105                 110

Gly Leu Gly Glu Ala Ala Ala Gly Ala Pro Arg Ala Ala Lys Ala Gln
        115                 120                 125

Val Val Gly Trp Pro Pro Val Arg Ser Tyr Arg Lys Asn Thr Leu Ala
    130                 135                 140

Ala Ser Ala Thr Lys Thr Lys Gly Glu Asp Gln Gly Lys Ser Glu Val
145                 150                 155                 160

Gly Cys Cys Tyr Val Lys Val Ser Met Asp Gly Ala Pro Tyr Leu Arg
                165                 170                 175

Lys Val Asp Leu Lys Thr Tyr Ser Ser Tyr Glu Asp Leu Ser Leu Ala
            180                 185                 190

Leu Glu Lys Met Phe Ser Cys Phe Ile Thr Gly Arg Ser Ser Ser His
        195                 200                 205

Lys Thr Ser Lys Arg Asp Arg Leu Thr Asp Gly Ser Arg Ala Asp Ala
    210                 215                 220

Leu Lys Asp Gln Glu Tyr Val Leu Thr Tyr Glu Asp Lys Asp Ala Asp
225                 230                 235                 240

Trp Met Leu Val Gly Asp Leu Pro Trp Asp Leu Phe Thr Thr Ser Cys
                245                 250                 255

Arg Lys Leu Arg Ile Met Arg Gly Ser Asp Ala Ala Gly Ile Ala Ser
            260                 265                 270

Asp Asn Leu Ser Asn Gly Asn Ser Leu Arg Asp His Trp Asn Arg Gln
        275                 280                 285

Pro Glu Ala Gln Asn Ser Asp Asp Tyr Pro Asn Leu Gly Lys Ile Ala
    290                 295                 300

Phe Leu Gln Cys Ser Trp Val Asp Leu Pro Tyr Ala Ser Leu Pro Glu
305                 310                 315                 320

Thr Arg Ser Ser Glu Ser Leu Met Thr Ile Pro Ile Leu Leu Ala Gly
                325                 330                 335

Ile Ser Ala Tyr Leu Cys Asn Ile Pro Tyr
            340                 345
```

<210> SEQ ID NO 77
<211> LENGTH: 648
<212> TYPE: DNA
<213> ORGANISM: maize

<400> SEQUENCE: 77

```
gccggtgcgc actgggagca tcgccggaaa aaaaattctt cggctaagag taacttcttt      60

ctccttttct tctctgatct cgcgagcagt gctgataacg tgttgtaatc tacttagcgg     120

taacgagatt gagagagaca aaatgacaga actattgtct ttattgcaga gtgtcatgta     180

tttatacagg ggatacaaag tctcccaagg ggtgtgtccc ttgggagtaa ctgccagttg     240

atcacaggac aatattttgt aacaaaacgt acacatcgtc aaaatagcga ggcatgaaac     300

tggccttggc catggacgcg tgaagcgcgc catgcgttgg atatgtggtc aataagtata     360

tacaatacaa tgtttaacag agctgatagt actgctttgg cacatttttg tccacgcttc     420

atgagagata aaacacctgc acgtaaattc acatgctgca ctgaaggccc gatcactgag     480

gagcgaactg ccgtaactcc cttctatata tacccccagt ccctgtttca gttttcgtca     540

agctagcagc accaagttgt cgatcacttg cctgctcttg agctcgatta agctatcatc     600

agctacagca tccgatccca aactgcaact gtagcagcga caactgcc                  648
```

<210> SEQ ID NO 78
<211> LENGTH: 324

-continued

```
<212> TYPE: DNA
<213> ORGANISM: maize

<400> SEQUENCE: 78

gcgcgccatg cgttggatat gtggtcaata agtatataca atacaatgtt taacagagct     60

gatagtactg ctttggcaca tttttgtcca cgcttcatga gagataaaac acctgcacgt    120

aaattcacat gctgcactga aggcccgatc actgaggagc gaactgccgt aactcccttc    180

tatatatacc cccagtccct gtttcagttt tcgtcaagct agcagcacca agttgtcgat    240

cacttgcctg ctcttgagct cgattaagct atcatcagct acagcatccg atcccaaact    300

gcaactgtag cagcgacaac tgcc                                           324


<210> SEQ ID NO 79
<211> LENGTH: 566
<212> TYPE: DNA
<213> ORGANISM: maize

<400> SEQUENCE: 79

aaatccttac agaattgctg tagtttcata gtgctagatg tggacagcaa agcgccgctg     60

tatgcttctg cttttctttt ttggtgtgtg tagccacatc ctttgttcct gcccggcgcc    120

atcccacttg gttgtttttt tttatgattg aaagccttca tgcttcctcg gtcaatcacc    180

ggtgcgcact gggagcatcg ccggaaaaaa aattcttcgg ctaagagtaa cttctttctc    240

cttttcttct ctgatctcgc gagcagtgct gataacgtgt tgtaatctac ttagcggtaa    300

cgagattgag agagacaaaa tgacagaact attgtcttta ttgcagagtg tcatgtattt    360

atacagggga tacaaagtct cccaaggggt gtgtcccttg ggagtaactg ccagttgatc    420

acaggacaat attttgtaac aaaacgtaca catcgtcaaa atagcgaggc atgaaactgg    480

ccttggccat ggacgcgtga agcgcgccat gcgttggata tgtggtcaat aagtatatac    540

aatacaatgt ttaacagagc tgatag                                         566
```

PLANTS WITH ALTERED ROOT ARCHITECTURE, INVOLVING THE RUM1 GENE, RELATED CONSTRUCTS AND METHODS

This application is a continuation-in-part of U.S. application Ser. No. 12/030,455, filed Feb. 13, 2008, pending, which claims priority to U.S. Provisional Application No. 60/889,637, filed Feb. 13, 2007, the entire contents of which are hereby incorporated by reference in their entirety.

FIELD OF THE INVENTION

This invention relates to compositions and methods useful in altering root architecture in plants. Additionally, the invention relates to plants that have been genetically transformed with the compositions of the invention.

BACKGROUND OF THE INVENTION

Relatively little is known about the genetic regulation of plant root development and function. Elucidation of the genetic regulation is important because roots serve important functions such as acquisition of water and nutrients and the anchorage of the plants in the soil.

Maize root architecture is composed of different root types formed at different plant developmental stages. A number of mutants affected in specific root types during different developmental stages have been described in maize (e.g. rtcs (rootless concerning crown and seminal roots), lrt1 (lateral rootless1)). The monogenic recessive rum1 ((rootless with undetectable meristems 1) mutant was first reported by Woll et al. (2004) *Maize Genetics Cooperation Newsletter* 78: 59-60. A more detailed description of the mutant phenotype was published by Woll et al. (2005) *Plant Physiology* 139 (3): 1255-1267. The maize mutant was shown to be impaired in the formation of seminal and lateral roots on the primary root. No obvious differences were detectable in aboveground development between rum1 and wild-type plants. Genetic analysis of the rum1 mutation indicated that it is inherited as a monogenic recessive trait. However, introduction of the rum1 mutation into different genetic backgrounds resulted in segregation ratios that suggested the presence of a recessive suppressor of the rum1 mutation in those backgrounds.

The plant hormone auxin plays a crucial role during embryogenesis and is involved in various aspects of root development. In the rum1 mutant, auxin transport toward the root tip is severely reduced. Mutations in members of the auxin-inducible Aux/IAA and ARF gene families of *Arabidopsis* result in phenotypes that resemble the maize rum1 phenotype in regard to the absence of lateral roots on the primary root. Several gain-of-function mutants lacking lateral roots or inhibited in lateral root formation have been described in *Arabidopsis* (Solitary-Root/IAA14 gene (SLR/IAA14) described by Fukaki et al. (2002) *The Plant Journal* 29(2): 153-168; Massugu2/IAA19 gene (MSG2/IAA19) described by Tatematsu et al. (2004) *Plant Cell* 16: 379-393. Okushima et al. (2005) *Plant Cell* 17: 444-463 described a arf7arf19 double mutant, that shows a phenotype similar to the slr/iaa14 and msg/iaa19 mutants.

In vitro experiments indicate that IAA14 interacts with both ARF7 and ARF19, and that IAA19 interacts with ARF7. Aux/IAA and ARFs are therefore considered major components of the auxin signaling pathway that controls plant growth responses to the hormone auxin.

Despite the extensive genetic and morphological characterization of the rum1 mutant, there has been no molecular analysis of the nucleic acid encoding the protein associated with the rum1 phenotype. Indeed, the identity of the protein encoded by rum1 has not been reported.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 85% sequence identity, based on the Clustal V method of alignment, when compared to SEQ ID NO: 73 and wherein said plant exhibits altered root architecture when compared to a control plant not comprising said recombinant DNA construct.

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO: 24, 29, 39, 67, 69, 71 or 73, and wherein said plant exhibits altered root architecture when compared to a control plant not comprising said recombinant DNA construct.

In another embodiment, a plant comprising in its genome a recombinant DNA construct comprising: (a) a polynucleotide operably linked to at least one regulatory element, wherein said polynucleotide encodes a polypeptide having an amino acid sequence of at least 50% sequence identity, based on the Clustal V method of alignment, when compared to SEQ ID NO: 24, 29, 39, 67, 69, 71 or 73 or (b) a suppression DNA construct comprising at least one regulatory element operably linked to: (i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73 or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide, and wherein said plant exhibits an alteration of at least one agronomic characteristic when compared to a control plant not comprising said recombinant DNA construct.

In another embodiment, a method of altering root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 24, 29, 39, 67, 69, 71 or 73; and (b) regenerating a transgenic plant from the regenerable plant cell after step (a), wherein the transgenic plant comprises in its genome the recombinant DNA construct and exhibits altered root architecture when compared to a control plant not comprising the recombinant DNA construct; and optionally, (c) obtaining a progeny plant derived from the transgenic plant, wherein said progeny plant comprises in its genome the recombinant DNA construct and exhibits altered root architecture when compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 24, 29, 39, 67, 69, 71 or 73; (b) regenerating a transgenic plant from the regenerable plant cell after step (a), wherein the transgenic plant comprises in its genome the recombinant DNA construct; and (c) evaluating root architecture of the transgenic plant compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating root architecture of the progeny plant compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 24, 29, 39, 67, 69, 71 or 73; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating root architecture of the progeny plant compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 24, 29, 39, 67, 69, 71 or 73; (b) regenerating a transgenic plant from the regenerable plant cell after step (a), wherein the transgenic plant comprises in its genome the recombinant DNA construct; and (c) determining whether the transgenic plant exhibits an alteration of at least one agronomic characteristic when compared to a control plant not comprising the recombinant DNA construct; and optionally, (d) obtaining a progeny plant derived from the transgenic plant, wherein the progeny plant comprises in its genome the recombinant DNA construct; and optionally, (e) determining whether the progeny plant exhibits an alteration of at least one agronomic characteristic when compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 24, 29, 39, 67, 69, 71 or 73; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct.

In another embodiment, a method of determining an alteration of an agronomic characteristic in a plant, comprising:

(a) introducing into a regenerable plant cell a suppression DNA construct comprising at least one regulatory element operably linked to:
- (i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73, or (B) a full complement of the nucleic acid sequence of (b)(i)(A); or
- (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide;

(b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared to a control plant not comprising the suppression DNA construct;

and optionally, (d) obtaining a progeny plant derived from the transgenic plant, wherein the progeny plant comprises in its genome the suppression DNA construct; and optionally, (e) determining whether the progeny plant exhibits an alteration of at least one agronomic characteristic when compared to a control plant not comprising the suppression DNA construct.

In another embodiment, a method of determining an alteration of an agronomic characteristic in a plant, comprising:

(a) introducing into a regenerable plant cell a suppression DNA construct comprising at least one regulatory element operably linked to:
- (i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73, or (B) a full complement of the nucleic acid sequence of (a)(i)(A); or
- (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide;

(b) regenerating a transgenic plant from the regenerable plant cell after step (a), wherein the transgenic plant comprises in its genome the suppression DNA construct and exhibits altered root architecture when compared to a control plant not comprising the suppression DNA construct;

(c) obtaining a progeny plant derived from the transgenic plant, wherein the progeny plant comprises in its genome the suppression DNA construct; and (d) determining whether the progeny plant exhibits an alteration of at least one agronomic characteristic when compared to a control plant not comprising the suppression DNA construct.

In another embodiment, a method of altering root architecture in a plant, comprising:

(a) introducing into a regenerable plant cell a suppression DNA construct comprising at least one regulatory element operably linked to:

(i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73; or (B) a full complement of the nucleic acid sequence of (a)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide; and (b) regenerating a transgenic plant from the regenerable plant cell after step (a), wherein the transgenic plant comprises in its genome the suppression DNA construct and wherein the transgenic plant exhibits altered root architecture when compared to a control plant not comprising the suppression DNA construct; and optionally, (c) obtaining a progeny plant derived from the transgenic plant, wherein said progeny plant comprises in its genome the recombinant DNA construct and wherein the progeny plant exhibits altered root architecture when compared to a control plant not comprising the suppression DNA construct.

In another embodiment, a method of evaluating root architecture in a plant, comprising:

(a) introducing into a regenerable plant cell a suppression DNA construct comprising at least one regulatory element operably linked to:

(i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73, or (B) a full complement of the nucleic acid sequence of (a)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide;

(b) regenerating a transgenic plant from the regenerable plant cell after step (a), wherein the transgenic plant comprises in its genome the suppression DNA construct; and (c) evaluating root architecture of the transgenic plant compared to a control plant not comprising the suppression DNA construct;

and optionally, (d) obtaining a progeny plant derived from the transgenic plant, wherein the progeny plant comprises in its genome the suppression DNA construct; and optionally, (e) evaluating root architecture of the progeny plant compared to a control plant not comprising the suppression DNA construct.

In another embodiment, a method of evaluating root architecture in a plant, comprising:

(a) introducing into a regenerable plant cell a suppression DNA construct comprising at least one regulatory element operably linked to:

(i) all or part of: (A) a nucleic acid sequence encoding a polypeptide having an amino acid sequence of at least 50% sequence identity, based on the Clustal V method of alignment, when compared to SEQ ID NO: 24, 29, 39, 67, 69, 71 or 73, or (B) a full complement of the nucleic acid sequence of (a)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a RUM1 or RUM1-like polypeptide;

(b) regenerating a transgenic plant from the regenerable plant cell after step (a), wherein the transgenic plant comprises in its genome the suppression DNA construct;

(c) obtaining a progeny plant derived from the transgenic plant, wherein the progeny plant comprises in its genome the suppression DNA construct; and (d) evaluating root architecture of the progeny plant compared to a control plant not comprising the suppression DNA construct.

Also included in the present invention is any progeny of the above plants, any seeds of the above plants, and cells from any of the above plants and progeny. A method of producing seed that can be sold as a product offering with altered root architecture comprising any of the preceding preferred methods, and further comprising obtaining seeds from said progeny plant, wherein said seeds comprise in their genome said recombinant DNA construct.

In another embodiment, a promoter driving transcription in a root-preferred manner, wherein said regulatory element comprises a nucleotide sequence selected from the group consisting of: a) sequences natively associated with, and that regulate expression of DNA coding for maize Nicotinamine Synthase 2 (NAS2); b) the nucleotide sequence set forth in SEQ ID NO:51; and c) a sequence comprising a fragment of the nucleotide sequence set forth in SEQ ID NO:51. In yet another embodiment the promoter comprises SEQ ID NO:77 (TR1). In a further embodiment, the promoter comprises SEQ ID NO:78 (TR2). In yet another embodiment, the promoter comprises SEQ ID NO:79 (TR3). Also included in the present invention are recombinant constructs, vectors, cells, plants and seeds comprising the sequences of the invention.

BRIEF DESCRIPTION OF THE FIGURES AND SEQUENCE LISTINGS

The invention can be more fully understood from the following detailed description and the accompanying drawings and Sequence Listing which form a part of this application.

FIG. 16 is the growth medium used for semi-hydroponics maize growth in Example 19.

FIG. 17 is a chart setting forth data relating to the effect of different nitrate concentrations on the growth and development of Gaspe Bay Flint derived maize lines in Example 19.

FIG. 18 shows the multiple alignment of the full length amino acid sequences of B73-Mu-wt RUM1 (SEQ ID NO:24), B73 RUM1 (SEQ ID NO:29), B73 RUL (SEQ ID NO:39), the mutant rum1 (SEQ ID NO:25) and the rice protein identified as belonging to the AUX-IM family (NCBI General identifier No. 34911088, SEQ ID NO:65). Amino acids conserved among all sequences are indicated with an asterisk (*) on the top row; dashes are used by the program to maximize alignment of the sequences. The L×L×L motif described in Example 24 is shown in bold letters. The method parameters used to produce the multiple alignment of the sequences below was performed using the Clustal method of alignment (Higgins and Sharp (1989) *CABIOS.* 5:151-153) with the default parameters (GAP PENALTY=10, GAP LENGTH PENALTY=10).

FIG. 19 shows a chart of the percent sequence identity for each pair of amino acid sequences displayed in FIG. 18.

Figure 20:
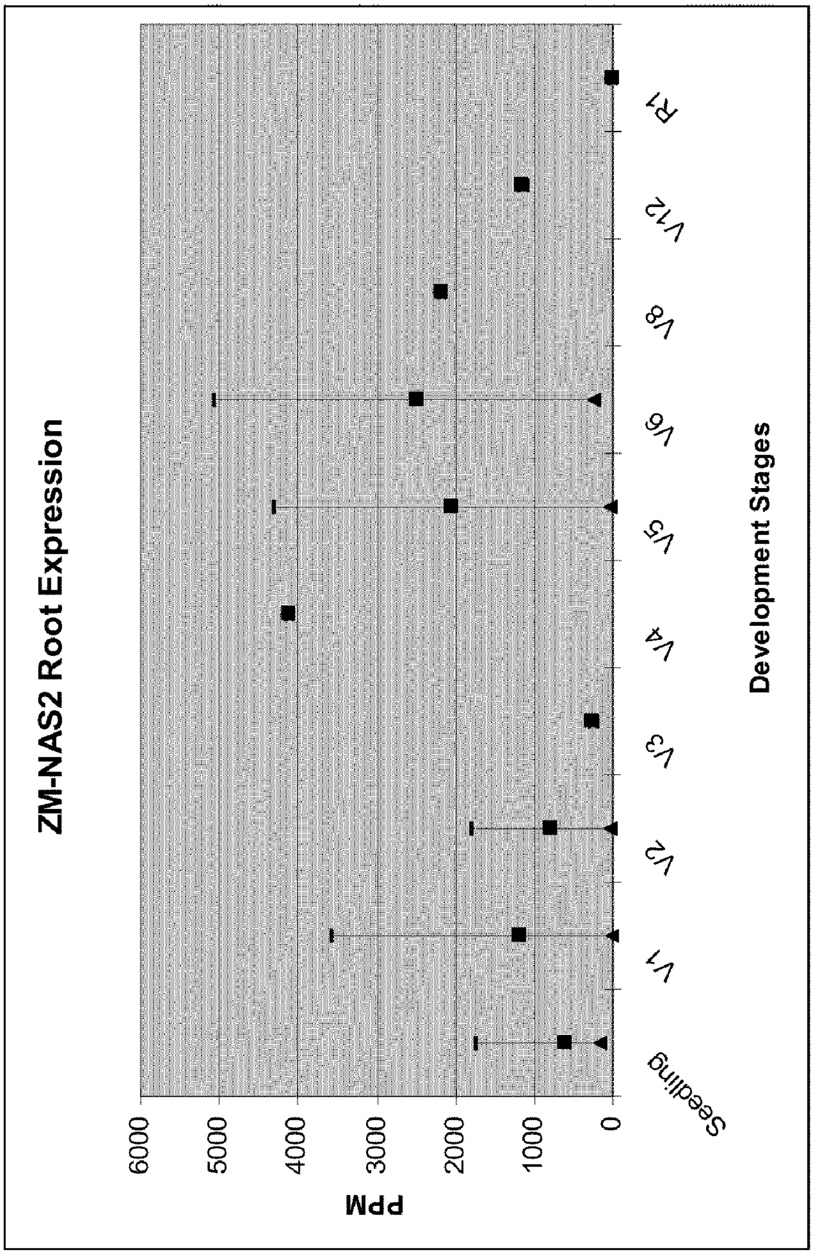

FIG. 20 shows the average expression levels of the maize NAS2 gene in MPSS libraries from root tissues at different developmental stages, shown with maximum PPM (bars, top), mean PPM (squares, middle) and minimum PPM (triangles, bottom). The peak expression is in a V6 root library at 5067 PPM, and the lowest level of expression was 9 PPM found in a V1 root library. The maize NAS 2 gene has expression in root tissues only.

Figure 21:
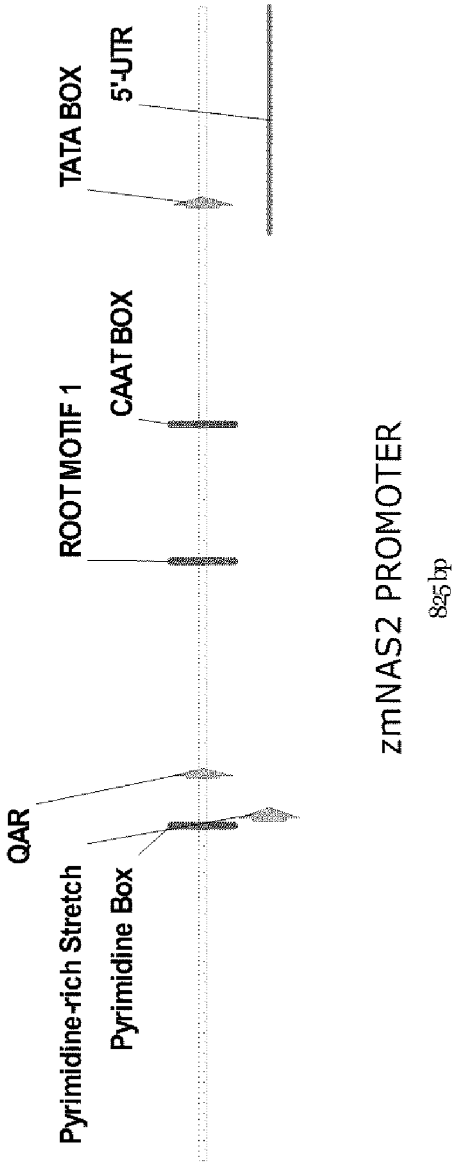

FIG. 21 shows a vector NTI map depicting the NAS2 promoter and motif locations (Pyrimidine Box at position 240-245, Pyrimidine-rich stretch at 243-252, QAR element at 274-280, and Root Motif 1 at 429-433).

Figure 22:
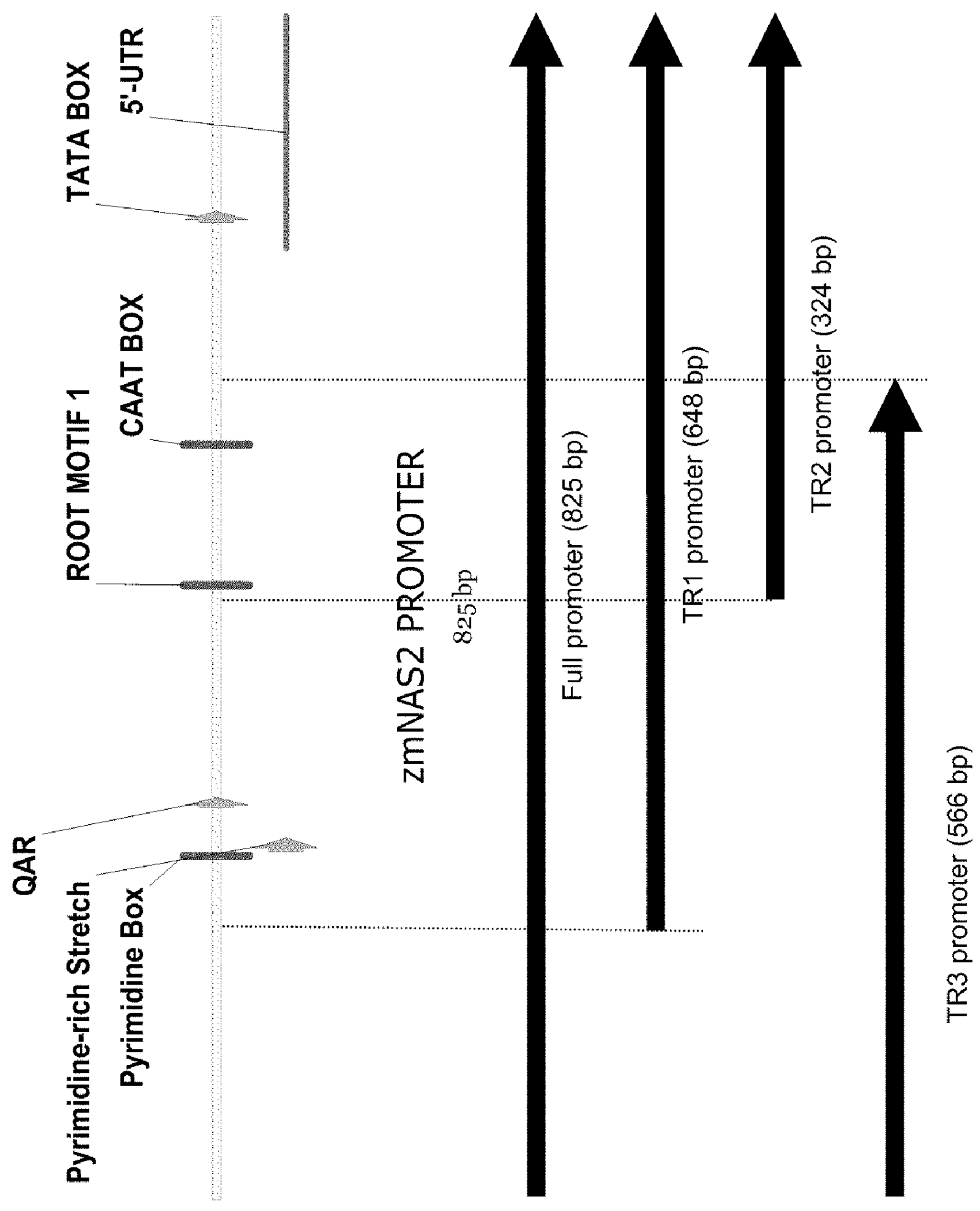

FIG. 22 shows a diagrammed illustration of the three variants of the promoter by truncations. TR1 (truncated 1, SEQ ID NO:77), TR2 (truncated 2, SEQ ID NO:78) and TR3 (truncated 3, SEQ ID NO:79).

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

SEQ ID NO:1 is the forward primer for SSR marker UMC1690 used in Example 1.

SEQ ID NO:2 is the reverse primer for SSR marker UMC1690 used in Example 1.

SEQ ID NO:3 is the forward primer for SSR marker BNLG 1108 used in Example 1.

SEQ ID NO:4 is the reverse primer for SSR marker BNLG 1108 used in Example 1.

SEQ ID NO:5 is the forward primer for marker UMC1844 used in Example 1.

SEQ ID NO:6 is the reverse primer for marker UMC1844 used in Example 1.

SEQ ID NO:7 is the forward primer for marker UMC1915 used in Example 1.

SEQ ID NO:8 is the reverse primer for marker UMC1915 used in Example 1.

SEQ ID NO:9 is the forward primer for marker PHP9257A used in Example 1.

SEQ ID NO:10 is the reverse primer for marker PHP9257A used in Example 1.

SEQ ID NO:11 is the forward primer for marker UMC2274 used in Example 1.

SEQ ID NO:12 is the reverse primer for marker UMC2274 used in Example 1.

SEQ ID NO:13 is the forward primer for CAP marker MZA8411 used in Example 1.

SEQ ID NO:14 is the reverse primer for CAP marker MZA8411 used in Example 1.

SEQ ID NO:15 is the forward primer for CAP marker b0568n15 used in Example 1.

SEQ ID NO:16 is the reverse primer for CAP marker b0568n15 used in Example 1.

SEQ ID NO:17 is the forward primer for CAP marker MZA8828 used in Example 1.

SEQ ID NO:18 is the reverse primer for CAP marker MZA8828 used in Example 1.

SEQ ID NO:19 is the 4098 bp genomic fragment of b0568n15 containing the RUM1 gene.

SEQ ID NO:20 is the sequence of the forward primer RUM1−70F as described in Example 3.

SEQ ID NO:21 is the sequence of the reverse primer RUM1+40R as described in Example 3.

SEQ ID NO:22 is the wild type RUM1 cDNA sequence obtained from the mutant line (B73-Mu) described in Example 3.

SEQ ID NO:23 is the mutant rum1 cDNA sequence obtained from the mutant line (B73-Mu) described in Example 3.

SEQ ID NO:24 is the amino acid sequence encoded by SEQ ID NO:22.

SEQ ID NO:25 is the amino acid sequence encoded by SEQ ID NO:23.

SEQ ID NO:26 is the partial EST corresponding to accession number CD439-449 described in Example 4.

SEQ ID NO:27 is the amino acid sequence encoded by SEQ ID NO:26.

SEQ ID NO:28 is the full length RUM1 cDNA from B73 described in Example 4.

SEQ ID NO:29 is the amino acid sequence encoded by SEQ ID NO:28.

SEQ ID NO:30 is the amino acid sequence of the *Arabidopsis* IAA8 protein (gi:15227275).

SEQ ID NO:31 is the amino acid sequence of the *Arabidopsis* protein SLRIAA14 (gi:22328628).

SEQ ID NO:32 is the amino acid sequence of the *Arabidopsis* protein MSG2/IAA1 g (gi:1532612 or 17365900).

SEQ ID NO:33 is the forward primer RUM1-354F used in Example 6.

SEQ ID NO:34 is the reverse RUM1 exon1-R1 used in Example 6.

SEQ ID NO:35 is the forward primer −132F used in Example 6.

SEQ ID NO:36 is the reverse primer RUM1 exon1-R2 used in Example 6.

SEQ ID NO:37 is the MuTIR primer used in Example 6.

SEQ ID NO:38 is the sequence of the RUM1-like (RUL) cDNA described in Example 7.

SEQ ID NO:39 is the amino acid sequence of the RUL protein encoded by SEQ ID NO:38.

SEQ ID NO:40 is the forward primer RUL−43F described in Example 8.

SEQ ID NO:41 is the reverse primer RUL+181R described in Example 8.

SEQ ID NO:42 is the attB1 sequence described in Example 9.

SEQ ID NO:43 is the attB2 sequence described in Example 9.

SEQ ID NO:44 is the sequence of the forward primer VC062 described in Example 9.

SEQ ID NO:45 is the sequence of the reverse primer VC063 described in Example 9.

SEQ ID NO:46 is the sequence of vector pDONOR™/Zeo described in Example 9.

SEQ ID NO:47 is the sequence of vector pDONOR™/221 described in Example 9.

SEQ ID NO:48 is the sequence of PHP27840 described in Example 9.

SEQ ID NO:49 is the sequence of PHP23236 described in Example 9.

SEQ ID NO:50 is the sequence of PHP10523.

SEQ ID NO:51 is the sequence of the NAS2 promoter.

SEQ ID NO:52 is the sequence of the GOS2 promoter.

SEQ ID NO:53 is the sequence of the ubiquitin promoter.

SEQ ID NO:54 is the sequence of the PINII terminator.

SEQ ID NO:55 is the sequence of PHP28408.

SEQ ID NO:56 is the sequence of PHP20234.

SEQ ID NO:57 is the sequence of PHP28529.

SEQ ID NO:58 is the sequence of PHP22020.

SEQ ID NO:59 is the sequence of PHP23112.

SEQ ID NO:60 is the sequence of PHP23235.

SEQ ID NO:61 is the sequence of PHP29635.

SEQ ID NO:62 is the sequence of pIIOXS2a-FRT87(ni)m.

SEQ ID NO:63 is the sequence of the S2A promoter.

SEQ ID NO:64 is the GAL4 DNA binding sequence.

SEQ ID NO:65 is the sequence corresponding to NCBI General identifier No. 34911088.

SEQ ID NO:66 is the cDNA corresponding to nucleotides 155 through 865 (Stop) of the RUM1 homolog ebb1c.pk008.p9:fis.

SEQ ID NO:67 is the amino acid sequence encoded by SEQ ID NO:66.

SEQ ID NO:68 is the cDNA corresponding to nucleotides 154 through 1218 (Stop) of the RUM1 homolog smj1c.pk013.h7.f:fis.

SEQ ID NO:69 is the amino acid sequence encoded by SEQ ID NO:68.

SEQ ID NO:70 is the cDNA corresponding to nucleotides 225 through 1304 (Stop) of the RUM1 homolog smj1c.pk007.k12.f:fis.

SEQ ID NO:71 is the amino acid sequence encoded by SEQ ID NO:70.

SEQ ID NO:72 is the cDNA corresponding to nucleotides 155 through 865 (Stop) of the RUM1 homolog wdk1c.pk023.b8:fis.

SEQ ID NO:73 is the amino acid sequence encoded by SEQ ID NO:72.

SEQ ID NO:74 is the sequence corresponding to NCBI General identifier No. 15229343.

SEQ ID NO:75 is the sequence corresponding to NCBI General identifier No. 2388689.

SEQ ID NO:76 is the sequence corresponding to NCBI General identifier No. 125553286.

SEQ ID NO:77 is the 648 bp sequence of the NAS2 promoter variant TR1 (truncated 1).

SEQ ID NO:78 is the 324 bp sequence of the NAS2 promoter variant TR2 (truncated 2).

SEQ ID NO:79 is the 566 bp sequence of the NAS2 promoter variant TR3 (truncated 3).

DETAILED DESCRIPTION OF PREFERRED EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "root architecture" refers to the arrangement of the different parts that comprise the root. The terms "root architecture", "root structure", "root system" or "root system architecture" are used interchangeably herewithin.

In general, the first root of a plant that develops from the embryo is called the primary root. In most dicots, the primary root is called the taproot. This main root grows downward and gives rise to branch (lateral) roots. In monocots the primary root of the plant branches, giving rise to a fibrous root system.

The term "altered root architecture" refers to aspects of alterations of the different parts that make up the root system at different stages of its development compared to a reference or control plant. It is understood that altered root architecture encompasses alterations in one or more measurable parameters, including but not limited to, the diameter, length, number, angle or surface of one or more of the root system parts, including but not limited to, the primary root, lateral or branch root, crown roots, adventitious root, and root hairs, all of which fall within the scope of this invention. These changes can lead to an overall alteration in the area or volume occupied by the root. The reference or control plant does not comprise in its genome the recombinant DNA construct or heterologous construct.

"Agronomic characteristics" is a measurable parameter including but not limited to greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, and harvest index.

"Harvest index" refers to the grain weight divided by the total plant weight.

"RUM1-mu-wt" and "RUM1" refer to the *Zea Mays* RUM1 wild type gene and includes without limitation SEQ ID NO:22 and SEQ ID NO:28, respectively). "RUM1-mu-wt" and "RUM1" and refer to the *Zea Mays* RUM1 wild type protein encoded by SEQ ID NO:24 and SEQ ID NO:29, respectively.

"RUM1-like" or RUL are used interchangeable herewithin and refer to the nucleotide homolog of the maize RUM1 and RUM1-mu-wt sequences and includes without limitation the nucleotide sequence of SEQ ID NO:38.

"RUM1-like" or RUL are used interchangeable herewithin and refer to the polypeptide homolog of the maize RUM1 and RUM1-mu-wt proteins and includes without limitation the amino acid sequence of SEQ ID NO:39.

"rum1" refers to the nucleotide sequence of the *Zea Mays* "footless with undetectable meristems 1" mutant and includes without limitation SEQ ID NO:23.

"rum1" refers to the polypeptide of the *Zea Mays* "footless with undetectable meristems 1" mutant and includes without limitation SEQ ID NO:25.

"Environmental conditions" refer to conditions under which the plant is grown, such as the availability of water, availability of nutrients (for example nitrogen or phosphate), or the presence of insects or disease.

"Root lodging" refers to stalks leaning from the center. Root lodging can occur as early as the late vegetative stages and as late as harvest maturity. Root lodging can be affected by hybrid susceptibility, environmental stress (drought, flooding), insect and disease injury. Root lodging can be attributed to corn rootworm injury in some cases.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase 1.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg, et al., (2004) "Identification of a 49-bp fragment of the HvLTP2 promoter directing aleurone cell specific expression" Gene 341:49-58. Such variants should retain promoter activity, particularly the ability to drive expression in root or root tissues. Activity can be measured by Northern blot analysis, reporter activity measurements when using transcriptional fusions, and the like. See, for example, Sambrook et al., (1989) Molecular Cloning: A Laboratory manual ($2^{nd}$ ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis, et al., (1987) Methods Enzymol. 155:335-350, and Ehrlich, ed. (1989) PCR Technology (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the Megalign® program of the LASARGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to preferred embodiments:

Preferred embodiments include isolated polynucleotides and polypeptides, recombinant DNA constructs, compositions (such as plants or seeds) comprising these recombinant DNA constructs, and methods utilizing these recombinant DNA constructs.

Preferred Isolated Polynucleotides and Polypeptides

The present invention includes the following preferred isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 and wherein expression of said polypeptide in a plant results in an altered root architecture when compared to a control plant not comprising said recombinant DNA construct, or (ii) a full complement of the nucleic acid sequence of (i), wherein the full complement and the nucleic acid sequence of (i) consist of the same number of nucleotides and are 100% complementary.

Any of the foregoing isolated polynucleotides may be utilized in any recombinant DNA constructs (including suppression DNA constructs) of the present invention.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 and wherein expression of said polypeptide in a plant results in an altered plant root architecture when compared to a control plant not comprising said recombinant DNA construct.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 22, 28, 38, 66, 68, 70 or 72 and wherein said polynucleotide encodes a polypeptide wherein expression of said polypeptide results in an altered root architecture when compared to a control plant not comprising said recombinant DNA construct or (ii) a full complement of the nucleic acid sequence of (i). Any of the foregoing isolated polynucleotides may be utilized in any recombinant DNA constructs (including suppression DNA constructs) of the present invention. The isolated polynucleotide encodes a RUM1 or RUM1-like protein.

Preferred Recombinant DNA Constructs and Suppression DNA Constructs

In one aspect, the present invention includes recombinant DNA constructs (including suppression DNA constructs).

In one preferred embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 or (ii) a full complement of the nucleic acid sequence of (i).

In another preferred embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 22, 28, 38, 66, 68, 70 or 72 or (ii) a full complement of the nucleic acid sequence of (i).

FIG. 18 shows the multiple alignment of the full length amino acid sequences of B73-Mu-wt RUM1 (SEQ ID NO:24), B73 RUM1 (SEQ ID NO:29), B73 RUL (SEQ ID NO:39), the mutant rum1 (SEQ ID NO:25) and the rice protein identified as belonging to the AUX-IAA family (NCBI General identifier No. 34911088, SEQ ID NO:65). Amino acids conserved among all sequences are indicated with an asterisk (*) on the top row; dashes are used by the program to maximize alignment of the sequences. The method parameters used to produce the multiple alignment of the sequences below was performed using the Clustal method of alignment (Higgins and Sharp (1989) *CABIOS.* 5:151-153) with the default parameters (GAP PENALTY=10, GAP LENGTH PENALTY=10), and the pairwise alignment default parameters of KTUPLE=1, GAP PENALTY=3, WINDOW=5 and DIAGONALS SAVED=5.

FIG. 19 shows a chart of the percent sequence identity for each pair of amino acid sequences displayed in FIG. 18.

In another preferred embodiment, a recombinant DNA construct comprises a polynucleotide operably linked to at least one regulatory sequence (e.g., a promoter functional in a plant), wherein said polynucleotide encodes a RUM1 or RUM1-like protein. Preferably, the RUM1 or RUM1-like protein is from *Arabidopsis thaliana, Zea mays, Glycine max, Glycine tabacina, Glycine soja* and *Glycine tomentella.*

In another aspect, the present invention includes suppression DNA constructs.

A suppression DNA construct preferably comprises at least one regulatory sequence (preferably a promoter functional in a plant) operably linked to (a) all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 protein; or (c) all or part of (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 22, 28, 38, 66, 68, 70 or 72 or (ii) a full complement of the nucleic acid sequence of (c)(i). The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) *Plant J.* 16:651-659; and Gura (2000) *Nature* 404:804-808).

Another variation describes the use of plant viral sequences to direct the suppression of proximal mRNA encoding sequences (PCT Publication WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published 3 Jan. 2002.

RNA interference refers to the process of sequence-specific post-transcriptional gene silencing in animals mediated by short interfering RNAs (siRNAs) (Fire et al., Nature 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., Nature 409:363 2001). Short interfering RNAs derived from dicer activity are typically about 21 to about 23 nucleotides in length and comprise about 19 base pair duplexes (Elbashir et al., Genes Dev. 15:188 2001). Dicer has also been implicated in the excision of 21- and 22-nucleotide small temporal RNAs (stRNAs) from precursor RNA of conserved structure that are implicated in translational control (Hutvagner et al., 2001, Science 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., Genes Dev. 15:188 2001). In addition, RNA interference can also involve small RNA (e.g., miRNA) mediated gene silencing, presumably through cellular mechanisms that regulate chromatin structure and thereby prevent transcription of target gene sequences (see, e.g., Allshire, Science 297:1818-1819 2002; Volpe et al., Science 297:1833-1837 2002; Jenuwein, Science 297:2215-2218 2002; and Hall et al., Science 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (Nature 391:806 1998) were the first to observe RNAi in *C. elegans*. Wianny and Goetz (Nature Cell Biol. 2:70 1999) describe RNAi mediated by dsRNA in mouse embryos. Hammond et al. (Nature 404:293 2000) describe RNAi in *Drosophila* cells transfected with dsRNA. Elbashir et al., (Nature 411:494 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., Science 294:853-858 2001, Lagos-Quintana et al., Curr. Biol. 12:735-739 2002; Lau et al., Science 294:858-862 2001; Lee and Ambros, Science 294:862-864 2001; Llave et al., Plant Cell 14:1605-1619 2002; Mourelatos et al., Genes. Dev. 16:720-728 2002; Park et al., Curr. Biol. 12:1484-1495 2002; Reinhart et al., Genes. Dev. 16:1616-1626 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., Cell 106:23-34 2001; Hutvagner et al., Science 293:834-838 2001; Ketting et al., Genes. Dev. 15:2654-2659 2001). Plants also have a Dicer-like enzyme, DCL1 (previously named CARPEL FACTORY/SHORT INTEGUMENTS1/SUSPENSORI ), and recent evidence indicates that it, like Dicer, is involved in processing the hairpin precursors to generate mature miRNAs (Park et al., Curr. Biol. 12:1484-1495 2002; Reinhart et al., Genes. Dev. 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., Science 294:853-858 2001; Lee et al., EMBO J. 21:4663-4670 2002). Recent work has also examined the selection of the miRNA strand from the dsRNA product arising from processing of the hairpin by DICER (Schwartz, et al. 2003 Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs appear to regulate target genes by binding to complementary sequences located in the transcripts produced by these genes. In the case of lin-4 and let-7, the target sites are located in the 3' UTRs of the target mRNAs (Lee et al., Cell 75:843-854 1993; Wightman et al., Cell 75:855-862 1993; Reinhart et al., Nature 403:901-906 2000; Slack et al., Mol. Cell. 5:659-669 2000), and there are several mismatches between the lin-4 and let-7 miRNAs and their target sites. Binding of the lin-4 or let-7 miRNA appears to cause down-regulation of steady-state levels of the protein encoded by the target mRNA without affecting the transcript itself (Olsen and Ambros, Dev. Biol. 216:671-680 1999). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, Science 297:2056-2060 2002; Llave et al., Plant Cell 14:1605-1619 2002). It seems likely that miRNAs can enter at least two pathways of target gene regulation: Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., Plant Cell 14:1605-1619 2002; Park et al., Curr. Biol. 12:1484-1495 2002; Rhoades et al., Cell 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

A recombinant DNA construct (including a suppression DNA construct) of the present invention preferably comprises at least one regulatory sequence.

A preferred regulatory sequence is a promoter.

A number of promoters can be used in recombinant DNA constructs (and suppression DNA constructs) of the present invention. The promoters can be selected based on the desired outcome, and may include constitutive, tissue-specific, inducible, or other promoters for expression in the host organism.

High level, constitutive expression of the candidate gene under control of the 35S promoter may have pleiotropic effects. Candidate gene efficacy may be tested when driven by different promoters.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); *PEMU* (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611 and maize GOS2 (WO0020571 A2).

In choosing a promoter to use in the methods of the invention, it may be desirable to use a tissue-specific or developmentally regulated promoter.

A preferred tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo specific and may be useful in the invention include soybean Kunitz trysin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Preferred promoters include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993)). "Structural characterization, chromosomal localization and phylogenetic evaluation of two pairs of AGAMOUS-like MADS-box genes from maize", Theissen et al., Gene 156(2): 155-166 (1995); NCBI GenBank Accession No. X80206)). Zag2 transcripts can be detected 5 days prior to pollination to 7 to 8 days after pollination (DAP), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional preferred promoters for regulating the expression of the nucleotide sequences of the present invention in plants are stalk-specific promoters. Such stalk-specific promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as “constitutive promoters”. New promoters of various types useful in plant cells are constantly being discovered; numerous examples may be found in the compilation by Okamuro, J. K., and Goldberg, R. B., Biochemistry of Plants 15:1-82 (1989).

Preferred promoters may include: RIP2, mLIP15, ZmCORI , Rab17, CaMV 35S, RD29A, B22E, Zag2, SAM synthetase, ubiquitin , CaMV 19S, nos, Adh, sucrose synthase, R-allele, root cell promoter, the vascular tissue preferred promoters S2A (Genbank accession number EF030816; SEQ ID NO:76) and S2B (Genbank accession number EF030817) and the constitutive promoter GOS2 from *Zea mays*. Other preferred promoters include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790, gi:1063664), Recombinant DNA constructs (and suppression DNA constructs) of the present invention may also include other regulatory sequences, including but not limited to, translation leader sequences, introns, and polyadenylation recognition sequences. In another preferred embodiment of the present invention, a recombinant DNA construct of the present invention further comprises an enhancer or silencer.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell. Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. Molecular Biotechnology 3:225 (1995)).

In another preferred embodiment of the present invention, a recombinant DNA construct of the present invention further comprises an enhancer or silencer.

Any plant can be selected for the identification of regulatory sequences and genes to be used in creating recombinant DNA constructs and suppression DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plants for the identification of regulatory sequences are *Arabidopsis*, corn, wheat, soybean, and cotton.

Preferred Compositions

A preferred composition of the present invention is a plant comprising in its genome any of the recombinant DNA constructs (including any of the suppression DNA constructs) of the present invention (such as those preferred constructs discussed above). Preferred composition also includes any progeny of the plant, and any seed obtained from the plant or its progeny. Progeny includes subsequent generations obtained by self-pollination or out-crossing of a plant. Progeny also includes hybrids and inbreds.

Preferably, in hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g. an increased agronomic characteristic under nitrogen or phosphate limiting conditions), or used in a breeding program to produce hybrid seed, which can be grown to produce plants that would exhibit altered root architecture. Preferably, the seeds are maize.

Preferably, the plant is a monocotyledonous or dicotyledonous plant, more preferably, a maize or soybean plant, even more preferably a maize plant, such as a maize hybrid plant or a maize inbred plant. The plant may also be sunflower, sorghum, canola, wheat, alfalfa, cotton, rice, barley or millet.

Preferably, the recombinant DNA construct is stably integrated into the genome of the plant.

Particularly preferred embodiments include but are not limited to the following preferred embodiments:

1. A plant (preferably a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, and wherein said plant exhibits an altered root architecture when compared to a control plant not comprising said recombinant DNA construct. Preferably, the plant further exhibits an alteration of at least one agronomic characteristic when compared to the control plant.

2. A plant (preferably a maize or soybean plant) comprising in its genome a recombinant DNA construct comprising a polynucleotide operably linked to at least one regulatory sequence, wherein said polynucleotide encodes a RUM1 or RUM1-like protein, and wherein said plant exhibits an altered root architecture when compared to a control plant not comprising said recombinant DNA construct. Preferably, the plant further exhibits an alteration of at least one agronomic characteristic when compared to the control plant. Preferably, the RUM1 or RUM1-like protein is from *Arabidopsis thaliana, Zea mays, Glycine max, Glycine tabacina, Glycine soja* or *Glycine tomentella.*

3. A plant (preferably a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 or RUM1-like protein, and wherein said plant exhibits an alteration of at least one agronomic characteristic when compared to a control plant not comprising said recombinant DNA construct.

4. A plant (preferably a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, or (b) a full complement of the nucleic acid sequence of (a), and wherein said plant exhibits an alteration of at least one agronomic characteristic when compared to a control plant not comprising said recombinant DNA construct.

5. Any progeny of the above plants in preferred embodiments 1-4, any seeds of the above plants in preferred embodiments 1-4, any seeds of progeny of the above plants in preferred embodiments 1-4, and cells from any of the above plants in preferred embodiments 1-4 and progeny thereof.

In any of the foregoing preferred embodiments 1-5 or any other embodiments of the present invention, the recombinant DNA construct (or suppression DNA construct) preferably comprises at least a promoter that is functional in a plant as a preferred regulatory sequence.

In any of the foregoing preferred embodiments 1-5 or any other embodiments of the present invention, the alteration of at least one agronomic characteristic is either an increase or decrease, preferably an increase.

In any of the foregoing preferred embodiments 1-5 or any other embodiments of the present invention, the at least one greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, and harvest index.

With greenness, harvest index, yield, biomass, resistance to root lodging being a particularly preferred agronomic characteristic for alteration (preferably an increase).

In any of the foregoing preferred embodiments 1-5 or any other embodiments of the present invention, the plant preferably exhibits the alteration of at least one agronomic characteristic irrespective of the for example water and nutrient availability when compared to a control plant .

One of ordinary skill in the art is familiar with protocols for determining alteration in plant root architecture. For example, alterations in root architecture can be determined by counting the nodal root numbers of the top 3 or 4 nodes of the greenhouse grown plants or the width of the root band. Other measures of alterations in root architecture include but are not limited to alterations in vigor, growth, size, yield, biomass, or resistance to root lodging when compared to a control or reference plant.

The Examples below describe some representative protocols and techniques for detecting alterations in root architecture.

One can also evaluate alterations in root architecture by the ability of the plant to maintain sufficient yield thresholds in field testing under various environmental conditions (e.g. nutrient over-abundance or limitation, water over-abundance or limitation, exposure to insects or disease) by measuring for substantially equivalent yield at those conditions compared to normal nutrient or water conditions, or by measuring for less yield drag under over-abundant or limiting nutrient and water conditions compared to a control or reference plant.

Alterations in root architecture can also be measured by determining the resistance to root lodging of the transgenic plants compared to reference or control plants.

One of ordinary skill in the art would readily recognize a suitable control or reference plant to be utilized when assessing or measuring an agronomic characteristic or phenotype of a transgenic plant in any embodiment of the present invention in which a control or reference plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the parent inbred or variety line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Preferred Methods

Preferred methods include but are not limited to methods for altering root architecture in a plant, methods for evaluating alteration of root architecture in a plant, methods for altering an agronomic characteristic in a plant, methods for evaluating an alteration of an agronomic characteristic in a plant, and methods for producing seed. Preferably, the plant is a monocotyledonous or dicotyledonous plant, more preferably, a maize or soybean plant, even more preferably a maize plant. The plant may also be sunflower, sorghum, canola, wheat, alfalfa, cotton, rice, barley or millet. The seed is preferably a maize or soybean seed, more preferably a maize seed, and even more preferably, a maize hybrid seed or maize inbred seed.

Particularly preferred methods include but are not limited to the following:

A method of altering root architecture of a plant, comprising: (a) introducing into a regenerable plant cell a recombinant DNA construct comprising a polynucleotide operably linked to at least one regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, and (b) regenerating a transgenic plant from the regenerable plant cell after step (a), wherein the transgenic plant comprises in its genome the recombinant DNA construct and exhibits in altered root architecture when compared to a control plant not comprising the recombinant DNA construct. The method may further comprise (c) obtaining a progeny plant derived from the transgenic plant.

A method of altering root architecture in a plant, comprising: (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 or (ii) a full complement of the nucleic acid sequence of (a)(i); and (b) regenerating a transgenic plant from the regenerable plant cell after step (a), wherein the transgenic plant comprises in its genome the recombinant DNA construct and exhibits an altered root architecture when compared to a control plant not comprising the recombinant DNA construct. The method may further comprise (c) obtaining a progeny plant derived from the transgenic plant.

A method of altering root architecture in a plant, comprising: (a) introducing into a regenerable plant cell a suppression DNA construct comprising at least one regulatory sequence (preferably a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 or RUM1-like protein; and (b) regenerating a transgenic plant from the regenerable plant cell after step (a), wherein the transgenic plant comprises in its genome the recombinant DNA construct and exhibits an altered root architecture when compared to a control plant not comprising the recombinant DNA construct. The method may further comprise (c) obtaining a progeny plant derived from the transgenic plant.

A method of evaluating altered root architecture in a plant, comprising (a) introducing into a regenerable plant cell a recombinant DNA construct comprising a polynucleotide operably linked to at least on regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 (b) regenerating a transgenic plant from the regenerable plant cell after step (a), wherein the transgenic plant comprises in its genome the recombinant DNA construct; and (c) evaluating the transgenic plant for altered root architecture compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for altered root architecture compared to a control plant not comprising the recombinant DNA construct.

A method of evaluating altered root architecture in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, or (ii) a full complement of the nucleic acid sequence of (a)(i); (b) regenerating a transgenic plant from the regenerable plant cell after step (a), wherein the transgenic plant comprises in its genome the suppression DNA construct; and (c) evaluating the transgenic plant for altered root architecture compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for altered root architecture compared to a control plant not comprising the suppression DNA construct.

A method of evaluating altered root architecture in a plant, comprising (a) introducing into a regenerable plant cell a suppression DNA construct comprising at least one regulatory sequence (preferably a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 or RUM1-like protein; (b) regenerating a transgenic plant from the regenerable plant cell after step (a), wherein the transgenic plant comprises in its genome the suppression DNA construct; and (c) evaluating the transgenic plant for altered root architecture compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for altered root architecture compared to a control plant not comprising the suppression DNA construct.

A method of evaluating altered root architecture in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for altered root architecture compared to a control plant not comprising the recombinant DNA construct.

A method of evaluating altered root architecture in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, or (ii) a full complement of the nucleic acid sequence of (a)(i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (e) evaluating the progeny plant for altered root architecture compared to a control plant not comprising the suppression DNA construct.

A method of evaluating altered root architecture in a plant, comprising (a) introducing into a regenerable plant cell a suppression DNA construct comprising at least one regulatory sequence (preferably a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 or RUM1-like protein; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) evaluating the progeny plant for altered root architecture compared to a control plant not comprising the recombinant DNA construct.

A method of evaluating an alteration of an agronomic characteristic in a plant, comprising (a) introducing into a regenerable plant cell a recombinant DNA construct comprising a polynucleotide operably linked to at least on regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 (b) regenerating a transgenic plant from the regenerable plant cell after step (a), wherein the transgenic plant comprises in its genome said recombinant DNA construct; and (c) determining whether the transgenic plant exhibits an alteration in at least one agronomic characteristic when compared to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration in at least one agronomic characteristic when compared to a control plant not comprising the recombinant DNA construct.

A method of evaluating an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared to a control plant not comprising the suppression DNA construct.

A method of evaluating alteration of an agronomic characteristic in a plant, comprising (a) introducing into a regenerable plant cell a suppression DNA construct comprising at least one regulatory sequence (preferably a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes RUM1 protein; (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared to a control plant not comprising the suppression DNA construct.

A method of evaluating an alteration of an agronomic characteristic in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration in at least one agronomic characteristic when compared to a control plant not comprising the recombinant DNA construct.

A method of evaluating an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 24, 29, 39, 67, 69, 71 or 73 or (ii) a full complement of the nucleic acid sequence of (i); (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared to a control plant not comprising the recombinant DNA construct.

A method of evaluating an alteration of an agronomic characteristic in a plant, comprising (a) introducing into a regenerable plant cell a suppression DNA construct comprising at least one regulatory sequence (preferably a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a RUM1 protein; (b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared to a control plant not comprising the suppression DNA construct.

A method of producing seed (preferably seed that can be sold as a product offering with altered root architecture) comprising any of the preceding preferred methods, and further comprising obtaining seeds from said progeny plant, wherein said seeds comprise in their genome said recombinant DNA construct (or suppression DNA construct).

In any of the preceding preferred methods, in said introducing step said regenerable plant cell preferably comprises a callus cell (preferably embryogenic), a gametic cell, a meristematic cell, or a cell of an immature embryo. The regenerable plant cells are preferably from an inbred maize plant.

In any of the preceding preferred methods or any other embodiments of methods of the present invention, said regenerating step preferably comprises: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

In any of the preceding preferred methods or any other embodiments of methods of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, and harvest index; with greenness, yield, biomass or resistance to root lodging being a particularly preferred agronomic characteristic for alteration (preferably an increase).

In any of the preceding preferred methods or any other embodiments of methods of the present invention, the plant preferably exhibits the alteration of at least one agronomic characteristic irrespective of the environmental conditions when compared to a control plant (e.g., water, nutrient availability, insect or disease), The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

Preferred techniques are set forth below in the Examples.

Other preferred methods for transforming dicots, primarily by use of *Agrobacterium tumefaciens*, and obtaining transgenic plants include those published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *Bio/Technology* 6:923 (1988), Christou et al., *Plant Physiol.* 87:671 674 (1988)); *Brassica* (U.S. Pat. No. 5,463,174); peanut (Cheng et al., *Plant Cell Rep.* 15:653 657 (1996), McKently et al., *Plant Cell Rep.* 14:699 703 (1995)); papaya; and pea (Grant et al., *Plant Cell Rep.* 15:254 258, (1995)).

Transformation of monocotyledons using electroporation, particle bombardment, and *Agrobacterium* have also been reported and are included as preferred methods, for example, transformation and plant regeneration as achieved in asparagus (Bytebier et al., *Proc. Natl. Acad. Sci. U.S.A.* 84:5354, (1987)); barley (Wan and Lemaux, *Plant Physiol.* 104:37 (1994)); *Zea mays* (Rhodes et al., Science 240:204 (1988), Gordon-Kamm et al., *Plant Cell* 2:603 618 (1990), Fromm et al., *Bio/Technology* 8:833 (1990), Koziel et al., *Bio/Technology* 11:194, (1993), Armstrong et al., Crop *Science* 35:550-557 (1995)); oat (Somers et al., *Bio/Technology* 10:1589 (1992)); orchard grass (Horn et al., *Plant Cell Rep.* 7:469 (1988)); rice (Toriyama et al., *Theor. Appl. Genet.* 205:34, (1986); Part et al., *Plant Mol. Biol.* 32:1135 1148, (1996); Abedinia et al., *Aust. J. Plant Physiol.* 24:133 141 (1997); Zhang and Wu, *Theor. Appl. Genet.* 76:835 (1988); Zhang et al., *Plant Cell Rep.* 7:379, (1988); Battraw and Hall, *Plant Sci.* 86:191 202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)), and wheat (Vasil et al., *Bio/Technology* 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Map-based Cloning of RUM1

The rum1 mutation was mapped using one mapping population and its corresponding corn seeds, segregating for the rum1 mutation. The mapping populations consisted of 3886 corn plants derived from a F1 cross between the line carrying the rum1 mutation, and the inbred line F7. The line carrying the rum1 mutation was isolated from mutagenized F2 families generated from selfed F1 crosses between the inbred line B73 and active Mutator stocks. For convenience this line was named B73-Mu.

Homozygous rum /rum1 plants were scored twice at 7 and 10 days after germination as plants with no visible lateral roots on primary roots when grown on paper rolls. A total of 630 plants were retrieved from the mapping population. These plants were selected for fine mapping of the rum1 locus.

DNA was extracted from those plants using standard molecular biology procedures.

To obtain F2 plants that carry recombination near the rum1 locus, public PCR-based DNA markers (SSRs) present in the Maize Genetics and Genomic Database (MaizeGDB), were used. When these were not available, CAP (allele-specific PCR primers) markers were developed from the DuPont proprietary sequences of BAC (Bacterial Artificial Chromosome) clones of known map positions. Both CAP and SSR primers were used in a PCR reaction containing ng of DNA.

Flanking SSR marker UMC1690 [UMC1690 forward primer (SEQ ID NO:1), UMC1690 reverse primer (SEQ ID NO:2)] and BNLG1108 [BNLG1108 forward primer (SEQ ID NO:3), BNLG1108 reverse primer (SEQ ID NO:4)] were retrieved from the MaizeGDB. These markers are localized at 544.6 cM and 618.6 cM of Chromosome 3 respectively, based on the public map IBM2 2004 neighbors 3.

SSR markers amplifications were performed in a 10 ul PCR reaction using the Qiagen HotStart mix (Qiagen, Valencia, Calif.) and 10 ng DNA. The thermal cycle conditions were: 95° C. 15 min (1 cycle), 94° C. 30 sec, 60° C. 30 sec, 72° C. 60 sec, (40 cycles) 72° C. 5 min. Amplification products were examined for polymorphisms on 4% high resolution agarose (Sigma-Aldrich, Saint Louis, Mo.).

When using these 2 primer sets on an initial population of 213 rum1 plants, a total of 16 out of 213 recombinants were obtained, 14 with marker UMC1690 and 2 from marker BNLG1108, indicating that rum1 was closer to BNLG1108.

In order to obtain genetic markers closer to rum 1, more primers were retrieved from the Maize GDB based on their position along chromosome 3 and tested on the above mentioned 213 rum1 plants plus an additional 204 rum1 plants, in a total of 417 rum1 plants. In particular, markers UMC1844 [UMC1844 forward primer (SEQ ID NO:5), UMC1844 reverse primer (SEQ ID NO:6)] gave 15 out of 417 recombinants and marker UMC1915 [UMC1915 forward primer (SEQ ID NO:7), UMC1915 reverse primer (SEQ ID NO:8)] gave 14 out of 417 recombinants, indicating a distance of 1.8 cM and 1.7 cM from the rum1 locus respectively. Marker UMC1844 and UMC1915 have been physically positioned by hybridization onto a single maize contig, named 320 (Dupont Genomix database).

Two more SSR markers reported to be localized between UMC1844 and UMC1915 on the public IBM2 2004 neighbors 3 map, but not physically positioned onto contig 320 were analyzed. Screening of the public BAC library using the marker PHP9257A [PHP9257A forward primer (SEQ ID NO:9), PHP9257A reverse primer (SEQ ID NO:10)] or marker UMC2274 [UMC2274 forward primer (SEQ ID NO:11), UMC2274 reverse primer (SEQ ID NO:12)] as probes, revealed that PHP9257A localizes immediately downstream of UMC1844 and UMC2274 localizes immediately upstream of UMC1915 on contig 320. Marker PHP9257A gave 11 recombinants while marker UMC2274 gave 6 recombinants, indicating a distance of 1.3 cM and 0.7 cM from the rum1 locus respectively. The physical distance comprising the two markers encompasses approximately 10 BACs.

Based on this information, new CAP markers were designed using available BAC-end sequences of the BACs constituting the region of contig 320 surrounded by markers PHP9257A and UMC2274.

Cap marker MZA8411 [MZA8411 forward primer (SEQ ID NO:13), MZA8411 reverse primer (SEQ ID NO:14)] was designed based on the MZA8411 sequence, which is downstream of PHP9257A. This primer set amplifies a region of 544 bp, showing polymorphism between F7 and the mutant background line after restriction with the 5-cutter enzyme TspRI (New England Biolabs, Ipswich, Mass.).

CAP marker amplifications were performed in a 20 ul PCR reaction using the Qiagen HotStart mix (Qiagen, Valencia, Calif.) and 10 ng DNA. Thermal cycle conditions were the same as described previously. Fifteen microliters of the amplification product were used for a restriction digest (total volume of 100 ul) with the 5-cutter restriction enzyme TspRI. Restriction reaction was carried out at 65° C. for one hour. Restricted amplification products were extracted one time in phenol/chlorophorm/isoamyl alcohol (25:24:1), precipitated in 100% ethanol/3M sodium acetate (2.5 vol:1/10 vol), rinsed in 70% ethanol and examined on 2% agarose gels. By screening the 17 previously obtained recombinants with this primers set, 7 recombination breakpoints were found, indicating that it is located at a distance of 0.8 cM from the rum1 locus on the same side of the marker PHP9257A.

Cap marker b0568n15 [b0568n15 forward primer (SEQ ID NO:15), b0568n15 reverse primer (SEQ ID NO:16)] was designed based on the BAC-end sequence of clone BAC b0568n15, which is localized upstream of UMC2274. This primer set amplifies a region of 706 bp, showing polymorphism between F7 and the mutant background line after restriction with the 5-cutter enzyme TspRI. Two recombination breakpoints were found using this primer set, indicating that b0568n15 is located at a distance of 0.2 cM from the rum1 locus on the same side of the marker UMC2274.

Cap marker MZA8828 [MZA8828 forward primer (SEQ ID NO:17), MZA8828 reverse primer (SEQ ID NO:18)] was designed based on the sequence of MZA8828, which is downstream of MZA8411. This primer set amplifies a region of 763 bp, showing polymorphism between F7 and the mutant background line after restriction with the 5-cutter enzyme Ncil (New England Biolabs, Ipswich, Mass.) at 37° C. One recombination breakpoint was found using this primer set, indicating that MZA8828 is located at a distance of 0.1 cM form the rum1 locus on the same side of MZA8411.

PCR amplification showed that the MZA8828 marker is also located on the BAC clone b0568n15. Therefore, the RUM1 locus could be narrowed down to the genomic region on Bac clone b0568n15 between marker MZA8828 marker (at a distance of 0.1 cM, one recombinant) and the BAC-end marker b0568n15 (at a distance of 0.2 cM, two recombinants).

Example 2

Identification of the RUM1 Gene

BAC clone b0568n15, to which the rum1 locus mapped, was sequenced. For this purpose, BAC DNA was nebulized using high-pressure nitrogen gas as described in Roe et al. 1996 (Roe et al. (1996) "DNA isolation and Sequencing" John Wiley and Sons, New York).

The region between the marker MZA8828 and BAC-end marker b0568n15 is about 69 kb long and comprises six genic regions according to BLAST searches of the BAC b0568n15 against maize EST databases (Public and DuPont proprietary EST databases). This region was also found to be syntenic with the rice chomosome 1 region: 27753126 to 27823073 bp by homology search of the markers against the rice genomic database. Among the six genic regions found in maize, four were also conserved in rice and annotated as: Os01g676200 (Conserved hypothetical protein), Os01g675800 (NAC domain containing protein), Os01g675700 (Auxin-responsive Solitary-root/IAA14-like protein (SLR/IAA14-like)), Os01g0675500 (Glycoprotein-specific UDP-glucoronyl-transferase-like protein).

Figure 1:
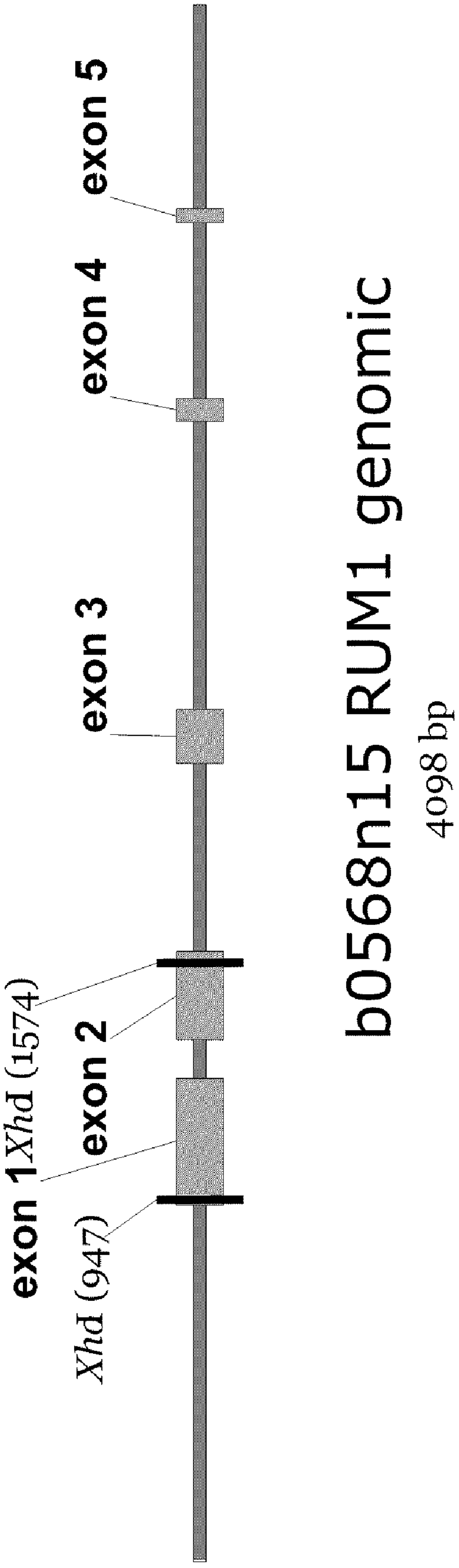
FIG. 1 shows a map of the RUM1 genomic sequence.
Figure 2:
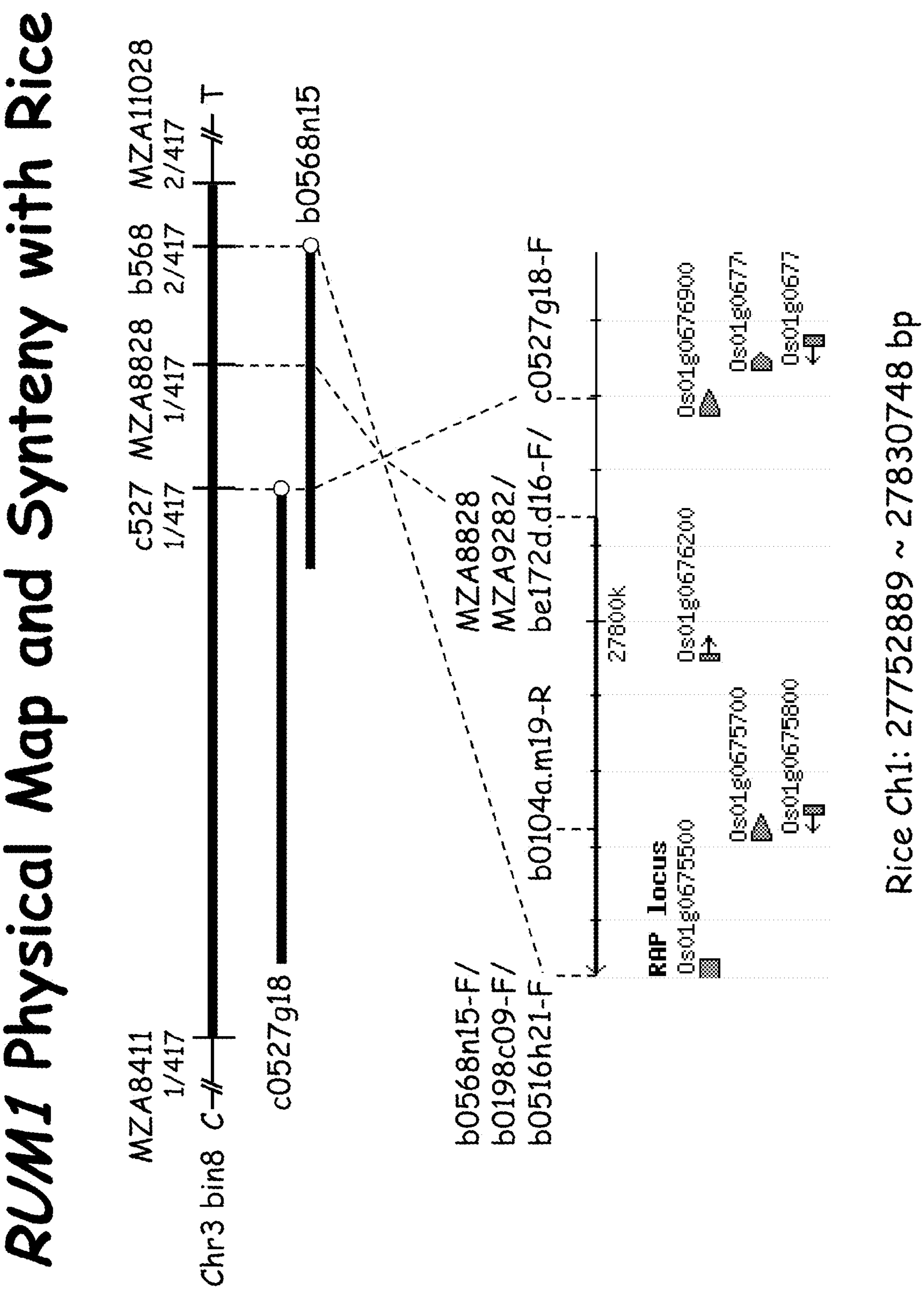
FIG. 2 shows the RUM1 physical map and its synteny with rice.

The gene homologous to the rice SLR/IAA14-like gene was selected as the strongest candidate to be the RUM1 gene due to its location regarding the distance from the markers MZA8828 and b0568n5 (⅓ and ⅔, respectively), as well as for the phenotypic similarity of the rum1 mutant to the sir from *Arabidopsis*, which is also defective in lateral root formation (Fukaki et al., 2002). The 4098 bp fragment of b0568n15 containing the RUM1 gene is shown in SEQ ID NO:19 and FIG. 1. FIG. 2 shows the RUM1 physical map and its synteny with Rice.

DNA extracted from B73-Mu, carrying a wild type allele for RUM1 (B73-Mu-wt), or from rum1 plants and digested with XhoI (Promega) was examined by Southern hybridization using a fragment comprising exons 1 and 2 of the RUM1 gene as probe. While a fragment of about 700 bp segregated with B73-Mu-wt DNA, a fragment of about 1.8 kb segregated with mutant rum1 plants, indicating the insertion of an exogenous element in the mutants. The element was amplified by PCR and consisted of a fragment of 1719 bp with terminal inverted repeats (TIRs) of 212 bp that show about 85% of identity with the TIRs of the maize transposable element Mu1.

RT-PCR of RUM1 with poly(A) RNA extracted from B73-Mu-wt and mutant rum1 plants primary roots, revealed that the rum1 transcript was shorter than the RUM1 B73-Mu-wt transcript.

Example 3

Cloning of the Full Length RUM1 and rum1 cDNAs

Primary roots B73-Mu-wt and rum1 sibling seedlings obtained from the selfed progeny of a heterozygote plant were used to extract total RNA using TRIzolI (Invitrogen™), containing phenol and guanidine thiocyanate. Poly(A) mRNA was purified from total RNA with a mRNA Purification kit obtained from Amersham Biosciences/GE Healthcare, Piscataway, N.J., 08855, which consists of oligo (dT)-cellulose spin columns. To perform RT-PCR, 0.5 μg of poly(A) RNA was used for cDNA synthesis using the Thermoscript® RT-PCR system (Invitrogen™). The cDNA was then amplified by PCR using the Platinum® Taq DNA polymerase combined with $PCR_x$ Enhancer System (Invitrogen™). Primers specific to the 5' and 3' UTR of RUM1 [RUM1−70F forward primer (SEQ ID NO:20), RUM1+40R reverse primer (SEQ ID NO:21)] were used in the PCR reaction. PCR products were cloned into the pPCROII-Topo® nt vector (Invitrogen™) and sequenced to confirm identity. The RUM1 B73-Mu-wt and rum1 mutant cDNAs are shown in SEQ ID NO:22 and 23, respectively. The corresponding amino acid sequences are shown in SEQ ID NO's: 24 and 25, respectively). The mutant has a deletion of 72 nucleotides. Therefore, the transposon insertion in rum1 plants results in an alternative splicing of the RUM1 transcript and consequently deletion of 24 amino acids from the protein sequence.

Example 4

Identification of the Full Length B73 RUM1 cDNA

Using BLAST N, the sequence of the full length RUM1 cDNA (SEQ ID NO.:22), obtained as described in Example 3, was used to search for ESTs in the public EST database, which is derived from the inbred line B73. The highest homology found was to a partial EST from B73 with the accession number CD439-449 (SEQ ID NO:26). The protein encoded by CD439-449 is shown in SEQ ID NO:27. The 5' terminus of the B73 RUM1 cDNA (SEQ ID NO.:26) was deduced from the sequence of the public BAC clone b0568n15 mentioned in Example 3 (SEQ ID NO:19). The full length coding sequence of B73 RUM1 is shown in SEQ ID NO:28 and the corresponding amino acid sequence in SEQ ID NO:29. The RUM1 amino acid sequence from B73 shares 99.3% identity with the wild type RUM1 sequence from the background line of the mutant (B73-Mu-wt) and 39.8%, 38.6% and 33.5% sequence identity with the *Arabidopsis* proteins IAA8 (NCBI General Identifier No. 15227275, SEQ ID NO:30), SLR/IAA14 (NCBI General Identifier No. 22328628, SEQ ID NO:31) and MSG2/IAA19 (NCBI General Identifier No. 1532612, SEQ ID NO:32), respectively. MSG2/IAA19 has been shown to be involved in the regulation of the differential growth responses of hypocotyl and formation of lateral roots in *Arabidopsis thaliana* (Tatematsu et al. Plant Cell. 2004 February; 16(2):379-93).

Percent identity calculations were performed using the Megalign program of the LASERGENE bioinformatics computing suite (DNASTAR Inc., Madison, Wis.). Multiple alignment of the sequences was performed using the Clustal V method of alignment (Higgins and Sharp (1989) *CABIOS.* 5:151-153) with the default parameters (GAP PENALTY=10, GAP LENGTH PENALTY=10).

Example 5

Expression Pattern of the RUM1 Gene

The expression pattern of RUM1 was analyzed via Lynx MPSS (Brenner et al (2000) *Proc Natl Acad Sci U S A* 97:1665-70). MPSS tags in the B73 RUM1 cDNA sequence were searched using the DuPont proprietary LynxMPSS database. RUM1 expression was detected at high levels in several tissues as summarized in Table 1 below.

TABLE 1

MPSS tags in B73 RUM1 cDNA sequence

| PPM | Tissue |
|---|---|
| 229 | meristem |
| 221 | embryo |
| 164 | seedling |
| 154 | tassel |
| 144 | ear |
| 111 | silk |
| 110 | root |
| 99 | leaf |
| 86 | cell culture |
| 70 | pericarp |
| 55 | kernel |
| 51 | endosperm |
| 46 | whorl |
| 41 | stem |
| 41 | pedicel |
| 40 | husk |
| 26 | vascular bundles |
| 19 | scutellum |
| 19 | stalk |

(PPM: parts per million)

Example 6

Identification of New rum1 Mutant Alleles

Four independent Mutator (Mu) insertion lines were identified by screening the Mu active TUSC populations: PV04 47 E-04, PV03 103 E-03, PV03 128 B-04 and BT94 104 G-05. Twenty five seeds from each line were planted in the 2006 Summer field to generate homozygous insertions by selfing, and also to introgress the insertion into the inbred line B73.

DNA was extracted from leaves of the seedlings that germinated in the field and insertion was confirmed by PCR using two combinations of nested RUM1 primers [set 1: RUM1-354F forward primer (SEQ ID NO:33), RUM1 exon1-R1 reverse primer (SEQ ID NO:34); set 2: RUM1-132F forward primer (SEQ ID NO:35), RUM1 exon1-R2 reverse primer (SEQ ID NO:36)], and two combinations of nested primers for RUM1 and for the Mu TIR [set 1: RUM1-354F forward primer (SEQ ID NO:33), MuTIR primer (SEQ ID NO:37); set 2: RUM1-132F forward primer (SEQ ID NO:35), MuTIR primer (SEQ ID NO:37)].

The progeny of these plants will be used for analyses of the insertion lines phenotype.

Example 7

Identification of the RUM1 Duplicate Gene RUL

The RUM1 cDNA from B73 was used to search the public EST database for additional maize RUM1 genes. An EST with accession number DR813588 was identified. The two sequences share 85.2% sequence identity. The DR813588 cDNA sequence was used to search homologous sequences in the public and proprietary DNA databases. The highest homology was obtained with AZM5_100875 from the TIGR Genomic Assembly Release 5.0. The predicted cDNA from AZM5_100875 shows around 70% of identity with the RUM1 cDNA from B73 and B73-Mu-wt. On the protein level the B73 and B73-Mu-wt RUM1 share 84.6% identity with the predicted protein encoded by the AZM5_100875 sequence.

Recently, a public BAC clone comprising the AZM5_100875 sequence has been released. The BAC clone c0491g17 (accession number AC187246) is physically mapped to chromosome 8 bin 5. Patterns of chromosome duplication between chromosomes 3 and 8 of maize have been reported [Gaut B. S. (2001) *Genomic Research* 11, 55-66.]. Therefore, AZM5_100875 appears to encode a duplicate gene of RUM1. The full length sequence of the RUM1 duplicate sequence was assembled from the alignment of the cDNA sequences from DR813588 and AZM5_100875 and was named Rum1-like (RUL). The full length cDNA sequence encoding the RUL protein is shown in SEQ ID NO:38 and the corresponding protein sequence in SEQ ID NO:39. All sequence alignments and % identity calculations were done using the Clustal method of alignment.

Example 8

Cloning of the Full Length RUL cDNA

Primers specific for the 5' and 3' UTR of RUL [RUL−43F forward primer (SEQ ID NO:40), RUL+181R reverse primer (SEQ ID NO:41)] were used for PCR amplification the RUL full length cDNA (SEQ ID NO:38) as described in Example 3. Primary roots of B73-Mu-wt and rum1 sibling seedlings obtained from the selfed progeny of a heterozygote plant were used as template. PCR products were cloned into the pPCRII-Topo vector obtained from Invitrogen, Carlsbad, Calif., 92008 and sequenced to confirm identity. RUL transcripts derived from wild type (B73-Mu-wt) or rum1 siblings were identical, indicating that the RUL gene is not altered in the rum1 mutants.

Example 9

Preparation of a Plant Expression Vector Containing the RUM1 or a RUM1-like Gene Sequences homologous to the RUM1 gene can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). The RUM1 gene (SEQ ID NO:22 or 28), or RUM1-like genes, such as the one disclosed in SEQ ID NO:38, can be PCR-amplified by either of the following methods.

Method 1 (RNA-based): Based on the 5' and 3' sequence information for the protein-coding region of RUM1 (SEQ ID NO:22 or 28) or a RUM1 homolog (for example RUL, SEQ ID NO:38, gene-specific primers can be designed. RT-PCR can be used with plant RNA to obtain a nucleic acid fragment containing the RUM1 protein-coding region flanked by attB1 (SEQ ID NO:42) and attB2 (SEQ ID NO:43) sequences. The primer may contain a consensus Kozak sequence (CAACA) upstream of the start codon.

Method 2 (DNA-based): Alternatively, the entire cDNA insert (containing 5' and 3' non-coding regions) of a clone encoding RUM1 or a polypeptide homolog (such as RUL, SEQ ID NO:38), can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBluescript SK+, the forward primer VC062 (SEQ ID NO:44) and the reverse primer VC063 (SEQ ID NO:45) can be used.

Methods 1 and 2 can be modified according to procedures known by one skilled in the art. For example, the primers of method 1 may contain restriction sites instead of attB1 and attB2 sites, for subsequent cloning of the PCR product into a vector containing attB1 and attB2 sites. Additionally, method 2 can involve amplification from a cDNA clone, a lambda clone, a BAC clone or genomic DNA.

Figure 3:
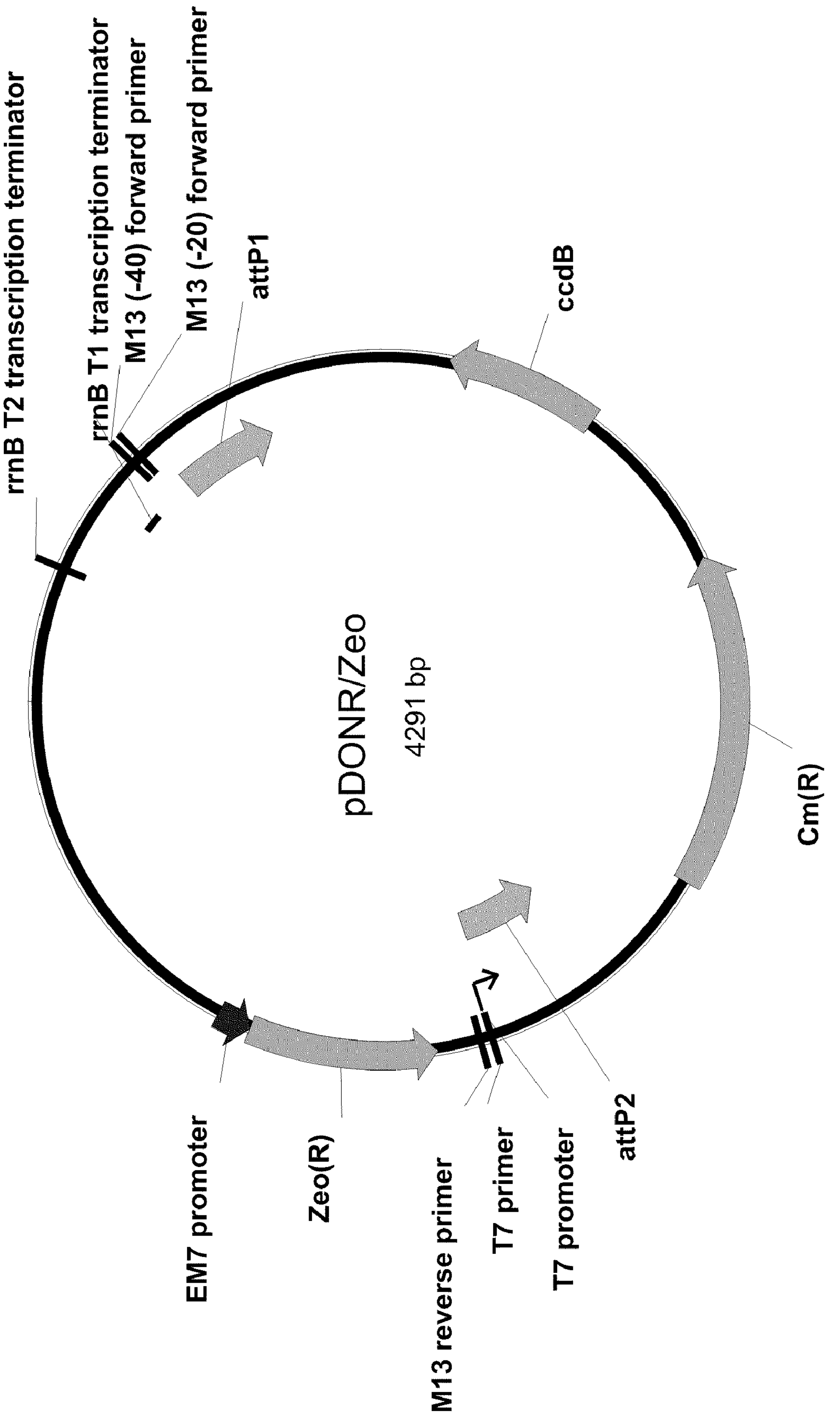
FIG. 3 depicts the vector pDONOR™/Zeo.
Figure 4:
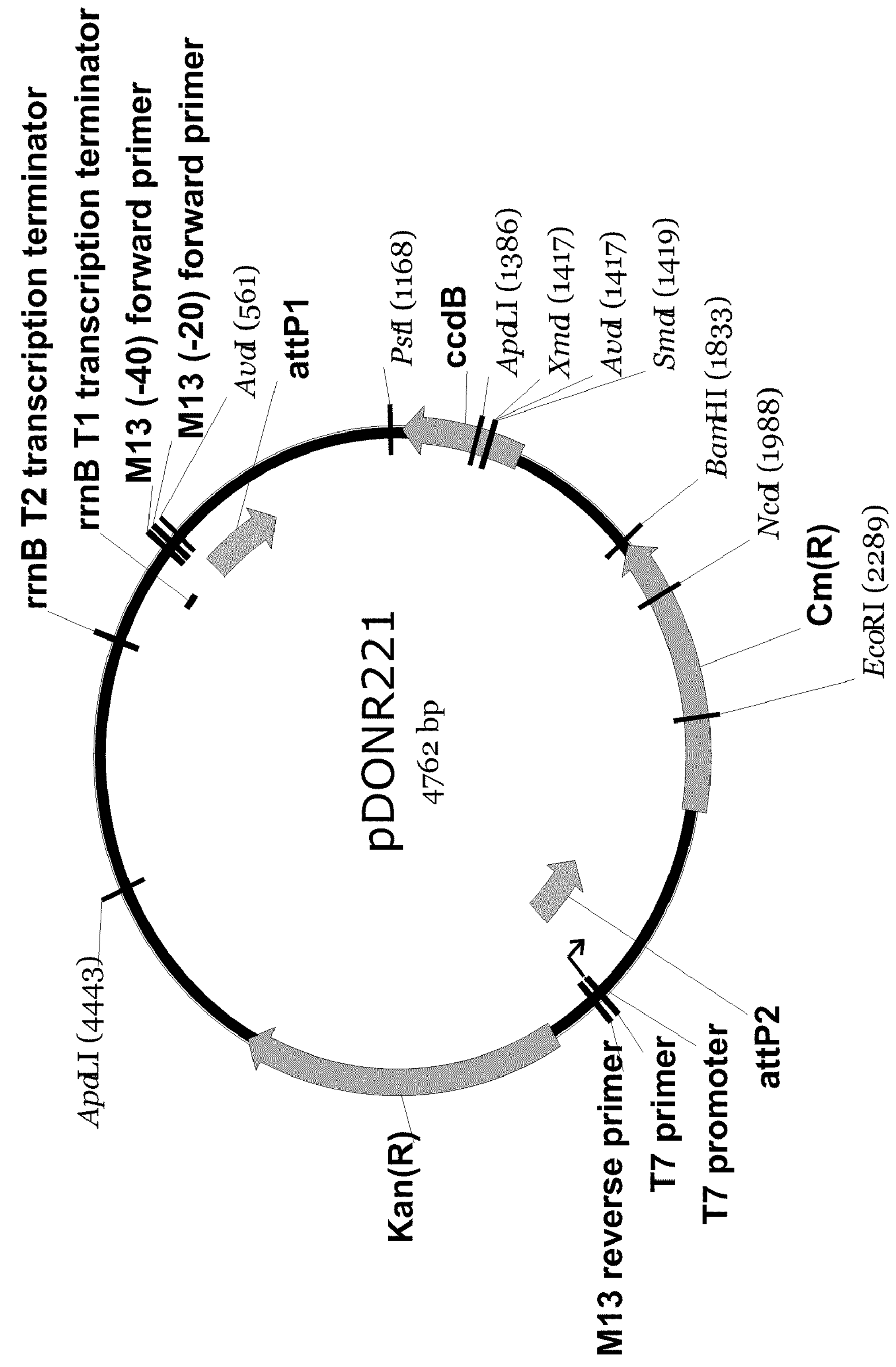
FIG. 4 depicts the vector pDONOR™221.
Figure 5:
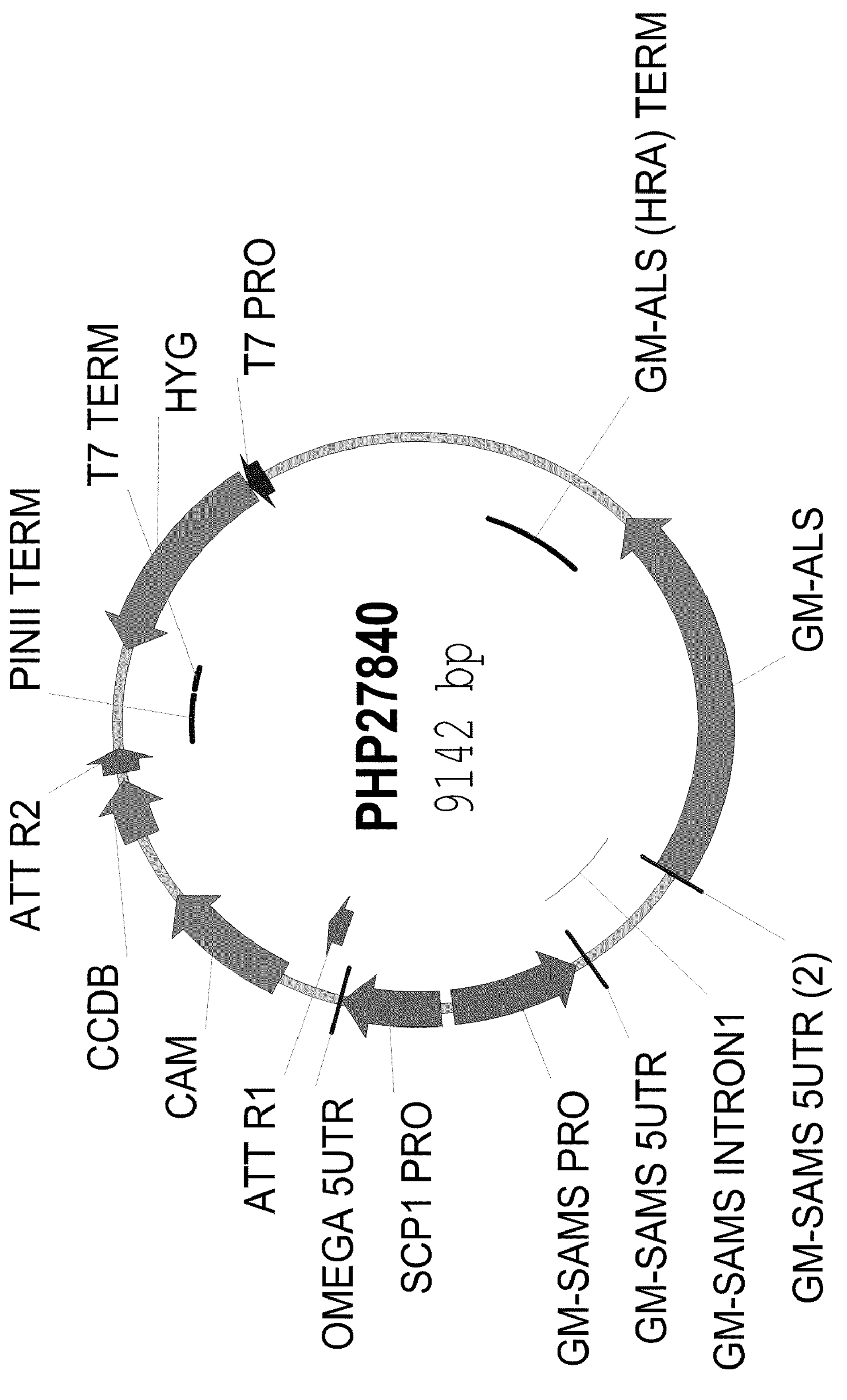
FIG. 5 depicts the vector PHP27840.
Figure 6:
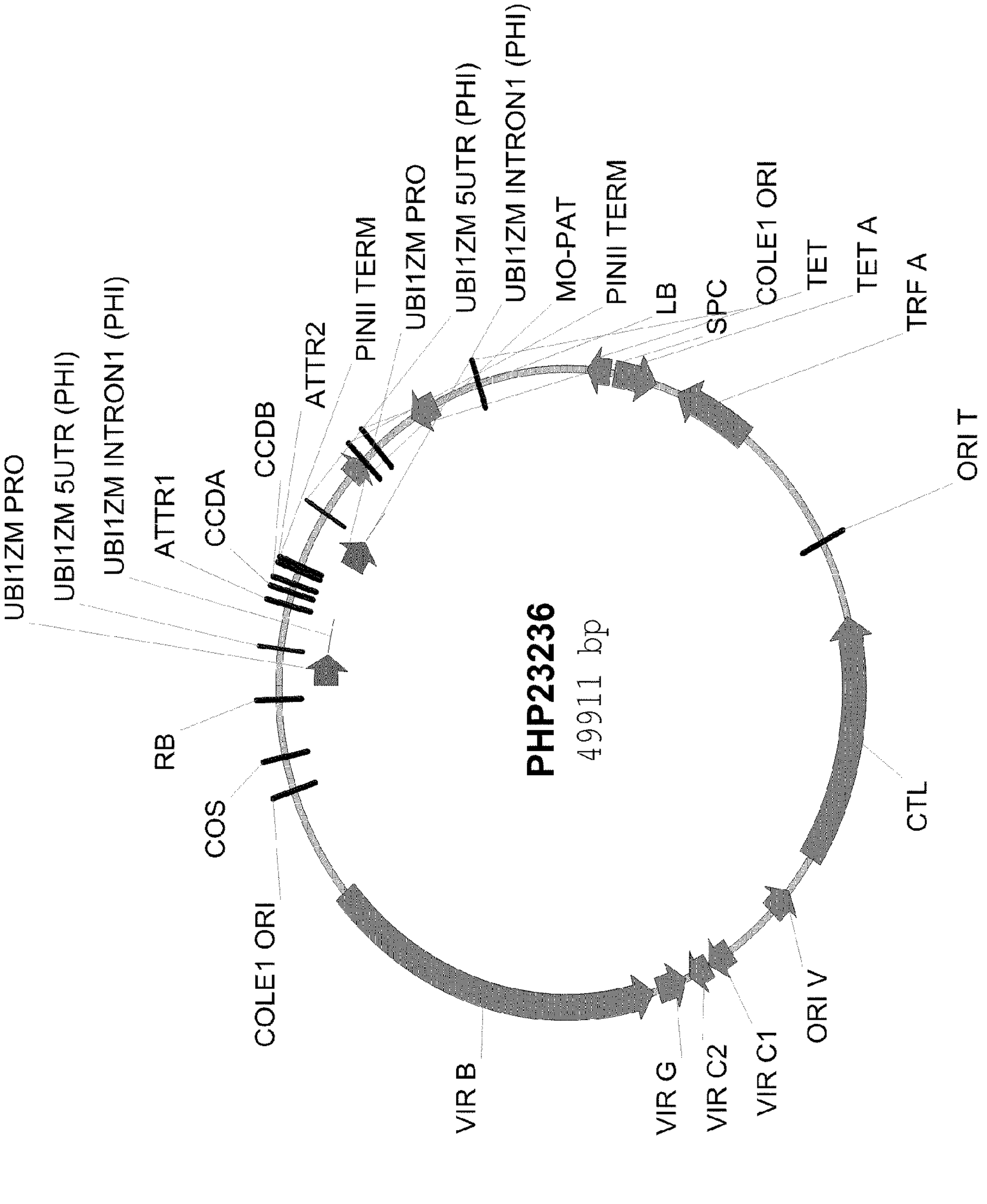
FIG. 6 depicts the vector PHP23236.

A PCR product obtained by either method above can be combined with the Gateway® donor vector, such as pDONR™/Zeo (Invitrogen™, FIG. 3; SEQ ID NO:46) or pDONR™221 (Invitrogen™, FIG. 4; SEQ ID NO:47) using a BP Recombination Reaction. This process removes the bacteria lethal ccdB gene as well as the chloramphenicol resistance gene (CAM) from the donor vectors and directionally clones the PCR product with flanking attB1 and attB2 sites to create an entry clone. Using the Invitrogen Gateway® Clonase™ technology, the RUM1 or RUM1-like gene from the entry clone can then be transferred to a suitable destination vector to obtain a plant expression vector for use with soy and corn, such as PHP27840 (FIG. 5; SEQ ID NO:48) or PHP23236 (FIG. 6; SEQ ID NO:49), respectively.

Alternatively a MultiSite Gateway® LR recombination reaction between multiple entry clones and a suitable destination vector can be performed to create an expression vector. An Example of this type of reaction is outlined in Example 14, which describes the construction of maize expression vectors for transformation of maize lines.

Example 10

Preparation of Soybean Expression Vectors and Transformation of Soybean with the RUM1 gene Soybean plants can be transformed to over-express the RUM1 and RUM1-like sequences in order to examine the resulting phenotype.

The entry clones described in Example 9 can be used to directionally clone each gene into PHP27840 vector (FIG. 5, SEQ ID NO:48) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Enhanced root architecture can be measured in soybean by growing the plants in soil and wash the roots before analysis of the total root mass with the software WinRHIZO® (Regent Instruments Inc), an image analysis system specifically designed for root measurement. WinRHIZO® uses the contrast in pixels to distinguish the light root from the darker background.

Soybean plants transformed with the RUM1 gene can then be assayed to study agronomic characteristics relative to control or reference plants. For example, nitrogen utilization efficacy, yield enhancement and/or stability under various environmental conditions (e.g. nitrogen limiting conditions, drought etc.).

Example 11

Transformation of Maize with the RUM1 and RUM1-like Gene Using Particle Bombardment Maize plants can be transformed to overexpress RUM1 and RUM1-like genes in order to examine the resulting phenotype.

The Gateway® entry clones described in Example 9 can be used to directionally clone each gene into a maize transformation vector. Expression of the gene in maize can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens.*

The particle bombardment method (Klein et al., *Nature* 327:70-73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the maize tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialophos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined following HTP procedures. T1 seed can be collected.

T1 plants can be grown and analyzed for phenotypic changes. The following parameters can be quantified using image analysis: plant area, volume, growth rate and color analysis can be collected and quantified. Expression constructs that result in an alteration of root architecture compared to suitable control plants, can be considered evidence that the RUM1 gene functions in maize to alter root architecture.

Furthermore, a recombinant DNA construct containing the RUM1 gene can be introduced into an maize line either by direct transformation or introgression from a separately transformed line.

Transgenic plants, either inbred or hybrid, can undergo more vigorous field-based experiments to study yield enhancement and/or resistance to root lodging under various environmental conditions (e.g. variations in nutrient and water availability).

Subsequent yield analysis can also be done to determine whether plants that contain the RUM1 gene have an improvement in yield performance, when compared to the control (or reference) plants that do not contain the RUM1 gene. Plants containing the RUM1 gene would have less yield loss relative to the control plants, preferably 50% less yield loss or would have increased yield relative to the control plants under varying environmental conditions.

Example 12

Electroporation of *Agrobacterium* LBA4404

Electroporation competent cells (40 μl), such as *Agrobacterium tumefaciens* LBA4404 (containing PHP10523, FIG. 7, SEQ ID NO:50), are thawn on ice (20-30 min). PHP10523 contains VIR genes for T-DNA transfer, an *Agrobacterium* low copy number plasmid origin of replication, a tetracycline resistance gene, and a cos site for in vivo DNA biomolecular recombination. Meanwhile the electroporation cuvette is chilled on ice. The electroporator settings are adjusted to 2.1 kV.

A DNA aliquot (0.5 μL JT (U.S. Pat. No. 7,087,812) parental DNA at a concentration of 0.2 μg-1.0 μg in low salt buffer or twice distilled $H_2O$) is mixed with the thawn *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2×YT medium (or SOCmedium) are added to cuvette and transferred to a 15 ml Falcon tube. The cells are incubated at 28-30° C., 200-250 rpm for 3 h.

Aliquots of 250 μl are spread onto #30B (YM+50 μg/mL. Spectinomycin) plates and incubated 3 days at 28-30° C. To increase the number of transformants one of two optional steps can be performed:

Option 1: overlay plates with 30 μl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plated are incubate at 28° C. for 2-3 days.

A single colony for each putative co-integrate is picked and inoculated with 4 ml #60A with 50 mg/l Spectinomycin. The mix is incubated for 24 h at 28° C. with shaking. Plasmid DNA from 4 ml of culture is isolated using Qiagen Miniprep+ optional PB wash. The DNA is eluted in 30 μl . Aliquots of 2 μl are used to electroporate 20 μl of DH10b+20 μl of dd$H_2O$ as per above.

Optionally a 15 μl aliquot can be used to transform 75-100 μl of Invitrogen Library Efficiency DH5α. The cells are spread on LB medium plus 50 mg/mL Spectinomycin plates (#34T medium) and incubated at 37° C. overnight.

Three to four independent colonies are picked for each putative co-integrate and inoculated 4 ml of 2×YT (#60A) with 50 μg/ml Spectinomycin. The cells are incubated at 37° C. overnight with shaking.

Isolate plasmid DNA from 4 ml of culture using QIAprep® Miniprep with optional PB wash (elute in 50 μl). Use 8 μl for digestion with SalI (using JT parent and PHP10523 as controls).

Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Alternatively, for high throughput applications, such as described for Gaspe Bay Flint Derived Maize Lines (Examples 16-18), instead of evaluating the resulting co-integrate vectors by restriction analysis, three colonies can be simultaneously used for the infection step as described in Example 13.

Example 13

*Agrobacterium* Mediated Transformation into Maize

Maize plants can be transformed to overexpress RUM1 and RUL in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation

Immature embryos are dissected from caryopses and placed in a 2 mL microtube containing 2 mL PHI-A medium.

2. *Agrobacterium* Infection and Co-Cultivation of Embryos 2.1 Infection Step

PHI-A medium is removed with 1 mL micropipettor and 1 mL *Agrobacterium* suspension is added. Tube is gently inverted to mix. The mixture is incubated for 5 min at room temperature.

2.2 Co-Culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events

To each plate of PHI-D medium in a 100×15 mm Petri dish, 10 embryos are transferred, maintaining orientation and the dishes are sealed with Parafilm. The plated are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 Plants

Embryonic tissue propagated on PHI-D medium is subcultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 μE from cool white or equivalent fluorescent lamps). In 7-10 days, regenerated plants, about 10 cm tall, are potted in horticultural mix and hardened-off using standard horticultural methods.

Media for Plant Transformation

1. PHI-A: 4 g/L CHU basal salts, 1.0 mL/L 1000× Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 μM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L gelrite, 100 μM acetosyringone (filter-sterilized), 5.8.
3. PHI-C: PHI-B without gelrite and acetosyringonee, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (fileter-sterilized), 8 g/L agar, pH 5.6.
6. PHI-F: PHI-E without zeatin, IAA, ABA; sucrose reduced to 40 g/L; replacing agar with 1.5 g/L gelrite; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis can be taken at multiple times during growth of the plants. Alteration in root architecture can be assayed as described In Example 21.

Subsequent analysis of alterations in agronomic characteristics can be done to determine whether plants containing the RUM1 or the RUL gene have an improvement of at least one agronomic characteristic, when compared to the control (or reference) plants that do not contain RUM1 or the RUL gene. The alterations may also be studied under various environmental conditions.

Example 14

Construction of Maize Expression Vectors with the RUM1 and RUL Gene Using *Agrobacterium* Mediated Transformation Maize expression vectors can be prepared with the RUM1 (SEQ ID NO:22 or 28 and RUM1-like genes (such as RUL, SEQ ID NO:38) under the control of the NAS2 (SEQ ID NO:51), GOS 2 (SEQ ID NO:52) or Ubiquitin (UBI1ZM; SEQ ID NO:53) promoter. PINII is the terminator (SEQ ID NO:54)

Figure 8:
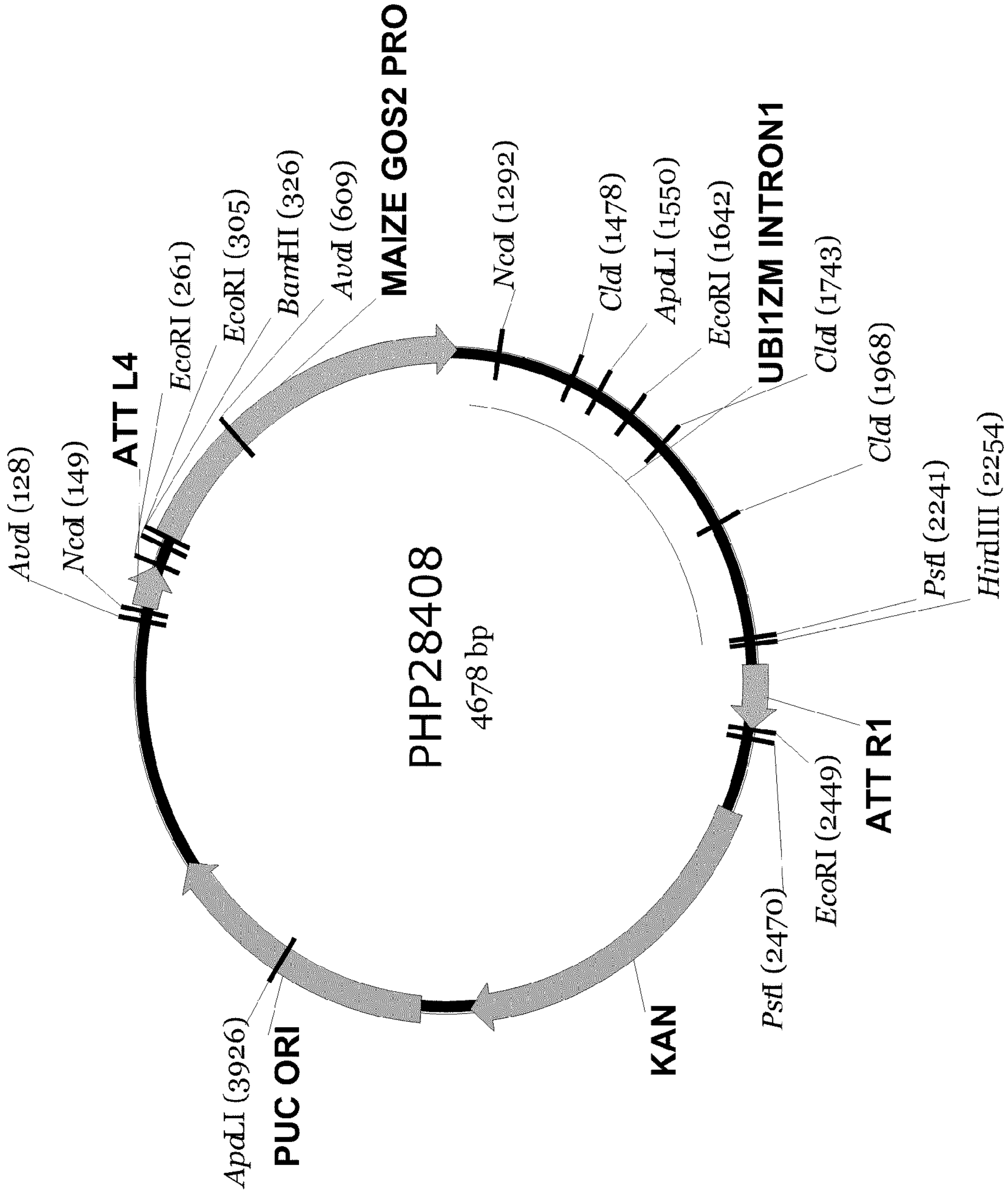
FIG. 8 depicts the vector PHP28408.
Figure 9:
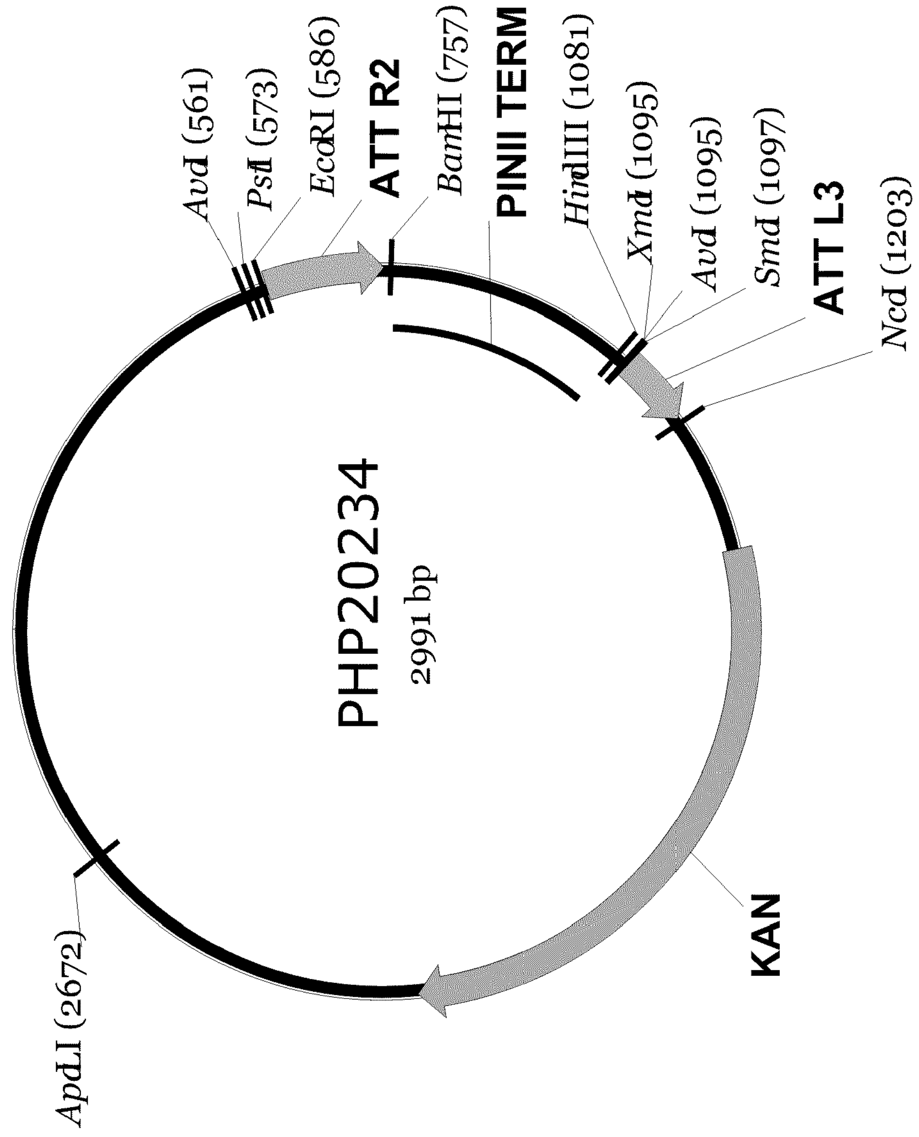
FIG. 9 depicts the vector PHP20234.
Figure 10:
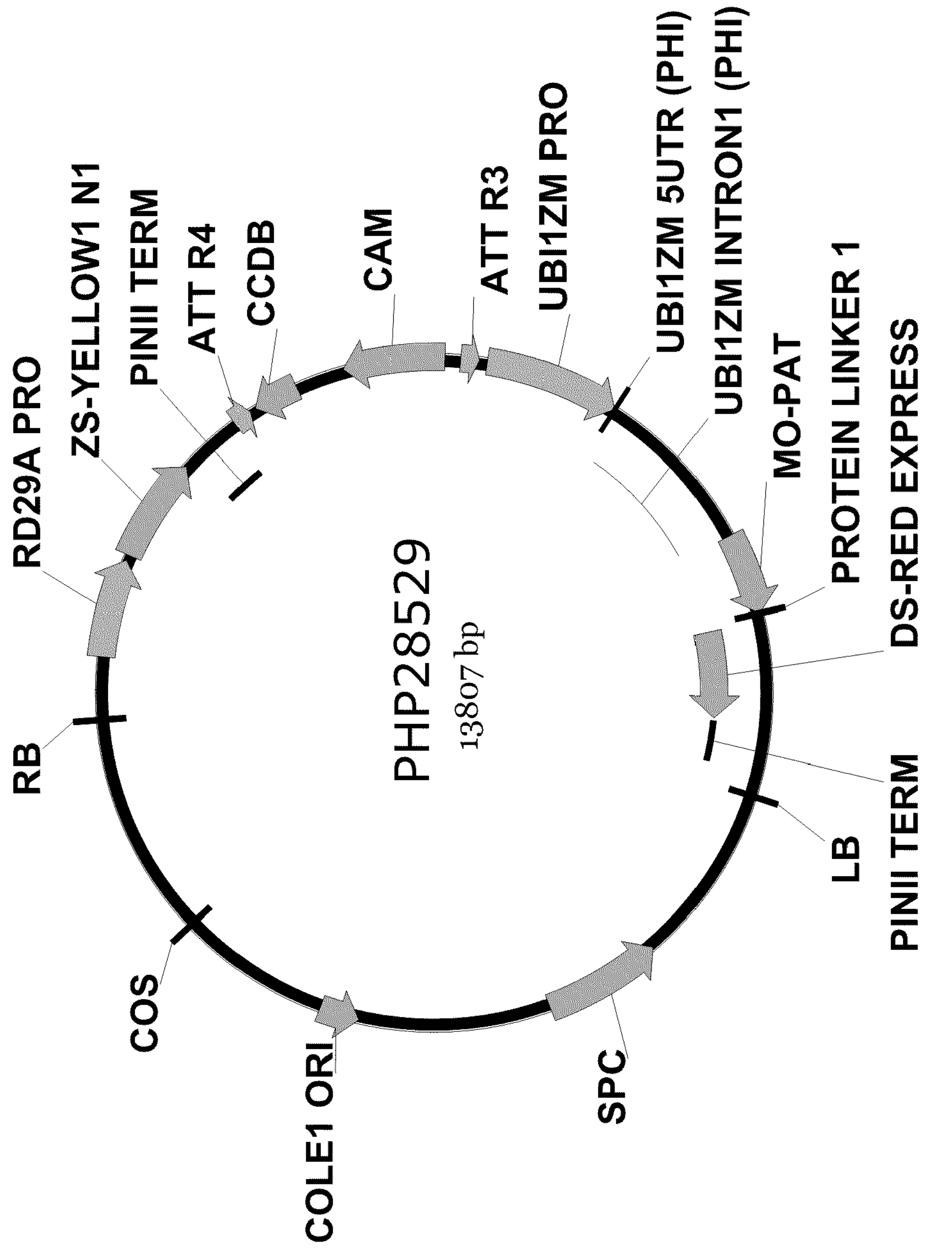
FIG. 10 depicts the vector PHP28529.

Using Invitrogen's™ Gateway® technology the entry clone, created as described in Example 9, containing the maize RUM1 gene or maize RUL gene can be used in separate Gateway® LR reactions with:

1) the constitutive maize GOS2 promoter entry clone PHP28408 (FIG. 8, SEQ ID NO:55) and the PinII Terminator entry clone PHP20234 (FIG. 9, SEQ ID NO:56), into the destination vector PHP28529 (FIG. 10, SEQ ID NO:57).

Figure 11:
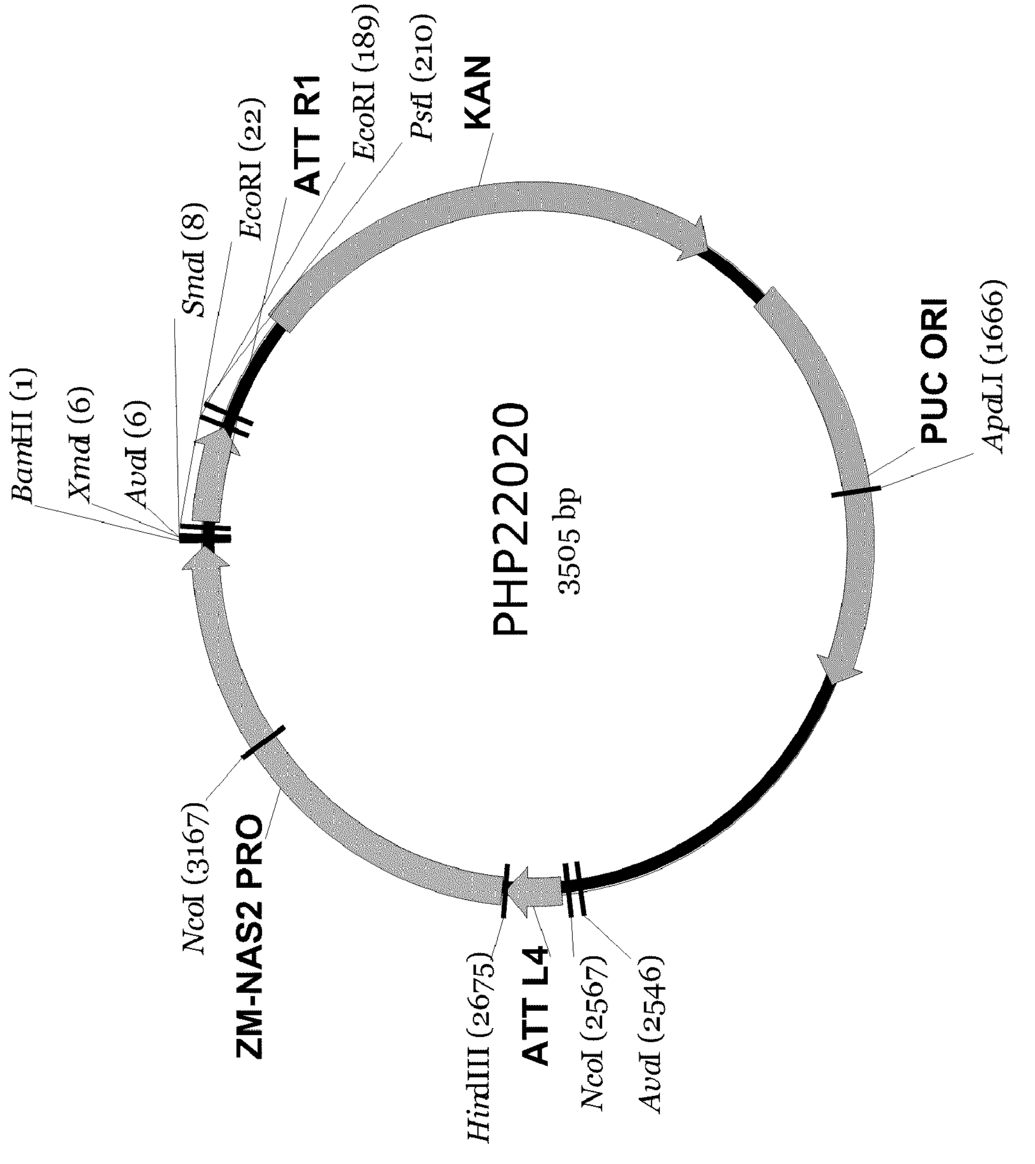
FIG. 11 depicts the vector PHP22020.

2) the root maize NAS2 promoter entry clone PHP22020 (FIG. 11, SEQ ID NO:58) and the PinII Terminator entry clone PHP20234 (FIG. 9, SEQ ID NO:56) into the destination vector PHP28529 (FIG. 10, SEQ ID NO:57).

Figure 12:
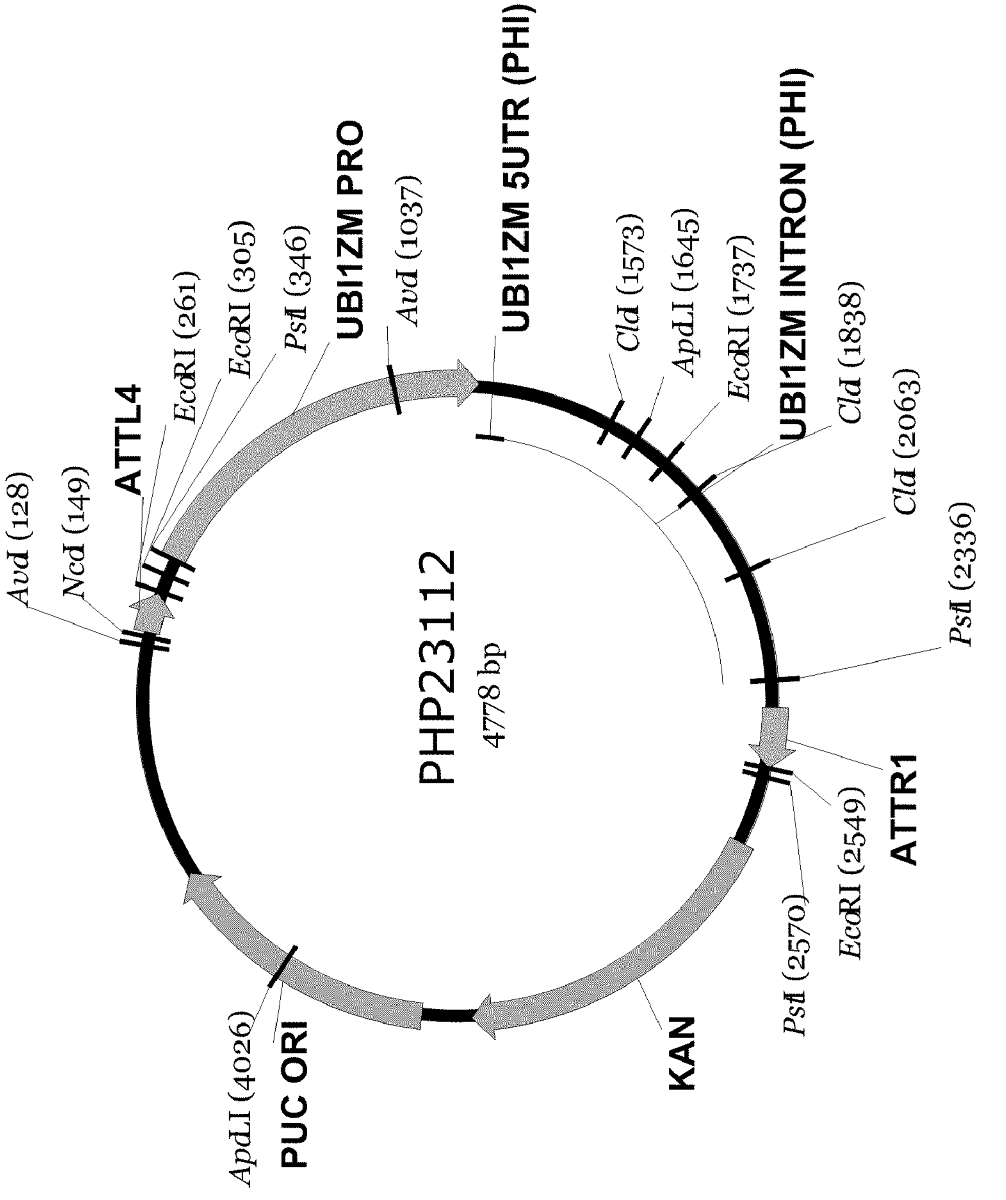
FIG. 12 depicts the vector PHP23112.

3) the constitutive maize UBI1ZM promoter entry clone PHP23112 (FIG. 12, SEQ ID NO:59) and the PinII Terminator entry clone PHP20234 (FIG. 9, SEQ ID NO:56) into the destination vector PHP28529 (FIG. 10, SEQ ID NO:57). The destination vector PHP28529 adds to each of the final vectors also an:

1) RD29A promoter::yellow fluorescent protein::PinII terminator cassette for *Arabidospis* seed sorting.
2) a Ubiquitin promoter::moPAT/red fluorescent protein fusion: :Pin II terminator cassette for transformation selection and *Z. mays* seed sorting.

In addition to the GOS2 or NAS2 promoter, other promoters such as, but not limited to the S2A and S2B promoter, the maize ROOTMET2 promoter, the maize Cyclo, the CR1BIO, the CRWAQ81 and the maize ZRP2.4447 are useful for directing expression of RUM1 and RUM1-like genes in maize. Furthermore, a variety of terminators, such as, but not limited to the PINII terminator, could be used to achieve expression of the gene of interest in maize.

Example 15

Figure 7:
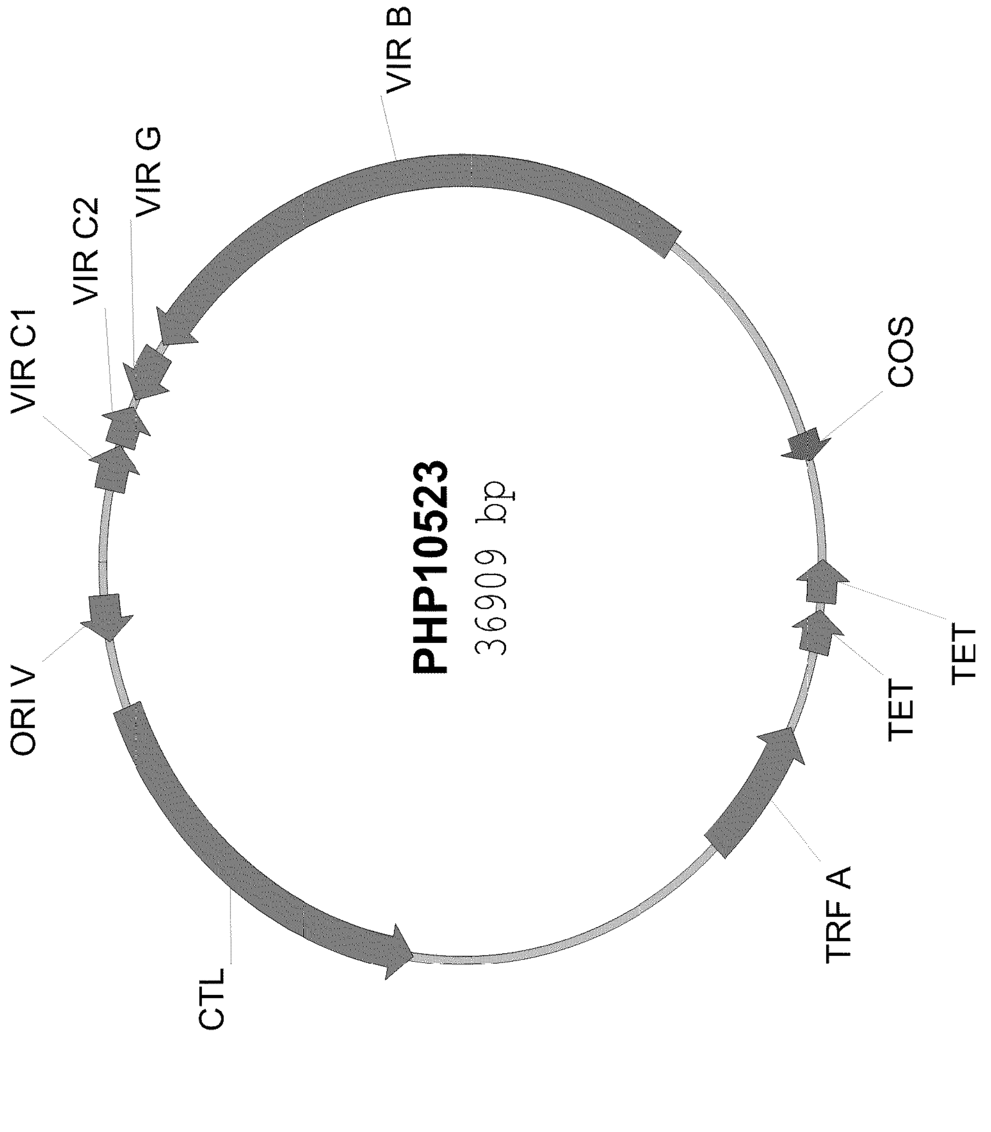
FIG. 7 depicts the vector PHP10523.

Transformation of Maize Lines with RUM1 and RUM1-like Genes Using *Agrobacterium* Mediated Transformation The final vectors (Example 14) can then electroporated separately into LBA4404 *Agrobacterium* containing PHP10523 (FIG. 7; SEQ ID NO:50, Komari et al. Plant J 10:165-174 (1996), *NCBI GI:* 59797027) to create the co-integrate vectors for maize transformation. The co-integrate vectors are formed by recombination of the final vectors (maize expression vectors) with PHP10523, through the COS recombination sites contained on each vector. The co-integrate vectors contain in addition to the expression cassettes described in Example 14, also genes needed for the *Agrobacterium* strain and the *Agrobacterium* mediated transformation, (TET, TET, TRFA, ORI terminator, CTL, ORI V, VIR C1, VIR C2, VIR G, VIR B). Transformation into a maize line can be performed as described in Example 13.

Example 16

Figure 13:
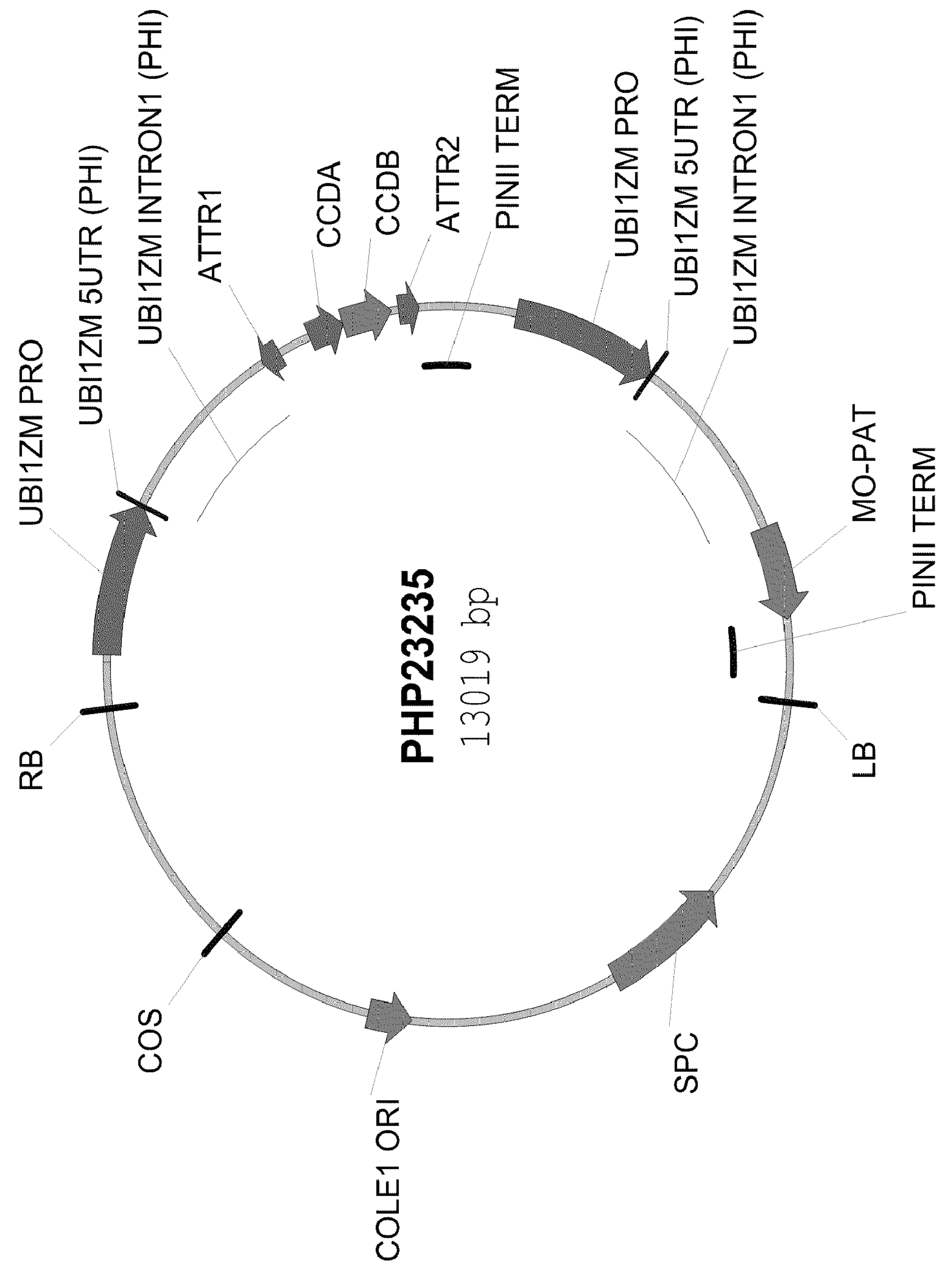
FIG. 13 depicts the vector PHP23235.

Preparation of the Destination Vectors PHP23236 and PHP29635 for Transformation of Gaspe Bay Flint Derived Maize Lines Destination vector PHP23236 (FIG. 6, SEQ ID NO:49) was obtained by transformation of *Agrobacterium* strain LBA4404 containing plasmid PHP10523 (FIG. 7, SEQ ID NO:50) with plasmid PHP23235 (FIG. 13, SEQ ID NO:60) and isolation of the resulting co-integration product. Destination vector PHP23236, can be used in a recombination reaction with an entry clone as described in Example 9 to create a maize expression vector for transformation of Gaspe Bay Flint derived maize lines. Expression of the gene of interest is under control of the ubiquitin promoter (SEQ ID NO:53).

Figure 14:
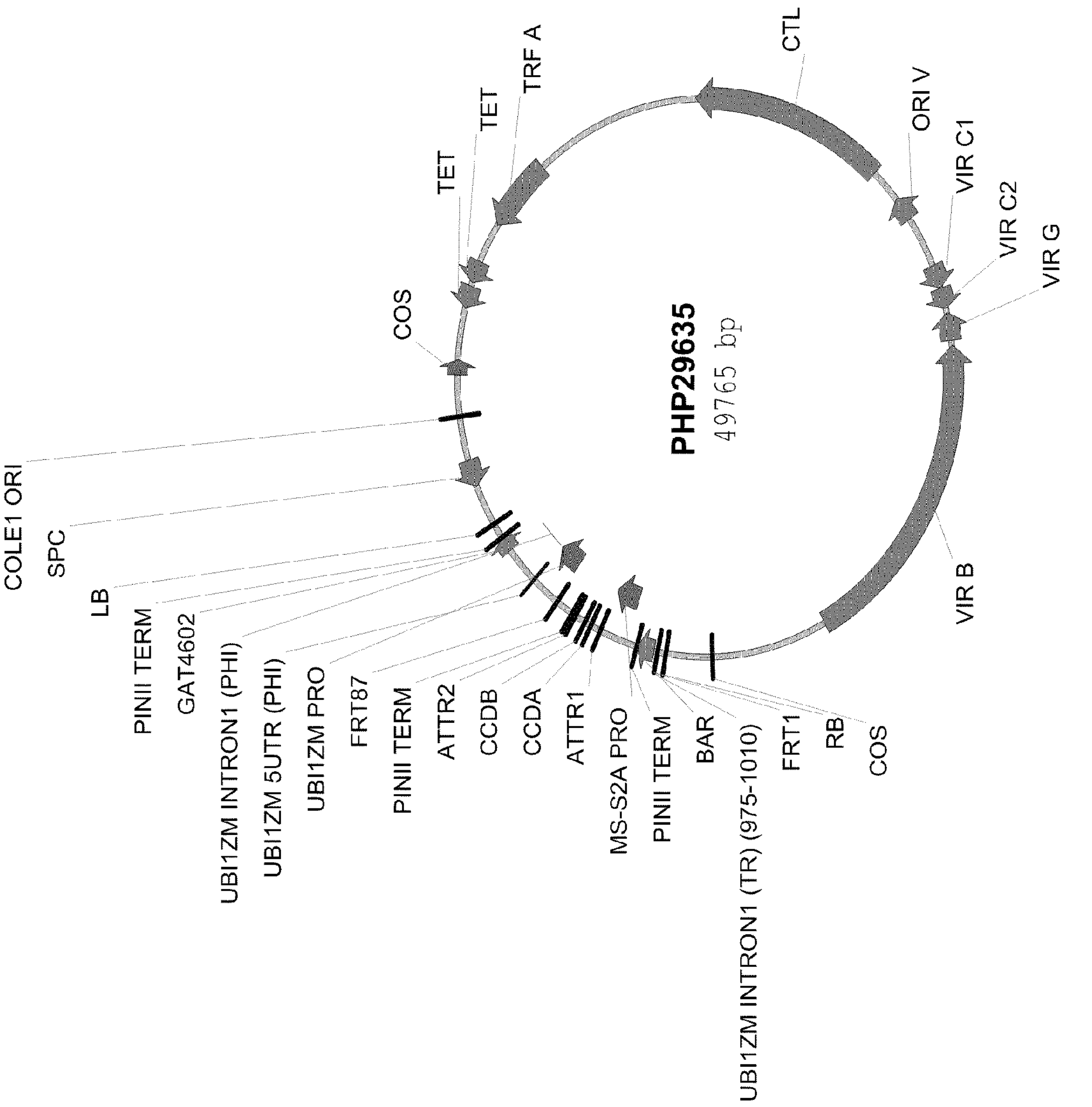
FIG. 14 depicts the vector PHP29635.
Figure 15:
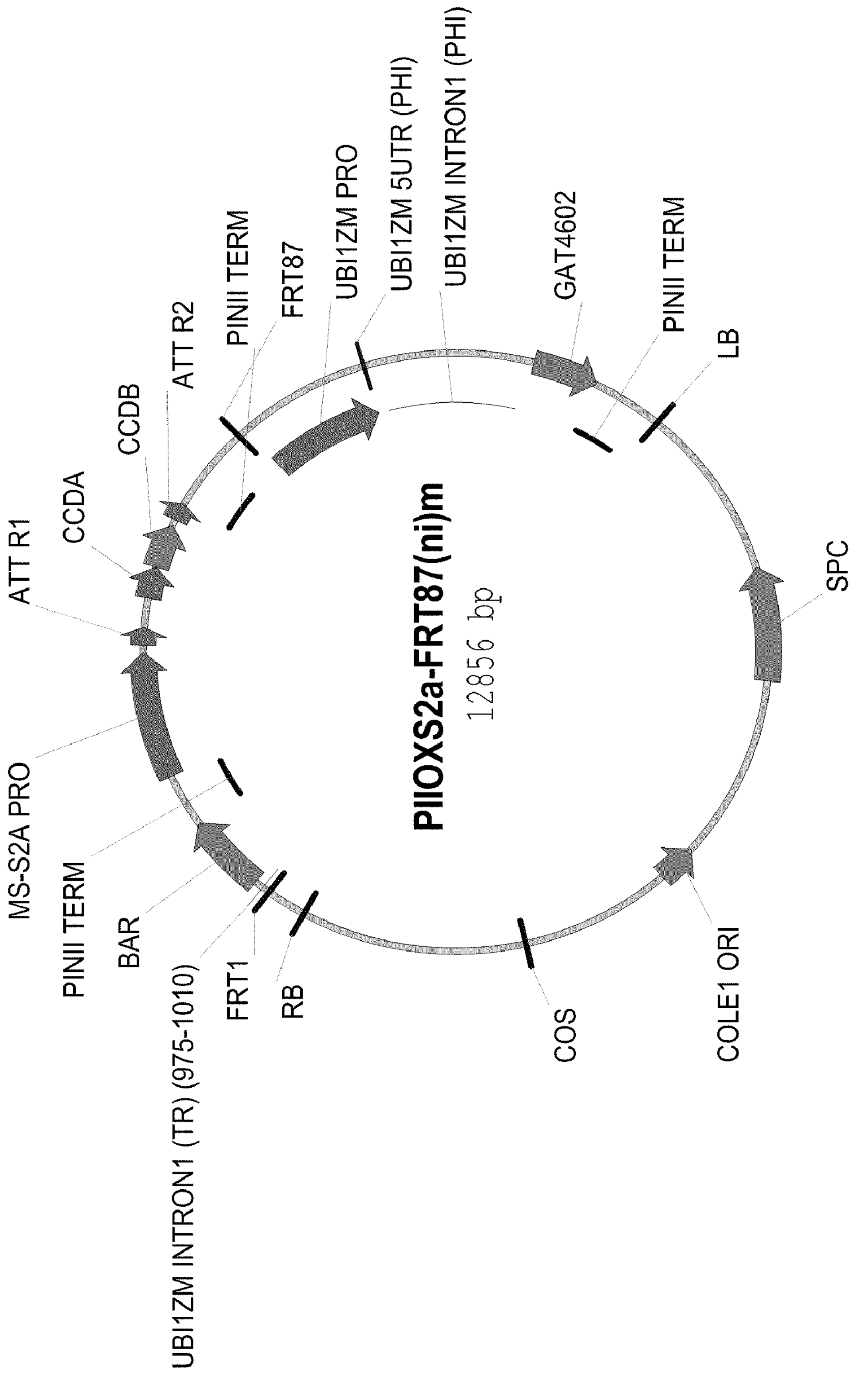
FIG. 15 depicts the vector pIIOXS2a-FRT87(ni)m.

PHP29635 (FIG. 14, SEQ ID NO:61) was obtained by transformation of *Agrobacterium* strain LBA4404 containing plasmid PHP10523 with plasmid PIIOXS2a-FRT87(ni)m (FIG. 15, SEQ ID NO:62) and isolation of the resulting co-integration product. Destination vector PHP29635 can be used in a recombination reaction with an entry clone as described in Example 9 to create a maize expression vector for transformation of Gaspe Bay Flint derived maize lines. Expression of the gene of interest is under control of the S2A promoter (SEQ ID NO:63).

Example 17

Preparation of Plasmids Containing RUM1 or RUL Genes for Transformation of Gaspe Bay Flint Derived Maize Lines Using Invitrogen's Gateway® Recombination technology, entry clones containing the RUM1 or RUM1-like genes can be created, as described in Example 9 and used to directionally clone each gene into destination vector PHP23236 (Example 16) for expression under the ubiquitin promoter or into destination vector PHP29635 (Example 16) for expression under the S2A promoter. Each of the expression vectors are T-DNA binary vectors for *Agrobacterium*-mediated transformation into corn.

Gaspe Bay Flint Derived Maize Lines can be transformed with the expression vectors as described in Example 18.

Example 18

Transformation of Gaspe Bay Flint Derived Maize Lines with RUM1 and RUM1-Like Genes Maize plants can be transformed to over-express the RUM1 and RUM1-like genes, in order to examine the resulting phenotype.

Recipient Plants

Recipient plant cells can be from a uniform maize line having a short life cycle ("fast cycling"), a reduced size, and high transformation potential. Typical of these plant cells for maize are plant cells from any of the publicly available Gaspe Bay Flint (GBF) line varieties. One possible candidate plant line variety is the F1 hybrid of GBF×QTM (Quick Turnaround Maize, a publicly available form of Gaspe Bay Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors as described in Example 17. Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. Preferably, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. Preferably, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging

For best estimation of biomass the plant images should be taken from at least three axes, preferably the top and two side (sides 1 and 2) views. These images are then analyzed to separate the plant from the background, pot and pollen control bag (if applicable). The volume of the plant can be estimated by the calculation:

$$Volume(voxels) = \sqrt{TopArea(pixels)} \times \sqrt{Side1Area(pixels)} \times \sqrt{Side2Area(pixels)}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 19

Screening of Gaspe Bay Flint Derived Maize Lines Under Nitrogen Limiting Conditions Transgenic plants will contain two or three doses of Gaspe Flint-3 with one dose of GS3 (GS3/(Gaspe-3)$_2$× or GS3/(Gaspe-3)3×) and will segregate 1:1 for a dominant transgene. Plants will be planted in Turface, a commercial potting medium, and watered four times each day with 1 mM $KNO_3$ growth medium and with 2 mM $KNO_3$, or higher, growth medium (see FIG. 16). Control plants grown in 1 mM $KNO_3$ medium will be less green, produce less biomass and have a smaller ear at anthesis (see FIG. 17 for an illustration of sample data).

Statistics are used to decide if differences seen between treatments are really different. FIG. 17 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal.

Expression of a transgene will result in plants with improved plant growth in 1 mM $KNO_3$ when compared to a transgenic null. Thus biomass and greenness will be monitored during growth and compared to a transgenic null. Improvements in growth, greenness and ear size at anthesis will be indications of increased nitrogen tolerance.

Example 20

Yield Analysis of Maize Lines with RUM1 or RUM1-like Genes

A recombinant DNA construct containing a RUM1 or RUM1-like Gene can be introduced into a maize line either by direct transformation or introgression from a separately transformed line.

Transgenic plants, either inbred or hybrid, can undergo more vigorous field-based experiments to study yield enhancement and/or stability under various environmental conditions, such as variations in water and nutrient availability.

Subsequent yield analysis can be done to determine whether plants that contain the RUM1 or RUM1-like gene have an improvement in yield performance under various environmental conditions, when compared to the control plants that do not contain the RUM1 or RUM1-like gene. Reduction in yield can be measured for both. Plants containing the RUM1 or RUM1-like gene have less yield loss relative to the control plants, preferably 50% less yield loss.

Example 21

Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.

1) Root mass (dry weights). Plants are grown in Turface, a growth media that allows easy separation of roots. Oven-dried shoot and root tissues are weighed and a root/shoot ratio calculated.

2) Levels of lateral root branching. The extent of lateral root branching (e.g. lateral root number, lateral root length) is determined by sub-sampling a complete root system, imaging with a flat-bed scanner or a digital camera and analyzing with WinRHIZO™ software (Regent Instruments Inc.).

3) Root band width measurements. The root band is the band or mass of roots that forms at the bottom of greenhouse pots as the plants mature. The thickness of the root band is measured in mm at maturity as a rough estimate of root mass.

4) Nodal root count. The number of crown roots coming off the upper nodes can be determined after separating the root from the support medium (e.g. potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with that of non-transgenic sibling plants. One-way ANOVA may also be used in cases where multiple events and/or constructs are involved in the analysis.

Example 22

Subcellular Localization of RUM1 and RUL

The Aux/IAA proteins of *Arabidopsis* and rice have been shown to be localized to the nucleus [Abel et al. (1994) *Proc Natl Acad Sci USA* 91:326-330; Thakur et al. (2005) *Biochim Biophys Acta* 1730:196-205]. Two types of putative nuclear localization signals (NLS) that are conserved in most of the rice Aux/IAA proteins [Jain et al. (2006) Funct Integr Genomics 6:47-59] are also present in the maize RUM1 and RUL proteins. A bipartite NLS comprises residues KR, at amino acid residues 80 and 84 in RUM1 and RUL, respectively and residues NYRKN, at amino acid residues 122 and 125 in RUM1 and RUL, respectively. A SV40-type NLS comprises residues RKLKIMR at amino acid residues 244 and 247 in Rum1 and RUL, respectively.

In order to confirm that the RUM1 and the RUL proteins localize to the nucleus, one can analyze the transient expression of the respective proteins in onion epidermal cells. First, vectors carrying full length cDNAs driven by the CaMV 35S promoter and fused translationally to the YFP reporter gene (Clontech) are constructed, and then introduced into onion epidermal cells by particle bombardment (Scott A. et al. (1999) Biotechniques 26(6):1125, 1128-32).

Example 23

Analysis of the Transcriptional Repressor Activity of RUM1 and RUL Proteins

The Aux/IAA proteins show a conserved L×L×L motif which has been shown to act as a transcriptional repressor domain [Tiwari et al (2004) Plant Cell 16:533-543]. The L×L×L motif is also present in the RUM1 and RUL proteins at residue 42 in RUM1 and 40 in RUL (FIG. 18).

In order to determine if RUM1 and RUL are transcriptional repressors, one can analyze their repressor activity by protoplast transfect ion assay. In this method, an *Arabidopsis* leaf macrophylla protoplast transfect ion assay system and a reporter construct containing the firefly luciferase reporter gene (glib 3, Promega, Madison Wis., 53711) driven by the CaMV 35S minimal promoter (nucleotides -46 to −1) with four GAL4 DNA binding sequences (SEQ ID NO:64) are used. The luciferase reporter is co-transfected with one effectors gene encoding a chimeric protein consisting of the yeast GAL4 DNA binding domain (amino acids 1 to 147 from pGBKT7, Clontech) fused in frame to either the RUM1, or the RUL cDNAs. Effectors genes are driven by a duplicated CaMV 35S enhancer sequence (nucleotides -206 to 46) followed by the CaMV 35S minimal promoter. A construct containing only the 35S promoter and the GAL4 DBD is used as an effectors control. Effectors plasmids (5 μg) are cotransfected with reporter plasmids (10 μg) at a ratio of 1:2. The efficiency of transfect ion is normalized by adding 100 ng of a pUbiquitin:Renilla LUC reporter gene (phRL-TK, Promega, Madison Wis., 53711), (Tiwari et al. (2005) *Methods in Mol Biol* 323: 237-244). If RUM1 and RUL function as transcriptional repressors, it is expected that the RUM1 and RUL effectors will reduce the relative luciferase activity of the reporter in comparison to the effectors control.

Example 24

Composition of cDNA Libraries; Isolation and Sequencing of cDNA Clones cDNA libraries representing mRNAs from various tissues of *Brassica napus* (canola), *Glycine max* (soybean), and *Triticum aestivum* (wheat) were prepared. The characteristics of the libraries are described below.

TABLE 2 cDNA Libraries from Canola, Soybean and Wheat.

| Library | Tissue | Clone |
|---|---|---|
| ebb1c | Immature buds of Canola Rf gene knock out mutant line, 02SM2. Isolation of genes involved in CMS restoration. | ebb1c.pk008.p9:fis |
| smj1c | Characterization of IPT transcripts from transgenic soybean. The lead Yield Enhancement (Soy YE2.1) construct is expressing *Agrobacterium* isopentenyl transferase gene, and we need to characterize all transcripts from the transgene. | smj1c.pk013.h7.f:fis<br>smj1c.pk007.k12.f:fis |
| wdk1c | Wheat (*Triticum aestivum* L.) developing kernel, 3 days after anthesis. | wdk1c.pk023.b8:fis |

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfect ion into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers.

Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 25

Identification of cDNA Clones cDNA clones encoding RUM1-like polypeptides were identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained as described in Example 24 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the Genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 24. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 26

Characterization of cDNA Clones Encoding RUM1 Polypeptides, RUL Polypeptides and Homologs Thereof The BLASTX search using the EST sequences from clones listed in Table 3 revealed similarity of the polypeptides encoded by the ORF to proteins from rice, *Arabidopsis* and soybean identified as belonging to the AUX-IAA family (NCBI General Identifier No's. 34911088, 125553286, 15229343, and 2388689, corresponding to SEQ ID NOs:65, 76, 74, and 75, respectively ).

Shown in Table 3 and 4 are the literature and patent BLAST results, respectively, for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results (Literature) and Percent Identity for Sequences Encoding RUM1 and RUL polypeptides and homologs thereof.

| Sequence | Status | BLAST pLOG Score to | % identity |
|---|---|---|---|
| B73-Mu-wt RUM1 (SEQ ID NO: 24) | cgs | 77 (NCBI GI No: 34911088, SEQ ID NO: 65) | 67.3 NCBI GI No: 34911088 (SEQ ID NO: 65) |
| B73 RUM1 (SEQ ID NO: 29) | cgs | 78 (NCBI GI No: 34911088, SEQ ID NO: 65) | 67.3 NCBI GI No: 34911088 (SEQ ID NO: 65) |
| B73 RUL (SEQ ID NO: 39) | cgs | 77 (NCBI GI No: 34911088, SEQ ID NO: 65) | 68.6 NCBI GI No: 34911088 (SEQ ID NO: 65) |
| ebb1c.pk008.p9:fis (SEQ ID NO: 67) | cgs | 100 (NCBI GI No: 15229343, SEQ ID NO: 74) | 90.3(NCBI GI No: 15229343, SEQ ID NO: 74) |
| smj1c.pk013.h7.f:fis (SEQ ID NO: 69) | cgs | >180 (NCBI GI No: 2388689, SEQ ID NO: 75) | 95.6 (NCBI GI No: 2388689, SEQ ID NO: 75) |
| smj1c.pk007.k12.f:fis (SEQ ID NO: 71) | cgs | >180 (NCBI GI No: 2388689, SEQ ID NO: 75) | 100 (NCBI GI No: 2388689, SEQ ID NO: 75) |
| wdk1c.pk023.b8:fis (SEQ ID NO: 73) | cgs | 79 (NCBI GI No: 125553286 SEQ ID NO: 76 | 64.4 (NCBI GI No: 125553286 SEQ ID NO: 76 |

The BLASTX search using the sequences from clones listed in Table 1 below revealed similarity of the polypeptides encoded by the Table 3 shows the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS").

TABLE 4

BLAST Results (patent) for Sequences Encoding Polypeptides Homologous to RUM1 and RUL Polypeptides and homologs thereof.

| Sequence | Status | Reference | Blast pLog Score | % identity |
|---|---|---|---|---|
| B73-Mu-wt RUM1 (SEQ ID NO: 24) | CGS | SEQ ID NO: 349502 in US2004214272 | 106 | 98.5 |
| B73 RUM1 (SEQ ID NO: 29) | CGS | SEQ ID NO: 349502 in US2004214272 | 106 | 99.3 |
| B73 RUL (SEQ ID NO: 39) | CGS | SEQ ID NO: 6770 in US2004034888-A1 | 106 | 100 |
| ebb1c.pk008.p9:fis (SEQ ID NO: 67) | CGS | G456 in US2007022495 | 101 | 90.3 |
| smj1c.pk013.h7.f:fis (SEQ ID NO: 69) | CGS | SEQ ID NO: 23940 in US2006107345 | >180 | 100 |
| smj1c.pk007.k12.f:fis (SEQ ID NO: 71) | CGS | SEQ ID NO: 23940 in US2006107345 | >180 | 100 |
| wdk1c.pk023.b8:fis (SEQ ID NO: 73) | CGS | SEQ ID NO: 33260 in US2006107345 | 83 | 66.4 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 27

Construction of Promoter Variants and Expression Data Using Promoter Sequences Deletion variants are made by truncating the promoter sequences at several positions in the promoter region as shown in FIG. 22. The truncations result in three promoter variants: (1) 648 nucleotides (TR1, SEQ ID NO:77), (2) 324 nucleotides (TR2, SEQ ID NO:78), and (3) 566 nucleotides (TR3, SEQ ID NO:79), in length. FIG. 22 also indicates correspondence of each truncation variant with Motifs found in the NAS2 promoter. Expression constructs are prepared as described below, using the truncated variant, linked with the GUS or YFP marker and PINII terminator. Although the foregoing has been described in some detail by way of illustration and example for purposes of understanding, it will be obvious that certain changes and modifications may be practiced within the scope of the appended claims. All references cited are incorporated herein by reference.

Promoter::reporter::terminator fusion constructs are prepared as set out below. All vectors are constructed using standard molecular biology techniques. The deletion variants are made by truncating the promoter sequence from 5'-end at three positions.

ZM-NAS2 PRO::YFP::PINII
ZM-NAS2 PRO::ADH1 INTRON::YFP::PINII
ZM-NAS2 PRO::GUS::PINII
ZM-NAS2 PRO:: ADH1 INTRON::GUS::PINII
ZM-NAS2 TR1 PRO::GUS::PINII
ZM-NAS2 TR2 PRO::GUS::PINII
ZM-NAS2 TR3 PRO::GUS::PINII

Successful subcloning is confirmed by restriction analysis. Transformation and expression is confirmed as discussed infra. It is expected that with both reporters (GUS and YFP) expression is highest in roots. No expression is expected in leaves. Any suitable method may be used to introduce the above described constructs into the maize cells, including but not limited to the transformation methods described in Examples 11, 12, and 13.

What is claimed is:

1. An isolated nucleic acid fragment comprising a root-preferred maize NAS2 promoter, said promoter comprising:

(a) a nucleotide sequence comprising the sequence set forth in SEQ ID NO:51 or the full-length complement thereof.

2. An isolated nucleic acid fragment comprising a root-preferred maize promoter wherein said promoter consists essentially of the nucleotide sequence set forth in SEQ ID NO:51.

3. A recombinant DNA construct comprising the polynucleotide of claim 1 or 2 operably linked to at least one polynucleotide of interest.

4. A vector comprising the recombinant DNA construct of claim 3.

5. A method of transforming a cell, comprising transforming a cell with the recombinant construct of claim 3.

6. An isolated cell comprising the recombinant DNA construct of claim 3.

7. A method for producing a plant comprising transforming a plant cell with the recombinant DNA construct of claim 3 and regenerating a plant from the transformed plant cell.

8. A plant comprising the recombinant DNA construct of claim 3.

9. A seed comprising the recombinant DNA construct of claim 3.

* * * * *